United States Patent
Kawai et al.

(10) Patent No.: US 6,215,016 B1
(45) Date of Patent: Apr. 10, 2001

(54) KETONE DERIVATIVES AND MEDICAL APPLICATION THEREOF

(75) Inventors: Hideki Kawai; Kiyoshi Okano; Yasumoto Adachi; Tsuyoshi Matsumoto; Yuji Sugawara, all of Kanagawa; Youhei Miyamoto, Shiga, all of (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/420,668

(22) Filed: Oct. 19, 1999

Related U.S. Application Data

(62) Division of application No. 08/973,321, filed on Dec. 22, 1997, now abandoned.

(30) Foreign Application Priority Data

Mar. 27, 1996 (JP) .................................................. 8-72212

(51) Int. Cl.[7] ........................... C07C 69/76; C07C 59/90; C07C 49/76; A61K 31/19; A61K 31/235
(52) U.S. Cl. ..................... 560/53; 562/463; 568/337; 514/570; 514/545; 514/689
(58) Field of Search .............................. 562/463; 560/53; 568/337; 514/570, 545, 689

(56) References Cited

U.S. PATENT DOCUMENTS 5,366,993  11/1994  Schiehser et al. .

OTHER PUBLICATIONS

Caputo et al., "IL Farmaco", Ed. Sc., vol. 37, No. 4, 1982, pp. 213–222.

Susnik et al., "Synthesis of some Schiff Bases of 3–Aroyl–6–aryl–4–hydroxy–2 H–pyran–2–ones", Chemical Monthly, 123, (1992), pp. 817–822.

*Primary Examiner*—Deborah C. Lambkin
(74) *Attorney, Agent, or Firm*—Arthur R. Miller

(57) ABSTRACT

The present invention relates to ketone derivatives represented by the following formula and medical agents containing the ketone derivatives or pharmacologically acceptable salts thereof as an active ingredient, and in particular, relates to a hematopoietic agent; it is shown that the present invention increases blood cells, such as platelets, white blood cells, and red blood cells, and is effective in preventing and treating cytopenia caused by cancer chemotherapy, radiation therapy, and the like.

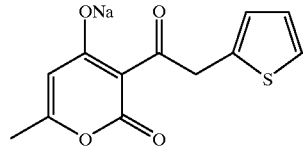

7 Claims, No Drawings

KETONE DERIVATIVES AND MEDICAL APPLICATION THEREOF

This application is a divisional of U.S. Ser. No. 08/973,221 Dec. 22, 1997 abandoned.

TECHNICAL FIELD

The present invention relates to ketone derivatives and an agent having the ketone derivatives or pharmaceutically acceptable salts thereof as an active ingredient, and in particular, relates to a hematopoietic agent.

BACKGROUND ART

Ketone derivatives include lactones and lactams. For example, carolic acid and carolynic acid are known as natural lactones and compounds disclosed in J. Chem. Soc. Perkin Trans. I, 14, 1485–1491 (1976) and Synth. Comm., 22(6), 809–816 (1992) are known as non-naturally derived compounds. In addition, compounds disclosed in J. Org. Chem., 40(13), 1927 (1975), Tetrahedron Lett., 33, 2821 (1975), Chem. Pharm. Bull., 32, 3724 (1984), Tetrahedron Lett., 163 (1973), and the like are known as compounds having the following general formula (I') wherein $R_4$ is an ester group:

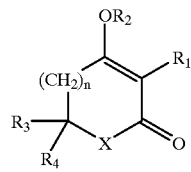

(I')

Lactams of the general formula (I) wherein X is nitrogen are disclosed in Japanese Patent Laid-Open Nos. 2-279691, 4-49289, 2-48591, and 1-313488, Chem. Pharm. Bull., 32(10), 4197–4204 (1984), Pharmazie, 43(7), 473–474 (1988), Monatsh. Chem., 123(1–2), 93–98 (1992), J. Inorg. Biochem., 24(3), 167–181 (1985), J. Am. Chem. Soc., 107(18), 5219–5224 (1985), J. Org. Chem., 50 (8), 1344–1346 (1985), and Chem. Rev., 95, 1981–2001 (1995).

Applications of lactones include, for example, a compound disclosed in Japanese Patent Laid-Open No.5-43568 and EP 0508690, which is known as an anti-inflammatory agent inhibiting phospholipase A2, a compound disclosed in Archive des Pharmazie (Weinhelm, Ger.) (1983), 316(2), 115–120, which is known as an anticoagulant, and a compound disclosed in Journal of Antibiotics (1994), 47(2), 143–7, which is known as an anti-AIDS agent inhibiting HIV-protease.

Applications of lactams include, for example, a compound disclosed in Chem. Pharm. Bull., 32(10), 4197–4204 (1984), which is known as an agent having antibacterial activity, and a compound disclosed in J. Antibiot., 33(2), 173–181 (1980), which is known as an anaerobic antibiotic. However, no ketone derivative has been known to have hematopoietic activity.

An object of the present invention is to provide ketone derivatives, medical agents which have such ketone derivatives or pharmaceutically acceptable salts thereof as an active ingredient, in particular, a hematopoietic agent used for preventing or treating cytopenia caused by cancer chemotherapy, radiation therapy, bone-marrow transplantation, drug therapy, immunological disorders, anemia, or the like.

DISCLOSURE OF INVENTION

The above-mentioned object is achieved by the following present invention. In other words, the present invention relates to: a medical agent composed of a ketone derivative of the following general formula (I) or a pharmacologically acceptable salt thereof

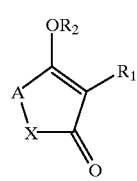

(I)

In the above general formula (I), $R_1$ is a hydrogen atom, a halogen atom, a hydrocarbon group having 1 to 19 carbon atoms (in which the hydrocarbon group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), —$CO(CH_2)_qQ$ (wherein q is an integer of from 0 to 10 and Q is a hydrogen atom, a hydrocarbon group having 1 to 6 carbon atoms (in which the hydrocarbon group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, a cyano group, a trifluoromethyl group, a methylthio group, a phenylthio group, and a t-butyl group), a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, a phosphoric ester group (in which the ester portion has 2 to 6 carbon atoms), a phosphoric group, a sulfonyl group having 1 to 7 carbon atoms, a t-butoxycarbonylamino group, a methylsulfoxide group, a primary amido group, or a secondary amido group), —$COCO(CH_2)_rV_3$ (wherein r is an integer of 0 or 1 and $V_3$ is a hydrogen atom, a linear or branched alkyl group having 1 to 6 carbon atoms, an aryl group having 6 to 12 carbon atoms (in which the aryl group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, a primary amido group, or a secondary amido group), —COCH=CHV$_4$ (wherein V$_4$ is an aryl group having 6 to 12 carbon atoms (in which the aryl group may have one or more substituents selected from the group essentially consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group) or a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), —CO$_2$G (wherein G is a hydrogen atom, a linear or branched alkyl group having 1 to 6 carbon atoms, or an aryl group having 6 to 12 carbon atoms (in which the aryl group may have one or more substituents selected from the group essentially consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group), —CONHV$_1$ (wherein V$_1$ is a hydrogen atom, a linear or branched alkyl group having 1 to 10 carbon atoms, an aryl group having 6 to 12 carbon atoms (in which the aryl group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), or a heterocyclic ring having 1 to 9 carbon atoms (which heterocyclic ring may have one or more substituents selected from the group essentially consisting of a chlorine atom, a bromine atom, a fluorine atom, a hydroxy group, a nitro group, a methoxy group, and an ethoxy group), —NHCOV$_2$ (wherein V$_2$ is a hydrogen atom, a linear or branched alkyl group having 1 to 10 carbon atoms, an aryl group having 6 to 12 carbon atoms (in which the aryl group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), or heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), or —(CH$_2$)$_t$J (wherein t is an integer of from 1 to 10, J is a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, a primary amido group, or a secondary amido group);

R$_2$ is a hydrogen atom, a hydrocarbon group having 1 to 6 carbon atoms, or an acyl group having 2 to 10 carbon atoms;

A is represented by the following general formula (II) or (III),

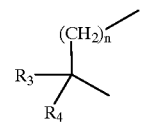

(II)

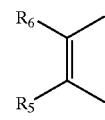

(III)

wherein n is an integer of 0 or 1, R$_3$ and R$_4$ are independently a hydrogen atom, a hydrocarbon group having 1 to 15 carbon atoms (in which the hydrocarbon group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), a 1-hydroxy-1-carboalkoxymethyl group, or a group represented by —(CH$_2$)$_m$Z (wherein m is an integer of from 1 to 6, Z is a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, an aldehyde group, a phosphoric group, a sulfonic group, a phosphoric ester group (in which the ester portion has 1 to 6 carbon atoms), a sulfonic ester group (in which the ester portion has 1 to 6 carbon atoms), a primary amido group, a secondary amido group, an indole group, a monosubstituted phenyl group, a disubstituted phenyl group, or a trisubstituted phenyl group (whose substituent is a chlorine atom, a bromine atom, a fluorine atom, a hydroxy group, a nitro group, a methoxy group, an ethoxy group, a carboxyl group, a carboethoxy group, a carbomethoxy group, and a cyano group), or R$_3$ and R$_4$ may together form —(CH$_2$)$_4$— or —(CH$_2$)$_5$—;

R$_5$ is independently a hydrogen atom, a hydrocarbon group having 1 to 15 carbon atoms (in which the hydrocarbon group may have one or more substituents selected from the group essentially consisting of a chlorine a atom, a bromine atom, a fluorine atom, a hydroxy group, a nitro group, a methoxy group, an ethoxy group, a carboxyl group, a carboethoxy group, a carbomethoxy group, and a cyano group), a 1-hydroxy-1-carboalkoxymethyl group, or a group represented by —(CH$_2$)$_l$Y (wherein l is an integer of from 1 to 6, Y is a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, an aldehyde group, a phosphoric group, a sulfonic group, a phosphoric ester group (in which the ester portion has 1 to 6 carbon atoms), a sulfonic ester group (in which the ester portion has 1 to 6 carbon atoms), a primary amido group, a secondary amido group, an indole group, a thiophene group, a furan group, a monosubstituted phenyl group, a disubstituted phenyl group, or a trisubstituted phenyl group (whose substituent is a chlorine atom, a bromine atom, a fluorine atom, a hydroxy group, a nitro group, a methoxy group, an ethoxy group, a carboxyl group, a carboethoxy group, a carbomethoxy group, and a cyano group)); $R_6$ is independently a hydrogen atom, a halogen atom, a hydrocarbon group having 1 to 6 carbon atoms, or an acyl group having 2 to 19 carbon atoms (in which the acyl group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group); or $R_5$ and $R_6$ may together form —CH=CH—CH=CH— or —CO(CH$_2$)$_3$—; and X is O, S, CH$_2$, or NL (wherein L is a hydrogen atom, a linear or branched alkyl group, or L may form —CH$_2$SC(CH$_3$)$_2$— or —(CH$_2$)$_3$— with $R_3$ or $R_4$);

a ketone derivative of the following general formula (I') or a pharmacologically acceptable salt thereof:

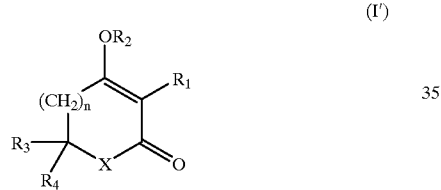

(I')

In the above general formula (I'), $R_1$ is a hydrocarbon group having 3 to 19 carbon atoms (in which the hydrocarbon group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), —CO(CH$_2$)$_q$Q (wherein q is an integer of 0, 1, or from 3 to 10 and Q is a hydrogen atom, a hydrocarbon group having 1 to 6 carbon atoms (in which the hydrocarbon group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, a cyano group, a trifluoromethyl group, a methylthio group, a phenylthio group, and a t-butyl group, however, the hydrocarbon group must have a substituent when (CH$_2$)$_q$Q is an ethyl group), a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, a phosphoric ester group (in which the ester portion has 2 to 6 carbon atoms), a phosphoric group, a sulfonyl group having 1 to 7 carbon atoms, a t-butoxycarbonylamino group, a methylsulfoxide group, a primary amido group, or a secondary amido group), —COCO(CH$_2$)$_r$V$_3$ (wherein r is an integer of 0 or 1 and V$_3$ is a hydrogen atom, a linear or branched alkyl group having 1 to 6 carbon atoms, an aryl group having 6 to 12 carbon atoms (in which the aryl group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbimethoxy group, and a cyano group), a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, a primary amido group, or a secondary amido group), —COCH=CHV$_4$ (wherein V$_4$ is an aryl group having 6 to 12 carbon atoms (in which the aryl group may have one or more substituents selected from the group essentially consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group) or a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), —CO$_2$G (wherein G is a hydrogen atom, a linear or branched alkyl group having 1 to 6 carbon atoms, or an aryl group having 6 to 12 carbon atoms (in which the aryl group may have one or more substituents selected from the group essentially consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group), —CONHV$_1$ (wherein V$_1$ is a hydrogen atom, a linear or branched alkyl group having 1 to 10 carbon atoms, an aryl group having 6 to 12 carbon atoms (in which the aryl group may have one or more substituents selected from the group essentially consisting of a chlorine atom, a bromine atom, a hydroxy group, a nitro group, a methoxy group, an ethoxy group, a carboxyl group, a carboethoxy group, a carbomethoxy group, and a cyano group), or a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group)), —NHCOV$_2$ (wherein V$_2$ is a hydrogen atom, a linear or branched alkyl group having 1 to 10 carbon atoms, an aryl group having 6 to 12 carbon atoms (in which the aryl group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group) or a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group)), or —(CH$_2$)$_t$J (wherein t is an integer of from 1 to 10, J is a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, a primary amido group, or a secondary amido group);

R$_2$ is a hydrogen atom, a hydrocarbon group having 1 to 6 carbon atoms, or an acyl group having 2 to 10 carbon atoms;

X is O, S, CH$_2$, or NL (wherein L is a hydrogen atom, a linear or branched alkyl group, or L may form —CH$_2$SC(CH$_3$)$_2$— or —(CH$_2$)$_3$— with R$_3$ or R$_4$); n is an integer of 0 or 1; and R$_3$ and R$_4$ are independently a hydrogen atom, a hydrocarbon group having 1 to 15 carbon atoms (in which the hydrocarbon group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), a 1-hydroxy-1-carboalkoxymethyl group, or a group represented by —(CH$_2$)$_m$Z (wherein m is an integer of from 1 to 6, Z is a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, an aldehyde group, a phosphoric group, a sulfonic group, a phosphoric ester group (in which the ester portion has 1 to 6 carbon atoms), a sulfonic ester group (in which the ester portion has 1 to 6 carbon atoms), a primary amido group, a secondary amido group, an indole group, a monosubstituted phenyl group, a disubstituted phenyl group, or a trisubstituted phenyl group (whose substituent is a chlorine atom, a bromine atom, a fluorine atom, a hydroxy group, a nitro group, a methoxy group, an ethoxy group, a carboxyl group, a carboethoxy group, a carbomethoxy group, and a cyano group), or R$_3$ and R$_4$ may together form —(CH$_2$)$_4$— or —(CH$_2$)$_5$—; and a ketone derivative of the following general formula (I″) or a pharmacologically acceptable salt thereof:

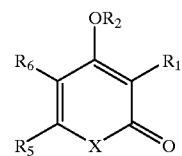

(I″)

In the above general formula (I″), R$_1$ is —CO(CH$_2$)$_q$Q (wherein q is an integer of 0, 1, or from 3 to 10 and Q is a hydrogen atom, a hydrocarbon group having 1 to 6 carbon atoms (in which the hydrocarbon group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, a cyano group, a trifluoromethyl group, a methylthio group, a phenylthio group, and a t-butyl group, however, the hydrocarbon group must have a substituent when (CH$_2$)$_q$Q is an ethyl group), a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group, a carboxyl group, a phosphoric ester group (in which the ester portion has 2 to 6 carbon atoms), a phosphoric group, a sulfonyl group having 1 to 7 carbon atoms, a t-butoxycarbonylamino group, a methylsulfoxide group, a primary amido group, or a secondary amide group), —COCO(CH$_2$)$_r$V$_3$ (wherein r is an integer of 0 or 1 and V$_3$ is a hydrogen atom, a linear or branched alkyl group having 1 to 6 carbon atoms, an aryl group having 6 to 12 carbon atoms (in which the aryl group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, a acetamido group, a cyano group, a carboxyl ester group (in which ester portion has 1 to 6 carbon atoms), a carboxyl group, a primary amide group, or a secondary amide group), —COCH=CHV$_4$ (wherein V$_4$ is an aryl group having 6 to 12 carbon atoms (in which the aryl group may have one or more substituents selected from the group essentially consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group) or a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), —CO₂G (wherein G is a hydrogen atom, a linear or branched alkyl group having 1 to 6 carbon atoms, an aryl group having 6 to 12 carbon atoms (in which the aryl group may have one or more substituents selected from the group essentially consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group), —CONHV₁ (wherein V₁ is a hydrogen atom, a linear or branched alkyl group having 1 to 10 carbon atoms, an aryl group having 6 to 12 carbon atoms (in which the aryl group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group) or a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group)), —NHCOV₂ (wherein V₂ is a hydrogen atom, a linear or branched alkyl group having 1 to 10 carbon atoms, an aryl group having 6 to 12 carbon atoms (in which the aryl group may have one or more substituents selected from the group essentially consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), or a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group)), or —(CH₂)ₜJ (wherein t is an integer of from 1 to 10, J is a heterocyclic ring having 1 to 9 carbon atoms (in which the heterocyclic ring may have one or more substituents selected from the group essentially consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, a primary amide group, or a secondary amide group);

R₂ is a hydrogen atom, a hydrocarbon group having 1 to 6 carbon atoms, or an acyl group having 2 to 10 carbon atoms;

X is O, S, CH₂, or NL (wherein L is a hydrogen atom or a linear or branched alkyl group); R₅ is independently a hydrogen atom, a hydrocarbon group having 1 to 15 carbon atoms, a 1-hydroxy-1-carboalkoxymethyl group, or a group represented by —(CH₂)ₗY (wherein l is an integer of from 1 to 6 and Y is a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, an aldehyde group, a phosphoric group, a sulfonic group, a phosphoric ester group (in which the ester portion has 1 to 6 carbon atoms), a sulfonic ester group (in which the ester portion has 1 to 6 carbon atoms), a primary amide group, a secondary amide group, an indole group, a thiophene group, a furan group, a monosubstituted phenyl group, a disubstituted phenyl group, or a trisubstituted phenyl group (whose substituent is a chlorine atom, a bromine atom, a fluorine atom, a hydroxy group, a nitro group, a methoxy group, an ethoxy group, a carboxyl group, a carboethoxy group, a carbomethoxy group, and a cyano group); R₆ is independently a hydrogen atom, a halogen atom, a hydrocarbon group having 1 to 6 carbon atoms, or an acyl group having 2 to 19 carbon atoms (in which the acyl group may have one or more substituents selected from the group essentially consisting of a chlorine atom, a bromine atom, a fluorine atom, a hydroxy group, a nitro group, a methoxy-group, an ethoxy group, a carboxyl group, a carboethoxy group, a carbomethoxy group, and a cyano group); or R₅ and R₆ may together form —CH=CH—CH=CH— or —CO(CH₂)₃—).

BEST MODE FOR CARRYING OUT THE INVENTION

When R₂ in general formula (I) of the present invention is a hydrogen atom, keto-enol tautomerism shown by the following formula is included.

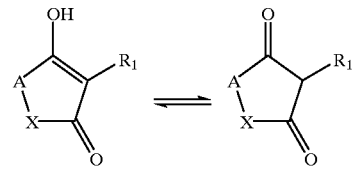

In R₁ in the general formula (I), the halogen atom may be a chlorine, a bromine, or an iodine atom; the hydrocarbon group having 1 to 19 carbon atoms may be a linear or branched alkyl group, an alkenyl group, an alkynyl group, a cycloalkyl group, an aryl group which may have one or more substituents, an alkylaryl group (whose aryl group may have one or more substituents), an arylalkyl group (whose aryl group may have one or more substituents), an arylalkenyl group (whose aryl group may have one or more substituents), or an alkenylaryl group (whose aryl may have a substituent); the alkyl group may be either linear or branched and examples thereof are methyl, ethyl, n-propyl, isopropyl, n-butyl, isobutyl, sec-butyl, t-butyl, n-pentyl, isopentyl, neopentyl, t-pentyl, n-hexyl, n-heptyl, n-octyl, n-nonyl, n-decyl, n-dodecyl, n-tetradecyl, n-pentadecyl, n-hexadecyl, n-heptadecyl, 15-methylhexadecyl, 7-methylhexadecyl, and n-octadecyl; and the alkenyl group may be either linear or branched, includes isomers (E and Z bodies) relating to a double bond, and examples thereof are ethenyl, 2-propenyl, 2-butenyl, 2-pentel, 2-hexenyl, 2-heptenyl, 2-octenyl, 2-nonenyl, 2-denyl, 3-butenyl, 3-pentel, 3-hexenyl, 3-heptenyl, 3-octenyl, 3-nonenyl, 3-denyl, 4-pentel, 4-hexenyl, 4-heptenyl, 4-octenyl, 4-nonenyl, 4-denyl, 1,3-butadienyl, 1,3-pentadienyl, 1,3-hexadienyl, 1,3-heptadienyl, 1,3-octadienyl, 1,3-nonadienyl, 1,3-decadienyl, 1,4-pentadienyl, 1,4- hexadienyl, 1,4-heptadienyl, 1,4-octadienyl, 1,4-nonadienyl, 1,4-decadienyl, 1,3,5-hexatrienyl, 1,3,5-heptatrienyl, 1,3,5-octatrienyl, 1,3,5-nonatrienyl, and 1,3,5-decatrienyl groups; and the cycloalkyl group includes, for example, cyclopropyl cyclobutyl, cyclohexyl, and cycloheptyl groups. Examples of the cycloalkenyl group are cyloputenyl, cyclopentenyl, cyclohexenyl, cycloheptenyl, cyclobutene-3-methyl, cyclopentene-4-methyl, cyclohexene-3-methyl, cyclohexene-4-methyl, cyclobutene-3-ethyl, cyclopentene-4-ethyl, cyclohexene-3-ethyl, and cyclohexene-4-ethyl groups. Examples of the aryl group are phenyl, naphthyl, and biphenyl groups, in addition to aryl groups monosubstituted by a chlorine atom, a bromine atom, a fluorine atom, a hydroxy group, a nitro group, a methoxy group, an ethoxy group, a carboxyl group, a carboethoxy group, a carbomethoxy group, or a cyano group.

Examples of the alkylaryl group are 2-methylphenyl, 3-methylphenyl, 4-methylphenyl, 2-ethylphenyl, 3-ethylphenyl, and 4-ethylphenyl groups, in addition to the following groups substutued by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups; examples of the arylalkyl group are benzyl, 2-phenylethyl, 3-phenylpropyl, 2-phenylpropyl, and 4-phenylbutyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups; and the arylalkenyl group includes isomers (E and Z bodies) relating to a double bond, examples of the arylalkyl group are 2-phenylethenyl, 1-phenylethenyl, 3-phenyl-2-propenyl, and 3-phenyl-1-propenyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups.

Examples of the hydrocarbon group having 1 to 6 carbon atoms in Q of $-CO(CH_2)_qQ$ are methyl, ethyl, propyl, butyl, pentyl, hexyl, cyclobutyl, cyclopentyl, cyclohexyl, ethylene, propylene, butylene, pentylene, hexylene, acetylenyl, propynyl, butynyl, pentynyl, hexynyl, and phenyl groups; examples of the heterocyclic ring are thiophene, furan, pyrrole, tetrahydrofuran, N-methylpyrrole, indole, imidazole, pyrrolidine, pyridine, benzothiophene, benzofuran, quinoline, isoquinoline, phthalimide, and phthalide groups; examples of the thioether group are thiomethyl, thioethyl, thiopropyl, thiophenyl, and thiobutyl groups; examples of the alkoxy group are methoxy, ethoxy, propoxy, and phenoxy groups; examples of the carboxyl ester groups are carbomethoxy, carboethoxy, carbopropoxy, carbobutoxy, and carbophenoxy groups; examples of the phosphoric ester groups are dimethylphosphate, diethylphosphate, and dipropylphosphate groups; and examples of the sulfonyl group having 1 to 7 carbon atoms are methylsulfonyl, ethylsulfonyl, cyclohexylsulfonyl, phenylsulfonyl, p-methylphenylsulfonyl, and o-methylphenylsulfonyl groups. Examples of the primary amido group are N-methylamido, N-ethylamido, and N-propylamido groups; and examples of second amido group are N,N-dimethylamido, N,N-diethylamido, N,N-methylethylamido, and N,N-dipropylamido groups.

Examples of the linear or branched alkyl group having 1 to 6 carbon atoms in $V_3$ of $-COCO(CH_2)_rV_3$ are methyl, ethyl, n-propyl, isopropyl, n-butyl, isobutyl, sec-butyl, t-butyl, n-pentyl, isopentyl, neopentyl, t-pentyl, and n-hexyl groups. Examples of the aryl group are phenyl, naphthyl, and biphenyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups. Examples of the heterocyclic ring are thiophene, furan, pyrrole, tetrahydrofuran, N-methylpyrrole, indole, imidazole, pyrrolidine, pyridine, benzothiophene, benzofuran, quinoline, isoquinoline, phthalimide, and phthalide groups; examples of the thioether group are thiomethyl, thioethyl, thiopropyl, thiophenyl, and thiobutyl groups; examples of the alkoxy group are methoxy, ethoxy, propoxy, and phenoxy groups; examples of the carboxyl ester group are carbomethoxy, carboethoxy, carbopropoxy, carbobutoxy, and carbophenoxy groups; examples of the phosphoric ester group are dimethylphosphate, diethylphosphate, and dipropylphosphate groups; examples of the primary amido group are N-methylamido, N-ethylamido, and N-propylamido groups; and examples of the second amido group are N,N-dimethylamido, N,N-diethylamido, N,N-methylethylamido, and N,N-dipropylamido groups.

Examples of the aryl group in $V_4$ of —COCH=CHV$_4$ are phenyl, naphthyl, and biphenyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups. Examples of the heterocyclic ring are thiophene, furan, pyrrole, tetrahydrofuran, N-methylpyrrole, indole, imidazole, pyrrolidine, pyridine, benzothiophene, benzofuran, quinoline, isoquinoline, phthalimide, and phthalide groups.

Examples of the linear or branched alkyl group having 1 to 6 carbon atoms in G of —CO$_2$G are propyl, butyl, and pentyl groups. Examples of the aryl group are phenyl, naphthyl, and biphenyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dlhydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups.

Examples of the linear or branched alkyl group having 1 to 6 carbon atoms in $V_1$ of —CONHV$_1$ are methyl, ethyl, n-propyl, isopropyl, n-butyl, isobutyl, sec-butyl, t-butyl, n-pentyl, isopentyl, neopentyl, t-pentyl, n-hexyl, n-heptyl, n-octyl, n-nonyl, and n-decyl groups. Examples of the aryl group are phenyl, naphthyl, and biphenyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups. Examples of the heterocyclic ring are thiophene, furan, pyrrole, tetrahydrofuran, N-methylpyrrole, indole, imidazole, pyrrolidine, pyridine, benzothiophene, benzofuran, quinoline, isoquinoline, phthalimide, and phthalide groups.

Examples of the linear or branched alkyl group having 1 to 10 carbon atoms in $V_2$ of —NHCOV$_2$ are methyl, ethyl, n-propyl, isopropyl, n-butyl, isobutyl, sec-butyl, t-butyl, n-pentyl, isopentyl, neopentyl, t-pentyl, n-hexyl, n-heptyl, n-octyl, n-nonyl, and n-decyl groups. Examples of the aryl group are phenyl, naphthyl, and biphenyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups. Examples of the heterocyclic ring are thiophene, furan, pyrrole, tetrahydrofuran, N-methylpyrrole, indole, imidazole, pyrrolidine, pyridine, benzothiophene, benzofuran, quinoline, isoquinoline, phthalimide, and phthalide groups.

Examples of the heterocyclic ring in J of —(CH$_2$)$_r$J are thiophene, furan, pyrrole, tetrahydrofuran, N-methylpyrrole, indole, imidazole, pyrrolidine, pyridine, benzothiophene, benzofuran, quinoline, isoquinoline, phthalimide, and phthalide groups; examples of the thioether group are thiomethyl, thioethyl, thiopropyl, thiophenyl, and thiobutyl groups; examples of the alkoxy group are methoxy, ethoxy, propoxy, and phenoxy groups; examples of the carboxyl ester group are carbomethoxy, carboethoxy, carbopropoxy, carbobutoxy, and carbophenoxy groups; examples of the primary amido group are N-methylamido, N-ethylamido, and N-propylamido groups; and examples of the second amido group are N,N-dimethylamido, N,N-diethylamido, N,N-methylethylamido, and N,N-dipropylamido groups.

Examples of the hydrocarbon group having 1 to 6 carbon atoms in R$_2$ in the general formula (I) are methyl, ethyl, n-propyl, isopropyl, n-butyl, isobutyl, sec-butyl, n-pentyl, isopentyl, t-pentyl, and n-hexyl groups, and the acyl group having 2 to 10 carbon atoms may be either saturated or unsaturated and either linear or branched; examples thereof are acetyl, propionyl, butyryl, valeryl, isovaleryl, pivaloyl, hexanoyl, heptanoyl, octanoyl, benzoyl, toluoyl, and naphthoyl groups.

Examples of the hydrocarbon group having 1 to 15 carbon atoms in R$_3$ and R$_4$ in the general formula (II) are a linear or branched alkyl group, an alkenyl group, an alkynyl group, a cycloalkyl group, a cycloalkenyl group, an aryl group which may have a substituent, an alkylaryl group (whose aryl group may have one or more substituents), an arylalkyl group (whose aryl group may have one or more substituents), an arylalkenyl group (whose aryl group may have one or more substituents), or an alkenylaryl group (whose aryl group may have one or more substituents); the alkyl group may be either linear or branched and includes methyl, ethyl, n-propyl, isopropyl, n-butyl, isobutyl, sec-butyl, t-butyl, n-pentyl, isopentyl, neopentyl, t-pentyl, n-hexyl, n-heptyl, n-octyl, n-nonyl, and n-decyl groups; and the alkenyl group may be either linear or branched, includes isomers (E and Z bodies) relating to a double bond, and examples thereof are, ethenyl, 2-propenyl, 2-butenyl, 2-pentel, 2-hexenyl, 2-heptenyl, 2-octenyl, 2-nonenyl, 2-denyl, 3-butenyl, 3-pentel, 3-hexenyl, 3-heptenyl, 3-octenyl, 3-nonenyl, 3-denyl, 4-pentel, 4-hexenyl, 4-heptenyl, 4-octenyl, 4-nonenyl, 4-denyl, 1,3-butadienyl, 1,3-pentadienyl, 1,3-hexadienyl, 1,3-heptadienyl, 1,3-octadienyl, 1,3-nonadienyl, 1,3-decadienyl, 1,4-pentadienyl, 1,4-hexadienyl, 1,4-heptadienyl, 1,4-octadienyl, 1,4-nonadienyl, 1,4-decadienyl, 1,3,5-hexatrienyl, 1,3,5-heptatrienyl, 1,3,5-octatrienyl, 1,3,5-nonatrienyl, and 1,3,5-decatrienyl groups.

The cycloalkyl group may be, for example, cyclopropyl, cyclobutyl, cyclohexyl, and cycloheptyl groups. Examples of the aryl group are phenyl, naphthyl, and biphenyl groups, in addition to the following groups substituted by a chlorine atom, a bromine atom, a fluorine atom, a hydroxy group, a nitro group, a methoxy group, an ethoxy group, a cyano group, a carboxyl group, a carboethoxy group, or a carbomethoxy group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups.

Examples of the alkylaryl group are 2-methylphenyl, 3-methylphenyl, 4-methylphenyl, 2-ethylphenyl, 3-ethylphenyl, and 4-ethylphenyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophonyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups.

Examples of the arylalkyl group are benzyl, 2-phenylethyl, 3-phenylpropyl, 2-phenylpropyl, and 4-phenylbutyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups; and the arylalkenyl groups includes isomers (E and Z bodies) relating to a double bond, such as 2-phenylethenyl, 1-phenylethenyl, 3-phenyl-2-propenyl, and 3-phenyl-1-propenyl groups.

Examples of the 1-hydroxy-1-carboalkoxymethyl group are 1-hydroxy-1-carbomethoxymethyl, 1-hydroxy-1-carbomethoxymethyl, and 1-hydroxy-1-carbopropoxymethyl groups.

Examples of the thioether group in Z in —(CH$_2$)$_m$Z are thiomethyl, thioethyl, thiopropyl, thiophenyl, and thiobutyl groups; examples of the alkoxy group are methoxy, ethoxy, propoxy, and phenoxy groups; examples of the carboxyl ester group are carbomethoxy, carboethoxy, carbopropoxy, carbobutoxy, and carbophenoxy groups; examples of the phosphoric ester group are methylphosphate, ethylphosphate, propylphosphate, butylphosphate, and phenylphosphate group; examples of the primary amido groups are N-methylamido, N-ethylamido, and N-propylamido groups; examples of the second amido group are N,N-dimethylamido, N,N-diethylamido, N,N-methylethylamido, and N,N-dipropylamido groups; examples of the monosubstituted phenyl group are the phenyl groups monosubstituted by a chlorine atom, a bromine atom, a fluorine atom, a hydroxy group, a nitro group, a methoxy group, an ethoxy group, a cyano group, a carboxyl group, a carboethoxy group, or a carbomethoxy group, such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; examples of the disubstituted phenyl group are phenyl groups disubstituted by a chlorine atom, a bromine atom, a fluorine atom, a hydroxy group, a nitro group, a methoxy group, an ethoxy group, a cyano group, a carboxyl group, a carboethoxy group, or a carbomethoxy group, such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and examples of the trisubstituted phenyl group are phenyl groups trisubstituted by a chlorine atom, a bromine atom, a fluorine atom, a hydroxy group, a nitro group, a methoxy group, an ethoxy group, a cyano group, a carboxyl group, a carboethoxy group, or a carbomethoxy group, such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups Examples of the hydrocarbon group having 1 to 15 carbon atoms in $R_5$ in general formula (III) are a linear or branched alkyl group, an alkenyl group, an alkynyl group, a cycloalkyl group, a cycloalkenyl group, an aryl group which may have one or more substituents, an alkylaryl group (whose aryl group may have one or more substituents), an arylalkyl group (whose aryl group may have one or more substituent), an arylalkenyl group (whose aryl group may have one or more substituent), or an alkenylaryl group (whose aryl group may have one or more substituent); the alkyl group may be either linear or branched and includes methyl, ethyl, n-propyl, isopropyl, n-butyl, isobutyl, sec-butyl, t-butyl, n-pentyl, isopentyl, neopentyl, t-pentyl, n-hexyl, n-heptyl, n-octyl, n-nonyl, and n-decyl groups; and the alkenyl group may be either linear or branched, includes isomers (E and Z bodies) relating to a double bond, and example thereof are ethenyl, 2-propenyl, 2-butenyl, 2-pentel, 2-hexenyl, 2-heptenyl, 2-octenyl, 2-nonenyl, 2-denyl, 3-butenyl, 3-pentel, 3-hexenyl, 3-heptenyl, 3-octenyl, 3-nonenyl, 3-denyl, 4-pentel, 4-hexenyl, 4-heptenyl, 4-octenyl, 4-nonenyl, 4-denyl, 1,3-butadienyl, 1,3-pentadienyl, 1,3-hexadienyl, 1,3-heptadienyl, 1,3-octadienyl, 1,3-nonadienyl, 1,3-decadienyl, 1,4-pentadienyl, 1,4-hexadienyl, 1,4-heptadienyl, 1,4-octadienyl, 1,4-nonadienyl, 1,4-decadienyl, 1,3,5-hexatrienyl, 1,3,5-heptatrienyl, 1,3,5-octatrienyl, 1,3,5-nonatrienyl, and 1,3,5-decatrienyl groups. The cycloalkyl group includes, for example, cyclopropyl cyclobutyl, cyclohexyl, and cycloheptyl groups.

Examples of the aryl group are phenyl, naphthyl, and biphenyl groups, in addition to the following groups substituted by a chlorine atom, a bromine atom, a fluorine atom, a hydroxy group, a nitro group, a methoxy group, an ethoxy group, a cyano group, a carboxyl group, a carboethoxy group, or a carbomethoxy group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups.

Examples of the alkylaryl group are 2-methylphenyl, 3-methylphenyl, 4-methylphenyl, 2-ethylphenyl, 3-ethylphenyl, and 4-ethylphenyl groups, in addition to the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups.

Examples of the arylalkyl group are benzyl, 2-phenylethyl, 3-phenylpropyl, 2-phenylpropyl, and 4-phenylbutyl groups, in addition to the following groups substituted by a chlorine atom, a bromine atom, a fluorine atom, a hydroxy group, a nitro group, a methoxy group, an ethoxy group, a cyano group, a carboxyl group, a carboethoxy group, or a carbomethoxy group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl groups; and the arylalkenyl group includes isomers (E and Z bodies) relating to a double bond, such as 2-phenylethenyl, 1-phenylethenyl, 3-phenyl-2-propenyl, and 3-phenyl-1-propenyl groups.

Examples of the thioether group in Y in —$(CH_2)_1Y$ are thiomethyl, thioethyl, thiopropyl, thiophenyl, and thiobutyl groups, examples of the alkoxy group are methoxy, ethoxy, propoxy, and phenoxy groups; examples of the carboxyl ester group are carbomethoxy, carboethoxy, carbopropoxy, carbobutoxy, and carbophenoxy groups; examples of the phosphoric ester group are methylphosphate, ethylphosphate, propylphosphate, butylphosphate, and phenylphosphate groups; examples of the sulfonic ester group are methylsulfate and ethylsulfate groups; examples of the primary amido group are N-methylamido, N-ethylamido, and N-propylamido groups; and examples of the second amido group are N,N-dimethylamido, N,N-diethylamido, N,N-methylethylamido, and N,N-dipropylamido groups.

Examples of the monosubstituted phenyl group are phenyl groups monosubstituted by a chlorine atom, a bromine atom, a fluorine atom, a hydroxy group, a nitro group, a methoxy group, an ethoxy group, a cyano group, a carboxyl group, a carboethoxy group, or a carbomethoxy group, such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; examples of the disubstituted phenyl group are phenyl groups disubstituted by a chlorine atom, a bromine atom, a fluorine atom, a hydroxy group, a nitro group, a methoxy group, an ethoxy group, a cyano group, a carboxyl group, a carboethoxy group, or a carbomethoxy group, such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and examples of the trisubstituted phenyl group are phenyl groups trisubstituted by a chlorine atom, a bromine atom, a fluorine atom, a hydroxy group, a nitro group, a methoxy group, an ethoxy group, a cyano group, a carboxyl group, a carboethoxy group, or a carbomethoxy group, such as o,m,p-trichlorophenyl, o,m,p-tribromophenyl, o,m,p-trifluorophenyl, o-chloro-m-hydroxy-p-methoxyphenyl, and o-hydroxy-m-hydroxy-p-methoxyphenyl.

In $R_6$ in the general formula (I), the halogen atom may be a chlorine, a bromine, or an iodine atom, and the hydrocarbon group having 1 to 6 carbon atoms may be methyl, ethyl, propyl, butyl, pentyl, hexyl, isopropyl, cyclopropyl, and phenyl groups. The acyl group having 2 to 19 carbon atoms may be either saturated or unsaturated and either linear or branched; examples thereof are acetyl, propionyl, butyryl, valeryl, isovaleryl, bivaloyl, hexanoyl, heptanoyl, octanoyl, benzoyl, toluoyl, and naphthoyl groups, in addition to acyl groups having the following groups substituted by a chlorine atom, a bromine atom, a fluorine atom, a hydroxy group, a nitro group, a methoxy group, an ethoxy group, a carboxyl group, a carboethoxy group, a carbomethoxy group, or a cyano group: monosubstituted aryl groups such as o-chlorophenyl, m-chlorophenyl, p-chlorophenyl, o-bromophenyl, m-bromophenyl, p-bromophenyl, o-hydroxyphenyl, m-hydroxyphenyl, p-hydroxyphenyl, o-nitrophenyl, m-nitrophenyl, p-nitrophenyl, o-methoxyphenyl, m-methoxyphenyl, p-methoxyphenyl, o-cyanophenyl, m-cyanophenyl, p-cyanophenyl, o-carbomethoxyphenyl, m-carbomethoxyphenyl, and p-carbomethoxyphenyl groups; disubstituted aryl groups such as o,m-dichlorophenyl, o,p-dichlorophenyl, m,p-dichlorophenyl, o,m-dihydroxyphenyl, o,p-dihydroxyphenyl, m,p-dihydroxyphenyl, o,m-dimethoxyphenyl, o,p-dimethoxyphenyl, m,p-dimethoxyphenyl, o-chloro-m-bromophenyl, o-chloro-m-hydroxyphenyl, o-chloro-m-cyanophenyl, o-chloro-m-methoxyphenyl, o-hydroxy-m-chlorophenyl, and o-methoxy-m-chlorophenyl groups; and trisubstituted aryl groups such as o,m,p-trichlorophenyl, o,m,p-tribromophenyl, o,m,p-trifluorophenyl, o-chloro-m- hydroxy-p-methoxyphenyl, and o-hydroxy-m-hydroxy-p-methoxyphenyl groups.

Examples of the linear or branched alkyl group having 1 to 6 carbon atoms in L in NL are methyl, ethyl, n-propyl, isopropyl, n-butyl, isobutyl, sec-butyl, n-pentyl, isopentyl, t-pentyl, and n-hexyl groups.

Examples of pharmacologically acceptable salts are base addition salts and acid addition salts. Base addition salts are those which retain biological availability and the properties of free bases and which do not have biologically adverse effects or other adverse effects; examples thereof are salts obtained from inorganic bases such as sodium, potassium, lithium, ammonium, calcium, magnesium, and the like. Furthermore, pharmacologically acceptable salts include salts obtained from organic bases, for example, substituted amines such as primary amine, secondary amine, tertiary amine, naturally substituted amine, cyclic amine, and basic ion exchange resin, and practically, isopropylamine, trimethylamine, diethylamine, tripropylamine, ethanol amine, 2-dimethylamino ethanol, 2-diethylamino ethanol, trimetamine, dicyclohexylamine, lysine, arginine, histidine, caffeine, procaine, hydravamine, choline, and betaine, and practically, isopropylamine, trimethylamine, diethylamine, tripropylamine, ethanol amine, 2-dimethylamino ethanol, 2-diethylamino ethanol, trimetamine, dicyclohexylamine, lysine, arginine, histidine, caffeine, procaine, hydravamine, choline, betaine, ethylenediamine, glucosamine, methylglucamine, theobromine, purine, piperazine, piperidine, N-ethylpiperidine, ornithine, and polyamine resin. However, pharmacologically acceptable salts in the present invention are not restricted to the above salts. Acid addition salts are those which retain biological availability and the properties of free acids and which do not have biologically adverse effects or other adverse effects; examples thereof are inorganic salts such as hydrochlorides, sulfates, nitrates, hydrobromates, hydrogen tetrafluoroborate, phosphates, and perchlorates. Furthermore, pharmacologically acceptable salts include, for example, oxalates, tartrates, lactates, and acetates as salts of organic acids. However, pharmacologically acceptable salts of the present invention are not limited to these salts.

When compounds of the present invention have an asymmetric carbon in their molecule, various types of optical isomers exist, furthermore, when compounds of the present invention have at least two asymmetric carbons, various types of diastereomers exist. The present invention also includes such optical isomers as well as each isomer. Moreover, the present invention includes stereoisomers.

Lactones of the present invention can be produced by a known method. For example, they can be produced by the methods disclosed in J. Chem. Soc. Perkin Trans. I. 121–129 (1987), J. Org. Chem., 59, 488–490 (1994), Bull. Chem. Soc. Japan, 52, 3601–3605 (1979), J. Chem. Soc. Perkin Trans. I. 1225–1231 (1987), Tetrahedron Lett., 5143–5146 (1983), Chem. Pharm. Bull., 38, 94–98 (1990), Chem. Pharm. Bull., 34, 5188–5190 (1986), Tetrahedron Lett., 8285–8296 (1991), Tetrahedron Lett., 4807–4810 (1988), Chem. Pharm. Bull., 34(12), 5188 (1986), J. Chem. Soc., (C), 1501 (1968), J. Org. Chem., 59, 4749 (1994), Chem. Pharm. Bull., 29(10), 2762 (1981), J. Chem. Soc., 4483 (1963), J. Am. Chem. Soc., 78, 3201 (1956), and J. Hetrocyclic Chem., 31, 1619 (1994).

Lactams can be produced by methods disclosed in Chem. Pharm. Bull., 32(10), 4197–4204 (1984), Pharmazie, 43(7), 473–474 (1988), Monatsh. Chem., 123(1–2), 93–98 (1992), J. Inorg. Biochem., 24(3), 167–181 (1985), J. Am. Chem. Soc., 107(18), 5219–5224 (1985), J. Org. Chem., 50(8), 1344–1346 (1985), J. Org. Chem., 58, 142–146 (1993), J. Org. Chem., 49, 3489 (1984), J. Hetrocycl. Chem., 19, 883 (1982), J. Am. Chem. Soc., 72, 1236 (1950), J. Am. Chem. Soc., 72, 4447 (1950), J. Chem. Soc. 850 (1954), J. Chem. Soc., Perkin Trans. 1. 2907 (1973), Tetrahedron Lett., 25, 2009 (1984), Bull. Chem. Soc. Jpn., 59, 2185 (1986), Bull. Chem. Soc. Jpn., 49, 1161 (1976), Chem. Pharm. Bull., 28, 2494 (1980), J. Am. Chem. Soc., 69, 2571 (1947), and Chem. Pharm. Bull., 30(4), 1315 (1982). Thiotetronic acids can be produced by a method disclosed in J. Chem. Soc. (C), 1501 (1968) or the like.

Acylmeldrum's acids can be produced by a method disclosed in J. Org. Chem., 43, 2087 (1978) or the like.

On clinical application, an agent containing an effective dose of a ketone of the present invention is administered orally or parenterally. Formulations of the agent include a tablet, a sugar-coated tablet, a pill, a capsule, a powder, a troche, a liquid, a suppository, or an injection solution, and they can be prepared by uniformly mixing with pharmaceutically acceptable excipients. As excipients, the following can be used: lactose, sucrose, glucose, sorbitol, mannitol, potato starch, amylopectin, other types of starches, cellulose derivatives (e.g., carboxymethyl cellulose and hydroxyethyl cellulose), gelatin, magnesium stearate, polyvinyl alcohol, polyethylene glycol wax, gum arabic, talc, titanium dioxide, vegetable oils including olive oil, peanut oil, and sesame oil, paraffin oils, neutral fat base, ethanol, propylene glycol, physiological saline, sterilized water, glycerine, coloring agents, flavoring materials, thickeners, stabilizing agents, isotonizing agents, buffers, and the like.

In the present invention, a hematopoietic agent means an agent which induces in vivo proliferation of platelets, white blood cells, red blood cells, and the like when administered to humans or to animals so as to prevent or to treat cytopenia caused by cancer chemotherapy, radiation therapy, bone-marrow transplantation, drug therapy, immunological disorders, anemia such as renal anemia, hemorrhagic anemia, hemolytic anemia, and deficiency anemia. In addition, a hematopoietic agent of the present invention can also be applied to the field of treatment of leukopenia, idiopathic thrombocytopenic purpura, and the like caused by aplastic anemia, thrombocytopenia, infectious diseases, viral diseases, nutritional disorder, etc. Furthermore, it can be used for autologous blood storage.

For preventing or treating cytopenia caused by cancer chemotherapy, radiation therapy, bone-marrow transplantation, drug therapy, immunological disorders, and anemia such as renal anemia, hemorrhagic anemia, hemolytic anemia, and deficiency anemia, a hemopoietic agent of the present invention can be used in combination with an EPO, i.e., an erythrocytopoietic agent, or a G-CSF, i.e., a leukocytopoietic agent.

Although the dosage of the agent of the present invention varies according to the symptoms, body weight, age, and the route of administration, the general daily dose for an adult is preferably 0.01 mg to 2000 mg per day.

EXAMPLES

The present invention will be further illustrated in detail with reference to the following comparative examples and examples.

Example 1

Synthesis of Compound 1

After 5.00 g (29.1 mmol) of L-cysteine methyl ester hydrochloride was heat-refluxed in 250 mL of acetone for 4 hours, the reaction solution was cooled in a refrigerator, and then, 5.57 g (26.3 mmol, 90.4%) of methyl 2,2-dimethylthiazolidinedione 4-carboxylate hydrochloride was recovered by filtration.

$^1$H-NMR(300 MHz, CDCl$_3$)δ: 1.86(3H, s), 1.87(3H, s), 3.59(1H, m), 3.72(1H, m), 3.94(3H, s), 5.11(1H, dd, J=8.71, 8.09).

To a mixed solution of 4.00 g (18.9 mmol) of methyl 2,2-dimethylthiazolidinedione 4-carboxylate hydrochloride, 25 mL of tetrahydrofuran, and 5.24 mL (37.8 mmol) of triethylamine, was added dropwise a solution of 1.44 mL (18.9 mmol) of diketene in 5 mL of tetrahydrofuran. After the addition of the diketene solution, the mixture was stirred at room temperature for 4 hours. Insoluble substances were removed by filtration and the filtrate was concentrated. To the residue, were added 5 mL of tetrahydrofuran and 25 mL of a 1.0 M tetrabutylammonium fluoride/tetrahydrofuran solution, followed by stirring at 40° C. for 9 hours. The reaction solution was concentrated; the residue was solubilized by adding water and extracted with dichloromethane. The resultant was dried over sodium sulfate anhydride and concentrated; the residue was purified by silica gel column chromatography (ethyl acetate:methanol=20:1) and recrystallized from ethyl acetate/diethyl ether. As a result, 2.14 g (mmol, %) of an orange tetrabutylammonium salt was obtained. In dichloromethane, was dissolved 2.14 g of the tetrabutylammonium salt, neutralized by adding 1 N hydrochloric acid, dried over sodium sulfate anhydride, and concentrated. The residue was purified by silica gel column chromatography (ethyl acetate:methanol=20:1) to obtain 445 mg (1.96 mmol, 10.3%) of the target compound in a free form.

Example 2

Synthesis of Compound 2

To a mixed solution of 1.50 g (6.21 mmol) of L-proline benzyl ester hydrochloride; 7.5 mL of tetrahydrofuran, and 1.72 mL (12.4 mmol) of triethylamine, was added dropwise a solution of 0.48 mL (6.21 mmol) of diketene in 1.5 mL of tetrahydrofuran, followed by stirring for 3 hours at room temperature. The reaction solution was filtered and the filtrate was concentrated. The residue was purified by silica gel column chromatography (diethyl ether) to give 1.61 g (5.56 mmol, 89.5%) of a colorless oily substance.

In 5 mL of tetrahydrofuran, was dissolved 1.42 g (4.91 mmol) of the oily substance, and mixed with 5 mL of a 1.0 M-tetrabutylammonium fluoride/tetrahydrofuran solution, followed by stirring for 63 hours at room temperature. The reaction solution was concentrated, and then, the residue was purified by silica gel column chromatography (dichloromethane:methanol=10:1) to give 167 mg (0.92 mmol, 18.7%) of the target compound as an orange oily substance.

Example 3

Synthesis of Compound 3

To a mixed solution of 1.50 g (6.26 mmol) of L-glutamic acid diethyl ester hydrochloride, 9 mL of tetrahydrofuran, and 1.74 mL (12.6 mmol) of triethylamine, was added dropwise a solution of 0.48 mL (6.26 mmol) of diketene in 1.5 mL of tetrahydrofuran, followed by stirring for 3 hours at room temperature. The reaction solution was filtered and the filtrate was concentrated. The residue was mixed with 6 mL of toluene and 4.1 mL of 2 N sodium methoxide/methanol and heat-refluxed for 3 hours. The mixture was cooled to room temperature and concentrated; the residue was washed with acetone and filtered to recover a solid. The solid was dissolved in water, acidified by adding 2 N hydrochloric acid, and extracted with dichloromethane. The resultant was dried over sodium sulfate anhydride, filtered, and concentrated. The residue was purified by silica gel column chromatography and the thus-obtained powder was washed with diethyl ether to give 205 mg (0.90 mmol, 14.4%) of the target compound.

Example 4

Synthesis of Compound 4

Similarly to Example 3, 1.75 g (7.20 mmol, 47.0%) of an acetamido derivative was obtained from 3.00 g (15.3 mmol) of L-leucine ethyl ester hydrochloride.

$^1$H-NMR(300 MHz, CDCl$_3$)δ: 0.95(6H, m, J=3.30), 1.28 (3H, t, J=7.14), 1.58–1.69(3H, m), 2.28(3H, s), 3.45(2H, s), 4.19(2H, q, J=7.14), 4.60(1H, m), 7.24(1H, br, NH)

In 7.5 mL of benzene, was dissolved 1.75 g (7.20 mmol) of the acetamido derivative, and the resulting solution was mixed with 5 mL of 2 N sodium methoxide/methanol, followed by heat-refluxing for 2 hours. The reaction solution was cooled and concentrated. The residue was dissolved in water, washed with diethyl ether, acidified by adding 2 N hydrochloric acid, and extracted with dichloromethane. The resultant was dried over sodium sulfate anhydride and concentrated to give 1.38 g of crude crystals. The crude crystals were recrystallized from ethyl acetate to give 228 mg (1.15 mmol, 1.16%) of colorless crystals.

Example 5

Synthesis of Compound 5

To a mixed solution of 3.00 g (17.5 mmol) of L-cysteine methyl ester hydrochloride, 20 mL of tetrahydrofuran, and 4.85 mL of triethylamine, was added dropwise 1.35 mL (17.6 mmol) of diketene, followed by stirring for 4 hours at room temperature. The reaction solution was filtered and the filtrate was concentrated. The residue was purified by silica gel column chromatography (diethyl ether) to give 2.45 g (11.2 mmol, 64.0%) of a pale yellow oily substance.

$^1$H-NMR(300 MHz, CDCl$_3$)δ: 2.30(3H, s), 3.02(2H, dd, J=4.39, 6.72), 3.50(2H, s), 3.80(3H, s), 4.89(1H, m), 7.43 (1H, br, NH).

In 20 mL of benzene, was dissolved 2.43 g (11.1 mmol) of the above oily substance, and then, 8 mL of 2 N sodium methoxide/methanol was added dropwise to the resulting solution, followed by heat-refluxing for 2 hours. After cooling the solution, the precipitate was recovered by filtration, dissolved in water, and washed with diethyl ether. The resultant was then acidified by adding concentrated hydrochloric acid for extraction with dichloromethane, however, it was not solubilized; thus the organic layer was recovered. The organic layer was concentrated; the residue was mixed with methanol, washed while being heated, and filtered for removing insoluble substances so as to give 475 mg (2.54 mmol, 22.9%) of the target compound as a pale yellow powder.

Example 6

Synthesis of Compound 6

Similarly to Example 3, 2.57 g (<6.26 mmol, <100%) of an acetamido derivative was obtained from 3.01 g (6.20 mmol) of L-asparaginic acid dibenzyl ester.p-toluenesulfonate.

¹H-NMR(300 MHz, CDCl$_3$)δ: 2.22(3H, s), 2.90(1H, dd, J=4.67, 17.03), 3.08(1H, dd, J=4.67, 17.03), 3.40(2H, s), 4.94(1H, m), 5.08(2H, s), 5.13(2H, s), 7.27–7.37(10H, m), 7.66(1H, d, J=8.24); IR(neat)3330, 1734, 1655, 1569, 1359, 741, 700 cm$^{-1}$.

In 10 mL of benzene, was dissolved 2.57 g (<6.20 mmol) of the acetamido derivative, and the resulting solution was mixed with 2 N sodium methoxide/methanol (512 mg/3.1 mL), followed by heat-refluxing for 2 hours. The reaction solution was cooled and mixed with acetone so as to filter insoluble substances. The thus-obtained solid was dissolved in methanol and insoluble substances were removed by filtration. After concentrating the resultant, the residue was dissolved in water, acidified by adding 6 N hydrochloric acid, extracted with dichloromethane, and dried over sodium sulfate anhydride. The resultant was filtered, the filtrate was concentrated, and the residue was washed with diethyl ether to give 317 mg (1.48 mmol, 24.0%) of the target compound.

Example 7

Synthesis of Compound 7

Similarly to Example 3, 1.95 g (6.45 mmol, 65.5%) of an acetamido derivative was obtained from 2.51 g (9.85 mmol) of L-tryptophane methyl ester.hydrochloride.

¹H-NMR(300 MHz, CDCl$_3$)δ: 2.16(3H, s), 3.32(2H, m), 3.33(2H, s), 3.69(3H, s), 4.92(1H, m), 7.05–7.36(4H, m), 7.54(1H, m), 8.22(1H, br).

In 10 mL of benzene, was dissolved 1.95 g (6.45 mmol) of the acetamido derivative, and the resulting solution was mixed with 2 N sodium methoxide/methanol (520 mg/4.8 mL), followed by heat-refluxing for 2 hours. The reaction solution was cooled and concentrated. The residue was dissolved in water, acidified by adding 6 N hydrochloric acid, extracted with dichloromethane, and dried over sodium sulfate anhydride. The resultant was filtered, the filtrate was concentrated, the residue was purified by silica gel column chromatography (ethyl acetate), and the thus-obtained solid was recrystallized from ethyl acetate. As a result, 312 mg (1.15 mmol, 17.9%) of the target compound was obtained.

Example 8

Synthesis of Compound 8

Sodium ethoxide was prepared from 35 mL of ethanol and 2.1 g (91.3 mmol) of sodium, and then, mixed with 10.7 g (93.0 mmol) of methyl 3-aminocrotonate and 14.2 mL (93.6 mmol) of dimethyl malonate, followed by heat-refluxing for 5 hours. The reaction solution was cooled to room temperature; the precipitated crystals were filtered and washed with ethanol. As a result, 5.27 g of a sodium salt of the target compound was obtained. The thus-obtained sodium salt was suspended in water, acidified by adding 3 N hydrochloric acid, filtered, washed with water, and recrystallized from ethanol. As a result, 1.63 g (8.26 mmol, 9.0%) of the target compound was obtained as colorless crystals.

Example 9

Synthesis of Compound 9

To 7.6 mL (109.3 mmol) of thioglycollic acid, was added dropwise 7.8 mL (109.7 mmol) of acetyl chloride while the mixture was stirred in an ice bath. After the addition of acetyl chloride, the mixture was heated to 35° C. and stirred for one and half hours. To the reaction solution, was added 9.5 mL of thionyl chloride and stirred for further three and half hours. The reaction solution was concentrated, the residue was mixed with benzene and evaporated, which procedure was repeated three times, and then, the residue was distilled under reduced pressure to give 5.10 g (33.4 mmol, 30.5%) of a thioacetyl derivative. In 65 mL of toluene, was dispersed 1.68 g (73.0 mmol) of metallic sodium and cooled to 5° C. To the mixture, 13.0 mL of ethyl acetoacetate was added dropwise while giving attention to temperature rise (5–10° C.), and was stirred for three and half hours in an ice bath. To the mixture, was further added dropwise 5.1 g (33.4 mmol) of the thioacetyl derivative, followed by stirring for one and half hours at 10–15° C. The reaction solution was subjected to extraction with 65 mL of 2 N hydrochloric acid, and then, with 10 w/v % sodium carbonate (20 mL×5). After adding 10.8 N-NaOH to the water layer, the resultant was allowed to stand for 3 days. The thus-precipitated crystals were filtered, dissolved in 80 mL of water, acidified by adding concentrated hydrochloric acid, and the thus-precipitated crystals were filtered. The thus-obtained crystals were recrystallized from ethyl acetate to give 1.92 g (12.1 mmol, 36.2%) of pale yellow needle crystals.

Example 10

Synthesis of Compound 10

To a mixed solution of 5.00 g (34.7 mmol) of meldrum's acid, 20 mL of dichloromethane, and 5.6 mL of pyridine, was added dropwise 5.2 mL (39.3 mmol) of phenacyl chloride while stirring the mixture in an ice bath. After the addition of phenacyl chloride, the mixture was poured in a separatory funnel, washed with 48 mL of 2 N hydrochloric acid, and dried over sodium sulfate anhydride. The resultant was filtered and concentrated; the residue was purified by silica gel column chromatography (diethyl ether). The resultant was recrystallized from diethyl ether to give 2.94 g (11.2 mmol, 32.3%) of phenacylmeldrum's acid.

¹H-NMR(300 MHz, CDCl$_3$)δ: 1.72(6H, s), 4.43(2H, s), 7.26–7.38(5H, m).

In 10 mL of benzene, was dissolved 501 mg (1.92 mmol) of phenacylmeldrum's acid, and the resulting solution was mixed with 0.25 mL (2.18 mmol) of (S)-ethyl lactate, followed by stirring for 1.5 hours. The reaction solution was concentrated and the residue was purified by silica gel column chromatography (diethyl ether:hexane=1:3) to give 513 mg (1.84 mmol, 96%) of a colorless oily substance.

¹H-NMR(300 MHz, CDCl$_3$)δ: 1.28(3H, t, J=7.14), 1.49 (3H, d, J=7.15), 3.53(2H, s), 3.88(2H, s), 4.21(2H, q, J=7.14), 5.11(1H, m), 7.21–7.35(5H, m).

To 497 mg (1.78 mmol) of the colorless oily substance, was added 4 mL of 1 M-tetrabutylammonium fluoride, followed by stirring for 2 days at room temperature. The reaction solution was concentrated; the residue was mixed with water, acidified by adding 3 N hydrochloric acid, and then, extracted with dichloromethane. The resultant was dried over sodium sulfate anhydride, filtered, and concentrated. It was revealed from NMR measurement that the thus-obtained oily substance was a tetrabutylammonium salt. Thus, the oily substance was mixed with 6 mL of 1 N hydrochloric acid/ethanol, stirred, and concentrated; water was added to the residue for filtration. The thus-obtained powder was dissolved in dichloromethane and dried over sodium sulfate anhydride. After filtration and concentration, the residue was recrystallized from diethyl ether/hexane to give 196 mg (0.844 mmol, 47.4%) of the target compound as pale orange crystals.

Example 11

Synthesis of Compound 11

Similarly to Example 10, 799 mg (2.48 mmol, 92.5%) of a colorless oily substance was obtained from 700 mg (2.43 mmol) of phenacylmeldrum's acid and 0.385 mL (2.94 mmol) of DL-dimethyl malonate.

$^1$H-NMR(300 MHz, CDCl$_3$)δ: 2.92(2H, d, J=6.04), 3.53 (2H, s), 3.71(3H, d, J=3.02), 3.78(3H, d, J=3.30), 3.87(2H, s), 5.55(1H, m), 7.20–7.35(5H, m); IR(neat)2960, 1744, 1628, 1497, 1439, 1056, 702 cm$^{-1}$.

Under similar conditions to Example 10, 783 mg (2.43 mmol) of the colorless oily substance was subjected to reaction and recrystallized from methanol to give 247 mg of pale orange crystals.

Example 12

Synthesis of Compound 12

In 5 mL of dichloromethane, was dissolved 705 mg (5.97 mmol) of monomethyl malonate, and mixed with 0.685 mL (5.97 mmol) of (S)-ethyl lactate; 0.94 mL (6.10 mmol) of diisopropylcarbodiimide was added dropwise to the resultant mixture while stirring the mixture in an ice bath, the mixture was stirred for 9 hours in the ice bath, and then, allowed to stand at room temperature overnight. After removing the precipitate by filtration, the filtrate was concentrated and the residue was purified by silica gel column chromatography (ethyl acetate:hexane=1:2) to give 1.19 g (5.45 mmol, 91.3%) of a colorless oily substance.

$^1$H-NMR(300 MHz, CDCl$_3$)δ: 1.28(3H, t, J=7.14), 1.51 (3H, d, J=7.14), 3.48(2H, s), 3.78(3H, s), 4.21(2H, q, J=7.14), 5.14(1H, q, J=7.14); IR(neat)2998, 2964, 1765, 1746, 1441, 1357, 1272, 1203, 1149, 1096, 1050, 1021 cm$^{-1}$.

Under similar conditions to Example 10, 1.18 g (5.40 mmol) of the colorless oily substance was subjected to reaction to give 214 mg (1.24 mmol, 23.0%) of colorless crystals.

Example 13

Synthesis of Compound 13

Similarly to Example 12, 18.2 g (69.4 mmol, 91.7%) of a colorless oily substance was obtained from 10.0 g (84.7 mmol) of monomethyl malonate and 9.90 mL (75.7 mmol) of dimethyl malate.

$^1$H-NMR(300 MHz, CDCl$_3$)δ: 0.93(2H, d, J=6.04), 3.48 (2H, s), 3.73(3H, s), 3.76(3H, s), 3.79(3H, s), 5.55(1H, t, J=6.04).

Under similar conditions to Example 10, 12.78 g (48.7 mmol) of the colorless oily substance was subjected to reaction and recrystallized from ethyl acetate to give 719 mg (3.12 mmol, 6.4%) of the target compound as colorless crystals.

Example 14

Synthesis of Compound 14

Similarly to Example 12, 2.45 g (9.20 mmol, 92.0%) of a colorless oily substance was obtained from 1.19 g (10.1 mmol) of monomethyl malonate and 1.66 g (10.0 mmol) of (S)-methyl mandelate.

$^1$H-NMR(300 MHz, CDCl$_{13}$)δ: 3.54(2H, s), 3.74(3H, s), 3.75(3H, s), 6.00(1H, s), 7.38–7.45(5H, m).

Under similar conditions to Example 10, 2.43 g (9.12 mmol) of the colorless oily substance was subjected to reaction and recrystallized from ethyl acetate/methanol to give 895 mg (3.82 mmol, 41.9%) of colorless crystals.

Example 15

Synthesis of Compound 15

To 5.57 g (37.8 mmol) of L-glutamic acid, was added 100 mL of a 20% aqueous acetic acid solution, and a 3.45 g (50.0 mmol)/100 ml aqueous sodium nitrite solution was slowly added dropwise to the resultant mixture while stirring the mixture in an ice bath. After the addition of the aqueous sodium nitrite solution, the mixture was stirred in the ice bath for 1 hour, removed from the ice bath, and further stirred at room temperature overnight without the ice bath. The reaction solution was concentrated and dried to a solid by a vacuum pump. To the residue, was added 50 mL of methanol, and the mixture was heat-refluxed for 5 hours in gaseous hydrochloric acid. After removing methanol by evaporation, 130 mL of methanol was further added, followed by heat-refluxing for 5 hours in gaseous hydrochloric acid. After removing methanol by evaporation, the residue was distilled (0.06 mmHg, 72–73° C.) to give 3.97 g (22.5 mmol, 59.5%) of dimethyl 2-hydroxyglutarate.

$^1$H-NMR(300 MHz, CDCl$_3$)δ: 1.95(1H, m), 2.17(1H, m), 2.48(2H, m), 3.69(3H, s), 3.80(3H, s), 4.25(1H, m).

To 1.97 g (11.2 mmol) of dimethyl-2-hydroxyglutarate, were added 10 mL of tetrahydrofuran and 0.1 mL of pyridine, and then, while stirring the mixture at 60° C., 0.86 mL (11.2 mmol) of diketene and 2 mL of tetrahydrofuran were added dropwise to the mixture, followed by stirring at 60° C. for 4 hours. The reaction solution was concentrated, and the residue was purified by silica gel column chromatography to give 2.67 g (10.2 mmol, 91.1%) of an acetoacetate derivative.

$^1$H-NMR(300 MHz, CDCl$_3$)δ: 2.12–2.29(2H, m), 2.31 (3H, s), 2.46(2H, m), 3.53(2H, s), 3.69(3H, s), 3.77(3H, s), 5.14(1H, m).

To 2.67 g (10.2 mmol) of the acetoacetate derivative, was added 11 mL of 1 M-tetrabutylammonium fluoride, and the mixture was stirred at room temperature overnight; the resultant was subjected to reaction under similar conditions to Example 10 to give 759 mg (3.33 mmol, 32.6%) of a white solid.

Example 16

Synthesis of Compound 16

The water layer of the compound 13 was allowed to stand overnight, and a white precipitate was filtered.

Example 17

Synthesis of Compound 17

In 50 mL of dichloromethane, was dissolved 5.00 g (42.3 mmol) of monomethyl malonate, and mixed with 4.85 mL (42.3 mmol) of methyl 2-hydroxyglutarate; 6.65 mL (43.2 mmol) of diisopropylcarbodiimide was added dropwise to the resulting mixture while stirring the mixture in an ice bath, the mixture was stirred in the ice bath for 1.5 hours, and then, stirred at room temperature overnight. After removing the precipitate by filtration, the filtrate was concentrated and the residue was purified by silica gel column chromatography (ethyl acetate:hexane=1:3) to give 7.93 g (36.3 mmol, 85.8%) of a monomethyl malonate derivative as a colorless liquid.

$^1$H-NMR(300 MHz, CDCl$_3$)δ: 1.58(6H, s), 3.40(2H, s), 3.74(3H, s), 3.76(3H, s); IR(neat)3000, 2960, 1744, 1439, 1131, 1023 cm$^{-1}$.

Under similar conditions to Example 10, 7.92 g (36.3 mmol) of the monomethyl malonate derivative was subjected to reaction to give 942 mg (5.06 mmol, 13.9%) of a colorless powder.

Example 18

Synthesis of Compound 18

To 5.02 g (30.2 mmol) of L (−)-3-phenylacetic acid, was added 50 mL of 1 N hydrochloric acid/ethanol, followed by heat-refluxing for 5 hours. The reaction solution was evaporated and the residue was purified by distillation under reduced pressure (0.01 mmHg, 79–81° C.) to give 4.26 g (21.9 mmol, 72.5%) of ethyl (−)-3-phenylacetate.

$^1$H-NMR(300 MHz, CDCl$_3$)δ: 1.28(3H, t, J=7.14), 2.97 (1H, dd, J=6.87, 14.00), 3.13(1H, dd, J=4.67, 14.00), 4.22 (2H, q, J=7.14), 4.43(1H, dd, J=4.70, 6.87), 7.21–7.32(5H, m).

To 1.00 g (5.15 mmol) of ethyl (−)-3-phenylacetate, were added 5 mL of tetrahydrofuran and 0.1 mL of pyridine, and then, while stirring the resulting mixture at 60° C., a solution of 0.4 mL (5.23 mmol) of diketene in 2 mL of tetrahydrofuran was added dropwise to the mixture. After the addition of the diketene solution, the resulting mixture was stirred at 60° C. for 4 hours and the reaction solution was evaporated. The residue was purified by silica gel column chromatography (ethyl acetate:hexane=1:2) to give 1.37 g (4.92 mmol, 95.5%) of a colorless oily acetoacetate derivative.

$^1$H-NMR(300 MHz, CDCl$_3$)δ: 1.24(3H, t, J=7.14), 2.18 (3H, s), 3.09–3.20(2H, m), 3.45(2H, s), 4.19(2H, q, J=7.14), 5.27(1H, dd, J=4.70, 8.78), 7.19–7.30(5H, m); IR(neat) 1746, 1721, 1195, 1151, 1071, 1033, 702 cm$^{-1}$.

In 5 mL of tetrahydrofuran, was dissolved 1.34 g (4.81 mmol) of the acetoacetate derivative, and then, the resulting solution was subjected to reaction under similar conditions to Example 10 to give 260 mg (1.12 mmol, 23.3%) of the target compound.

Example 19

Synthesis of Compound 19

In 10 mL of dichloromethane, was dissolved 1.01 g (8.55 mmol) of 1-hydroxycinnamic acid, and mixed with 1.66 g (8.54 mmol) of monomethyl malonate; 1.34 mL (8.70 mmol) of diisopropylcarbodiimide was added dropwise to the resulting mixture while stirring the mixture in an ice bath, the mixture was stirred in the ice bath for 10 min., removed from the ice bath, and further stirred overnight. After removing insoluble substance by filtration, the filtrate was concentrated. The residue was purified by silica gel column chromatography (ethyl acetate:hexane=1:3) to give 2.52 g (8.56 mmol, 100%) of a malonic acid derivative.

$^1$H-NMR(300 MHz, CDCl$_3$)δ: 1.23(3H, t, J=7.14), 3.16 (2H, m), 3.42(2H, s), 3.69(3H, s), 4.18(2H, q, J=7.14), 7.19–7.33(5H, m); IR(neat)1742, 1456, 1439, 1280, 1195, 1152, 1031, 702 cm$^{-1}$.

Under similar conditions to Example 10, 2.50 g (8.49 mmol) of the malonic acid derivative was subjected to reaction and recrystallized form ethyl acetate to give 527 mg (2.12 mmol, 25.0%) of colorless crystals.

Example 20

Synthesis of Compound 20

To 1.21 g (4.99 mmol) of methyl benzilate, were added 5 mL of tetrahydrofuran and 0.1 mL of pyridine, and then, while stirring the mixture at 50° C., 0.4 mL (5.23 mmol) of diketene was added dropwise to the mixture, followed by stirring at 50° C. for 7 hours. The reaction solution was concentrated and the residue was purified by silica gel column chromatography (ethyl acetate:hexane=1:4) to give 1.39 g (4.26 mmol, 85.4%) of an acetoacetic acid derivative.

$^1$H-NMR(300 MHz, CDCl$_3$)δ: 2.22(3H, s), 3.53(2H, s), 3.76(3H, s), 3.53(2H, s), 7.30–7.33(6H, m), 7.49–7.53(4H, m); IR(KBr)1760, 1744, 1725, 1315, 1267, 1143, 69 cm$^{-1}$.

Under similar conditions to Example 10, 1.26 g (3.86 mmol) of the acetoacetic acid derivative was subjected to reaction to give 865 mg (2.94 mmol, 76.1%) of a pale yellow powder.

Example 21

Synthesis of Compound 21

In ether, was suspended 974 mg (4.86 mmol) of DL-3-(4-hydroxyphenyl)lactic acid monohydrate, and then, diazomethane was added to the resulting suspension until the bubbling stopped. After removing insoluble substances by filtration, the resultant was condensed, and the residue was purified by silica gel column chromatography (ethyl acetate:hexane=1:2) to give 977 mg (4.86 mmol, 100%) of a methyl ester compound.

$^1$H-NMR(300 MHz, CDCl$_3$)δ: 2.74(1H, d, J=6.32), 2.90 (1H, dd, J=6.59, 14.00), 3.06(1H, dd, J=4. 39, 14.00), 3.78(3H, s), 4,43(1H, m), 5.08(1H, s), 6.72–6.76(2H, m), 7.05–7.09(2H, m); IR(neat): 3400, 1734, 1615, 1518, 1446, 1224, 1108, 828, 803 cm$^{-1}$.

To a mixed solution of 449 mg (2.28 mmol) of the methyl ester compound, 3 mL of tetrahydrofuran, and 0.05 mL of pyridine, was added 0.2 mL of diketene while stirring the mixture at 60° C., followed by stirring for 4 hours. The reaction solution was concentrated, and the residue was purified by silica gel column chromatography to give 534 mg (1.90 mmol, 83.3%) of an acetoacetic acid derivative.

$^1$H-NMR(300 MHz, CDCl$_3$)δ: 2.20(3H,S), 3.04(1H, dd, J=8.24, 14.00), 3.14(1H, dd, J=4.39, 14.00), 3.46(2H, d, J=0.55), 3.74(3H, s), 5.25(1H, dd, J=4.67, 8.24), 6.74–6.77 (2H, m), 7.04–7.07(2H, m); IR(neat): 3416, 1748, 1734, 1717, 1518, 1228 cm$^{-1}$.

Under similar conditions to Example 10, 520 mg (1.85 mmol) of an acetamidoacetic acid derivative was subjected to reaction to give 225 mg (0.906 mmol, 49.0%) of the target compound as a colorless powder.

Example 22

Synthesis of Compound 22

To a mixed solution of 510 mg (2.60 mmol) of methyl 1-hydroxy-p-hydroxycinnamate, 339 mg (2.87 mmol) of monomethyl malonate, and 4 mL of dichloromethane, was added 0.5 mL of diisopropylcarbodiimide while stirring the mixture in an ice bath; the mixture was stirred in the ice bath for 10 min., removed from the ice bath, and stirred at room temperature for 1 day. Insoluble substances were filtered and washed with ethyl acetate. The mother liquor was concentrated, and the residue was purified by silica gel column chromatography (ethyl acetate:hexane=1:2) to give 631 mg of a mixed compound containing a malonic acid derivative. Under similar conditions to Example 10, the mixed compound was subjected to reaction to give 188 mg (0.711 mmol, 27.3%) of the target compound as a colorless powder.

Example 23

Synthesis of Compound 23

To 25.4 g (approximately 95.8 mmol) of 40% glyceric acid water, were added 200 mL of ethanol and 100 mL of 1 N hydrochloric acid/ethanol, followed by heat-refluxing for 2 hours. The mixture was cooled to room temperature, concentrated, mixed with 200 mL of ethanol and 25 mL of 1 N hydrochloric acid/ethanol, and heat-refluxed for 2 hours, which procedure was repeated twice; the reaction solution was concentrated, mixed with 200 mL of ethanol and 100 mL of 1 N hydrochloric acid/ethanol, and heat-refluxed for 5 hours. The reaction solution was concentrated and dried to a solid under reduced pressure to give 15.98 g (119 mmol) of an ethyl ester compound. To the ethyl ester compound, were added 20 mL of dichloromethane and 1.55 mL of pyridine, and then, while stirring the mixture in an ice bath, 9.0 mL (95.4 mmol) of acetic acid anhydride was added dropwise to the mixture. The mixture was stirred for 3 hours in the ice bath, removed from the ice bath, and stirred at room temperature overnight. Insoluble substances were removed by filtration; the mother liquor was mixed with dichloromethane and washed with diluted hydrochloric acid. The dichloromethane layer was dried over sodium sulfate anhydride and concentrated. The residue was purified by silica gel column chromatography (ethyl acetate:hexane= 1:1) to give 7.21 g (45.0 mmol, 47.0%) of a monoacetyl compound.

$^1$H-NMR(300 MHz, CDCl$_3$)δ: 1.29(3H, td, J=5.49, 6.32), 4.23–4.46(6H, m).

A mixed solution of 721 mg (4.50 mmol) of the monoacetyl compound, 1.07 g (4.10 mmol) of phenylmeldrum's acid, and 20 mL of benzene was heat-refluxed for 3 hours. The reaction solution was cooled to room temperature and concentrated; the residue was purified by silica gel column chromatography (ethyl acetate:hexane=1:4) to give 1.04 g (75.4 mmol) of an acetoacetic acid derivative.

$^1$H-NMR(300 MHz, CDCl$_3$)δ: 1.29(3H, t, J=6.32), 2.07 (3H, s), 3.57(2H, s), 3.88(2H, s), 4.25(2H, q, J=6.32), 4.45(2H, d, J=4.39), 5.35(1H, m), 7.21–7.35(5H, m); IR(neat): 1748, 1373, 1216, 1096, 702 cm$^{-1}$.

Under similar conditions to Example 10, 1.02 g (3.03 mmol) of the acetoacetic acid derivative was subjected to reaction to give 352 mg (1.21 mmol, 39.3%) of the target compound as a colorless powder.

Example 24

Synthesis of Compound 24

In a mixed solution of 5.00 g (34.7 mmol) of meldrum's acid, 20 mL of dichloromethane, and 5.6 mL of pyridine, was added dropwise 5.8 mL (39.0 mmol) of hydrocinnamyl chloride while stirring the mixed solution in an ice bath. After the addition of hydrocinnamyl chloride, the mixture was stirred for 1 hour in the ice bath and for 6 hours at room temperature. The reaction solution was mixed with 6 N hydrochloric acid and extracted with dichloromethane. The resultant was dried over sodium sulfate anhydride, filtered, and concentrated; the residue was purified by silica gel column chromatography (ethyl acetate:hexane=1:20) to give 6.68 g (24.1 mmol, 69.4%) of pale yellow oily acylmeldrum's acid.

$^1$H-NMR(300 MHz, CDCl$_3$)δ: 1.67(s, 6H), 3.02(m, 2H), 3.41(m, 2H), 7.20–7.30(m, 5H) 1154, 1031, 926, 700 cm$^{-1}$.

A mixed solution of 3.11 g (11.2 mmol) of acylmeldrum's acid, 45 mL of benzene, 1.55 mL (13.5 mmol) of (S)-ethyl lactate was heat-refluxed for 4 hours. The reaction solution was concentrated and the residue was purified by silica gel column chromatography (ethyl acetate:hexane=1:3) to give 3.02 g (10.3 mmol, 92.0%) of a colorless oily substance.

$^1$H-NMR(300 MHz, CDCl$_3$)δ: 1.26(t, J=7.14, 3H), 1.48 (d, J=7.14, 3H), 2.91–3.02(m, 4H), 3.61(s, 2H), 4.22(q, J=7.14, 2H), 5.08(m, 1H), 7.19–7.32(m, 5H); IR(neat)1748, 1721, 1456, 1212, 1096, 700 cm$^{-1}$.

Under similar conditions to Example 10, 3.01 g (10.3 mmol) of the colorless oily substance was subjected to reaction and recrystallized from ethyl acetate/hexane to give 1.26 g (5.11 mmol, 49.6%) of colorless crystals.

Example 25

Synthesis of Compound 25

In a mixed solution of 3.37 g (12.2 mmol) of 3-phenylpropionylmeldrum's acid, 45 mL of benzene, and 1.92 mL (14.6 mmol) of dimethyl malate was heat-refluxed for 4 hours. The reaction solution was concentrated and the residue was purified by silica gel column chromatography (ethyl acetate:hexane=1:4) to give 3.04 g (9.04 mmol, 74.1%) of a colorless oily substance.

$^1$H-NMR(300 MHz, CDCl$_3$)δ: 2.89–2.92(m, 6H), 3.50(s, 2H), 3.70, 3.72(s, s, 3H), 3.76, 3.79(s, s, 3H), 5.54(t, J=6.31, 1H), 7.17–7.28(m, 5H); IR(neat)1748, 1439, 1286, 1176, 1058, 702 cm$^{-1}$.

Under similar conditions to Example 10, 3.01 g (10.3 mmol) of the colorless oily substance was subjected to reaction and recrystallized from ethyl acetate/hexane to give 1.26 g (5.11 mmol, 49.6%) of colorless crystals.

Example 26

Synthesis of Compound 26

To a mixed solution of 5.00 g (34.7 mmol) of meldrum's acid, 20 mL of dichloromethane, and 5.6 mL of pyridine, was added dropwise 4.8 mL (39.0 mmol) of 2-thiopheneacetyl chloride while stirring the mixed solution in an ice bath. After the addition of 2-thiopheneacetyl chloride, the mixture was stirred for 1 hour in the ice bath and for 4 hours at room temperature. The reaction solution was mixed with 2 N hydrochloric acid and extracted with dichloromethane. The resultant was dried over sodium sulfate anhydride, filtered, and concentrated; the residue was purified by silica gel column chromatography (ethyl acetate:hexane=1:20) to give 3.61 g (13.4 mmol, 38.6%) of acylmeldrum's acid as a pale brown oily substance.

$^1$H-NMR(300 MHz, CDCl$_3$)δ: 1.74(s, 6H), 4.61(s, 2H), 6.97(dd, J=3.57, 5.21, 1H), 7.07(m, 1H), 7.23(dd, J=1.37, 5.21, 1H); IR(neat)1744, 1676, 1659, 1572, 1410, 1270, 1201, 1025, 934, 704 cm$^{-1}$.

A mixture of 3.60 g (13.4 mmol) of acylmeldrum's acid, 45 mL of benzene, 1.76 mL (13.4 mmol) of dimethyl malate was heat-refluxed for 2 hours. The reaction solution was concentrated and the residue was purified by silica gel column chromatography (ethyl acetate:hexane=1:4) to give 3.87 g (11.8 mmol, 88.0%) of a colorless oily substance.

$^1$H-NMR(300 MHz, CDCl$_3$)δ: 2.92(d, J=6.04, 2H), 3.57 (s, 2H), 3.71, 3.72(s, s, 3H), 3.78, 3.79(s, s, 3H), 4.08(s, 2H), 5.55(t, J=6.04, 1H), 6.93(m, 1H), 6.99(m, 1H), 7.25(m, 1H); IR(neat)1767-1717, 1437, 1054, 853, 1096, 704 cm$^{-1}$.

Under similar conditions to Example 10, 3.86 g (11.7 mmol) of the colorless oily substance was subjected to reaction and recrystallized from ethyl acetate to give 1.17 g (3.95 mmol, 33.8%) of pale brown crystals.

Example 27

Synthesis of Compound 27

Similar to Example 26, 3.07 g (14.3 mmol, 20.6%) of colorless oily acylmeldrum's acid was obtained from 10.0 g (69.4 mmol) of meldrum's acid and 8.8 mL (83.4 mmol) of isobutyryl chloride.

$^1$H-NMR(300 MHz, CDCl$_3$)δ: 1.24(d, J=6.86, 6H), 1.74 (s, 6H), 4.09(m, 1H), 7.07(m, 1H), 7.23(dd, J=1.37, 5.21, 1H); IR(neat)1744, 1667, 1576, 1421, 1332, 1207, 1021, 953, 922 cm$^{-1}$.

A mixture of 3.06 g (14.2 mmol) of acylmeldrum's acid, 40 mL of benzene, and 2.1 mL (16.0 mmol) of dimethyl malate was heat-refluxed for 4 hours. The reaction solution was concentrated and.the residue was purified by silica gel column chromatography (ethyl acetate:hexane=1:4) to give 3.05 g (11.1 mmol, 78.1%) of a colorless oily substance.

$^1$H-NMR(300 MHz, CDCl$_3$)δ: 1.14(d, J=6.86, 6H), 2.76 (m, 1H), 2.92(d, J=6.04, 2H), 3.58(s, 2H), 3.72, 3.73(s, s, 3H), 3.78, 3.79(s, s, 3H), 5.54(t, J=6.04, 1H), IR(neat)1750, 1717, 1216, 1174, 1046 cm$^{-1}$.

Under similar conditions to Example 10, 3.04 g (11.0 mmol) of the colorless oily substance was subjected to reaction to give 2.33 g (9.62 mmol, 87.4%) of a pale orange oily substance.

Example 28

Synthesis of Compound 28

In 50 mL of ether, was dissolved 2.50 g (15.8 mmol) of hexahydromandelic acid, and then, a solution of diazomethane in ether was added to the resulting solution until the bubbling stopped, followed by concentration. The residue was mixed with 1.87 g (15.8 mmol) of monomethyl malonate and 20 mL of dichloromethane, and then, 3.75 mL of N,N'-diisopropylcarbodiimide was added to the mixture while stirring the mixture in an ice bath, followed by stirring at room temperature overnight. The reaction solution was filtered, washed with ethyl acetate, and concentrated. The residue was purified by silica gel column chromatography (ethyl acetate:hexane=1:4) to give 4.13 g (15.1 mmol, 95.5%) of a colorless oily substance.

$^1$H-NMR(300 MHz, CDCl$_3$)δ: 1.01–1.91(m, 11H), 3.49 (d, J=3.84, 2H), 3.75(s, 3H), 3.77(s, 3H), 4.90(d, J=4.94, 1H); IR(neat)1744, 1439, 1272, 1210, 1149, 1023 cm$^{-1}$.

Under similar conditions to Example 10, 4.12 g (15.1 mmol) of the colorless oily substance was subjected to reaction and recrystallized from ethyl acetate to give 1.18 g (4.91 mmol, 32.5%) of colorless crystals.

Example 29

Synthesis of Compound 29

In 50 mL of ether, 2.50 g (15.8 mmol) of hexahydromandelic acid was dissolved, and then, a solution of diazomethane in ether was added to the resulting solution until the bubbling stopped, followed by concentration. To the residue, were added 15 mL of tetrahydrofuran and 0.2 mL of pyridine, and then, 1.27 mL (16.6 mmol) of diketene was added dropwise to the mixture over 20 min. while stirring the mixture at 60. After stirring for 4 hours at 60, the reaction solution was concentrated. The residue was purified by silica gel column chromatography (ethyl acetate:hexane=1:5) to give 3.90 g (15.2 mmol, 96.2%) of a colorless oily substance.

$^1$H-NMR(300 MHz, CDCl$_3$)δ: 1.13–1.95(m, 11H), 2.32 (s, 3H), 3.53(s, 2H), 3.75(s, 3H), 4.89(d, J=4.67, 1H); IR(neat)2932, 2860, 1744, 1723, 1452, 1363, 1152, 1106, 1017 cm$^{-1}$.

Under similar conditions to Example 10, 3.89 g (15.1 mmol) of the colorless oily substance was subjected to reaction and recrystallized from ethyl acetate to give 1.00 g (4.46 mmol, 29.5%) of pale yellow crystals.

Example 30

Synthesis of Compound 30

To 10.00 g (58.6 mmol) of 2-chlorophenylacetic acid, was added 100 mL of thionyl chloride, and the mixture was heat-refluxed for 4 hours. After removing excessive thionyl chloride by distillation, the residue was distilled under reduced pressure to give 8.91 g (80.4%) of a pale red liquid.

Similar to Example 26, 8.27 g (59.6%) of colorless oily acylmeldrum's acid was obtained from 6.71 g (mmol) of meldrum's acid and 8.8 g (46.6 mmol) of 2-chlorophenacyl chloride.

$^1$H-NMR(300 MHz, CDCl$_3$)δ: 1.77(s, 6H), 4.61(s, 2H), 7.24–7.29(m, 3H), 7.39–7.43(m, 1H).

A mixed solution of 3.00 g (10.1 mmol) of acylmeldrum's acid, 40 mL of benzene, and 1.32 mL (10.1 mmol) of dimethyl malate was heat-refluxed for 5 hours. The reaction solution was concentrated and the residue was purified by silica gel column chromatography (ethyl acetate:hexane= 1:3) to give 3.56 g (98.8%) of a colorless oily substance.

$^1$H-NMR(300 MHz, CDCl$_3$)δ: 2.93(d, J=6.046, 2H), 3.60 (s, 2H), 3.72(s, 3H), 3.79(s, 3H), 4.02(s, 2H), 5.56(t, J=6.04, 1H), 7.22–7.33(m, 3H), 7.37–7.41(m, 1H).

Under similar conditions to Example 10, 3.55 g (9.96 mmol) of the colorless oily substance was subjected to reaction and recrystallized from ethyl acetate to give 2.41 g (74.5%) of colorless crystals.

Example 31

Synthesis of Compound 31

In 40 mL of dichloromethane, was dissolved 10.00 g (69.4 mmol) of meldrum's acid, and the resulting solution was mixed with 11.2 mL of pyridine, and then, 9.6 mL (69.4 mmol) of monomethyl glutarate was added dropwise to the mixture while stirring the mixture in an ice bath. After the addition of monomethyl glutarate, the mixture was stirred for 1 hour in the ice bath, removed from the ice bath, and stirred for further 24 hours. The reaction solution was mixed with 75 mL of 2 N hydrochloric acid, extracted with dichloromethane, and dried over sodium sulfate anhydride. After being concentrated under reduced pressure, the residue was purified twice by silica gel column chromatography (ethyl acetate:hexane=1:9) to give 9.71 g (35.7 mmol, 51.3%) of acylmeldrum's acid as a yellow oily substance.

$^1$H-NMR(300 MHz, CDCl$_3$)δ: 1.74(d, J=6.87, 6H), 2.05 (quiNt, J=7.14, 2H), 2.44(t, J=7.14, 2H), 3.15(t, J=7.14, 2H), 3.69(s, 3H), IR(neat)1736, 1669, 1576, 1274, 1205, 1156, 1029, 924 cm$^{-1}$.

A mixed solution of 3.00 g (11.0 mmol) of acylmeldrum's acid, 40 mL of benzene, and 1.44 mL (11.0 mmol) of DL-dimethyl malate was heat-refluxed for 5 hours. The reaction solution was concentrated and the residue was purified by silica gel column chromatography (ethyl acetate:hexane=1:3) to give 3.06 g (9.20 mmol, 83.6%) of a colorless oily β-ketoester.

$^1$H-NMR(300 MHz, CDCl$_3$)δ: 1.92(q, J=7.14, 2H), 2.36 (t, J=7.14, 2H), 2.67(t, J=7.14, 2H), 2.92(d, J=6.04, 2H), 3.51(s, 2H), 3.67(s, 3H), 3.73(s, 3H), 3.78(s, 3H), 5.54(s, 1H); IR(neat)1744, 1439, 1176, 1058 cm$^{-1}$.

Under similar conditions to Example 10, 3.06 g (9.20 mmol) of the β-ketoester was subjected to reaction to give 1.68 g (5.60 mmol, 60.8%) of an orange oily substance.

Example 32

Synthesis of Compound 32

A mixed solution of 3.01 g (11.0 mmol) of 3-carbomethoxybutyric meldrum's acid, 40 mL of benzene, and 1.83 g (11.0 mmol) of (S)-methyl mandelate was heat-refluxed for 5 hours. The reaction solution was concentrated and the residue was purified by silica gel column chromatography (ethyl acetate:hexane=1:3) to give 3.63 g (98.2%) of a colorless solid β-ketoester.

$^1$H-NMR(300 MHz, CDCl$_{13}$)δ: 1.93(q, J=7.14, 2H), 2.35 (t, J=7.14, 2H), 2.69(t, J=7.14, 2H), 3.57(d, J=0.82, 2H), 3.66(s, 3H), 3.73(s, 3H), 5.97(s, 1H), 7.38–7.45(m, 5H); IR(KBr)1734, 1719, 1222, 1180, 1042, 733, 698 cm$^{-1}$.

Under similar conditions to Example 10, 3.62 g (10.7 mmol) of the β-ketoester was subjected to reaction and recrystallized from methanol to give 1.60 g (49.2%) of colorless crystals.

Example 33

Synthesis of Compound 33

A mixed solution of 2.29 g (8.76 mmol) of phenylacetylmeldrum's acid, 45 mL of benzene, and 1.48 mL (8.79 mmol) of DL-diethyl malate was heat-refluxed for 5 hours. The reaction solution was concentrated and the residue was purified by silica gel column chromatography (ethyl acetate:hexane=1:3) to give 2.34 g (6.68 mmol, 76.2%) of a colorless oily β-ketoester.

$^1$H-NMR(300 MHz, CDCl$_3$)δ: 1.23–1.30(m, 6H), 2.89(d, J=6.04, 2H), 35.3(s, 2H), 3.88(s, 3H), 4.11–4.25(m, 4H), 5.53(t, J=6.04, 1H), 7.20–7.35(m, 5H); IR(neat)1738, 1377, 1183, 1054, 1029, 702 cm$^{-1}$.

Under similar conditions to Example 10, 2.33 g (6.65 mmol) of the β-ketoester was subjected to reaction and recrystallized from methanol to give 1.35 g (66.6%) of colorless crystals.

Example 34

Synthesis of Compound 34

A mixed solution of 3.87 g (14.8 mmol) of phenylacetylmeldrum's acid, 70 mL of benzene, and 3.95 g (22.2 mmol) of (L)-(+)-dimethyl tartrate was heat-refluxed for 5 hours. The reaction solution was concentrated and the residue was purified by silica gel column chromatography (ethyl acetate:hexane=1:3 to 1:1) to give 4.12 g of a colorless oily substance. It was supposed from the results of NMR that the substance was a mixed compound.

Under similar conditions to Example 10, 4.12 g of the oily substance was subjected to reaction and recrystallized from methanol to give 1.51 g (4.93 mmol, 33.3%) of colorless crystals.

Example 35

Synthesis of Compound 35

In 8 mL of ethanol, was dissolved 834 mg (2.78 mmol) of 3-(4-methoxycarbonyl)butyryl-5-methoxycarbonylmethyltetronic acid, and then, mixed with 83 mg of 5% Pd—C (containing water), followed by stirring for 4 hours in a hydrogen atmosphere. Since the result of thin-layer chromatography was not different from that of the raw material, 158 mg of 10% Pd—C (containing water) was added to the resultant, followed by stirring for 3 hours in a hydrogen atmosphere. Although the result of thin-layer chromatography was not different from that of the raw material, the catalyst was removed by filtration and the filtrate was concentrated under reduced pressure. The residue was purified by silica gel column chromatography (ethyl acetate:hexane=1:1) to give 365 mg of colorless crystals. (1.27 mmol, 45.7%)

Example 36

Synthesis of Compound 36

A mixed solution of 2.87 g (10.9 mmol) of phenylacetylmeldrum's acid, 40 mL of benzene, and 1.94 g (11.0 mmol) of dimethyl 2-hydroxyglutarate was heat-refluxed for 5 hours. The reaction solution was concentrated and the residue was purified by middle-pressure column chromatography (silica gel, ethyl acetate:hexane=1:3) to give 2.91 g (8.65 mmol, 79.3%) of an orange oily P-ketoester.

$^1$H-NMR(300 MHz, CDCl$_3$)δ: 2.15–2.24(m, 2H), 2.44(m, 2H), 3.54(s, 2H), 3.69(s, 3H), 3.76(s, 3H), 3.87(s, 2H), 5.13(dd, J=4.67, 7.96, 1H), 7.21–7.36(m, 5H); IR(neat) 1744, 1439, 1212, 1077, 702 cm$^{-1}$.

Under similar conditions to Example 10, 2.91 g (8.65 mmol) of the β-ketoester was subjected to reaction and recrystallized from methanol to give 1.52 g (4.99 mmol, 57.7%) of colorless crystals.

Example 37

Synthesis of Compound 37

In 27 mL of ethanol, was dissolved 1.27 g (4.38 mmol) of 5-methoxycarbonylmethyl-3-phenacyltetronic acid, and then, mixed with 254 mg of 5% Pd—C (containing water), followed by stirring for 20 hours in a hydrogen atmosphere. After removing the catalyst by filtration, the mother liquor was concentrated. The residue was recrystallized from ethyl acetate to give 785 mg (2.84 mmol, 65.0%) of colorless crystals.

Example 38

Synthesis of Compound 38

A mixed solution of 3.00 g (20.8 mmol) of meldrum's acid, 257 mg (2.10 mmol) of 4-dimethylaminopyridine, 3.55 g (20.8 mmol) of 4-chlorophenylacetic acid, 4.72 g (22.8 mmol) of dicyclohexylcarbodiimide, and 50 mL of dichloromethane was stirred for 30 min. in an ice bath, removed from the ice bath, and stirred for further 2 days. After removing insoluble substances by filtration, the mother liquor was concentrated under reduced pressure, and the residue was purified by silica gel column chromatography (ethyl acetate:hexane=1:9) to give 1.73 g (5.83 mmol, 28.0%) of acylmeldrum's acid as colorless crystals.

$^1$H-NMR(300 MHz, CDCl$_3$)δ: 1.72(s, 6H), 4.38(s, 2H), 7.31–7.33(m, 4H); IR(neat)1744, 1651, 1593, 1427, 1383, 1319, 1154, 1019 cm$^{-1}$.

A mixed solution of 1.72 g (5.80 mmol) of acylmeldrum's acid, 23 mL of benzene, and 0.77 mL (5.88 mmol) of DL-dimethyl malate was heat-refluxed for 5 hours. The reaction solution was concentrated and the residue was purified by silica gel column chromatography (ethyl acetate:hexane=1:3) to give 2.00 g (5.60 mmol, 96.5%) of a colorless oily β-ketoester.

$^1$H-NMR(300 MHz, CDCl$_3$)δ: 2.92(dd, J=6.04, 7.96, 2H), 3.54(s, 2H), 3.72(s, 3H), 3.79(s, 3H), 3.87(s, 2H), 5.55(m, 1H), 7.13–7.20(m, 2H), 7.29–7.33(m, 2H); IR(neat)1746, 1493, 1439, 1199, 1176, 1091, 1056 cm$^{-1}$.

Under similar conditions to Example 10, 1.99 g (5.58 mmol) of the β-ketoester was subjected to reaction and recrystallized from methanol to give 1.51 g (83.3%) of colorless crystals.

Example 39

Synthesis of Compound 39

A mixed solution of 3.30 g (22.9 mmol) of meldrum's acid, 279 mg (2.29 mmol) of 4-dimethylaminopyridine, 3.80 g of 4-methoxyphenylacetic acid, 5.20 g (25.2 mmol) of dicyclohexylcarbodiimide, and 50 mL of dichloromethane was stirred for 30 min. in an ice bath, removed from the ice bath, and stirred for further 2 days. After removing insoluble substances by filtration, the mother liquor was concentrated under reduced pressure, and the residue was purified by silica gel column chromatography (ethyl acetate:hexane= 1:9) to give 2.23 g (7.63 mmol, 33.3%) of acylmeldrum's acid as colorless crystals.

$^1$H-NMR(300 MHz, CDCl$_3$)δ: 1.72(s, 6H), 3.79(s, 3H), 4.36(s, 2H), 6.84–6.88(m, 2H), 7.30–7.33(m, 2H); IR(neat) 1742, 1676, 1551, 1512, 1406, 1203, 1027, 932 cm$^{-1}$.

A mixed solution of 2.22 g (7.60 mmol) of acylmeldrum's acid, 30 mL of benzene, and 1.0 mL (7.65 mmol) of DL-dimethyl malate was heat-refluxed for 5 hours. The reaction solution was concentrated and the residue was purified by medium-pressure column chromatography (silica gel, ethyl acetate:hexane=1:3) to give 2.34 g (6.64 mmol, 87.4%) of a colorless oily β-ketoester.

$^1$H-NMR(300 MHz, CDCl$_3$)δ: 2.91(d, J=6.04, 2H), 3.52 (s, 2H), 3.72(s, 3H), 3.78(s, 3H), 3.80(m, 5H), 5.54(t, J=6.04, 1H), 6.85–6.89(m, 2H), 7.11–7.14(m, 2H); IR(neat) 1750, 1516, 1439, 1251, 1180, 1054 cm$^{-1}$.

Under similar conditions to Example 10, 2.32 g (6.58 mmol) of the β-ketoester was subjected to reaction and recrystallized from methanol to give 1.76 g (83.4%) of colorless crystals.

Example 40

Synthesis of Compound 40

To a mixed solution of 10.0 g (69.4 mmol) of meldrum's acid, 40 mL of dichloromethane, and 11.2 mL of pyridine, was added dropwise 21.0 mL (69.5 mmol) of palmitoyl chloride while stirring the mixed solution in an ice bath. After the addition of palmitoyl chloride, the resulting mixture was stirred for 1 hour in the ice bath, removed from the ice bath, and stirred for further 24 hours. The reaction solution was mixed with 75 mL of 2 N hydrochloric acid and extracted with dichloromethane. The resultant was dried over sodium sulfate anhydride and concentrated under reduced pressure to give 25.7 g (67.3 mmol, 97.0%) of acylmeldrum's acid as colorless crystals.

A mixed solution of 6.59 g (17.2 mmol) of acylmeldrum's acid, 40 mL of benzene, and 2.74 g (17.1 mmol) of ethyl 3-acetoxy-2-hydroxypropanate was heat-refluxed for 4 hours. The reaction solution was concentrated and the residue was purified by silica gel column chromatography (ethyl acetate:hexane=1:5) to give 5.04 g (11.0 mmol, 64.5%) of a β-ketoester as a pale yellow solid.

$^1$H-NMR(300 MHz, CDCl$_3$)δ: 0.88(t, J=6.31, 3H), 1.25–1.32(m, 27H), 1.60(m, 2H), 2.08(s, 3H), 2.58(t, J=7.14, 2H), 3.56(s, 2H), 4.24(m, 2H), 4.47(m, 2H), 5.36(m, 1H); IR(neat)2920, 2852, 1744, 1234 cm$^{-1}$.

Under similar conditions to Example 10, 5.04 g (11.0 mmol) of the β-ketoester was subjected to reaction and recrystallized from methanol to give 3.45 g (8.39 mmol, 76.3%) of colorless crystals.

Example 41

Synthesis of Compound 41

A mixed solution of 2.91 g (7.61 mmol) of palmitoylmeldrum's acid, 40 mL of benzene, and 1.0 mL (7.65 mmol) of DL-dimethyl malate was heat-refluxed for 5 hours. The reaction solution was concentrated and the residue was purified by medium-pressure column chromatography (silica gel, ethyl acetate:hexane=1:5) to give 2.72 g (6.14 mmol, 80.7%) of a β-ketoester as a pale yellow solid.

$^1$H-NMR(300 MHz, CDCl$_3$)δ: 0.88(t, J=6.87, 3H), 1.25–1.32(m, 27H), 1.57(m, 2H), 2.56(t, J=7.14, 3H), 2.92 (d, J=5.77, 2H), 3.5(s, 2H), 3.73(s, 3H), 3.78(s, 3H), 5.55(t, J=5.77, 1H); IR(neat)2920, 2854, 1748, 1255, 1234, 1205 cm$^{-1}$.

Under similar conditions to Example 10, 2.70 g (6.10 mmol) of the β-ketoester was subjected to reaction and recrystallized from methanol to give 2.13 g (85.1%) of pale orange crystals.

Example 42

Synthesis of Compound 42

Triethylamine (0.75 mL, 5.5 mmol) was added to a suspension of tetronic acid (500 mg, 5.00 mmol) in dichloromethane (25 mL) to obtain a homogeneous solution. The solution was cooled to 0° C., mixed with 4-N,N-dimethylaminopyridine (200 mg, 1.7 mmol), 3-cyclohexne-1-carboxylic acid (0.65 mL, 5.6 mmol), and then, diisopropylcarbodiimide (1.0 mL, 6.3 mmol), followed by stirring for 30 min. The resulting mixture was removed from the ice bath, stirred for 14 hours at room temperature, and filtered to remove thus-produced insoluble diisopropyl urea; the reaction solution was washed twice with 5% hydrochloric acid (20 mL) and the water layer was extracted twice with dichloromethane (10 mL). The organic layers were combined, dried over sodium sulfate anhydride, and concentrated; the thus-obtained residue was purified by silica gel column chromatography (silica gel, ethyl acetate:methanol=15:1). The resultant was arranged to be a sodium salt by adding an excess amount of sodium hydrogencarbonate and distilled water (100 mL), and then washed with dichloromethane; the water layer was acidified by adding 5% hydrochloric acid and extracted four times with dichloromethane (20 mL). The resultant was dried over sodium sulfate anhydride and concentrated to give pale yellow crystals (394 mg, 38%).

Example 43

Synthesis of Compound 43

Similarly to Example 42, brown crystals (1.13 g) were obtained from tetronic acid (500 mg, 5.00 mmol) and monomethyl glutarate (0.70 mL, 5.6 mmol).

Example 44

Synthesis of Compound 44

Similarly to Example 42, brown crystals (744 mg, 66%) were obtained from tetronic acid (500 mg, 5.00 mmol) and 2-thiopheneacetic acid (782 mg, 5.5 mmol).

Example 45

Synthesis of Compound 45

Similarly to Example 42, orange crystals (900 mg, 80%) were obtained from tetronic acid (500 mg, 5.00 mmol) and 3-thiopheneacetic acid (782 mg, 5.5 mmol).

Example 46

Synthesis of Compound 46

For removing mineral oil, 509 mg (12.7 mmol) of 60% sodium hydride was washed several times with hexane and dried under reduced pressure. The resultant was mixed with 15 mL of toluene, and then, 1.15 mL (6.70 mmol) of ethyl benzoylacetate was added dropwise to the mixture while stirring the mixture in an ice bath. Stirring was carried out for 1 hour in the ice bath after the addition of ethyl benzoylacetate. To the resulting slurry, was added dropwise 1 g (6.64 mmol)/3 mL of a solution of 2-acetoxy-propionyl chloride in toluene. After the addition of 2-acetoxy-propionyl chloride, the mixture was stirred for 1 hour in the ice bath and further 4 hours at room temperature. The reaction was stopped by adding methanol to the reaction solution and the reaction solution was concentrated under reduced pressure. The residue was dissolved in ethyl acetate, washed with 2 N hydrochloric acid, dried over sodium sulfate anhydride, and concentrated. The residue was roughly purified by silica gel column chromatography. The thus-obtained oily substance was mixed with 12.5 mL of 2 N sodium hydroxide and stirred overnight. The reaction solution was acidified by adding 6 N hydrochloric acid, extracted with dichloromethane, dried over sodium sulfate anhydride, and concentrated. The residue was distilled by Kugel Rohr under reduced pressure (0.2 mmHg, 145° C.) to give 197 mg (0.903 mmol, 13.6%) of the target compound as an orange oily substance.

Example 47

Synthesis of Compound 47

To a mixed solution of 4.5 mL (26.7 mmol) of diethyl malate, 20 mL of dichloromethane, and 2.4 mL of pyridine, was added dropwise 3.45 mL (26.9 mmol) of monoethyl malonyl chloride while stirring the mixed solution in an ice bath; the resulting mixture was stirred for 1 hour in the ice bath, removed from the ice bath, and stirred for further 3 hours. The resultant was mixed with 6 N hydrochloric acid, extracted with dichloromethane, dried over sodium sulfate anhydride, filtered, and concentrated to give 7.25 g of a malonic acid derivative. The malonic acid derivative was mixed with 30 mL of a 1 mol solution of tetrabutylammonium fluoride/tetrahydrofuran and stirred overnight at room temperature. The reaction solution was concentrated; the residue was mixed with 30 mL of 6 N hydrochloric acid and extracted with ether. After removing ether by evaporation, the residue was dissolved in dichloromethane and washed with saturated sodium chloride water. The organic layer was dried over sodium sulfate anhydride, filtered, and concentrated; the residue was purified by silica gel column chromatography (ethyl acetate:hexane=1:1). As a result, 1.09 g (15.8%) of the target compound was obtained as an orange oily substance.

Example 48

Synthesis of Compound 26

Dichloromethane (40 mL) was added to a mixture of meldrum's acid (5.00 g, 34.7 mmol) and 2-thiopheneacetic acid (4.95 g, 34.7 mmol), the resulting mixture was mixed with dicyclohexylcarbodiimide (7.5 g, 36 mmol) and 4-N,N-dimethylaminopyridine (0.42 g, 3.5 mmol), and stirred for 19 hours at 25° C. After removing the thus-produced insoluble dicyclohexyl urea by filtration, the reaction solution was washed with 1 N hydrochloric acid (50 mL), the water layer was extracted three times with dichloromethane (30 mL), and the organic layers were combined and dried over sodium sulfate anhydride. After concentrating the resulting solution, the thus-obtained residue was purified by silica gel column chromatography (dichloromethane) to give a substantially pure oily substance (5.04 g).

The oily substance (5.04 g) was dissolved in benzene (70 mL), mixed with DL-diethylmalate (2.58 mL, 19.7 mmol), and heat-refluxed for 9 hours. After removing the solvent by evaporation, the residue was purified by silica gel column chromatography (hexane:ethyl acetate=4:1 to 2:1) to give an oily substance (3.53 g).

The oily substance (3.53 g) was dissolved in tetrahydrofuran (5 mL), mixed with tetrabutylammonium fluoride (1 M tetrahydrofuran, 13.0 mL, 13.0 mmol), stirred for 24 hours at room temperature. After removing the solvent by evaporation, the residue was mixed with 6 N hydrochloric acid; the thus-produced precipitate was filtered, washed with hexane, and recrystallized from ethanol to give pale brown crystals (2.41 g, 23% from meldrum's acid).

Example 49

Synthesis of Compound 49

At room temperature, 4-N,N-dimethylaminopyridine (74 mg, 0.61 mmol), propionic acid (0.41 mL, 5.5 mmol), and then, dicyclohexylcarbodiimide (1.2 g, 5.8 mmol) were added to a suspension of 4-hydroxy-6-methyl-2-pyrone (634 mg, 5.02 mmol) in toluene (15 mL). After stirring for 10 min., the resulting mixture was heated at 70° C. for 18 hours. After cooling the mixture to room temperature, the thus-produced insoluble dicyclohexyl urea was removed by filtration; the reaction solution was washed with 5% hydrochloric acid (20 mL), the water layer was extracted twice with dichloromethane (10 mL), and the organic layers were combined and dried over sodium sulfate anhydride. The solution was concentrated and the residue was purified by silica gel column chromatography (hexane/ethyl acetate=6/1) to give a white solid (574 mg, 63%). The solid was recrystallized from hexane/ethyl acetate to give white crystals.

Example 50

Synthesis of Compound 50

Similarly to Example 49, a white solid (890 mg, 86%) was obtained from 4-hydroxy-6-methyl-2-pyrone (631 mg, 5.00 mmol) and 4-pentenoic acid (0.51 mL, 5.0 mmol). The solid was recrystallized from hexane/ethyl acetate to give white crystals.

Example 51

Synthesis of Compound 51

Similarly to Example 49, an orange solid (550 mg, 44%) was obtained from 4-hydroxy-6-methyl-2-pyrone (634 mg, 5.02 mmol) and 2-thiopheneacetic acid (0.79 mg, 5.6 mmol). The solid was recrystallized from hexane/ethyl acetate to give pale yellow crystals.

Example 52

Synthesis of Compound 52

Similarly to Example 49, yellow crystals (2.88 g, 80%) were obtained from 4-hydroxy-6-methyl-2-pyrone (2.00 g, 15.9 mmol) and 2-acetoxyacetic acid (1.9 g, approximately 16 mmol, unpurified synthesized material).

Example 53

Synthesis of Compound 53

Similarly to Example 49, 1.27 g of colorless crystals (5.98 mg, 33.8%) were obtained from 1.99 g (17.7 mmol) of 1,3-cyclohexanedion and 2.3 mL of monomethyl glutarate (18.4 mmol).

Example 54

Synthesis of Compound 54

Similarly to Example 49, 1.47 g (5.27 mmol, 33.3%) of pale yellow crystals were obtained from 2.00 g (15.8 mmol) of 4-hydroxy 6-methyl-2-pyrone and 2.70 g (15.8 mmol) of 4-chlorophenylacetic acid by recrystallization from ethyl acetate.

Example 55

Synthesis of Compound 55

Similarly to Example 49, a pale yellow solid (2.46 g, 91%) was obtained from 4-hydroxy-6-methyl-2-pyrone (1.50 g, 11.9 mmol) and methylthiopropionic acid (1.30 mL, 12.5 mmol). The solid was recrystallized from ethanol to give yellow crystals.

Example 56

Synthesis of Compound 56

Similarly to Example 49, a yellow solid (2.00 g, 71%) was obtained from 4-hydroxy-6-methyl-2-pyrone (1.50 g, 11.9 mmol) and dichloroacetic acid (1.25 mL, 12.1 mmol). The solid was recrystallized from ethanol to give white crystals.

Example 57

Synthesis of Compound 57

Similarly to Example 49, white crystals (2.10 g, 79%) were obtained from 4-hydroxy-6-methyl-2-pyrone (1.50 g, 11.9 mmol) and tetrahydrofuran carboxylic acid (1.20 mL, 12.5 mmol).

Example 58

Synthesis of Compound 58

Similarly to Example 49, white crystals (1.50 g, 50%) were obtained from 4-hydroxy-6-methyl-2-pyrone (1.50 g, 11.9 mmol) and cyclohexylacetic acid (1.70 g, 12.0 mmol).

Example 59

Synthesis of Compound 59

Similarly to Example 49, white crystals (1.30 g, 46%) were obtained from 4-hydroxy-6-methyl-2-pyrone (1.50 g, 11.9 mmol) and cyclopentylacetic acid (1.50 mL, 11.9 mmol).

Example 60

Synthesis of Compound 60

Similarly to Example 49, yellow crystals (0.75 g, 26%) were obtained from 4-hydroxy-6-methyl-2-pyrone (1.50 g, 11.9 mmol) and phenylacetyl chloride (1.57 mL, 11.9 mmol).

Example 61

Synthesis of Compound 61

Similarly to Example 49, yellow crystals (300 mg, 10%) were obtained from 4-hydroxy-6-methyl-2-pyrone (2.00 g, 15.9 mmol) and butyric acid (1.45 mL, 15.9 mmol).

Example 62

Synthesis of Compound 62

Similarly to Example 49, yellow crystals (2.44 g, 73%) were obtained from 4-hydroxy-6-methyl-2-pyrone (2.00 g, 15.9 mmol) and n-valerianic acid (1.72 mL, 15.8 mmol).

Example 63

Synthesis of Compound 63

Similarly to Example 49, white crystals (450 mg, 13%) were obtained from 4-hydroxy-6-methyl-2-pyrone (2.00 g, 15.9 mmol) and monomethyl malonate (1.87 g, 15.9 mmol).

Example 64

Synthesis of Compound 64

Similarly to Example 49, white crystals (600 mg, 19%) were obtained from 4-hydroxy-6-methyl-2-pyrone (2.00 g, 15.9 mmol) and isobutyric acid (1.40 mL, 15.1 mmol).

Example 65

Synthesis of Compound 65

Similarly to Example 49, white crystals (1.04 g, 69%) were obtained from 4-hydroxy-6-methyl-2-pyrone (657 mg, 5.21 mmol) and 2-(4-methylthiophenyl)acetic acid (950 mg, 5.21 mmol).

Example 66

Synthesis of Compound 66

Similarly to Example 49, yellow crystals (2.16 g, 43%) were obtained from 4-hydroxy-6-methyl-2-pyrone (2.00 g, 15.9 mmol) and N-phthaloyl glycine (3.25 g, 15.8 mmol).

Example 67

Synthesis of Compound 67

From 2.00 g (15.8 mmol) of 5-methyl-1,3-cyclohexanedione and 1.2 mL (16.2 mmol) of propionic acid, 1.71 g (9.38 mmol, 59.3%) of 5-methyl-2-propionyl-1,3-cyclohexanedione was obtained as colorless crystals similarly to Example 49.

Example 68

Synthesis of Compound 68

From 2.00 g (15.8 mmol) of 5-methyl-1,3-cyclohexanedione and 0.95 mL (16.2 mmol) of acetic acid, 1.29 g (7.67 mmol, 48.5%) of 2-acetyl-5-methyl-1,3-cyclohexanedione was obtained as colorless crystals similarly to Example 49.

Example 69

Synthesis of Compound 69

From 2.00 g (15.8 mmol) of 5-methyl-1,3-cyclohexanedione and 2.25 g (15.9 mmol) of thiopheneacetic acid, 1.22 g (4.87 mmol, 30.8%) of 5-methyl-2-propionyl-1,3-cyclohexanedione was obtained as pale yellow crystals similarly to Example 49.

Example 70

Synthesis of Compound 70

Similarly to Example 49, yellow crystals (3.58 g, 90%) were obtained from 4-hydroxy-6-methyl-2-pyrone (1.80 g, 14.3 mmol) and 5-(2-thiophene)-butyric acid (2.1 mL, 14.3 mmol).

Example 71

Synthesis of Compound 71

In an argon atmosphere, sodium hydride (5.2 g, 60%) was washed with tetrahydrofuran, and to the resulting suspension in tetrahydrofuran (200 mL), was added dropwise a solution of ethyl acetoacetate (12.6 mL, 100 mmol) in tetrahydrofuran (10 mL) at room temperature. After the addition of the ethyl acetoacetate solution, stirring was carried out for 1 hour at room temperature. The solution was cooled to 0° C. and butyl lithium (2.5 M hexane solution, 42 mL, 105 mmol) was added dropwise to the solution; after the addition of butyl lithium, the mixture was stirred for 20 min. as it was, and then, for further 10 min. at room temperature. The solution was cooled to 0° C. again, mixed with acetone (7.4 mL, 100 mmol), and stirred for 20 min. at room temperature. By adding 5% hydrochloric acid and then concentrated hydrochloric acid, the resulting mixture was acidified, and extracted with ethyl acetate; the organic layer was dried over sodium sulfate anhydride. The solution was concentrated and the thus-obtained oily substance was mixed with a 1 N sodium hydroxide solution (200 mL) and methanol, followed by stirring for 4 hours at room temperature. The reaction solution was concentrated as it was, evaporated to remove methanol, acidified by adding 5% hydrochloric acid, and extracted with dichloromethane; the organic layer was dried over sodium sulfate anhydride. The resulting solution was concentrated and the thus-obtained solid was recrystallized from hexane-ethyl acetate to give white crystals (4.8 g, 34%).

Example 72

Synthesis of Compound 72

From 4-hydroxy-6-methyl-2-pyrone (2.00 g, 15.9 mmol) and N-Boc-glycine (2.78 g, 15.9 mmol), white crystals (1.25 g, 28%) were obtained similarly to Example 49.

Example 73

Synthesis of Compound 73

From 4-hydroxycoumarin (2.00 g, 12.3 mmol) and acetic acid (0.71 mL, 12.3 mmol), white crystals (1.12 g, 49%) were obtained similarly to Example 49.

Example 74

Synthesis of Compound 74

From Compound 71 (1.00 g, 7.03 mmol) and 2-thiopheneacetic acid (1.00 g, 7.03 mmol), white crystals (1.27 g, 68%) were obtained similarly to Example 49.

Example 75

Synthesis of Compound 75

Similarly to Example 49, 1.66 g (8.37 mmol, 53.0%) of 2-methoxyacetyl-5-methyl-1,3-cyclohexanedion was obtained as a pale yellow liquid from 2.00 g (15.8 mmol) of 5-methyl-1,3-cyclohexanedion and 1.22 mL (15.9 mmol) of methoxyacetic acid.

Example 76

Synthesis of Compound 76

In 500 mL of dichloromethane, was dissolved 22.0 mL (207 mmol) of 2-pentanone. While stirring the resulting solution in an ice bath, 44 mL (317 mmol) of triethylamine was added to the solution, and then, 42 mL (232 mmol) of trimethylsilyl trifluoromethanesulfonate was added dropwise to the solution. After the addition of trimethylsilyl trifluoromethanesulfonate, the mixture was stirred for 1 hour at room temperature, poured into ether (500 mL)/a saturated aqueous sodium hydrogencarbonate solution (300 mL) so as to extract the ether layer. The ether layer was washed with saturated sodium chloride water and water, dried over sodium sulfate anhydride, filtered, and concentrated. The residue was distilled under normal pressure to collect fractions of 110 to 125° C. As a result, 8.43 g (53.2 mmol, 49.4%) of 2-trimethylsilyloxy-2-pentene was obtained. According to a similar method, 5.33 g (33.6 mmol, 32.3%) of 2-trimethylsilyloxy-2-pentene was obtained from 11.0 mL (103.8 mmol) of 2-pentanone.

In 200 mL of ether, was dissolved 13.6 g (85.9 mmol) of 2-trimethylsilyloxy-2-pentene, and 4.6 mL (47.3 mmol) of malonyl chloride was added dropwise to the solution while stirring the solution at −78° C. After the addition of malonyl chloride, the solution was stirred for 1 hour at −78° C., and then, stirred over night while gradually heating the solution to room temperature. The precipitate was filtered and washed with ether. As a result, 3.08 g (20.0 mmol, 42.3%) of 5-ethyl-4-hydroxy-6-methyl-2-pyrone was obtained.

Example 77

Synthesis of Compound 77

Similarly to Example 49, 1.03 g (5.25 mmol, 81.0%) of 3-acetyl-5-ethyl-4-hydroxy-6-methyl-2-pyrone was obtained as a pale yellow liquid from Compound 76 (1.00 g, 6.48 mmol) and 0.38 mL (6.55 mmol) of acetic acid.

Example 78

Synthesis of Compound 78

Similarly to Example 49, 1.11 g (5.28 mmol, 81.5%) of 5-ethyl-4-hydroxy-6-methyl-3-propanoyl-2-pyrone was obtained as a pale yellow oily substance from Compound 76 (1.00 g, 6.48 mmol) and 0.5 mL (6.48 mmol) of propionic acid.

Example 79

Synthesis of Compound 79

Similarly to Example 49, white crystals (0.96 g, 76%) were obtained from Compound 71 (1.00 g, 7.03 mmol) and acetic acid (0.40 mL, 7.03 mmol).

Example 80

Synthesis of Compound 80

Similarly to Example 49, yellow crystals (1.21 g, 24%) were obtained from 4-hydroxy-6-methyl-2-pyrone (2.00 g, 15.9 mmol) and p-toluenesulfonylacetic acid (3.40 g, 15.9 mmol).

Example 81

Synthesis of Compound 81

Similarly to Example 49, white crystals (0.71 g, 15%) were obtained from 4-hydroxy-6-methyl-2-pyrone (2.00 g, 15.9 mmol) and phthalide-3-acetic acid (3.04 g, 15.9 mmol).

Example 82

Synthesis of Compound 82

Similarly to Example 49, yellow crystals (0.96 g, 26%) were obtained from 4-hydroxy-6-methyl-2-pyrone (2.00 g, 15.9 mmol) and 4-cyclohexenecarboxylic acid (1.9 mL, 15.9 mmol).

Example 83

Synthesis of Compound 83

Similarly to Example 49, 608 mg (2.17 mmol, 33.5%) of 5-ethyl-4-hydroxy-6-methyl-3-(2-thiopheneacetyl)-2-pyrone was obtained as an orange oily substance from Compound 76 (1.00 g, 6.48 mmol) and 922 mg (6.48 mmol) of 2-thiopheneacetic acid.

Example 84

Synthesis of Compound 84

When 7.0 mL (72.0 mmol) of malonyl chloride was added to 7.0 mL (67.8 mmol) of acetylacetone, a violent exothermic reaction occurred to give a black solid within a few minutes. The solid was cooled to room temperature, washed with ether and then ethyl acetate, and filtered. The thus-obtained brown solid was recrystallized from ethyl acetate/methanol to give 1.75 g (10.4 mmol, 15.3%) of 5-acetyl-4-hydroxy-6-methyl-2-pyrone as brown crystals. The filtrates from washing and the recrystallized mother liquor were combined and concentrated; the residue was purified by silica gel column chromatography to give 2.87 g (17.1 mmol, 25.2%) of 5-acetyl-4-hydroxy-6-methyl-2-pyrone as orange crystals.

Example 85

Synthesis of Compound 85

Similarly to Example 49, 242 mg (1.15 mmol, 19.3%) of 3,5-diacetyl-4-hydroxy-6-methyl-2-pyrone was obtained as pale yellow needle crystals from Compound 84 (1.00 g, 5.95 mmol) and 0.35 mL (6.11 mmol) of acetic acid by recrystallization from hexane.

Comparative Example 1

Synthesis of 1-oxa-2,4-oxospiro[5,5]undecane

In an argon atmosphere, sodium hydride (5.2 g) was washed with tetrahydrofuran, and to the resulting suspension in tetrahydrofuran (200 mL), was added dropwise a solution of ethyl acetoacetate (12.6 mL, 100 mmol) in tetrahydrofuran (10 mL) at room temperature. After the addition of the ethyl acetoacetate solution, stirring was carried out for 1 hour at room temperature. The solution was cooled to 0° C. and butyl lithium (2.5 M hexane solution, 44 mL, 110 mmol) was added dropwise to the solution; after the addition of butyl lithium, the solution was stirred for 20 min., and then, for further 10 min. at room temperature. The solution was cooled to 0° C. again, mixed with cyclohexanone (11.5 mL, 110 mmol), and stirred at room temperature for 30 min. By adding 5% hydrochloric acid and then concentrated hydrochloric acid, the resulting mixture was acidified, mixed with sodium chloride, and extracted with ethyl acetate; the organic layer was dried over sodium sulfate anhydride. The solution was concentrated and the thus-obtained oily substance was mixed with a 1 N aqueous sodium hydroxide solution (200 mL) and methanol, followed by stirring for 4 hours at room temperature. The reaction solution was concentrated as it was and evaporated to remove methanol, acidified by adding 5% hydrochloric acid, and extracted with dichloromethane; the organic layer was dried over sodium sulfate anhydride. The solution was concentrated and the thus-obtained solid was recrystallized from hexane-ethyl acetate to give white crystals (9.96 g, 55%).

Example 86

Synthesis of Compound 86

Similarly to Example 49, white crystals (697 mg, 71%) were obtained from 1-oxa-2,4-oxospiro[5,5]undecane (800 mg, 4.39 mmol) and acetic acid (0.25 mL, 4.39 mmol).

Example 87

Synthesis of Compound 87

Similarly to Example 49, white crystals (0.83 g, 53%) were obtained from 6-phenetyl-4-oxa-δ-valerolactone (1.00 g, 4.58 mmol) and 2-thiopheneacetic acid (650 mg, 4.58 mmol).

Example 88

Synthesis of Compound 88

Similarly to Example 49, white crystals (3.39 g, 91%) were obtained from 4-hydroxy-6-methyl-2-pyrone (2.00 g, 15.9 mmol) and thenoyl chloride (1.96 mL, 15.9 mmol) by recrystallization from ethanol.

Example 89

Synthesis of Compound 89

In 150 mL of acetic acid, were suspended 11.7 g (121 mmol) of furfural and 16.25 g (122 mmol) of rhodanine. To the suspension, was added 31.0 g (378 mmol) of sodium acetate, and the mixture was stirred at 85° C. for 1 hour and 40 min. After confirming the appearance of a bright orange precipitate, the reaction suspension was cooled to room temperature and poured into 200 mL of water. After thorough stirring, the resulting precipitate was filtered under reduced pressure, and the residue was washed with 300 mL of water, 20 mL of 99.5% ethanol, and then 10 mL of diethyl ether. The residue was dried to give 20.0 g (94.8 mmol) of furfural rhodanine with a crude yield of 78%. The furfural rhodanine was used for the subsequent reaction without being further purified.

After 20.0 g (94.8 mmol) of furfural rhodanine was suspended in 120 mL of a 4.8 N aqueous sodium hydroxide solution, the suspension was stirred at 80° C. for 1 hour and 30 min. While the reaction solution was stirred in an ice bath, 4 N hydrochloric acid (200 mL) was poured into the reaction solution at once; the resultant was stirred at room temperature and extracted with ether. The ether layer was washed with water, a 10% aqueous sodium thiosulfate solution, and saturated sodium chloride water in that order, dried over sodium sulfate anhydride, and concentrated under reduced pressure. The thus-obtained solid was recrystallized from ethanol to give 12.0 g (70.6 mmol) of 3-α-furyl-2-thioketopropionic acid with a yield of 75%.

$^1$H-NMR(300 MHz, CDCl$_3$)δ: 4.73(1H, s), 6.58(1H, m), 6.88(1H, m), 7.61(1H, m), 7.72(1H, s).

To 200 mL of ethanol, were slowly added 8.0 g (350 mmol) of finely chopped sodium chips over 3 hours, and after sodium ethoxide was produced, the mixture was stirred for further 1 hour and 30 min. To the resulting solution, was added 23.2 g (333 mmol) of hydroxylamine hydrochloride at room temperature, and then, stirred for 1 hour. To the resulting suspension, was added dropwise 120 mL of a solution of 10.7 g (63.1 mmol) of 3-α-furyl-2-thioketopropionic acid in ethanol, and then stirred for 3 hours while being heat-refluxed. The reaction suspension was cooled to room temperature and poured into 60 mL of a 5% aqueous sodium hydroxide solution. After the precipitate was removed by filtration under reduced pressure, the filtrate was acidified by adding 80 mL of 4 N hydrochloric acid and extracted with ether. The ether layer was dried over magnesium sulfate anhydride and filtered under reduced pressure to give 7.62 g (38.7 mmol) of ethyl 3-α-furyl-2-oxyminopropionate.

$^1$H-NMR(300 MHz, CDCl$_3$)δ: 1.213(3H, t, J=7.2 Hz), 3.49(2H, q, J=7.2 Hz), 4.093(1H, s), 6.15(1H, m), 6.29(1H, m), 7.31(1H, m).

To a flask, was added 7.62 g (38.7 mmol) of the thus-obtained ethyl 3-α-furyl-2-oxyminopropionate and it was mixed with 85 mL of acetic acid anhydride and 1 mL of water, followed by thorough stirring. The mixture was heat-refluxed for 7 hours. After the completion of the reaction, the mixture was cooled to room temperature and subjected to steam distillation. While heating a still pot at 125° C. and stirring the mixture, fractions each 350 mL were collected. Each fraction was extracted with ether (150 mL×3); thus-collected ether was concentrated under reduced pressure to approximately a third, neutralized by adding a saturated aqueous sodium hydrogencarbonate solution, and dried over magnesium sulfate anhydride. The target compound was contained in the first to the fourth fractions collected from steam distillation. Then, 4.4 g of the thus-obtained residue was subjected to silica gel column chromatography, using 100 g of silica gel and hexane/dichloromethane=1/1 to 1/2 as a solvent, to give 3.79 g (35.4 mmol) of 2-α-furylacetonitrile with a yield of 91.5.

$^1$H-NMR(300 MHz, CDCl$_3$)δ: 3.77(2H, s), 6.33(1H, m), 6.37(1H, m), 7.40(1H, m); IR(KBr)2260, 1603 cm$^{-1}$.

In a mixed solution of 30 mL of a 3 N sodium hydroxide solution and 30 mL of methanol, was dissolved 3.34 g (31.2 mmol) of 2-α-furylacetonitrile and the resulting solution was heat-refluxed for 2 hours and 30 min. while stirring the solution. The solution was cooled to room temperature and extracted with ether. The water layer was mixed with 20 mL of concentrated hydrochloric acid to liberate organic substances, followed by extraction with ether. The ether layer was collected, dried over magnesium sulfate anhydride, concentrated under reduced pressure to give 3.84 g (30.5 mmol) of 2-α-furylacetic acid with a yield of 97.8%.

In 100 mL of toluene, were dissolved 1.00 g (7.91 mmol) of the thus-prepared 2-α-furylacetic acid and 1.04 g (8.24 mmol) of 4-hydroxy-6-methyl-2-pyrone, and then, 1.65 g (7.99 mmol) of dicyclohexylcarbodiimide and 0.18 g (1.44 mmol) of 4-N dimethylaminopyridine were added to the resulting solution, followed by stirring at room temperature for 1 hour and at 80° C. for 14 hours. The resultant was cooled to room temperature, filtered to remove residue, and the thus-obtained filtrate was concentrated under reduced pressure, followed by extraction with dichloromethane. The resultant was washed with a saturated aqueous ammonium chloride solution and a saturated aqueous sodium chloride solution, dried over sodium sulfate anhydride, and concentrated under reduced pressure to give 2.35 g of a mixed product. The product was purified by silica gel column chromatography using 108 g of silica gel. Hexane/ethyl acetate=3/1 to 1/1 was used as a solvent; the thus-obtained substance was concentrated and dissolved in ethyl acetate. With a saturated aqueous sodium hydrogencarbonate solution, the target compound was extracted to the water layer, and then, the water layer was acidified by adding hydrochloric acid, followed by extraction with ethyl acetate. By recrystallization from ethanol, 0.52 g of the target compound was obtained.

Example 90

Synthesis of Compound 90

Similarly to Example 49, pale yellow crystals (1.10 g, 32%) were obtained from 4-hydroxy-6-methyl-2-pyrone (2.00 g, 15.9 mmol) and 2-methylthioacetic acid (1.3 mL, 16 mmol).

Example 91

Synthesis of Compound 91

Similarly to Example 49, yellow crystals (950 mg, 23%) were obtained from 4-hydroxy-6-methyl-2-pyrone (2.00 g, 15.9 mmol) and 2-phenylpropionic acid (2.17 g, 15.9 mmol).

Example 92

Synthesis of Compound 92

Similarly to Example 49, white crystals (4.66 g, 67%) were obtained from 4-hydroxy-6-methyl-2-pyrone (3.00 g, 23.8 mmol) and N-undecanoic acid (4.8 g, 24 mmol).

Example 93

Synthesis of Compound 93

Similarly to Example 49, white crystals (3.43 g, 64%) were obtained from 4-hydroxy-6-methyl-2-pyrone (3.00 g, 23.8 mmol) and tetrahydro-3-furancarboxylic acid (2.25 mL, 23.8 mmol).

Example 94

Synthesis of Compound 94

Similarly to Example 49, white crystals (5.05 g, 58%) were obtained from 4-hydroxy-6-methyl-2-pyrone (3.00 g, 23.8 mmol) and palmitic acid (6.10 g, 23.8 mmol).

Example 95

Synthesis of Compound 95

Similarly to Example 49, white crystals (3.13 g, 81%) were obtained from 4-hydroxycoumarin (2.00 g, 12.3 mmol) and capric acid (2.13 g, 12.3 mmol).

Example 96

Synthesis of Compound 96

Similarly to Example 49, white crystals (3.13 g, 85%) were obtained from 4-hydroxycoumarin (2.00 g, 12.3 mmol) and palmitic acid (3.16 g, 12.3 mmol).

Example 97

Synthesis of Compound 97

Similarly to Example 49, pale yellow crystals (430 mg, 16%) were obtained from 4-hydroxy-6-methyl-2-pyrone (1.00 g, 7.93 mmol) and 3-(6-chlorobenzothiophene)acetic acid (1.80 g, 7.93 mmol).

Example 98

Synthesis of Compound 98

Similarly to Example 49, pale yellow crystals (1.48 g, 33%) were obtained from 4-hydroxy-6-methyl-2-pyrone (2.00 g, 15.9 mmol) and 3-indoleacetic acid (2.8 g, 16 mmol).

Example 99

Synthesis of Compound 99

Similarly to Example 49, pale yellow crystals (6.21 g, 57%) were obtained from 4-hydroxy-6-methyl-2-pyrone (5.00 g, 39.7 mmol) and phenylthioacetic acid (6.7 g, 40 mmol).

Example 100

Synthesis of Compound 100

Similarly to Example 49, pale yellow crystals (1.63 g, 44%) were obtained from 4-hydroxy-6-methyl-2-pyrone (1.50 g, 11.9 mmol) and 3-methylbenzo[b]thiophene-2-acetic acid (2.45 g, 11.9 mmol).

Example 101

Synthesis of Compound 101

Similarly to Example 49, 1.82 g of the target compound was obtained from 2.20 g (11.8 mmol) of undecanoic acid and 1.20 g (12.0 mmol) of tetronic acid by recrystallization from methanol.

Example 102

Synthesis of Compound 102

Similarly to Example 49, 0.58 g of crystals were obtained from 1.22 g (7.71 mmol) of pelargonic acid and 0.78 g (7.79 mmol) of tetronic acid by recrystallization from methanol.

Example 103

Synthesis of Compound 103

Similarly to Example 49, 0.62 g of the target compound was obtained from capric acid (0.97 g, 6.7 mmol) and tetronic acid (0.71 g, 7.1 mmol) by recrystallization from methanol.

Example 104

Synthesis of Compound 104

Similarly to Example 49, pale yellow crystals (5.03 g, 44%) were obtained from 4-hydroxy-6-methyl-2-pyrone (5.00 g, 40.0 mmol) and 4-nitrophenylacetic acid (7.2 g, 40 mmol).

Example 105

Synthesis of Compound 105

Similarly to Example 49, pale yellow crystals (2.50 g, 57%) were obtained from 4-hydroxy-6-methyl-2-pyrone (2.00 g, 15.9 mmol) and 4-methoxyphenylacetic acid (2.65 g, 15.9 mmol).

Example 106

Synthesis of Compound 106

Similarly to Example 49, pale yellow crystals (2.57 g, 29%) were obtained from 4-hydroxy-6-methyl-2-pyrone (5.00 g, 40.0 mmol) and levulinic acid (4.1 mL, 40 mmol).

Example 107

Synthesis of Compound 107

Similarly to Example 49, pale yellow crystals (3.22 g, 52%) were obtained from 4-hydroxy-6-methyl-2-pyrone (3.00 g, 23.8 mmol) and 4-fluorophenylacetic acid (3.7 g, 24 mmol).

Example 108

Synthesis of Compound 108

In an argon atmosphere, 1.06 g (9.45 mmol) of 5-hexynoic acid was dissolved in 90 mL of dry tetrahydrofuran and the resulting solution was cooled to −78° C. To the solution, was added dropwise 10 mL (25.0 mmol) of a 5 N butyl lithium hexane solution, followed by stirring at −78° C. for 15 min. After that, the solution was mixed with 10 mL of HMPA and stirred; then 20 mL of a solution of 1.5 mL (d=1.617, 2.42 g, 13.2 mmol) of butyl iodide in tetrahydrofuran was added dropwise to the solution. The reaction solution was stirred at −78° C. for 1 hour, and then, stirred overnight while gradually elevating the temperature to room temperature. The reaction solution was poured into ice-1 N hydrochloric acid and extracted with dichloromethane. The resultant was washed with saturated sodium bicarbonate water to liberate acidic components; the water layer was acidified by adding concentrated hydrochloric acid and extracted with dichloromethane again. The collected organic layers were washed with a 10% aqueous sodium thiosulfate solution and a saturated aqueous sodium chloride solution in that order, dried over manganese sulfate anhydride, and concentrated under reduced pressure to give a crude product. The product was used in the subsequent reaction without being further purified. The thus-obtained crude product was dissolved in 50 mL of dry methanol, mixed with 1 mL of concentrated sulfuric acid, and heat-refluxed for 2 hours. The resultant was cooled, poured into saturated sodium bicarbonate water, and extracted with ethyl acetate. The resultant was washed with water, a saturated aqueous ammonium chloride solution, and a saturated aqueous sodium chloride solution in that order, dried over manganese sulfate anhydride, and concentrated under reduced pressure. The residue was purified by silica gel column chromatography using 110 g of silica gel. Hexane/ethyl acetate was used as a solvent to give 1.02 g (59%) of the target compound.

$^1$H-NMR(300 MHz, CDCl$_3$)δ: 0.91(3H, t, J=6.8 Hz), 1.4(m, 4H), 1.80(2H, g, J=7.4 Hz), 2.14(2H, m), 2.22(2H, m), 2.44(2H, t, J=7.4 Hz), 3.68(3H, s).

To a 2.1% aqueous sodium hydroxide solution, was added 0.99 g (5.4 mmol) of methyl 5-decynate, and the mixture was heat-refluxed for 3 hours. The reaction solution was acidified by adding concentrated hydrochloric acid and extracted with ether. The organic layer was washed with a saturated aqueous sodium chloride solution, dried over magnesium sulfate, and concentrated under reduced pressure to give 0.87 g (96%) of the target compound.

$^1$H-NMR(300 MHz, CDCl$_3$)δ: 0.91(3H, t, J=7.1 Hz), 1.4(4H, m), 1.81(2H, q, J=7.4 Hz), 2.14(2H, m), 2.24(2H, m), 2.50(2H, t, J=7.4 Hz).

Similarly to Example 49, 0.51 g (36%) of the target compound was obtained from 5-decynoic acid (0.87 g, 5.1 mmol) and tetronic acid (0.52 g, 5.2 mmol).

Example 109

Synthesis of Compound 109

To a 100 mL, two-neck flask, was added 1.32 g of sodium hydride, and it was mixed with 10 mL of hexane in an argon atmosphere, followed by stirring using a magnetic stirrer so as to wash off paraffin contained in NaH. Hexane used for washing was removed from the flask by a Pasteur pipet. This procedure was repeated twice, and then, 50 mL of tetrahydrofuran was added to the flask. Using a Pasteur pipet, 4.48 g of ethyl ester of diethylphosphonoacetic acid was added slowly to the mixture. When hydrogen stopped being generated, 2.96 g of 4-isopropylbenzaldehyde was added slowly to the mixture. (Generated heat was cooled by icy water.) After 1 hour, stirring was stopped, and the reaction solution was added to 150 mL of distilled water. Extraction was carried out three times using 50 mL of ethyl acetate. The ethyl acetate layers were washed twice with 50 mL of distilled water, dried over sodium sulfate, concentrated by an evaporator, and dried by a vacuum pump. As a result, 3.4 g (78%) of ethyl p-isopropylcinnamate was obtained.

To 100 mL of ethyl acetate, were added 3.0 g of ethyl p-isopropylcinnamate and 300 mg of 5%-Pd/C. The resulting mixture was stirred in a hydrogen atmosphere. Three hours after the reaction, the hydrogen atmosphere was replaced with argon atmosphere, and the resulting mixture was filtered, concentrated, and dried. As a result, 2.9 g (y=97.6%) of ethyl p-isopropyldehydrocinnamate was obtained. To 2.9 g of ethyl p-isopropyldehydrocinnamate, were added 20 mL of distilled water and 20 mL of tetrahydrofuran, and the mixture was hydrolyzed by 0.70 g of lithium hydroxide to give 2.1 g (82.6%) of p-isopropyldehydrocinnamic acid.

Similar to Example 49, 0.211 g (15.4%) of the target compound was obtained from 0.968 g (5.0 mmol) of p-isopropyldehydrocinnamic acid and tetronic acid.

Example 110

Synthesis of Compound 110

To 200 mL of methanol, was added 6.3 g of p-hydroxyphenylacetic acid. Ten droplets of concentrated hydrochloric acid was added to the resulting mixture by a Pasteur pipet and reaction proceeded at 80° C. for 1 hour. The mixture was concentrated, mixed with 100 mL of ethyl acetate, and washed twice with 50 mL of distilled water. The resultant was dried over sodium sulfate, filtered, concentrated, and dried under reduced pressure. As a result, 6.5 g (95.1%) of methyl p-hydroxyphenylacetate was obtained.

In an argon atmosphere, 1.32 g of sodium hydride was weighed, mixed with 10 mL of hexane, and stirred by using a magnetic stirrer so as to wash off paraffin contained in sodium hydride. Hexane used for washing was removed from the flask by a Pasteur pipet. This procedure was repeated twice, and then, 50 mL of dimethylformamide was added to the flask. By using a Pasteur pipet, 2.49 g of methyl p-hydroxyphenylacetate was added slowly to the mixture. When hydrogen stopped being generated, 2.27 g of 1-bromo-3-methylbuthane was added slowly to the mixture. After stirring overnight, the reaction solution was added to 150 mL of distilled water. The resultant was neutralized by adding 1 N hydrochloric acid and extracted three times with 80 mL of ether. The ether layers were washed twice with 50 mL of distilled water, dried over sodium sulfate, concentrated by an evaporator, and dried by a vacuum pump. As a result, 1.4 g (39.5%) of an ether compound was obtained.

To 1.4 g of the ether compound, were added 10 mL of distilled water and 5 mL of ethanol, and the resultant was hydrolyzed by adding 0.32 g of sodium hydroxide and heating at 50° C. to give 0.533 g (40.5%) of a carboxylic acid.

Similarly to Example 49, 0.173 g (32.3%) of the target compound was obtained from 0.389 g (1.75 mmol) of the carboxylic acid and 0.176 g (1.75 mmol) of tetronic acid.

Example 111

Synthesis of Compound 111

Similarly to Example 49, pale yellow crystals (495 mg, 11%) were obtained from 4-hydroxy-6-methyl-2-pyrone (2.00 g, 15.9 mmol) and 4-dimethylaminophenylacetic acid (2.85 g, 15.9 mmol).

Example 112

Synthesis of Compound 112

Similarly to Example 49, white crystals (1.60 g, 30%) were obtained from 4-hydroxy-6-methyl-2-pyrone (2.00 g, 15.9 mmol) and 4-(trifluoromethyl)phenylacetic acid (3.24 g, 15.9 mmol).

Example 113

Synthesis of Compound 113

Similarly to Example 49, a brown oily substance (7.08 g) was obtained from 4-hydroxy-6-methyl-2-pyrone (5.00 g, 40.0 mmol) and diethylphosphonoacetic acid (6.4 mL, 40 mmol). However, since complete purification was impossible, the oily substance was subjected to the subsequent reaction as it was.

$^1$H-NMR(300 MHz, CD3OD)δ: 2.35(d, J=0.82 Hz, 3H), 2.39(m, 3H), 4.71(s, 2H), 6.22(q, J=0.82 Hz, 1H), 7.29–7.42 (m, 2H), 7.71–7.74(m, 1H), 7.78–7.82(m, 1H).

The oily substance (7.08 g) was dissolved in dichloromethane (20 mL) in an argon atmosphere, mixed with bromotrimethylsilane (11 mL, 85 mmol), and stirred for 24 hours at room temperature. After stopping the reaction by adding absolute methanol, the mixture was stirred for 1 hour in an argon atmosphere, and evaporated under reduced pressure for removing the solvent. The thus-obtained solid was recrystallized from ethyl acetate/ethanol to give pale brown crystals (3.47 g, 35%).

Example 114

Synthesis of Compound 114

Similarly to Example 49, pale yellow crystals (3.77 g, 36%) were obtained from 4-hydroxy-6-methyl-2-pyrone (5.00 g, 40.0 mmol) and pelargonic acid (6.9 mL, 40 mmol).

Example 115

Synthesis of Compound 115

To give 0.116 g of the target compound, 3.32 g (20 mmol) of the p-hydroxyphenylacetate used in Example 110 was reacted and the succeeding steps were followed similarly to Example 110.

Example 116

Synthesis of Compound 116

To 5 mL of thionyl glutarate, was added 2.92 (20 mmol) of monomethyl glutarate and then the mixture was heated at 80° C. for 30 min. Thionyl chloride was removed by distillation. To 2.54 g (20 mmol) of diisobutylamine, was added 20 mL of pyridine, and then the mixture was stirred. The monomethyl ester of glutaryl chloride synthesized by the above procedure was slowly added to the mixture, and then stirred overnight. After removing pyridine by evaporation, the resultant was mixed with 50 mL of distilled water and acidified by adding 1 N HCl. The mixture was extracted with ethyl acetate, dried over sodium sulfate, filtered, concentrated, and dried under reduced pressure. As a result, 4.1 g (79.7%) of a methyl ester of 3-(N,N-diisopropylamino)butyric acid was obtained.

By using lithium hydroxide, 2.03 g (7.89 mmol) of the above methyl ester was hydrolyzed to give 1.4 g (72.9%) of 3-(N,N-diisopropylamino)butyric acid. Similarly to Example 109, 0.8 g (3.29 mmol) of the above acid was subjected to reaction to give 0.154 g of the target compound.

Example 117

Synthesis of Compound 117

Similarly to Example 49, 0.170 g (11.3%) of the target compound was obtained from 0.961 g (5.0 mmol) of isopropyldehydrocinnamic acid and 0.63 g (5.0 mmol) of 4-hydroxy-6-methylpyrone.

Example 118

Synthesis of Compound 118

Similarly to Example 49, white crystals (6.5 g, 72%) were obtained from 4-hydroxycoumarin (5.00 g, 31.3 mmol) and p-tolueneacetic acid (4.7 g, 31.3 mmol).

Example 119

Synthesis of Compound 119

Similarly to Example 49, white crystals (7.51 g, 66%) were obtained from 4-hydroxy-6-methyl-2-pyrone (5.00 g, 39.6 mmol) and o-nitrophenylacetic acid (7.20 g, 39.6 mmol).

Example 120

Synthesis of Compound 120

Similarly to Example 49, white crystals (0.85 g, 25%) were obtained from 4-hydroxy-6-methyl-2-pyrone (1.50 g, 11.9 mmol) and 3,4-(methylenedioxy)phenylacetic acid (2.15 g, 11.9 mmol).

Example 121

Synthesis of Compound 121

To a mixture of meldrum's acid (8.00 g, 55.5 mmol) and p-nitrophenylacetic acid (10.3 g, 56 mmol), was added dichloromethane (120 mL); the resultant was mixed with dicyclohexylcarbodiimide (12 g, 59 mmol) and 4-N,N-dimethylaminopyridine (1.0 g, 8.2 mmol) and stirred at 25° C. for 19 hours. After removing the thus-produced insoluble dicyclohexyl urea by filtration, the reaction solution was washed with 1 N hydrochloric acid (50 mL), the water layer was extracted three times with dichloromethane (30 mL), and the organic layers were combined and dried over sodium sulfate anhydride. After concentrating the solution, the thus-obtained residue was purified by silica gel column chromatography (dichloromethane) to give substantially pure crystals (3.8 g).

$^1$H-NMR(300 MHz, CDCl$_3$)δ: 1.74(s, 6H), 4.51(s, 2H), 7.58(d, J=8.8 Hz, 2H), 8.22(d, J=8.8 Hz, 2H).

The crystals (3.8 g, 12.5 mmol) were dissolved in benzene (80 mL), mixed with DL-diethylmalate (1.72 mL, 13 mmol), and heat-refluxed for 4.5 hours. After removing the solvent by evaporation, the residue was purified by silica gel column chromatography (silica gel, hexane/ethyl acetate=4:1 to 2:1) to give an oily substance (4.30 g).

$^1$H-NMR(300 MHz, CDCl$_3$)δ: 1.74(s, 6H), 4.51(s, 2H), 7.58(d, J=8.8 Hz, 2H), 8.22(d, J=8.8 Hz, 2H).

The oily substance (4.30 g) was dissolved in tetrahydrofuran (8 mL), mixed with tetrabutylammonium fluoride (1 M tetrahydrofuran, 13.0 mL, 13.0 mmol) and stirred at room temperature for 3 hours. After removing the solvent by evaporation, the residue was mixed with 6 N hydrochloric acid and the thus-produced precipitate was collected by filtration, washed with hexane, and recrystallized from ethanol to give pale brown crystals (2.76 g, 15% from meldrum's acid).

$^1$H-NMR(300 MHz, CD3OD)δ: 2.87(dd, J1=6.9 Hz, J2=17.0 Hz, 1H), 3.08(dd, J1=3.8 Hz, J2=17.0 Hz, 1H), 3.72(s, 3H), 5.07(dd, J1=3.8 Hz, J2=6.9 Hz, 1H), 7.61(d, J=8.8 Hz, 2H), 8.22(d, J=8.8 Hz, 2H); Elemental analysis Found: C;53.59, H;3.93, N;4.14. Calcd. as C15H13NO8 C;53.73, H;3.9, N;4.18. IR(KBr)1746, 1661, 1609, 1520, 1448, 1352, 1245, 1114, 1025, 884 cm$^{-1}$.

To the pale brown crystals (1.00 g, 2.99 mmol), were added methanol (30 mL) and distilled water (15 mL), and the mixture was mixed with lithium hydroxide (180 mg, 7.5 mmol), followed by stirring at room temperature for 8 hours. After stopping the reaction by adding 1 N hydrochloric acid, methanol was removed by evaporation; the thus-obtained suspension was filtered and washed with 1 N hydrochloric acid to give pale brown crystals (901 mg, 94%).

Comparative Example 2

Synthesis of 4-hydroxy-6-methyl-2-pyrone

A solution of 1-phenyl-1-trimethylsiloxyethylene (25.0 g, 130 mmol) in absolute ether (400 mL) was cooled to −78° C., and malonyl dichloride (6.40 mL, 65.0 mmol) was added dropwise to the resulting solution by using a dropping funnel. The mixture was gradually heated to room temperature, stirred at room temperature (5 to 10° C.) for 14 hours, and further stirred at 30° C. for 24 hours. The thus-produced yellow precipitate was filtered and washed with absolute ether to give the target 4-hydroxy-6-methyl-2-pyrone (8.40 g, 67%) as a yellow solid.

Example 122

Synthesis of Compound 122

Triethylamine (0.57 mL, 4.0 mmol) and then propionyl chloride (0.33 mL, 3.7 mmol) were added to a suspension of 4-hydroxy-6-methyl-2-pyrone (0.70 g, 3.72 mmol) in toluene (50 mL) at room temperature. The mixture was stirred for 3.5 hours as it was and then mixed with 4-N,N-dimethylaminopyridine (170 mg, 1.39 mmol), followed by heating at 90° C. for 15 hours. After cooling the mixture to room temperature, insoluble substances were removed by filtration, the filtrate was washed with 5% hydrochloric acid (30 mL), and extracted four times with dichloromethane (20 mL); the organic layers were combined and dried over sodium sulfate anhydride. After concentrating the solution, the thus-obtained residue was purified by silica gel column chromatography (dichloromethane) and recrystallized from ethanol to give pale red crystals (550 mg, 61%).

Example 123

Synthesis of Compound 123

Similarly to Example 122, yellow crystals (1.82 g, 15%) were obtained from 4-hydroxy-6-methyl-2-pyrone (2.00 g, 15.9 mmol) and monoethyl succinyl chloride (2.20 mL, 15.6 mmol).

Example 124

Synthesis of Compound 124

Similarly to Example 122, yellow crystals (1.91 mg, 23%) were obtained from 4-hydroxy-6-methyl-2-pyrone (5.00 g, 39.6 mmol) and propyl chloroformate (5.4 mL, 40 mmol).

Example 125

Synthesis of Compound 125

Similarly to Example 122, white crystals (480 mg, 7.2%) were obtained from 4-hydroxy-6-methyl-2-pyrone (3.00 g, 23.8 mmol) and capryl chloride (4.9 mL, 24 mmol).

Example 126

Synthesis of Compound 126

Dichloromethane (15 mL) was added to a mixture of Compound 90 (400 mg, 1.87 mmol) and trimethyloxotetrafluoroborate (289 mg, 1.96 mmol), followed by stirring at room temperature for 21 hours. The thus-produced precipitate was filtered and washed with dichloromethane to give white crystals (530 mg, 90%).

Example 127

Synthesis of Compound 127

A solution of 3-carbomethoxy-4-hydroxy-6-methylpyrone (0.500 g, 2.72 mmol) in aniline (5 mL) was stirring for 2 hours while heating at 150° C., and then, after removing aniline by evaporation under reduced pressure, the residue was purified by silica gel column chromatography (dichloromethane) and recrystallized from ethanol to give yellow crystals (0.432 g, 65%).

Example 128

Synthesis of Compound 128

Ethanedithiol (0.4 mL, 4.8 mmol) was added to a solution of Compound 72 (300 mg, 1.06 mmol) in trifluoroacetic acid (9 mL) at room temperature and stirred at room temperature for 2 hours. After concentrating the solution, the thus-obtained residue was mixed with 1 N hydrochloric acid and concentrated again; the thus-obtained crystals were washed with hexane and acetone to give white crystals (220 mg, 95%).

Example 129

Synthesis of Compound 129

At −78° C., a solution of 3-(2-methoxyphenylacetyl)-4-hydroxy-6-methyl-pyrone (500 mg, 1.82 mmol) in tetrahydrofuran (10 mL) was added dropwise to a solution of lithium diisopropylamide in tetrahydrofuran (10 mL) prepared from diisopropylamine (0.56 mL, 3.98 mmol) and n-butyl lithium (2.5 M hexane solution, 1.75 mL, 4.38 mmol); the resulting mixture was stirred as it was for 30 min., heated to 0° C., stirred for further 30 min., and mixed with methyl iodide (0.27 mL, 4.3 mmol). The mixture was heated to room temperature and stirred for 2 hours; after stopping the reaction by adding 1 N hydrochloric acid (30 mL), the water layer was extracted twice with dichloromethane (20 mL), the organic layers were combined, and dried over sodium sulfate anhydride. After concentrating the solution, the thus-obtained residue was purified by flash silica gel column chromatography (dichloromethane/hexane=1:1) and recrystallized from ethanol/hexane to give yellow crystals (150 mg, 29%). This reaction was also carried out by using dimethyl sulfate instead of methyl iodide, and a similar result was obtained.

Example 130

Synthesis of Compound 130

While cooling in ice, a solution of 3-(2-methoxyphenylacetyl)-4-hydroxy-6-methyl-pyrone (1.00 g, 3.65 mmol) in tetrahydrofuran (10 mL) was added dropwise to a suspension of sodium hydride (0.18 g, 60% 4.4 mmol) in tetrahydrofuran (10 mL), stirred at room temperature for 1 hour, cooled to 0° C. again, and mixed with n-butyl lithium (2.5 M hexane solution, 1.6 mL, 4.0 mmol). After stirring for 10 min., ethyl iodide (0.65 mL, 8.0 mmol) was added to the mixture followed by stirring for 30 min.; since red anion seeds seemed to still remain unreacted, triamide hexamethyl phosphate (1.9 mL, 21 mmol) was added to the mixture followed by stirring for 1 hour. The reaction was stopped by adding concentrated hydrochloric acid (30 mL) at 0° C. and the water layer was extracted twice with dichloromethane (20 mL); the organic layers were combined and dried over sodium sulfate anhydride. After concentrating the solution, the thus-obtained residue was purified by silica gel column chromatography (dichloromethane/hexane=2:1) and recrystallized from ethanol/hexane to give pale yellow crystals (827 mg, 75%).

Example 131

Synthesis of Compound 131

While cooling in ice, a solution of Compound 51 (0.800 g, 3.20 mmol) in tetrahydrofuran (10 mL) was added dropwise to a suspension of sodium hydride (0.155 g, 60%) in tetrahydrofuran (15 mL), stirred at room temperature for 1 hour, cooled to 0° C. again, and mixed with triamide hexamethyl phosphate (1.7 mL, 18 mmol) and then n-butyl lithium (2.5 M hexane solution, 1.4 mL, 3.5 mmol). Ten min. after that, methyl iodide (0.44 mL, 7.1 mmol) was added to the mixture followed by stirring for 30 min. The reaction was stopped by adding concentrated hydrochloric acid (30 mL) at 0° C. and the water layer was extracted twice with dichloromethane (20 mL); the organic layers were combined and dried over sodium sulfate anhydride. After concentrating the solution, the thus-obtained residue was purified by silica gel column chromatography (dichloromethane/hexane=3:2) and recrystallized from ethanol/hexane to give a pale yellow oily substance (710 mg, 84%).

Example 132

Synthesis of Compound 132

To 11.6 g (60.3 mmol) of ethyl benzoylacetate, was added 60 mL of a 1 N aqueous sodium hydroxide solution, and the mixture was stirred at room temperature for 16 hours. After removing organic substances by ether, the reaction solution was acidified by adding concentrated hydrochloric acid while cooling the solution in an ice bath to give a precipitate. The precipitate was collected by filtration, washed with cold water, and dried under reduced pressure. As a result, 6.56 g (40.0 mmol, 66.3%) of benzoylacetic acid was obtained as a pale yellow powder.

In 40 mL of tetrahydrofuran, was dissolved 6.56 g (40.0 mmol) of benzoylacetic acid, and the resulting solution was mixed with 7.13 g (44.0 mL) of carbonyldiimidazole, followed by stirring at room temperature for 2 hours. The reaction solution was acidified by adding 6 N hydrochloric acid and extracted with ethyl acetate. As a result, a large amount of insoluble crystals precipitated and were not solubilized; the crystals were concentrated under reduced pressure and the residue was recrystallized from methanol to give 3.90 g (13.3 mmol, 66.6%) of yellow crystals.

Example 133

Synthesis of Compound 133

To 10.83 g (41.4 mmol) of phenylacetylmeldrum's acid, was added 70 mL of methanol, and the mixture was stirred for two and a half hours. Under reduced pressure, the reaction solution was concentrated and the residue was distilled (0.4 mmHg, 94 to 98° C). As a result, 5.96 g (31.0 mmol, 75.6%) of methyl 3-oxo-4-phenyl butyrate was obtained.

$^1$H-NMR(300 MHz, CDCl$_3$)δ: 3.46(s, 2H), 3.71(s, 3H), 3.83(s, 2H), 7.19–7.35(m, 5H).

From 5.96 g (31.0 mmol) of methyl 3-oxo-4-phenyl butyrate, 2.73 g (8.52 mmol, 65.0%) of yellow crystals were obtained similarly to Example 132.

Example 134

Synthesis of Compound 134

From 10.5 g (72.8 mmol) of ethyl 3-oxopentanate, 2.72 g (13.8 mmol, 68.2%) of colorless crystals were obtained similarly to Example 132.

Example 135

Synthesis of Compound 135

From 10.0 g (63.2 mmol) of ethyl 3-butyryl-4-hydroxy-6-propyl-2-pyrone 3-oxohexanate, 3.86 g (17.2 mmol, 76.0%) of a pale yellow liquid was obtained by distillation (0.02 mmHg, 91 to 98° C.) similarly to Example 132.

Example 136

Synthesis of Compound 136

From 10.0 g (63.2 mmol) of methyl 6-butyl-4-hydroxy-6-pentanoyl-2-pyrone 3-oxoenanthate, 2.87 g (11.3 mmol, 64.0%) of pale yellow crystals were obtained similarly to Example 132.

Example 137

Synthesis of Compound 137

To 5.00 g (34.7 mmol) of 4-hydroxy-3-isobutyryl-6-isopropyl-2-pyrone meldrum's acid, were added 20 mL of dichloromethane and 5.6 mL of pyridine, and then, 3.67 mL (34.8 mmol) of isobutyryl chloride was added dropwise to the mixture while stirring the mixture in an ice bath. After the addition of isobutyryl chloride, the mixture was stirred for 1 hour in the ice bath, and then, stirred for further 6.5 hours at room temperature. The reaction solution was mixed with 60 mL of 2 N hydrochloric acid, extracted with dichloromethane, washed with saturated sodium chloride water, dried over sodium sulfate anhydride, filtered, and concentrated. The residue was mixed with 50 mL of methanol, heat-refluxed for 3 hours, and evaporated for removing the reaction solution. The residue was distilled (1.0 mmHg, 40 to 49° C.) to give 3.08 g (21.3 mmol, 61.4%) of methyl 4-methyl 3-oxopentanate as a colorless liquid.

From 3.08 g (21.3 mmol) of methyl 4-methyl 3-oxopentanate, 1.15 g (5.13 mmol, 58.0%) of a colorless liquid was obtained similarly to Example 133.

Example 138

Synthesis of Compound 138

From 10.0 g (69.4 mmol) of meldrum's acid and 6.25 mL (69.4 mmol) of cyclopropanecarbonyl chloride, 1.59 g (7.22 mmol, 59.8%) of colorless crystals were obtained similarly to Example 137.

Example 139

Synthesis of Compound 139

From 10.0 g (69.4 mmol) of meldrum's acid and 8.45 mL (69.4 mmol) of isovaleryl chloride, 2.06 g (8.16 mmol, 53.4%) of a colorless liquid was obtained by distillation (0.07 mmHg, 103 to 104° C.) similarly to Example 137.

Example 140

Synthesis of Compound 140

With hexane, was washed several times 2.48 g (62.0 mmol) of 60% sodium hydride and dried under reduced pressure. The resultant was mixed with 100 mL of tetrahydrofuran, and then, 8.15 mL (50.0 mmol) of tertbutyl acetoacetate was added dropwise to the mixture. The mixture was stirred at room temperature for 1 hour, and while stirring the mixture in an ice bath, 33 mL of a 15% n-butyl lithium hexane solution was added dropwise to the mixture. The mixture was stirred for 15 min. in the ice bath, and then, poured onto an excess amount of dry ice. The mixture was allowed to stand until the dry ice disappeared, and then, neutralized by adding 3 N hydrochloric acid. The resultant was extracted with ethyl acetate, dried over sodium sulfate anhydride, filtered, and concentrated. As a result, 9.71 g of an orange oily substance was obtained. The orange oily substance was mixed with 60 mL of tetrahydrofuran and then with 9.34 g (57.6 mmol) of carbonyldiimidazole. The mixture was stirred at room temperature for 17 hours. The mixture was acidified by adding 3 N hydrochloric acid, extracted with ethyl acetate, dried over sodium sulfate anhydride, filtered, and concentrated. The residue was subjected to medium-pressure chromatography to give 3.24 g of an orange oily substance. The residue was dissolved in methanol and an aqueous sodium hydrogencarbonate solution, and then, concentrated; the residue was dissolved in water and extracted with ethyl acetate. The water layer was acidified and extracted with dichloromethane, dried over sodium sulfate anhydride, filtered, and concentrated. As a result, 423 mg (1.18 mmol) of a pale yellow oily substance was obtained.

Example 141

Synthesis of Compound 141

In 100 mL of methanol, was dissolved 5.90 g (50.0 mmol) of monomethyl malonate, and the resulting solution was mixed with 2.86 g (25 mmol) of magnesium ethoxide followed by stirring at room temperature for 4 hours. The reaction solution was concentrated and the residue was dried under reduced pressure. In 100 mL of tetrahydrofuran, was dissolved 2.80 g (25 mmol) of 2-furancarboxylic acid and the resulting solution was mixed with 4.45 g (27.4 mmol) of carbonyldiimidazole, followed by stirring for 1 hour. The reaction solution was added to a dry magnesium salt and stirred at room temperature for 19 hours. The reaction solution was concentrated; the residue was mixed with 100 mL of 1.5 N hydrochloric acid, extracted with ethyl acetate, and washed with an aqueous sodium hydrogencarbonate solution and saturated sodium chloride water. The resultant was dried over sodium sulfate anhydride, filtered, and concentrated. The residue was distilled (0.06 mmHg, 69 to 75) to give 2.93 g (17.4 mmol, 69.6%) of methyl 2-furancarbonylacetate as an anhydrous liquid. Similarly to Example 133, 65 mg (1.34 mmol, 58.1%) of dark yellow crystals were obtained from 2.93 g (17.4 mmol) of methyl 2-furancarbonylacetate.

Example 142

Synthesis of Compound 142

In 200 mL of methanol, was dissolved 8.90 g (75.4 mmol) of monomethyl malonate, and the resulting solution was mixed with 4.30 g (37.5 mmol) of magnesium ethoxide, followed by stirring for 4 hours at room temperature. The reaction solution was concentrated and the residue was dried under reduced pressure. In 150 mL of tetrahydrofuran, was dissolved 4.80 g (37.5 mmol) of 2-thiophenecarboxylic acid and the resulting solution was mixed with 6.69 g (41.2 mmol) of carbonyldiimidazole, followed by stirring for 1 hour. The reaction solution was added to a dry magnesium salt and stirred at room temperature for 21 hours. The reaction solution was concentrated; the residue was mixed with 150 mL of 1.5 N hydrochloric acid, extracted with ethyl acetate, and washed with an aqueous sodium hydrogencarbonate solution and then saturated sodium chloride water. The resultant was dried over sodium sulfate anhydride, filtered, and concentrated. The residue was distilled (0.06 mmHg, 87) to give 5.95 g (32.3 mmol, 86.1%) of methyl 2-thiophenecarbonylacetate as an anhydrous liquid. Similarly to Example 133, 2.52 g (8.28 mmol, 81.2%) of yellow crystals were obtained from 5.95 g (32.2 mmol) of methyl 2-thiophenecarbonylacetate by recrystallization from methanol.

Example 143

Synthesis of Compound 143

From 10.0 g (69.4 mmol) of meldrum's acid and 9.45 mL (69.9 mmol) of cyclohexanecarbonyl chloride, 3.85 g (12.6 mmol, 63.4%) of colorless crystals were obtained by recrystallization from methanol similarly to Example 137.

Example 144

Synthesis of Compound 144

In 200 mL of methanol, was dissolved 8.91 g (75.4 mmol) of monomethyl malonate, and the resulting solution was mixed with 4.30 g (37.5 mmol) of magnesium ethoxide, and stirred for 4 hours at room temperature. The reaction solution was concentrated and the residue was dried under reduced pressure. In 120 mL of tetrahydrofuran, was dissolved 4.10 mL (37.7 mmol) of cyclopentanecarboxylic acid, and the resulting solution was mixed with 6.69 g (41.2 mmol) of carbonyldiimidazole, followed by stirring for 2.5 hours. The reaction solution was added to a dry magnesium salt and the resulting mixture was stirred at room temperature for 221 hours. The reaction solution was concentrated; the residue was mixed with 150 mL of 2 N hydrochloric acid, extracted with ethyl acetate, and washed with an aqueous sodium hydrogencarbonate solution and then saturated sodium chloride water. The resultant was dried over sodium sulfate anhydride, filtered, and concentrated. The residue was distilled (0.15 mmHg, 51 to 55° C.) to give 5.72 g (33.4 mmol, 88.8%) of methyl 2-cyclopentanecarbonylacetate as an anhydrous liquid. Similarly to Example 133, 2.32 g (8.39 mmol, 57.0%) of pale yellow crystals were obtained from 5.72 g (33.4 mmol) of methyl 2-cyclopentanecarbonylacetate.

Example 145

Synthesis of Compound 145

To 600 mg (3.63 mmol) of an oxazolopyrone derivative, was added 6 mL of 10% hydrochloric acid, followed by stirring at 90° C. for 30 min. The reaction solution was concentrated and the residue was recrystallized from methanol. Since NMR of the thus-obtained crystals had peaks due to impurities, the crystals were recrystallized from methanol again. As a result, 296 mg (1.61 mmol, 44.3%) of colorless crystals were obtained.

Example 146

Synthesis of Compound 146

While cooling in an ice bath, 37 g of concentrated sulfuric acid was added to 28 g of nitric acid, and then, 12.7 g (100 mmol) of 4-hydroxy-6-methyl-2-pyrone was slowly added to the mixture over several times. Since furious heat generation occurred during the reaction, the temperature of the reaction was controlled by using the ice bath. After the addition of the whole amount of 4-hydroxy-6-methyl-2-pyrone, the mixture was stirred at 40 to 50° C. for 1 hour, and cooled to room temperature. The reaction solution was poured into icy water; the precipitate was filtered, washed, and recrystallized from methanol. As a result, 9.69 g (56.6 mmol, 56.6%) of a 3-nitro compound was obtained as colorless crystals.

$^1$H-NMR(CD3OD)δ: 2.34(d, J=0.82, 3H), 6.25(d, J=0.82, 1H).

In 50 mL of ethanol and 35 mL of dichloromethane, was dissolved 2.09 g (12.2 mmol) of the 3-nitro compound, the resulting solution was mixed with 510 mg of 5% Pd—C (wet), followed by stirring for 7 hours in a hydrogen atmosphere. A product was generated from the reaction solution as a precipitate. The catalyst was filtered and washed with a large amount of warm ethanol, however it was not solubilized. It was solubilized by washing with water. The filtrate was concentrated and the residue was recrystallized from water. As a result, 1.16 g (8.22 mmol, 67.4%) of a 3-amino compound was obtained as brown crystals. The filtrate was concentrated and the residue was washed with methanol to recover 166 mg (1.2 mmol, 9.8%).

$^1$H-NMR(CD3OD)δ: 2.18(d, J=0.82, 3H), 5.88(d, J=0.82, 1H).

In 3 mL of tetrahydrofuran, was dissolved 128 mmol (1.00 mmol) of tenoylic acid, and the resulting solution was mixed with 178 mg (1.10 mmol) of N,N'-carbonyldiimidazole; after washing the wall with 1 mL of tetrahydrofuran, the mixture was stirred at room temperature for 1 hour, mixed with 141 mg (1.00 mmol) of the 3-amino compound, and stirred at room temperature for 3 hours. The 3-amino compound was not solubilized by tetrahydrofuran and it existed as a precipitate; the reaction product was suspended and was not solubilized. The reaction solution became homogeneous by adding 3 N hydrochloric acid. The resultant was extracted with ethyl acetate and concentrated. The residue was recrystallized from dichloromethane/methanol to give 161 mg (0.64 mmol, 64%) of colorless crystals.

Example 147

Synthesis of Compound 147

In 6 mL of tetrahydrofuran, was dissolved 224 mg (2.00 mmol) of 3-(2-furancarboamide)-4-hydroxy-6-methyl-2-pyrone, 2-furancarboxylic acid, and the resulting solution was mixed with 356 mg (2.20 mmol) of N,N'-carbonyldiimidazole; after washing the wall with 1 mL of tetrahydrofuran, the solution was stirred at room temperature for 0.5 hours, mixed with 282 mg (2.00 mmol) of the 3-amino compound, and stirred at room temperature for 6.5 hours. Similarly to Example 146, the reaction product was suspended and was not solubilized. The reaction solution was concentrated, mixed with 3 N hydrochloric acid, and extracted with dichloromethane. The resultant was dried over sodium sulfate anhydride, filtered, and concentrated. The residue was recrystallized from methanol to give 319 mg (1.35 mmol, 67.5%) of pale yellow crystals.

Example 148

Synthesis of Compound 148

In 6 mL of tetrahydrofuran, was dissolved 246 mg (2.00 mmol) of picolinic acid, and the resulting solution was mixed with 356 mg (2.20 mmol) of N,N'-carbonyldiimidazole, stirred at room temperature for 0.5 hours, mixed with 282 mg (2.00 mmol) of 3-amino-4-hydroxy-2-pyrone, mixed with 4 mL of tetrahydrofuran, and stirred at room temperature for 4 hours. The reaction solution was concentrated, mixed with 3 N hydrochloric acid, and extracted with dichloromethane. The resultant was dried over sodium sulfate anhydride, filtered, and concentrated. The residue was recrystallized from chloroform to give 295 mg (1.20 mmol, 60.0%) of pale yellow needle crystals.

Example 149

Synthesis of Compound 149

In 6 mL of tetrahydrofuran, was dissolved 513 mg (2.00 mmol) of palmitic acid, and the resulting solution was mixed with 356 mg (2.20 mmol) of carbonyldiimidazole, followed by stirring at room temperature for 1 hour. The reaction solution was mixed with 282 mg (2.00 mmol) of 3-amino-4-hydroxy-6-methyl-2-pyrone and stirred at room temperature for 5 hours. Although the reaction solution once became homogeneous, crystals precipitated again. The reaction solution was concentrated; the residue was mixed with 3 N hydrochloric acid to filter the crystals, washed with water, and recrystallized from methanol. As a result, 574 mg (1.51 mmol, 75.5%) of the target compound was obtained as colorless crystals.

Example 150

Synthesis of Compound 150

In 100 mL of toluene, were suspended 5.6 g (30 mmol) of monoethyl pimelate, 3.8 g (30 mmol) of 4-hydroxy-6-methyl-2-pyrone, 6.8 g (33 mmol) of dicyclohexanecarbodiimide, and 368 mg (3 mmol) of dimethylaminopyridine, followed by stirring at room temperature for 1 hour and at 80° C. for 2 days. The resultant was filtered to remove insoluble substances and concentrated. The residue was dissolved in ethyl acetate, washed with 3 N hydrochloric acid, dried over manganese sulfate anhydride, filtered, and concentrated. The residue was purified by silica gel column chromatography to give 6.66 g (22.5 mmol, 75%) of an ethyl ester compound as an yellow oily substance.

$^1$H-NMR(300 MHz, CDCl$_3$)δ: 1.26(t, J=7.30, 3H), 1.42 (m, 2H), 1.60–1.75(m, 4H), 2.27(d, J=0.77, 3H), 2.31(t, J=7.30, 2H), 3.08(t, J=7.30, 2H), 4.12(q, J=7.30, 2H), 5.93 (d, J=0.77, 1H), 16.80(s, 1H).

Using 306 mg (1.03 mmol) of the thus-obtained ethyl ester compound, preliminary investigation was made concerning hydrolysis. To the ester, was added 4 mL of a 1 N aqueous sodium hydroxide solution, and the resulting mixture was stirred for 3 days. The reaction solution was acidified by adding 3 N hydrochloric acid; the precipitate was filtered and washed with water. The resultant was dried by a vacuum pump and recrystallized from ethyl acetate. As a result, 177 mg (0.66 mmol, 64%) of the target carboxylic acid was obtained as pale yellow crystals.

Similarly, 6.28 g (21.2 mmol) of the ester compound was hydrolyzed to give 4.60 g (17.1 mmol, 80.7%).

Example 151

Synthesis of Compound 151

Similar to Example 150, 6.81 g (21.9 mmol, 73%) of a methyl ester compound was obtained as orange crystals from 6.08 g (0.0 mmol recrystallized from 3 methanol) of monomethyl ester of azelaic acid and 3.78 g (30.0 mmol) of 4-hydroxy-6-methyl-2-pyrone by recrystallization from methanol.

$^1$H-NMR(300 MHz, CDCl$_3$)δ: 1.28–1.44(m, 4H), 1.57–1.70(m, 4H), 2.27(d, J=0.67, 3H), 2.31(t, J=7.30, 2H), 3.07(t, J=7.30, 2H), 3.67(s, 3H), 5.93(d, J=0.67, 1H), 16.86 (s, 1H).

With 40 mL of a 1 N aqueous sodium hydroxide solution, was mixed 4.81 g (15.5 mmol) of the thus-obtained methyl ester compound and the resulting mixture was stirred for 6 hours. The reaction solution was acidified by adding 3 N hydrochloric acid, extracted with dichloromethane, dried over sodium sulfate anhydride, filtered, and concentrated. The residue was recrystallized from ethyl acetate to give 3.23 g (10.9 mmol, 70%) of the target carboxylic acid as pale yellow crystals.

Comparative Example 3

Synthesis of 6-phenyl-4-oxa-d-valerolactone

In an argon atmosphere, sodium hydride (5.2 g, 60%, 120 mmol) was washed with tetrahydrofuran, and to the resulting suspension in 200 mL of tetrahydrofuran, an ethyl acetoacetate solution (12.6 mL, 100 mmol) in 10 mL of tetrahydrofuran was added dropwise at room temperature. After the addition of the ethyl acetoacetate solution, the resulting solution was stirred at room temperature for 1 hour. The solution was cooled to 0° C. and butyl lithium (2.5 M hexane solution, 44 mL, 110 mmol) was added dropwise to the solution; after the addition of butyl lithium, the mixture was stirred for 20 min. as it was, and then, for further 10 min. at room temperature. The solution was cooled to 0° C. again, mixed with benzaldehyde (11.0 mL, 110 mmol), and stirred at room temperature for 30 min. By adding 5% hydrochloric acid and then concentrated hydrochloric acid, the resultant was acidified, mixed with sodium chloride, and extracted with ethyl acetate; the organic layer was dried over sodium sulfate anhydride. The solution was concentrated and the thus-obtained oily substance was mixed with a 1 N aqueous sodium hydroxide solution (200 mL) and methanol, followed by stirring for 4 hours at room temperature. The reaction solution was concentrated as it was and evaporated for removing methanol, acidified by adding 5% hydrochloric acid, and extracted with dichloromethane; the organic layer was dried over sodium sulfate anhydride. The solution was concentrated and the thus-obtained solid was recrystallized from hexane-ethyl acetate to give white crystals (14.9 g, 78%).

Example 152

Synthesis of Compound 152

Similarly, white crystals (44 mg, 2.3%) were obtained from 1-oxa-2,4-oxospiro[5,5]undecane (800 mg, 4.39 mmol) and 2-thiopheneacetic acid (630 mg, 4.39 mmol).

Comparative Example 4

Synthesis of 6-methyl-4-oxa-d-valerolactone

10% Pd/C (1.0 g) was added to a suspension of 4-hydroxy-6-methyl-2-pyrone (10.0 g, 7.93 mmol) in ethyl acetate (35 mL) and stirred in an hydrogen atmosphere at normal pressure for 24 hours. The precipitate was filtered and the filter paper was washed with ethyl acetate and then ethanol. The thus-obtained filtrates were concentrated under reduced pressure; the thus-obtained solid was recrystallized from hexane-ethyl acetate to give 6-methyl-4-oxa-δ-valerolactone (74%) containing a small amount of raw material.

Example 153

Synthesis of Compound 153

To a suspension of 4-hydroxy-6-methyl-2-pyrone (1.00 g, 7.93 mmol) in toluene (30 mL), were added 4-N,N-dimethylaminopyridine (130 mg, 1.06 mmol), benzoic acid (970 mg, 7.94 mmol), and then, dicyclohexylcarbodiimide (2.0 g, 9.7 mmol) at room temperature. The mixture was stirred as it was for 10 min. and heated to 80° C. for 17 hours. After cooling the mixture to room temperature, the thus-produced insoluble dicyclohexyl urea was removed by filtration, the reaction solution was washed with 5% hydrochloric acid (30 mL), the water layer was extracted twice with dichloromethane (20 mL), and the organic layers were combined and dried over sodium sulfate anhydride. After concentrating the solution, the thus-obtained residue was purified by silica gel column chromatography (dichloromethane) to give a yellow solid (847.1 mg, 46%). Furthermore, the solid was recrystallized from ethanol to give yellow crystals.

Example 154

Synthesis of Compound 154

From 4-hydroxy-6-methyl-2-pyrone (1.50 g, 11.9 mmol) and 3-cyclohexenecarboxylic acid (1.40 mL, 12.0 mmol), a yellow solid (2.40 g, 86%) was obtained similarly to Example 153. Furthermore, the solid was recrystallized from ethanol to give yellow crystals.

Example 155

Synthesis of Compound 155

From 4-hydroxy-6-methyl-2-pyrone (1.50 g, 11.9 mmol) and cyclohexylacetic acid (1.70 g, 12.0 mmol), a yellow solid (1.80 g, 60%) was obtained similarly to Example 153. Furthermore, the solid was recrystallized from ethanol to give white crystals.

Example 156

Synthesis of Compound 156

Compound 104 (1.00 g, 3.46 mmol) was mixed with tetrahydrofuran (50 mL), methanol (15 mL), concentrated hydrochloric acid (5 mL), and then, Pd—C (5%, containing 100% water, 200 mg), followed by hydrogen replacement. Three hours later, the raw material disappeared, and hydrogen was replaced with argon. The precipitate was filtered, washed with hot methanol, and the filtrate was concentrated. The thus-obtained solid was recrystallized from ethanol/methanol to give a hydrochloride (760 mg, 74%) of the target compound.

Example 157

Synthesis of Compound 157

In 25 mL of chloroform, were added 3.36 g (20.0 mmol) of dehydroacetic acid and 5.68 g (20.0 mmol) of 3,5-di-tert-butyl-4-hydroxy-benzaldehyde, and the resulting solution was mixed with 0.2 mL of piperidine and heated while being

Example 158

Synthesis of Compound 158 dehydrated by using a Dean-Stark dehydrating tube; since dehydration could not proceed efficiently, the solution was evaporated for removing chloroform and mixed with 25 mL of benzene for 4-hour azeotropic dehydration. The reaction solution was cooled, concentrated, and the residue was recrystallized from methanol to give 3.93 g (10.2 mmol, 51%) of the target compound as yellow crystals.

Example 158

Synthesis of Compound 158

From 1.68 g (10.0 mmol) of dehydroacetic acid and 1.33 mL (10.0 mmol) of 4-methylthiobenzaldehyde, 1.41 g (4.66 mmol, 46.6%) of the target compound was obtained as orange crystals by recrystallization from ethyl acetate similar to Example 157.

Example 159

Synthesis of Compound 159

Compound 157 (1.03 g, 2.68 mmol) was dissolved in 50 mL of ethyl acetate, mixed with 210 mg of 5% Pd—C (wet), and stirred in a hydrogen atmosphere for 1 hour. After removing the catalyst by filtration, the filtrate was concentrated and the residue was recrystallized from methanol. As a result, 835 mg (2.16 mmol, 80.6%) of a hydrogenated compound was obtained as pale yellow crystals.

Example 160

Synthesis of Compound 160

With 240 mL of methanol and 50 mL of a 1 N aqueous sodium hydroxide solution, was mixed 2.36 g (5.76 mmol) of acetoxymethyl-3-palmitoyltetrdnic acid, and the mixture was stirred for 5 hours at room temperature. The reaction solution was concentrated; the residue was mixed with water and acidified by adding 3 N hydrochloric acid. The resultant was extracted with dichloromethane, dried over sodium sulfate anhydride, filtered, and concentrated. The residue was recrystallized from methanol to give 2.03 g (5.50 mmol, 95.4%) of yellow crystals.

Example 161

Synthesis of Compound 161

Methanol (30 mL) and distilled water (20 mL) were added to a mixture of Compound 52 (500 mg, 2.21 mmol) and calcium carbonate (760 mg, 5.5 mmol), and stirred for 15 hours at room temperature. After removing the stirrer, the mixture was concentrated as it was and evaporated to remove methanol. The resultant was acidified by adding 5% hydrochloric acid, extracted three times with dichloromethane (30 mL), and the organic layers were dried over sodium sulfate anhydride. The resultant was concentrated and the thus-obtained residue was recrystallized from ethanol to give white crystals (338 mg, 83%).

Example 162

Synthesis of Compound 162

In 20 mL of benzene, was suspended 5.00 g (44.6 mmol) of 1,3-cyclohexanedione, and the suspension was mixed with 4.4 mL (45 mmol) of malonyl chloride, followed by heat-refluxing for 2 hours. The reaction solution was mixed with methanol to solubilize insoluble substances, mixed with silica gel, evaporated for remove the solvent, and subjected to silica gel column chromatography using ethyl acetate. The thus-obtained crude product was dissolved in methanol again, mixed with silica gel, evaporated for remove the solvent, and purified by silica gel column chromatography using ethyl acetate:hexane=1:1. The thus-obtained crystals were washed with ether and filtered. As a result, 1.57 g (8.72 mmol, 19.6%) of yellow crystals were obtained.

Example 163

Synthesis of Compound 163

To a 100 mL, egg-plant type flask, was added 1.56 g of acetylmethyltetronic acid weighed by a balance, and mixed with 30 mL of ethanol. In 30 mL ethanol, was dissolved 0.57 g of diethoxy magnesium, and the solution was added to the flask containing acetylmethyltetronic acid. The mixture was stirred at room temperature and a solid precipitated. The mixture was filtered and dried to give 2.01 g of the target compound.

Example 164

Synthesis of Compound 164

To a 200 mL, egg-plant type flask, was added 1.56 g of acetylmethyltetronic acid weighed by a balance, and mixed with 30 mL of ethanol. In 120 mL methanol, was suspended 0.88 g of calcium diacetate, and the suspension was added to the flask containing acetylmethyltetronic acid. The mixture was solubilized by stirring at room temperature. The solution was concentrated and dried. The resultant was washed with ethyl acetate and dried to give 1.496 g of the target compound.

Example 165

Synthesis of Compound 165

Compound 51 (0.50 g, 2.00 mmol) was arranged to be a sodium salt by adding mixed sodium hydrogencarbonate, and then, an aqueous solution of the sodium salt was allowed to stand at room temperature in an oxygen atmosphere for 10 days. The solution was mixed with 1 N hydrochloric acid, extracted with dichloromethane, dried over sodium sulfate anhydride, and recrystallized from ethanol/hexane to give pale brown crystals (416 mg, 79%).

Example 166

Synthesis of Compound 166

Dimethylsulfoxide (5 mL) was added to a mixture of Compound 118 (1.00 g, 3.42 mmol) and N-bromosuccinimide (0.61 g, 3.4 mmol) in argon at room temperature and stirred for 20 hours. The reaction solution was mixed with distilled water and the thus-produced precipitate was recrystallized from ethanol to give pale yellow crystals (850 mg, 81%).

Example 167

Synthesis of Compound 167

Similarly to Example 166, pale yellow crystals (734 mg, 88) were obtained from 3-thiophenylacetyl-4-hydroxy-coumarin (800 mg, 2.79 mmol).

Example 168

Synthesis of Compound 168

Similarly to Example 166, pale yellow crystals (240 mg, 23%) were obtained from 3-(2-methoxyphenylacetyl)-4-hydroxy-6-methyl-pyrone (1.00 g, 3.65 mmol).

Example 169

Synthesis of Compound 169

Similarly to Example 166, pale yellow crystals (510 mg, 49%) were obtained from Compound 105 (1.00 g, 3.65 mmol).

Example 170

Synthesis of Compound 170

While cooling in ice, m-chloroperbenzoic acid (300 mg, >purity 80% >1.38 mmol) was added to a solution of Compound 55 (300 mg, 1.31 mmol) in dichloromethane (15 mL) and stirred for 2 hours. The reaction solution was subjected to silica gel chromatography as it was; fractions of dichloromethane/methanol (10:1) were collected and recrystallized from ethanol to give white crystals (338 mg, 83%).

Example 171

Synthesis of Compound 171

While cooling in ice, m-chloroperbenzoic acid (370 mg, >purity 80% >1.71 mmol) was added to a solution of Compound 90 (350 mg, 1.63 mmol) in dichloromethane (15 mL) and stirred for 3 hours. The reaction solution was subjected to silica gel chromatography as it was; fractions of dichloromethane/methanol (10:1) were collected and recrystallized from ethanol.to give white crystals (339 mg, 90%).

Comparative Example 5

Synthesis of 4-hydroxy-3-(1-oxopropionyl)-2(5H) furanone (Compound 172)

5-(1-oxopropionyl)-2,2-dimethyl-1,3-dioxane-4,6-dione (12.15 g) and ethyl glycolate (8.25 g) were added to 25 mL of toluene and stirred at 80° C. for 4 hours. After the completion of the reaction, toluene was removed by evaporation and the residue was purified by silica gel column chromatography (hexane:ethyl acetate=3:1) to give 9.91 g of an acetoacetic acid derivative. The thus-obtained acetoacetic acid derivative was dissolved in 31 mL of t-buthanol, mixed with 5.33 g of potassium t-buthoxide, and heat-refluxed for 4 hours. After the completion of the reaction, the reaction mixture was cooled by ice and the thus-produced precipitate was filtered. The resultant was mixed with 36.8 mmol of 1 N hydrochloric acid ethanol and tetrahydrofuran, stirred for 1 hour, and evaporated under reduced pressure for removing the solvent. The residue was distilled under reduced pressure and recrystallized from ethanol-hexane to give 3.32 g of 3-propionyltetronic acid.

Example 172

Synthesis of Compound 173

5-(1-oxobutyryl)-2,2-dimethyl-1,3-dioxane-4,6-dione (12.58 g) and ethyl glycolate (8.01 g) were added to 20 mL of toluene, and 9.91 g of an acetoacetic acid derivative was obtained similarly to Comparative Example 5. The thus-obtained acetoacetic acid derivative was dissolved in 28 mL of t-buthanol, mixed with 5.33 g of potassium t-buthoxide, and heat-refluxed for 4 hours. After the completion of the reaction, the reaction mixture was cooled by ice and the thus-produced precipitate was filtered. The resultant was mixed with 36.8 mmol of 1 N hydrochloric acid ethanol and tetrahydrofuran, stirred for 1 hour, and evaporated under reduced pressure for removing the solvent. The residue was distilled under reduced pressure and recrystallized from ethanol-hexane to give 2.88 g of 3-butyryltetronic acid.

Example 173

Synthesis of Compound 174

5-(1-oxo-2-methylpropionyl)-2,2-dimethyl-1,3-dioxane-4,6-dione (8.60 g) and ethyl glycolate (12 mL) were added to 40 mL of toluene and 7.71 g of an acetoacetic acid derivative was obtained similarly to Comparative Example 5. The thus-obtained acetoacetic acid derivative was dissolved in 20 mL of t-buthanol and 2.55 g of 3-isobutyryltetronic acid was obtained similarly to Comparative Example 1.

Example 174

Synthesis of Compound 175

5-(1-oxocyclopropionyl)-2,2-dimethyl-1,3-dioxane-4,6-dion (17.04 g) and ethyl glycolate (10.88 g) were added to 40 mL of toluene and 16.81 g of an acetoacetic acid derivative was obtained similarly to Comparative Example 5. The thus-obtained acetoacetic acid derivative was dissolved in 20 mL of t-buthanol and 2.32 g of 3-cyclopropylcarbonyltetronic acid was obtained similarly to Comparative Example 1.

Example 175

Synthesis of Compound 176

Compound 43 (1.0 g) was dissolved in 100 mL of methanol, mixed with 200 mg of 5% Pd carbon, and stirred in a hydrogen atmosphere for 2 hours. After removing Pd carbon, methanol was removed by evaporation, and the residue was purified by silica gel column chromatography to give 800 mg of the target compound. The compound was arranged to be a sodium salt by adding an equivalent amount of sodium hydrogencarbonate and lyophilized.

Examples 176 to 179

Synthesis of Compounds 177 to 180

By known methods, the above compounds were synthesized.

Example 180

Similarly to Example 42, Compound 181 was obtained from tetronic acid and 4-heptaenolic acid.

Example 181

Synthesis of Compound 182

Similarly to Example 42, Compound 182 was obtained from 5-carbomethoxymethyltetronic acid and phenacylacetic acid.

Example 182

Synthesis of Compound 183

Similarly to Example 42, Compound 183 was obtained from tetronic acid and 4-cyclohexenecarboxylic acid.

Example 183

Synthesis of Compound 184

Similarly to Example 42, Compound 184 was obtained from tetronic acid and methoxyacetic acid 2-thipheneacetic acid.

Example 184

Synthesis of Compound 185

Similarly to Example 49, crystals (1.56 g, 60%) were obtained from 4-hydroxy-6-methyl-2-pyrone (1.26 g, 10.0 mmol) and phenoxyacetic acid (1.52 g, 10.0 mmol).

Example 185

Synthesis of Compound 186

Similarly to Example 49, crystals (1.09 g, 55%) were obtained from 4-hydroxy-6-methyl-2-pyrone (1.26 g, 10.0 mmol) and 2-methoxyphenylacetic acid (0.9 g, 10 mmol).

Example 186

Synthesis of Compound 187

Similarly to Example 49, crystals (1.86 g, 54%) were obtained from 4-hydroxy-coumarin (1.62 g, 10.0 mmol) and 2-thiopheneacetic acid (1.42 g, 10 mmol).

Example 187

Synthesis of Compound 188

Similarly to Example 49, crystals (1.12 g, 48%) were obtained from 4-hydroxy-coumarin (1.62 g, 10.0 mmol) and methoxyacetic acid (0.9 g, 10 mmol).

Example 188

Synthesis of Compound 189

Similarly to Example 49, crystals (1.16 g, 49%) were obtained from 4-hydroxy-6-methyl-2-pyrone (1.26 g, 10.0 mmol) and tetrazoleacetic acid (1.28 g, 10 mmol).

Example 189

Synthesis of Compound 190

Similarly to Example 49, crystals (1.55 g, 60%) were obtained from 4-hydroxy-6-methyl-2-pyrone (1.26 g, 10.0 mmol) and p-trylacetic acid (1.50 g, 10 mmol).

Example 190

Synthesis of Compound 191

Similarly to Example 49, crystals (1.62 g, 52%) were obtained from 4-hydroxy-6-methyl-2-pyrone (1.26 g, 10.0 mmol) and 2-trifluorophenylacetic acid (2.04 g, 10 mmol).

Example 191

Synthesis of Compound 192

Similarly to Example 49, crystals (2.53 g, 91%) were obtained from 4-hydroxy-6-methyl-2-pyrone (1.26 g, 10.0 mmol) and methyl chloroformate (0.945 g, 10 mmol).

Example 192

Synthesis of Compound 195

Similarly to Example 49, white crystals (1.82 g, 68%) were obtained from 2,4-dioxo-6-methyl-6-lactone (1.44 g, 10 mmol) and 2-thiopheneacetic acid (1.42 g, 10 mmol).

Example 193

Synthesis of Compound 196

From 1.68 g (10.0 mmol) of dehydroacetic acid and 2-thiophenecarboaldehyde (1.46 g, 10.0 mmol), 1.39 g (47%) of the target compound was obtained as orange crystals by recrystallization from ethyl acetate similarly to Example 157.

Example 194

Synthesis of Compound 197

From 1.68 g (10.0 mmol) of dehydroacetic acid and 3-hydroxybenzaldehyde (1.22 g, 10.0 mmol), 1.55 g (57%) of the target compound was obtained as orange crystals by recrystallization from ethyl acetate similarly to Example 157.

Example 195

Synthesis of Compound 198

From 1.68 g (10.0 mmol) of dehydroacetic acid and 2-furalaldehyde (0.96 g, 10.0 mmol), 1.48 g (60%) of the target compound was obtained as orange crystals by recrystallization from ethyl acetate similarly to Example 157.

Example 196

Synthesis of Compound 199

From 1.68 g (10.0 mmol) of dehydroacetic acid and 2-thiazolecarboaldehyde (1.13 g, 10.0 mmol), 1.21 g (46%) of the target compound was obtained as orange crystals by recrystallization from ethyl acetate similarly to Example 157.

Example 197

Synthesis of Compound 200

From 1.82 g (10.0 mmol) of 3-propylyl-4-hydroxy-6-methylpyrone and 2-thiophenecarboaldehyde (1.46 g, 10.0 mmol), 1.40 g (45%) of the target compound was obtained as orange crystals by recrystallization from ethyl acetate similarly to Example 157.

Example 198

Synthesis of Compound 201

From 1.68 g (10.0 mmol) of dehydroacetic acid and 3,4-dihydrobenzaldehyde (1.38 g, 10.0 mmol), 1.07 g (37%) of the target compound was obtained as orange crystals by recrystallization from ethyl acetate similarly to Example 157.

Example 199

Synthesis of Compound 202

Compound 201 (0.576 g, 2 mmol) was dissolved in 30 mL of ethyl acetate, mixed with 210 mg of 5% Pd—C (wet), and stirred for 1 hour in a hydrogen atmosphere. After removing the catalyst by filtration, the filtrate was concentrated and the residue was recrystallized from methanol. As a result, 522 mg (90%) was obtained.

Example 200

Synthesis of Compound 203

From 1.68 g (10.0 mmol) of dehydroacetic acid and 2-nitrobenzaldehyde (1.51 g, 10.0 mmol), 2.35 g (78%) of the target compound was obtained as orange crystals by recrystallization from ethyl acetate similarly to Example 157.

Example 201

Synthesis of Compound 204

Compound 203 was dissolved in ethyl acetate, mixed with palladium carbon, mixed with several drops of concentrated hydrochloric acid, and stirred for 1 hour in a hydrogen atmosphere. After removing the catalyst by filtration, the filtrate was concentrated and the residue was recrystallized from methanol.

Example 202

Synthesis of Compound 205

Benzphenonesilyl ether was dissolved in ether and cooled to −78° C. Malonyl dichloride was added dropwise to the resulting solution and stirred as it was for 5 hours. The thus-produced precipitate was filtered and purified by column chromatography to give Compound 205.

Example 203

Synthesis of Compound 206

Dehydroacetic acid was dissolved in tetrahydrofuran and mixed with potassium carbonate. At room temperature, the mixture was mixed with methyl iodide and stirred as it was. The resultant was extracted with ethyl acetate and purified by column chromatography to give the target compound.

Example 204

Synthesis of Compound 207

Malonyl dichloride was added dropwise to a solution of acetobenzophenone in ether and stirred at room temperature. The solution was concentrated and purified by column chromatography to give Compound 207.

Example 205

Synthesis of Compound 208

Similarly to Example 49, white crystals (800 mg, 50%) were obtained from 4-hydroxy-6-methyl-2-pyrone (1.26 g, 10.0 mmol) and ethyl chloroformate (750 mg, 10.0 mmol).

Example 206

Synthesis of Compound 209

Similarly to Example 49, white crystals (800 mg, 48%) were obtained from 4-hydroxy-6-methyl-2-pyrone (1.26 g, 10.0 mmol) and methyl chloroformate (765 mg, 10.0 mmol).

Example 207

Synthesis of Compound 210

3-ethoxycarbonyl-4-hydroxy-6-methyl-pyridone and aniline were stirred in toluene for 5 hours. The solution was concentrated and the residue was purified by column chromatography to give Compound 210.

Example 208

Synthesis of Compound 211

Similarly to Example 42, Compound 211 was obtained from tetronic acid and dehydrocinnamic acid.

Example 209

Synthesis of Compound 212

Similarly to Example 42, Compound 212 was obtained from 5,5-dimethyltetronic acid and acetic acid.

Example 210

Synthesis of Compound 214

Compound 212 was dissolved in ethyl acetate and stirred for 1 hour in a hydrogen atmosphere. The solution was treated similarly to Example 201 to give Compound 214.

Example 211

Synthesis of Compound 216

Similarly to Example 49, white crystals (1.18 g, 48%) were obtained from 4-hydroxy-6-methyl-2-pyrone (1.26 g, 10.0 mmol) and N-methyl pyrroleacetic acid (1.37 g, 10.0 mmol).

Example 212

Synthesis of Compound 217

Similarly to Example 49, white crystals (1.48 g, 54%) were obtained from 4-hydroxy-6-methyl-2-pyrone (1.26 g, 10.0 mmol) and α-methoxyphenylacetic acid (1.66 g, 10.0 mmol).

Example 213

Synthesis of Compound 218

Similarly to Example 49, white crystals (1.97 g, 54%) were obtained from 4-hydroxy-6-methyl-2-pyrone (1.26 g, 10.0 mmol) and palmitic acid (2.56 g, 10.0 mmol).

Example 214

Synthesis of Compound 219

Similarly to Example 42, Compound 219 was obtained from 5-methyltetronic acid and acetic acid.

Example 215

Synthesis of Compound 220

Similarly to Example 42, Compound 220 was obtained from coumarin and methoxyhydrogen glutamate.

Example 216

Synthesis of Compound 221

Similarly to Example 49, white crystals (1.21 g, 49%) were obtained from 4-hydroxy-6-methyl-2-pyrone (1.26 g, 10.0 mmol) and 2-pyridineacetic acid (1.37 g, 10.0 mmol).

Example 217

Synthesis of Compound 222

Similarly to Example 49, Compound 222 was obtained from tetronic acid and acetic acid.

Example 218

Synthesis of Compound 224

Similarly to Example 49, Compound 224 was obtained from 5-carbomethoxytetronic acid and acetic acid.

Example 219

Synthesis of Compound 225

Similarly to Example 49, Compound 225 was obtained from 5-phenyltetronic acid and acetic acid.

Example 220

Synthesis of Compound 227

Similarly to Example 49, Compound 227 was obtained from 5-butyltetronic acid and acetic acid.

Example 221

Synthesis of Compound 228

Similarly to Example 49, Compound 228 was obtained from tetronic acid and dodecanoic acid.

Example 222

Synthesis of Compound 229

Similarly to Example 49, white crystals (1.29 g, 50.0%) were obtained from 4-hydroxy-6-methyl-2-pyrone (1.26 g, 10.0 mmol) and dehydrocinnamic acid (1.50 g, 10.0 mmol).

Example 223

Synthesis of Compound 230

Similarly to Example 49, Compound 230 was obtained from tetronic acid and heptanoic acid.

Example 224

Synthesis of Compound 231

Similarly to Example 49, white crystals (2.25 g, 68%) were obtained from 4-hydroxy-6-methyl-2-pyrone (1.26 g, 10.0 mmol) and 3-nitrophenylacetic acid (1.81 g, 10.0 mmol).

Example 225

Synthesis of Compound 232

Compound 231 (1.00 g, 3.3 mmol) was dissolved in ethyl acetate and mixed with 100 mg of Pd/C. Several drops of concentrated hydrochloric acid was added to the mixture and the resultant was allowed to react for 5 hours in a hydrogen atmosphere. After removing the active carbon by filtration, the filtrate was concentrated to give 960 mg of the target compound.

Example 226

Synthesis of Compound 233

Similarly to Example 49, white crystals (1.52 g, 58%) were obtained from 4-hydroxy-6-methyl-2-pyrone (1.26 g, 10.0 mmol) and 3-fluorophenylacetic acid (1.54 g, 10.0 mmol).

Example 227

Synthesis of Compound 235

Compound 232 (1.00 g) was dissolved in 10 mL of methylene chloride. The resulting solution was mixed with 1 mL of triethylamine and then with 920 mg of trifluoromethanesulfonate anhydride, and stirred as it was for 5 hours. The reaction solution was mixed with water and extracted with methylene chloride; the organic layer was washed three times with water and then with saturated sodium chloride water, and dried over sodium sulfate anhydride.

After removing the desiccating agent by filtration, the solution was concentrated and the residue was recrystallized from ethanol to give 1.00 g of the target compound.

Example 228

Synthesis of Compound 236

Similarly to Example 49, white crystals (1.44 g, 48%) were obtained from 4-hydroxy-6-methyl-2-pyrone (1.26 g, 10.0 mmol) and 3-thianaphthalenylacetic acid (1.92 g, 10.0 mmol).

Example 229

Synthesis of Compound 237

From 1.68 g (10.0 mmol) of dehydroacetic acid and 1-trifluorobenzaldehyde (1.74 g, 10.0 mmol), 2.52 g (78%) of the target compound was obtained as orange crystals by recrystallization from ethyl acetate similarly to Example 157.

Example 230

Synthesis of Compound 238

From 1.68 g (10.0 mmol) of dehydroacetic acid and 2-trifluorobenzaldehyde (1.74 g, 10.0 mmol), 2.43 g (75%) of the target compound was obtained as orange crystals by recrystallization from ethyl acetate similarly to Example 157.

Example 231

Synthesis of Compound 239

From 1.68 g (10.0 mmol) of dehydroacetic acid and 3-trifluorobenzaldehyde (1.74 g, 10.0 mmol), 2.46 g (76%) of the target compound was obtained as orange crystals by recrystallization from ethyl acetate similarly to Example 157.

Structural formulae and spectral data of the above test compounds are shown below.

| | | |
|---|---|---|
| Compound 1 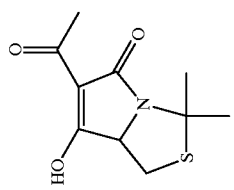 | NMR (ppm) (300 MHz, CDCl$_3$)<br>1.72(s, 3H), 1.98(s, 3H), 2.34(s, 3H), 2.88(dd, J = 10.43, 10.71, 1H), 3.16(dd, J = 6.04, 7.69, 1H), 4.41(dd, J = 6.04, 7.14, 1H)<br><br>IR(cm$^{-1}$) (KBr)<br>1715, 1638, 1597, 1431, 1408, 1386, 1241, 1214, 1203, 1098, 878<br><br>Mass (EI) 227(M$^+$) | mp. 66.5–73.5° C.<br>Molecular formula C$_{10}$H$_{13}$NO$_3$S<br>Calcd. C, 52.85; H, 5.77; N, 6.16; S, 14.11<br>Found |
| Compound 2 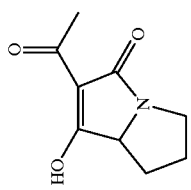 | NMR (ppm) (300 MHz, CDCl$_3$)<br>1.52(m, 1H), 2.04–2.23(m, 3H), 2.44(s, 3H), 3.27(m, 1H), 3.74(m, 1H), 3.97(dd, J = 6.87, 7.00, 1H)<br><br>IR(cm$^{-1}$) (neat)<br>3476, 1715, 1649, 1626, 1437, 1375, 1338, 1247, 946, 739<br><br>Mass (EI) 181(M$^+$) | mp.<br>Molecular formula C$_9$H$_{11}$NO$_3$<br>Calcd.<br>Found |
| Compound 3 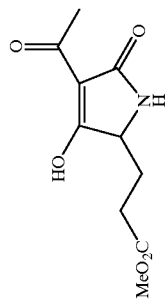 | NMR (ppm) (300 MHz, CDCl$_3$)<br>1.99(m, 1H), 2.18(m, 1H), 2.28–2.49(m, 2H), 2.46(s, 3H), 3.70(s, 3H), 3.88(dd, J = 4.94, 6.59, 1H), 6.36(br, 1H)<br><br>IR(cm$^{-1}$) (KBr)<br>1738, 1721, 1673, 1611, 1452, 1243, 1166, 1085<br><br>Mass (EI) 227(M$^+$) | mp. 69–76° C.<br>Molecular formula C$_{10}$H$_{13}$NO$_5$<br>Calcd. C, 52.86; H, 5.77; N, 6.16<br>Found |

-continued

| | | |
|---|---|---|
| Compound 4 | 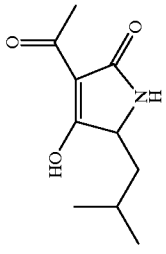 | NMR (ppm) (300 MHz, CDCl₃) 0.96(d, J = 3.30, 3H), 0.98(d, J = 2.75, 3H), 1.43(m, 1H), 1.74(m, 2H), 2.46(s, 3H), 3.85(m, 1H), 6.02(br, 1H)<br><br>IR(cm⁻¹) (KBr) 1715, 1692, 1665, 1628, 1280<br><br>Mass (EI) 197(M⁺) | mp. 138–138.5° C.<br>Elemental analysis<br>Molecular formula C₁₀H₁₅NO₃<br>Calcd. C, 60.90; H, 7.67; N, 7.10<br>Found C, 60.82; H, 7.48; N, 7.15 |
| Compound 5 | 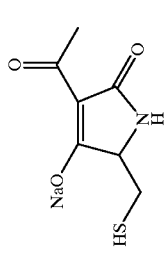 | NMR (ppm) (300 MHz, CD₃OD) 2.35(s, 3H), 2.70(m, 1H), 3.07(m, 1H), 3.79(m, 1H)<br><br>IR(cm⁻¹) (KBr) 1673, 1613, 1468<br><br>Mass | mp.<br><br>Molecular formula C₇H₈NNaO₃S<br>Calcd. C, 40.19; H, 3.85; N, 6.70; S, 15.33<br>Found |
| Compound 6 | 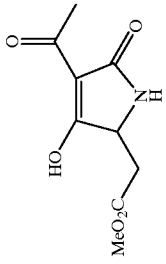 | NMR (ppm) (300 MHz, CDCl₃) 2.48(dd, J = 8.24, 28.29, 1H), 2.47(s, 3H), 3.03(dd, J = 3.02, 17.58, 1H), 3.75(s, 3H), 4.14(m, 1H), 6.38(br, 1H)<br><br>IR(cm⁻¹) (KBr) 1742, 1713, 1665, 1626, 1226<br><br>Mass (EI) 213(M⁺) | mp. 108–111° C.<br>Elemental analysis<br>Molecular formula C₉H₁₁NO₅<br>Calcd. C, 50.71; H, 5.20; N, 6.57<br>Found C, 50.66; H, 5.24; N, 6.65 |
| Compound 7 | 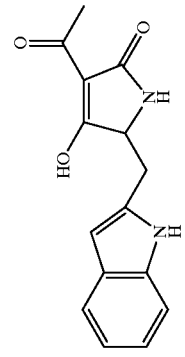 | NMR (ppm) (300 MHz, CDCl₃) 2.48(s, 3H), 2.83(dd, J = 10.44, 14.55, 1H), 3.46(dd, J = 3.57, 14.83, 1H), 4.12(m, 1H), 5.80(br, 1H), 7.06–7.24(m, 3H), 7.39(d, J = 7.96, 1H), 7.62(d, J = 7.69, 1H), 8.11(br, 1H)<br><br>IR(cm⁻¹) (KBr) 3300, 1707, 1655, 1618, 748<br><br>Mass (EI) 270(M⁺) | mp. 175–176° C.<br>Elemental analysis<br>Molecular formula C₁₅H₁₄N₂O₃<br>Calcd. C, 66.66; H, 5.22; N, 10.36<br>Found C, 66.19; H, 5.33; N, 10.19 |

-continued

| Compound 8 | 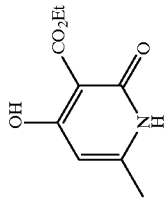 | NMR (ppm) (300 MHz, CD$_3$OD) 1.41(t, J = 7.14, 3H), 2.28(d, J = 0.82, 3H), 4.43(q, J = 7.14, 2H), 5.95(d, J = 0.82, 1H)<br><br>IR(cm$^{-1}$) (KBr) 1680, 1644, 1499, 1282, 1238<br><br>Mass (EI) 197(M$^+$) | mp. 193–198° C.<br>Elemental analysis<br>Molecular formula C$_9$H$_{11}$NO$_4$<br>Calcd. C, 54.82; H, 5.62; N, 7.10<br>Found C, 54.36; H, 5.58; n, 7.08 |
|---|---|---|---|
| Compound 9 | 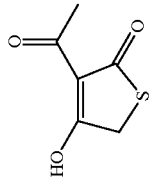 | NMR (ppm) (300 MHz, CD$_3$OD) 2.56(s, 0.50H), 2.58(s, 2.50H), 3.78(s, 0.33H), 3.99(s, 1.67H)<br><br>IR(cm$^{-1}$) (KBr) 1692, 1678, 1615, 1657, 1651, 1628, 1593, 1437, 1392, 1359, 1305<br><br>Mass (EI) 158(M$^+$) | mp. 89–91° C.<br>Elemental analysis<br>Molecular formula C$_6$H$_6$O$_3$S<br>Calcd. C, 45.56; H, 3.82; S, 20.27<br>Found C, 45.56; H, 3.93; S, 19.74 |
| Compound 10 | 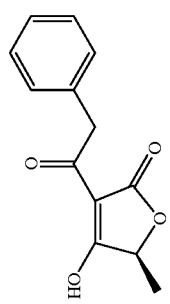 | NMR (ppm) (300 MHz, CDCl$_3$) 1.53(d, J = 6.87, 3H), 4.21 (s, 2H), 4.80(q, J = 6.87, 1H), 7.26–7.39(m, 5H)<br><br>IR(cm$^{-1}$) (KBr) 1752, 1665, 1609, 1464, 1249, 1091, 1021, 714<br><br>Mass (EI) 232(M$^+$) | mp. 102–104° C.<br>Elemental analysis<br>Molecular formula C$_{13}$H$_{12}$O$_4$<br>Calcd. C, 67.23; H, 5.21<br>Found C, 67.10; H, 5.35 |
| Compound 11 | 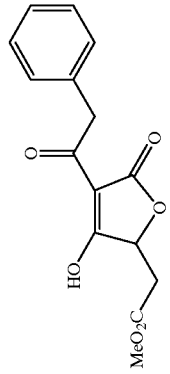 | NMR (ppm) (300 MHz, CD$_3$OD) 2.94(dd, J = 6.04, 17.30, 1H), 3.09(dd, J = 4.39, 17.30, 1H), 3.69(s, 3H), 3.72(m, 0.5H), 4.24(m, 0.5H), 5.09(m, 1H), 7.25–7.40(m, 5H)<br><br>IR(cm$^{-1}$) (KBr) 1760, 1734, 1661, 1618, 1448, 1390, 1249, 1238, 1178, 1023, 719<br><br>Mass (EI) 290(M$^+$) | mp. 115–116° C.<br>Elemental analysis<br>Molecular formula C$_{15}$H$_{14}$O$_6$<br>Calcd. C, 62.07; H, 4.86<br>Found C, 61.82; H, 4.84 |

-continued

Compound 12

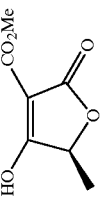

NMR (ppm) (300 MHz, CDCl$_3$)
1.57(d, J = 6.86, 3H), 3.95(s, 3H), 4.98(q, J = 6.86, 1H)

IR(cm$^{-1}$) (KBr)
1725, 1705, 1632, 1464, 1441, 1412, 1328, 1077

Mass (EI) 172(M$^+$)

mp. 130–133° C.
Elemental analysis
Molecular formula C$_7$H$_8$O$_5$
Calcd. C, 48.84; H, 4.68
Found C, 46.64; H, 4.39

Compound 13

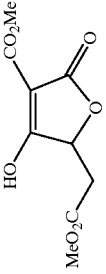

NMR (ppm) (300 MHz, CDCl$_3$)
2.78(dd, J = 7.41, 16.47, 1H), 3.00(dd, J = 4.39, 16.74, 1H), 3.75(s, 3H), 3.96(s, 3H), 5.30(dd, J = 4.39, 7.69, 1H)

IR(cm$^{-1}$) (KBr)
1769, 1734, 1620, 1477, 1255, 1201, 1176, 1064, 801

Mass (EI) 230(M$^+$)

mp. 122–126° C.
Elemental analysis
Molecular formula C$_9$H$_{10}$O$_7$
Calcd. C, 46.96; H, 4.38
Found C, 46.64; H, 4.39

Compound 14

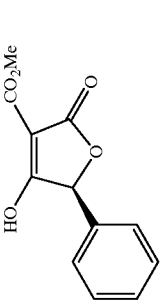

NMR (ppm) (300 MHz, CDCl$_3$)
3.98(s, 3H), 5.85(s, 1H), 7.35–7.45(m, 5H)

IR(cm$^{-1}$) (KBr)
1760, 1717, 1615, 1473, 1458, 1251, 1189, 1172, 1062, 1009, 702

Mass (EI) 234(M$^+$)

mp. 152–155° C.
Elemental analysis
Molecular formula C$_{12}$H$_{10}$O$_5$
Calcd. C, 61.54; H, 4.30
Found C, 61.40; H, 4.32

Compound 15

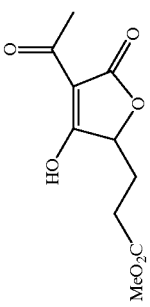

NMR (ppm) (300 MHz, CDCl$_3$)
2.02(m, 1H), 2.34(m, 1H), 2.53(m, 3H), 2.56(s, 3H), 3.69(s, 1.17H), 3.70(s, 1.83H), 4.71(dd, J = 4.39, 8.24, 0.39H), 4.85(dd, J = 4.39, 8.24, 0.61H)

IR(cm$^{-1}$) (KBr)
1765, 1738, 1667, 1622, 1346, 1168, 1023

Mass (EI) 228(M$^+$)

mp. 76–78° C.
Elemental analysis
Molecular formula C$_{10}$H$_{12}$O$_6$
Calcd. C, 52.63; H, 5.30
Found C, 52.50; H, 5.32

-continued

Compound 16

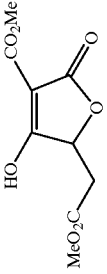

NMR (ppm) (300 MHz, CD$_3$OD) 2.75(dd, J = 7.41, 16.75, 1H), 3.05(dd, J = 3.84, 16.75, 1H), 3.85(s, 3H), 5.24(dd, J = 3.84, 7.41, 1H)

IR(cm$^{-1}$) (KBr) 1773, 1698, 1626, 1470, 1261, 1199, 1089, 1050

Mass (EI) 216(M$^+$)

mp. 149–151° C.
Elemental analysis
Molecular formula C$_8$H$_8$O$_7$
Calcd. C, 44.45; H, 3.73
Found C, 44.41; H, 3.77

Compound 17

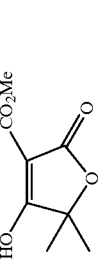

NMR (ppm) (300 MHz, CDCl$_3$) 1.57(s, 6H), 3.95(s, 3H)

IR(cm$^{-1}$) (KBr) 1771, 1620, 1489, 1323, 1158, 1069, 988

Mass (EI) 186(M$^+$)

mp. 112–115° C.
Elemental analysis
Molecular formula C$_8$H$_{10}$O$_5$
Calcd. C, 51.61; H, 5.41
Found C, 51.61; H, 5.43

Compound 18

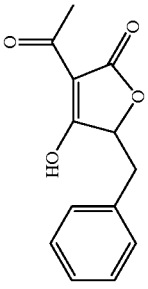

NMR (ppm) (300 MHz, CD$_3$OD) 2.33(s, 3H), 2.92(dd, J = 7.14, 14.55, 1H), 3.25(dd, J = 3.84, 14.55, 1H), 4.63(m, 1H), 7.18–7.31(m, 5H)

IR(cm$^{-1}$) (KBr) 1719, 1638, 1475

Mass (EI) 232(M$^+$)

mp. 195–200° C.
Molecular formula C$_{13}$H$_{12}$O$_4$
Calcd. C, 67.23; H, 5.21
Found Compound 19

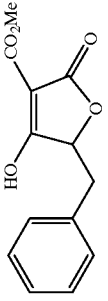

NMR (ppm) (300 MHz, CDCl$_3$) 3.07(dd, J = 6.04, 14.55, 1H), 3.34(dd, J = 4.12, 14.55, 1H), 3.89(s, 3H), 5.13(dd, J = 4.12, 6.04, 1H), 7.22–7.32(m, 5H)

IR(cm$^{-1}$) (KBr) 1760, 1717, 1601, 1065

Mass (EI) 248(M$^+$)

mp. 129–133° C.
Elemental analysis
Molecular formula C$_{13}$H$_{12}$O$_5$
Calcd. C, 62.90; H, 4.87
Found C, 62.77; H, 4.95

-continued

Compound 20

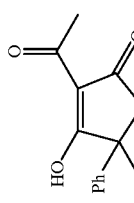

NMR (ppm) (300 MHz, CDCl$_3$)
2.62(s, 3H), 7.39–7.48(m, 10H)

IR(cm$^{-1}$) (KBr)
1698, 1599, 1172, 977, 760

Mass (EI) 294(M$^+$)

mp. 100–110° C.
Elemental analysis
Molecular formula C$_{18}$H$_{14}$O$_4$
Calcd. C, 73.46; H, 4.79
Found C, 73.42; H, 5.14

Compound 21

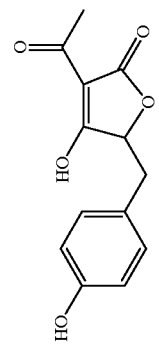

NMR (ppm) (300 MHz, CD$_3$OD)
2.42(s, 3H), 3.01(dd, J = 5.49, 14.55, 1H), 3.22(dd, J = 4.12, 14.55, 1H), 5.02(dd, J = 4.39, 5.76, 1H), 6.69–6.72(m, 2H), 7.04–7.07(m, 2H)

IR(cm$^{-1}$) (KBr)
3284, 1750, 1661, 1603, 1518, 1446, 1230

Mass (EI) 248(M$^+$)

mp. 195–196° C.
Elemental analysis
Molecular formula C$_{13}$H$_{12}$O$_5$
Calcd. C, 62.90; H, 4.87
Found C, 62.86; H, 4.87

Compound 22

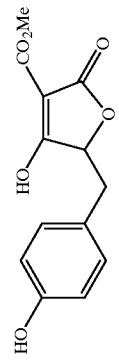

NMR (ppm) (300 MHz, CD$_3$OD)
2.99(dd, J = 5.49, 14.83, 1H), 3.27(dd, J = 4.12, 14.55, 1H), 3.78(s, 3H), 5.13(dd, J = 4.12, 5.49, 1H), 6.69–6.72(m, 2H), 7.05–7.08(m, 2H)

IR(cm$^{-1}$) (KBr)
3462, 1721, 1707, 1618, 1599, 1520, 1423, 1044

Mass (EI) 264(M$^+$)

mp. 146–152° C.
High resolution mass spectrum
Molecular formula C$_{13}$H$_{12}$O$_6$
Calcd. 264.063
Found 264.061

Compound 23

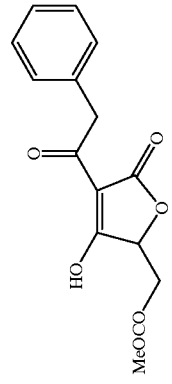

NMR (ppm) (300 MHz, CDCl$_3$)
1.99(s, 3H), 4.16–4.28(m, 3H), 4.37(br, 1H), 4.56(m, 1H), 4.90(br, 1H), 7.28–7.39(m, 5H)

IR(cm$^{-1}$) (KBr)
1760, 1734, 1661, 1618, 1448, 1390, 1249, 1238, 1178, 1023, 719

Mass (EI) 290(M$^+$)

mp.
Molecular formula C$_{15}$H$_{14}$O$_6$
Calcd. C, 62.07; H, 4.86
Found

-continued

| Compound 24 | 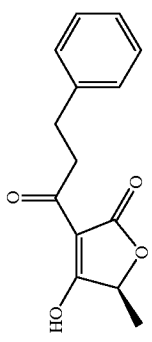 | NMR (ppm) (300 MHz, CDCl$_3$)<br>1.50(d, J = 7.14, 3H), 3.02(m, 2H), 3.26(m, 2H), 4.77(m, 1H), 7.19–7.39(m, 5H)<br>IR(cm$^{-1}$) (KBr)<br>1746, 1663, 1607, 1468, 1216, 1093, 700<br>Mass (EI) 246(M$^+$) | mp. 84–91° C.<br>Elemental analysis<br>Molecular formula C$_{14}$H$_{14}$O$_4$<br>Calcd. C, 68.28; H, 5.73<br>Found C, 68.28; H, 5.75 |
|---|---|---|---|
| Compound 25 | 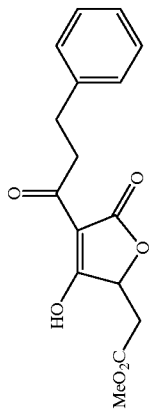 | NMR (ppm) (300 MHz, CD$_3$OD)<br>2.89(dd, J = 6.32, 11.03, 1H), 2.99–3.10(m, 3H), 3.24(m, 2H), 5.05(dd, J = 4.39, 6.31, 1H), 7.21–7.32(m, 5H)<br>IR(cm$^{-1}$) (KBr)<br>1754, 1736, 1661, 1611, 1274, 1174, 1025<br>Mass (EI) 304(M$^+$) | mp. 54–57° C.<br>Elemental analysis<br>Molecular formula C$_{16}$H$_{16}$O$_6$<br>Calcd. C, 63.15; H, 5.30<br>Found C, 63.16; H, 5.26 |
| Compound 26 | 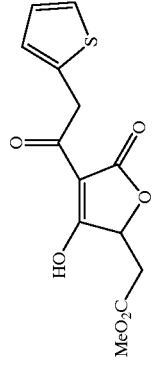 | NMR (ppm) (300 MHz, CD$_3$OD)<br>2.90(dd, J = 6.32, 17.02, 1H), 3.08(dd, J = 4.12, 17.30, 1H), 3.71, 3.73(s, 3H), 5.04, 5.12(m, 1H), 6.86–7.05(m, 2H), 7.25–7.33(m, 1H)<br>IR(cm$^{-1}$) (KBr)<br>1756, 1734, 1659, 1613, 1454, 1245, 1178, 1021, 719<br>Mass (EI) 296(M$^+$) | mp. 103–104° C.<br>Elemental analysis<br>Molecular formula C$_{13}$H$_{12}$O$_6$S<br>Calcd. C, 52.70; H, 4.08; S, 10.82<br>Found C, 52.70; H, 4.05; S, 10.75 |
| Compound 27 | 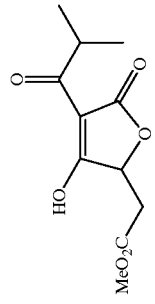 | NMR (ppm) (300 MHz, CD$_3$OD)<br>1.25(dd, J = 0.55, 6.86, 6H), 2.95(dd, J = 6.32, 17.30, 1H), 3.09(dd, J = 4.12, 17.30, 1H), 3.70(m, 1H),3.72(s, 3H), 5.09(dd, J = 4.12, 6.04, 1H)<br>IR(cm$^{-1}$) (KBr)<br>1771, 1744, 1696, 1603, 1330, 1226, 1178, 1087, 1021<br>Mass (EI) 242(M$^+$) | mp.<br>Molecular formula C$_{11}$H$_{14}$O$_6$<br>Calcd. 242.079<br>Found 242.080 |

-continued

Compound 28

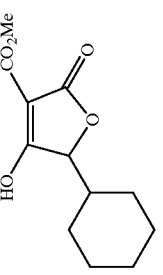

NMR (ppm) (300 MHz, CD$_3$OD)
1.12–2.05(m, 11H), 3.85(s, 3H), 4.81(d, J = 3.30, 1H)

IR(cm$^{-1}$) (KBr)
1754, 1717, 1601, 1477, 1259, 1207, 1170, 1058, 1011

Mass (CI) 241(M + H)* mp. 126–128° C.
Elemental analysis
Molecular formula C$_{12}$H$_{16}$O$_5$
Calcd. C, 59.99; H, 6.71
Found C, 59.90; H, 6.68

Compound 29

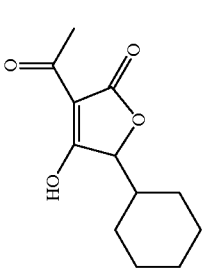

NMR (ppm) (300 MHz, CD$_3$OD)
1.13–2.05(m, 11H), 2.53(s, 3H), 4.68(d, J = 3.84, 1H)

IR(cm$^{-1}$) (KBr)
1750, 1663, 1599, 1456, 1156, 1048, 1011, 404

Mass (EI) 224(M$^+$)

mp. 92–95° C.
Elemental analysis
Molecular formula C$_{12}$H$_{16}$O$_4$
Calcd. C, 64.27; H, 7.19
Found C, 64.33; H, 7.09

Compound 30

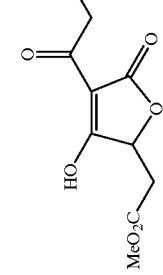

NMR (ppm) (300 MHz, CD$_3$OD)
2.92(dd, J = 6.59, 17.02, 1H), 3.11(dd, J = 4.12, 17.02, 1H), 3.75(s, 3H), 5.19(dd, J = 4.12, 6.59, 1H), 7.29–7.46(m, 4H)

IR(cm$^{-1}$) (KBr)
1765, 1738, 1661, 1604, 1027

Mass (EI) 324(M$^+$)

mp. 110.5–112.5° C.
Elemental analysis
Molecular formula C$_{15}$H$_{13}$ClO$_6$
Calcd. C, 55.48; H, 4.04; Cl, 10.92
Found C, 55.34; H, 4.05; Cl, 11.09

Compound 31

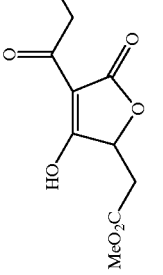

NMR (ppm) (300 MHz, CD$_3$OD)
2.02(quint, J = 7.14, 2H), 2.47(t, J = 7.14, 2H), 2.88–3.12(m, 4H), 3.70(s, 3H), 3.73(s, 3H), 5.08(dd, J = 4.12, 6.31, 1H)

IR(cm$^{-1}$) (neat)
1769, 1742, 1700 1605, 1439, 1377, 1019

Mass (EI) 300(M$^+$)

mp.

Molecular formula C$_{13}$H$_{16}$O$_8$
Calcd. C, 52.00; H, 5.37
Found

-continued

| | | |
|---|---|---|
| Compound 32 | 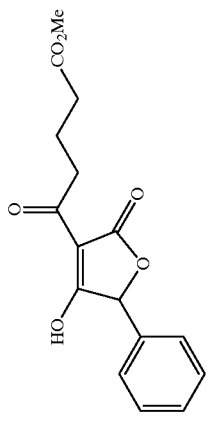 | NMR (ppm) (300 MHz, CD$_3$OD) 2.02(quint, J = 7.14, 2H), 2.47(t, J = 7.14, 2H), 3.03(t, J = 7.14, 2H), 3.69(s, 3H), 5.83(s, 1H), 7.38–7.47(m, 5H)<br>IR(cm$^{-1}$) (KBr) 1742, 1651, 1609, 1170<br>Mass (EI) 304(M$^+$) | mp. 87–90° C.<br>Elemental analysis<br>Molecular formula C$_{16}$H$_{16}$O$_6$<br>Calcd. C, 63.15; H, 5.30<br>Found C, 63.14; H, 5.29 |
| Compound 33 | 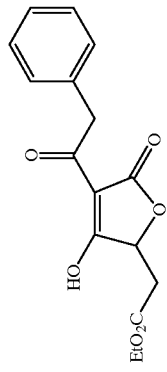 | NMR (ppm) (300 MHz, CD$_3$OD) 1.22(t, J = 7.14, 3H), 2.94(dd, J = 5.77, 17.02, 1H), 3.04(dd, J = 4.39, 17.02, 1H), 4.10–4.26(m, 3H), 5.08(m, 1H), 7.28–7.39(m, 5H)<br>IR(cm$^{-1}$) (KBr) 1748, 1725, 1661, 1247, 1187, 1019<br>Mass (EI) 304(M$^+$) | mp. 80–81° C.<br>Elemental analysis<br>Molecular formula C$_{16}$H$_{16}$O$_6$<br>Calcd. C, 63.15; H, 5.30<br>Found C, 63.16; H, 5.34 |
| Compound 34 | 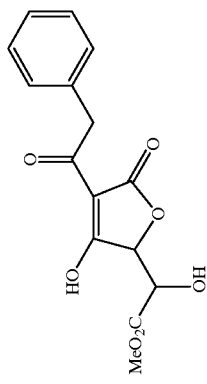 | NMR (ppm) (300 MHz, CD$_3$OD) 3.86(s, 3H), 4.25(d, J = 3.84, 1H), 4.71(d, J = 1.92, 1H), 5.21(d, J = 1.92, 1H), 7.29–7.35(m, 5H)<br>IR(cm$^{-1}$) (KBr) 1771, 1742, 1649, 1620, 1122, 988, 727<br>Mass (EI) 306(M$^+$) | mp. 108–111° C.<br>Elemental analysis<br>Molecular formula C$_{15}$H$_{14}$O$_7$<br>Calcd. C, 58.83; H, 4.61<br>Found C, 58.72; H, 4.70 |
| Compound 35 | 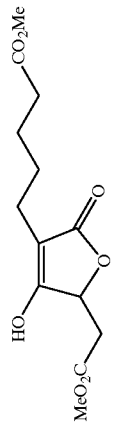 | NMR (ppm) (300 MHz, CD$_3$OD) 1.53(m, 2H), 1.63(m, 2H), 2.22(t, J = 7.14, 2H), 2.38(t, J = 7.14, 2H), 2.58(dd, J = 8.51, 16.20, 1H), 3.02(dd, J = 3.57, 16.20), 3.69(d, J = 0.82, 3H), 3.75(d, J = 0.82, 3H), 5.11(dd, J = 3.57, 8.51)<br>IR(cm$^{-1}$) (KBr) 1742, 1644, 1278, 1238, 1174, 1098<br>Mass (EI) 286(M$^+$) | mp. 35° C.<br>Elemental analysis<br>Molecular formula C$_{13}$H$_{18}$O$_7$<br>Calcd. C, 54.54; H, 6.34<br>Found C, 54.60; H, 6.32 |

| Compound 36 | 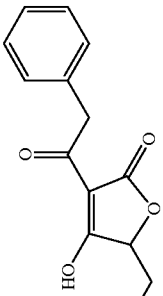 | NMR (ppm) (300 MHz, CD₃OD) 2.02(m, 1H), 2.31(m, 1H), 2.52(t, J = 7.14, 2H), 3.70(s, 3H), 4.20(m, 1H), 493(m, 1H), 7.27–7.37(m, 5H) IR(cm⁻¹) (KBr) 1744, 1661, 1609, 1444, 1245, 1027, 729, 712 Mass (EI) 304(M⁺) | mp. 86–88° C. Elemental analysis Molecular formula C₁₆H₁₆O₆ Calcd. C, 63.15; H, 5.30 Found C, 63.15; H, 5.30 |
|---|---|---|---|
| Compound 37 | 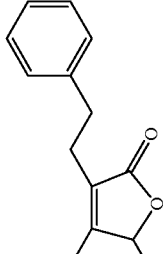 | NMR (ppm) (300 MHz, CD₃OD) 2.41–2.52(m, 3H), 2.80(t, J = 7.69, 2H), 2.94(dd, J = 3.30, 16.20), 3.75(s, 3H), 5.06(dd, J = 3.30, 8.78), 7.19–7.32(m, 5H) IR(cm⁻¹) (KBr) 1740, 1711, 1632, 1276 Mass (EI) 276(M⁺) | mp. 128–132° C. Elemental analysis Molecular formula C₁₅H₁₆O₅ Calcd. C, 65.21; H, 5.84 Found C, 65.07; H, 5.84% |
| Compound 38 | 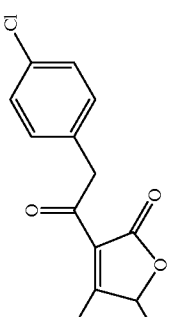 | NMR (ppm) (300 MHz, CD₃OD) 2.92(dd, J = 6.31, 17.30, 1H), 3.09(dd, J = 4.39, 17.30, 1H), 3.71(s, 3H), 3.72(m, 1H), 5.09(dd, J = 4.39, 6.31, 1H), 7.26–7.44(m, 4H) IR(cm⁻¹) (KBr) 1740, 1661, 1609, 1444, 1243, 1021 Mass (EI) 324(M⁺) | mp. 140–144° C. Elemental analysis Molecular formula C₁₅H₁₃ClO₆ Calcd. C, 55.48; H, 4.04; Cl, 10.92 Found C, 55.42; H, 4.07; Cl, 10.95 |
| Compound 39 | 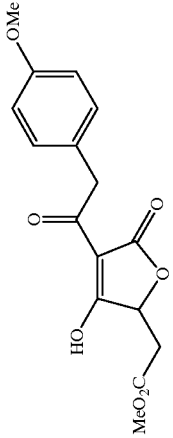 | NMR (ppm) (300 MHz, CD₃OD) 2.94(dd, J = 6.31, 17.30, 1H), 3.08(dd, J = 4.39, 17.30, 1H), 3.69(s, 3H), 3.80(s, 3H), 5.07(dd, J = 4.39, 6.31, 1H), 6.88–6.92(m, 2H), 7.28–7.31(m, 2H) IR(cm⁻¹) (KBr) 1748, 1729, 1661, 1613, 1518, 1439, 1247 Mass (EI) 320(M⁺) | mp. 104–167° C. Elemental analysis Molecular formula C₁₆H₁₆O₇ Calcd. C, 60.00; H, 5.03 Found C, 60.06; H, 5.03 |

-continued

| Compound | Structure | Data | Properties |
|---|---|---|---|
| Compound 40 | 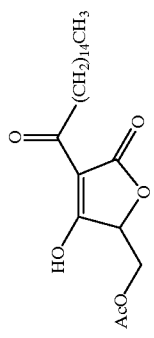 | NMR (ppm) (300 MHz, CD$_3$OD) 0.94(t, J = 6.87, 3H), 1.27–1.40(m, 27H), 1.72(m, 2H), 2.04(s, 3H), 2.95(t, J = 7.14, 2H), 4.39(dd, J = 3.84, 12.35, 1H), 4.58(dd, J = 2.74, 12.35, 1H), 5.03(dd, J = 2.74, 3.83, 1H) IR(cm$^{-1}$) (KBr) 2920, 2852, 1750, 1665, 1613 Mass (EI) 410(M$^+$) | mp. 82–83° C. Elemental analysis Molecular formula C$_{23}$H$_{38}$O$_6$ Calcd. C, 67.29; H, 9.33 Found C, 67.28; H, 9.32 |
| Compound 41 | 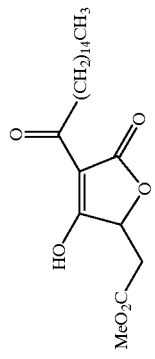 | NMR (ppm) (300 MHz, CD$_3$OD) 0.94(t, J = 6.87, 3H), 1.28–1.40(m, 27H), 1.73(m, 2H), 2.90–2.98(m, 3H), 3.08(dd, J = 4.39, 17.30, 1H), 3.72(s, 3H), 5.04(dd, J = 4.39, 6.21, 1H) IR(cm$^{-1}$) (KBr) 2920, 2852, 1752, 1731, 1620 Mass (EI) 410(M$^+$) | mp. 79–80° C. Elemental analysis Molecular formula C$_{23}$H$_{38}$O$_6$ Calcd. C, 67.29; H, 9.33 Found C, 67.33; H, 9.31 |
| Compound 42 | 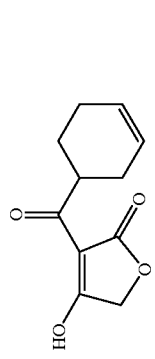 | NMR (ppm) (300 MHz, CD$_3$OD) 1.62–1.79 (m, 1H), 1.91–2.06(m, 1H), 2.14–2.37 (m, 4H), 3.62-3.69 (m, 1H), 4.76 (s, 2H), 5.76–5.77 (m, 1H). IR(cm$^{-1}$) (KBr) 3028, 2928, 1750, 1661, 1601, 1466, 1433, 1348, 1263, 1251, 1205, 1116, 1048, 843, 830, 644 Mass (EI) 208 (M$^+$) | mp. 111.0–112.0° C. Elemental analysis Molecular formula C$_{11}$H$_{12}$O$_4$ Calcd. C, 63.45; H, 5.81 Found C, 63.41; H, 5.93. |
| Compound 43 | 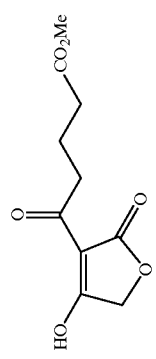 | NMR (ppm) (300 MHz, CD$_3$OD) 2.00 (quint, J = 7.4 Hz, 2H), 2.46 (t, J = 7.4 Hz, 2H), 2.97 (t, J = 7.4 Hz, 2H), 3.70 (s, 2H), 4.74 (s, 2H) IR(cm$^{-1}$) (KBr) 3174, 3146, 2950, 1781, 1740, 1661, 1615, 1460, 1441, 1390, 1305, 1249, 1207, 1125, 1054, 1017, 841, 766 Mass (EI) 228 (M$^+$) | mp. 51.0–53.0° C. Elemental analysis Molecular formula C$_{10}$H$_{10}$O$_6$ Calcd. C, 52.63; H, 5.30. Found C, 52.56; H, 5.38. |

-continued

| Compound | Structure | Data |
|---|---|---|
| Compound 44 | 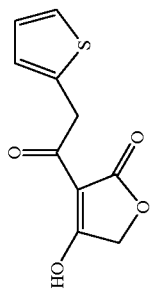 | NMR (ppm) (300 MHz, $CD_3OD$) 4.76 (s, 2H), 4.91 (s, 2H), 6.96–7.02 (m, 2H), 7.29–7.32 (m, 1H). IR($cm^{-1}$) (KBr) 3110, 1748, 1663, 1607, 1466, 1431, 1352, 1257, 1218, 1100, 1042, 948, 857, 694 Mass (EI) 224 ($M^+$) mp. 107.0–109.0° C. Elemental analysis Molecular formula $C_{10}H_8O_4S$ Calcd. C, 53.56; H, 3.60; S, 14.30. Found C, 53.61; H, 3.65; S, 14.10. |
| Compound 45 | 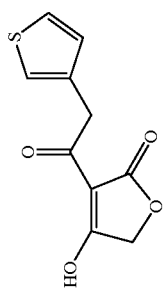 | NMR (ppm) (300 MHz, $CD_3OD$) 4.75 (s, 2H), 4.91 (s, 2H), 7.07–7.10 (m, 1H), 7.28–7.30 (m, 1H), 7.37–7.40 (m, 1H) IR($cm^{-1}$) (KBr) 3108, 1752, 1698, 1667, 1603, 1466, 1431, 1255, 1214, 1102, 1044, 1023, 837, 752 Mass (EI) 224 ($M^+$) mp. 70.5–71.0° C. Elemental analysis Molecular formula $C_{10}H_8O_4S$ Calcd. C, 53.56; H, 3.60; S, 14.30. Found C, 53.62; H, 3.62; S, 14.05. |
| Compound 46 | 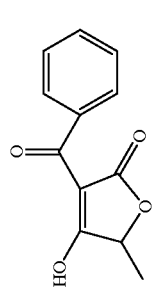 | NMR (ppm) (300 MHz, $CDCl_3$) 1.56(d, J = 6.87, 1.59H), 1.60(d, J = 6.87, 1.41H), 4.76(q, J = 6.87, 0.47H), 4.92(q, J = 6.87, 0.53H), 7.51–7.57(m, 3H), 7.66(m, 1H), 8.27–8.34(m, 2H) IR($cm^{-1}$) (neat) 1767, 1684, 1595, 1560, 1450, 1052, 851, 775, 698, 600 Mass (EI) 218($M^+$) mp. 145° C.(0.2 mmHg) Molecular formula $C_{12}H_{10}O_4$ Calcd. C, 66.05; H, 4.62 Found |
| Compound 47 | 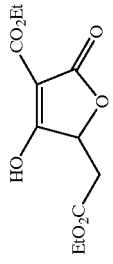 | NMR (ppm) (300 MHz, $CDCl_3$) 1.28(t, J = 7.14, 3H), 1.41(t, J = 7.14, 3H), 2.76(dd, J = 7.41, 16.48, 1H), 2.98(dd, J = 4.39, 16.48, 1H), 4.21(q, J = 7.14, 2H), 4.43(q, J = 7.14, 2H), 5.29(m, 1H) IR($cm^{-1}$) (neat) 1760, 1734, 1452, 1381, 1187, 1038, 806 Mass (EI) 258($M^+$) mp. Molecular formula $C_{11}H_{14}O_7$ Calcd. C, 51.16; H, 5.46 Found |

-continued

| | | |
|---|---|---|
| Compound 49 | 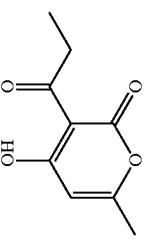 | NMR (ppm) (300 MHz, CD$_3$OD) 1.17 (t, J = 7.14 Hz, 3H), 2.32 (d, J = 0.82 Hz, 3H), 3.10 (q, J = 7.14 Hz, 2H), 6.18 (q, J = 0.82 Hz, 1H).<br><br>IR(cm$^{-1}$)<br>既知物質<br><br>Mass 182 (M$^+$) | mp. 104.0–106.0° C.<br>Molecular formula<br>Calcd.<br>Found |
| Compound 50 | 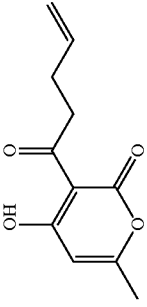 | NMR (ppm) (300 MHz, CD$_3$OD) 2.32 (d, J = 0.82 Hz, 3H), 2.34–2.48 (m, 2H), 3.16–3.20 (m, 2H), 4.66–5.14 (m, 2H), 5.86–6.00 (m, 1H), 6.19 (q, J = 0.82 Hz, 1H).<br><br>IR(cm$^{-1}$) (KBr)<br>3084, 1715, 1711, 1651, 1609, 1570, 1456, 1390, 1344, 1236, 996, 940, 919, 861, 712<br><br>Mass (EI) 208 (M$^+$) | mp. 72.5–73.0° C.<br>Elemental analysis<br>Molecular formula C$_{11}$H$_{12}$O$_4$<br>Calcd. C, 63.45 H, 5.81.<br>Found C, 63.48; H, 5.87. |
| Compound 51 | 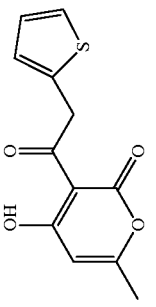 | NMR (ppm) (300 MHz, CD$_3$OD) 2.33 (d, J = 0.82 Hz, 3H), 4.61 (s, 2H), 6.20 (q, J = 0.82 Hz, 1H), 6.95–7.00 (m, 2H), 7.30–7.33 (m, 1H).<br><br>IR(cm$^{-1}$) (KBr)<br>3082, 1711, 1626, 1533, 1454, 1369, 1321, 1238, 1170, 990, 932, 855, 795, 772, 721, 712<br><br>Mass (EI) 250 (M$^+$) | mp. 126.0–127.5° C.<br>Elemental analysis<br>Molecular formula C$_{12}$H$_{10}$O$_4$S<br>Calcd. C, 57.59; H, 4.03; S, 12.81.<br>Found C, 57.57; H, 4.04; S, 12.72. |
| Compound 52 | 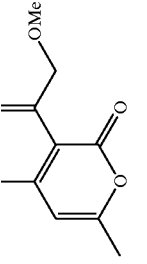 | NMR (ppm) (300 MHz, CD$_3$OD) 2.34 (d, J = 0.82 Hz, 3H), 3.51 (s, 3H), 4.73 (s, 2H), 6.24 (q, J = 0.82 Hz, 1H).<br><br>IR(cm$^{-1}$) (KBr)<br>1750, 1736, 1638, 1578, 1460, 1342, 1137, 996, 984, 940, 919, 845<br><br>Mass (EI) 198 (M$^+$) | mp. 91.0–93.5° C.<br>Elemental analysis<br>Molecular formula C$_9$H$_{10}$O$_5$<br>Calcd. C, 54.54; H, 5.08.<br>Found C, 54.62; H, 5.11. |

-continued

Compound 53

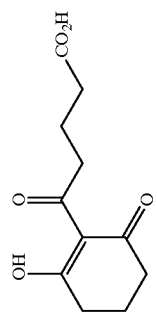

NMR (ppm) (300 MHz CD$_3$OD)
1.91–2.05(m, 4H), 2.40(t, J = 7.41, 2H), 2.4–2.9(br, 4H), 3.1(t, J = 7.41, 2H)

IR(cm$^{-1}$) (KBr)
1723, 1632, 1560, 1446, 1423, 1274, 1197, 1168

Mass (EI) 226(M$^+$)

mp. 78–79° C.
Elemental analysis
Molecular formula C$_{11}$H$_{14}$O$_5$
Calcd. C, 58.40; H, 6.24
Found C, 58.34; H, 6.25

Compound 54

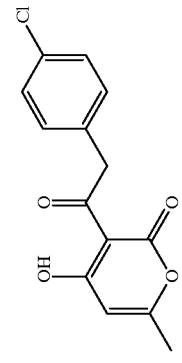

NMR (ppm) (300 MHz, CD$_3$OD)
2.32(d, J = 0.82, 3H), 4.40(s, 2H), 6.19(d, J = 0.82, 1H), 7.27–7.35(m, 4H)

IR(cm$^{-1}$) (KBr)
1742, 1719, 1638, 1615, 1570, 996, 779

Mass (EI) 278(M$^+$)

mp. 137–139° C.
Elemental analysis
Molecular formula C$_{14}$H$_{11}$ClO$_4$
Calcd. C, 60.34; H, 3.98; Cl, 12.72
Found C, 60.22; H, 4.04; Cl, 12.66

Compound 55

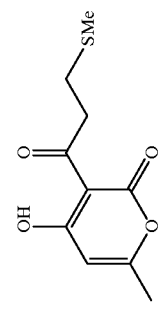

NMR (ppm) (300 MHz, CD$_3$OD)
2.16 (s, 3H), 2.33 (d, J = 0.82 Hz, 3H), 2.83 (t, J = 7.14 Hz, 2H), 3.39 (t, J = 7.14 Hz, 2H), 6.20 (q, J = 0.82 Hz, 1H).

IR(cm$^{-1}$) (KBr)
1715, 1647, 1560, 1460, 1421, 1247, 998, 973, 942, 847

Mass (EI) 228 (M$^+$)

mp. 80.0–81.0° C.
Elemental analysis
Molecular formula C$_{10}$H$_{12}$O$_4$S
Calcd. C, 52.61; H, 5.30; S, 14.05.
Found C, 52.45; H, 5.33; S, 13.84.

Compound 56

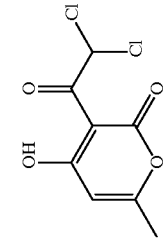

NMR (ppm) (300 MHz, CD$_3$OD)
2.37 (d, J = 0.82 Hz, 3H), 6.33 (q, J = 0.82 Hz, 1H), 7.54 (s, 1H).

IR(cm$^{-1}$) (KBr)
1711, 1647, 1562, 1450, 1253, 1000, 837, 810, 770, 752

Mass (EI) 236 (M$^+$)

mp. 91.0–92.5° C. (dec)
Elemental analysis
Molecular formula C$_8$H$_6$Cl$_2$O$_4$
Calcd. C, 40.54; H, 2.55; Cl, 29.91.
Found C, 40.62; H, 2.63; Cl, 29.82.

-continued

| Compound | Structure | Data |
|---|---|---|
| Compound 57 | 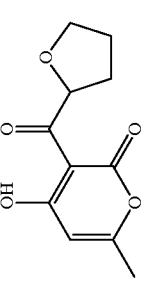 | NMR (ppm) (300 MHz, CD$_3$OD) 1.85–2.03 (m, 3H), 2.34 (d, J = 0.82 Hz, 3H), 2.44–2.62 (m, 1H), 3.94–4.16 (m, 2H), 5.47–5.52 (m, 1H), 6.23 (q, J = 0.82 Hz, 1H).<br>IR(cm$^{-1}$) (KBr) 2984, 2878, 1725, 1642, 1620, 1564, 1460, 1238, 1098, 1083, 1000, 880, 849<br>Mass (EI) 224 (M$^+$) | mp. 128.5–130.0° C.<br>Elemental analysis<br>Molecular formula C$_{11}$H$_{12}$O$_5$<br>Calcd. C, 58.92; H, 5.40.<br>Found C, 58.88; H, 5.46. |
| Compound 58 | 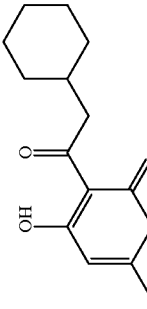 | NMR (ppm) (300 MHz, CD$_3$OD) 0.98–1.22 (m, 5H), 1.63–1.83 (m, 5H), 1.93 (m, 1H), 2.32 (d, J = 0.82 Hz, 3H), 2.95 (d, J = 6.59 Hz, 2H), 6.17 (q, J = 0.82 Hz, 1H).<br>IR(cm$^{-1}$) (KBr) 2926, 2854, 1725, 1651, 1611, 1562, 1448, 1340, 1249, 1236, 996, 932, 859<br>Mass (EI) 250 (M$^+$) | mp. 66.0–66.5° C.<br>Elemental analysis<br>Molecular formula C$_{14}$H$_{18}$O$_4$<br>Calcd. C, 67.18; H, 7.25.<br>Found C, 67.17; H, 7.24. |
| Compound 59 | 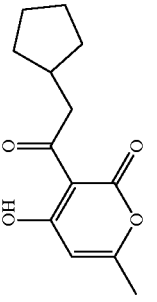 | NMR (ppm) (300 MHz, CD$_3$OD) 0.97–1.15 (m, 2H), 1.56–1.75 (m, 4H), 1.83–1.98 (m, 2H), 2.32 (d, J = 0.82 Hz, 3H), 2.36 (sept, J = 0.82 Hz, 1H), 3.10 (d, J = 7.14 Hz, 2H), 6.17 (q, J = 0.82 Hz, 1H).<br>IR(cm$^{-1}$) (KBr) 3082, 2954, 2870, 1717, 1649, 1613, 1566, 1454, 1354, 1238, 996, 936, 866, 775, 716<br>Mass (EI) 236 (M$^+$) | mp. 57.0–57.5° C.<br>Elemental analysis<br>Molecular formula C$_{13}$H$_{16}$O$_4$<br>Calcd. C, 66.08; H, 6.83.<br>Found C, 66.04; H, 6.80. |
| Compound 60 | 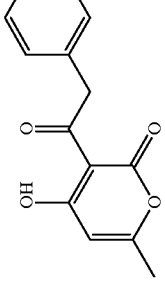 | NMR (ppm) (300 MHz, CD$_3$OD) 2.32 (d, J = 0.82 Hz, 3H), 4.41 (s, 2H), 6.18 (q, J = 0.82 Hz, 1H), 7.22–7.39 (m, 5H).<br>IR(cm$^{-1}$) (KBr) 3082, 3034, 2932, 1707, 1655, 1560, 1460, 1238, 1170, 998, 946, 862, 727, 702, 542<br>Mass (EI) 244 (M$^+$) | mp. 148–149° C.<br>Elemental analysis<br>Molecular formula C$_{14}$H$_{12}$O$_4$<br>Calcd. C, 68.84; H, 4.95.<br>Found C, 68.90; H, 5.02. |

-continued

Compound 61

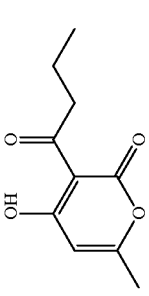

NMR (ppm) (300 MHz, CD$_3$OD)
1.03 (t, J = 7.42 Hz, 3H), 1.72 (sext, J = 7.42 Hz, 2H), 2.32 (d, J = 0.82 Hz, 3H), 3.05 (t, J = 7.42 Hz, 2H), 6.18 (q, J = 0.82 Hz, 1H).

IR(cm$^{-1}$) (KBr)
3078, 2974, 2942, 2916, 2882, 1725, 1655, 1613, 1557, 1462, 1381, 1348, 1238, 994, 920, 861, 777

Mass (EI) 196 (M$^+$)

mp. 59.0–59.5° C.
Elemental analysis
Molecular formula C$_{10}$H$_{12}$O$_4$
Calcd. C, 61.21; H, 6.17.
Found C, 61.18; H, 6.13.

Compound 62

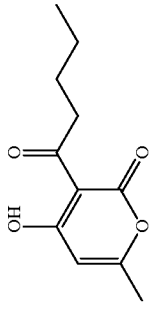

NMR (ppm) (300 MHz, CD$_3$OD)
0.99 (t, J = 7.42 Hz, 3H), 1.44 (sext, J = 7.42 Hz, 2H), 1.67 (quint, J = 7.42 Hz, 2H), 2.32 (d, J = 0.82 Hz, 3H), 3.07 (t, J = 7.42 Hz, 2H), 6.18 (q, J = 0.82 Hz, 1H).

IR(cm$^{-1}$) (KBr)
3090, 2964, 2874, 1719, 1653, 1609, 1564, 1454, 1361, 1332, 1234, 1189, 996, 934, 861, 772, 714, 640

Mass (EI) 210 (M$^+$)

mp. 75.0–75.5° C.
Elemental analysis
Molecular formula C$_{11}$H$_{14}$O$_4$
Calcd. C, 62.84; H, 6.71.
Found C, 62.77; H, 6.63.

Compound 63

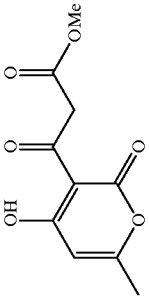

NMR (ppm) (300 MHz, CD$_3$OD)
2.34 (d, J = 0.82 Hz, 3H), 3.75 (s, 3H), 4.02 (s, 2H), 6.25 (q, J = 0.82 Hz, 1H).

IR(cm$^{-1}$) (KBr)
1717, 1640, 1618, 1572, 1448, 1386, 1299, 1251, 1158, 998, 988, 944, 777

Mass (EI) 226 (M$^+$)

mp. 91.5–92.0° C.
Elemental analysis
Molecular formula C$_{10}$H$_{10}$O$_6$
Calcd. C, 53.10; H, 4.46.
Found C, 53.04; H, 4.47.

Compound 64

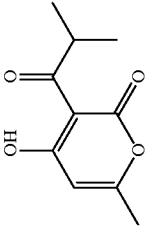

NMR (ppm) (300 MHz, CD$_3$OD)
1.18 (d, J = 6.73 Hz, 6H), 2.32 (d, J = 0.82 Hz, 3H), 3.94 (sept, J = 6.73 Hz, 1H), 6.18 (q, J = 0.82 Hz, 1H).

IR(cm$^{-1}$) (KBr)
1721, 1647, 1611, 1562, 1458, 1425, 1365, 1236, 1000, 982, 930, 859

Mass (EI) 196 (M$^+$)

mp. 74.5–75.0° C.
Elemental analysis
Molecular formula C$_{10}$H$_{12}$O$_4$
Calcd. C, 61.21; H, 6.17.
Found C, 61.06; H, 6.09.

-continued

Compound 65

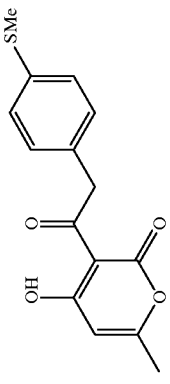

NMR (ppm) (300 MHz, CD$_3$OD)
2.32 (d, J = 0.82 Hz, 3H), 2.49 (s, 3H, SMe), 4.37 (s, 2H), 6.19 (q, J = 0.82 Hz, 1H), 7.24 (brs, 4H).

IR(cm$^{-1}$) (KBr)
1709, 1651, 1560, 1497, 1460, 1238, 996, 948, 936, 862, 777

Mass (EI) 290 (M$^+$)

mp. 134.5–135.5° C.
Elemental analysis
Molecular formula C$_{15}$H$_{14}$O$_4$S
Calcd. C, 62.05; H, 4.86; S, 11.05.
Found C, 61.83; H, 4.87; S, 11.05.

Compound 66

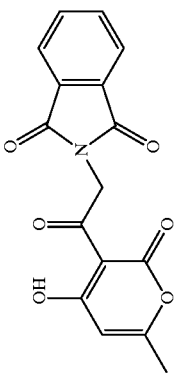

NMR (ppm) (300 MHz, CD$_3$OD)
2.38 (d, J = 0.82 Hz, 3H), 5.14 (s, 2H), 6.27 (q, J = 0.82 Hz, 1H), 7.87–7.98 (m, 4H).

IR(cm$^{-1}$) (KBr)
1730, 1715, 1638, 1620, 1458, 1419, 1406, 1110, 994, 949, 721, 530, 514

Mass (EI) 313 (M$^+$)

mp. 194.5–195.5° C.
Elemental analysis
Molecular formula C$_{13}$H$_{11}$NO$_6$
Calcd. C, 61.34; H, 3.54; N, 4.47.
Found C, 61.59; H, 3.65; N, 4.46.

Compound 67

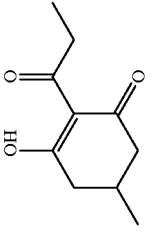

NMR (ppm) (300 MHz, CD$_3$OD)
1.11(d, J = 6.31, 3H), 1.14(t, J = 7.14, 3H), 2.26(m, 2H), 2.54(m, 2H), 2.58(s, 3H), 2.75(m, 1H), 3.05(dq, J = 0.82, 7.14, 2H), 7.36–7.39(m, 2H)

IR(cm$^{-1}$) (KBr)
1657, 1555, 1543

Mass (EI) 182(M$^+$)

mp. 41–43° C.
Elemental analysis
Molecular formula C$_{10}$H$_{14}$O$_3$
Calcd. C, 65.92; H, 7.74
Found C, 65.92; H, 7.76

Compound 68

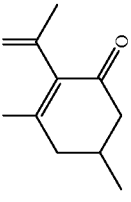

NMR (ppm) (300 MHz, CD$_3$OD)
1.12(d, J = 6.04, 3H), 2.26(m, 2H), 2.57(m, 2H), 2.58(s, 3H), 2.75(m, 1H), 3.05(dq, J = 0.82, 7.14, 2H), 7.36–7.39(m, 2H)

IR(cm$^{-1}$)
1642, 1562, 1458

Mass (EI) 168(M$^+$)

mp. 43–44° C.
Elemental analysis
Molecular formula C$_9$H$_{12}$O$_3$
Calcd. C, 64.27; H, 7.19
Found C, 64.20; H, 7.15

-continued

| Compound 69 | 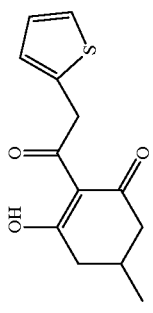 | NMR (ppm) (300 MHz, CD₃OD) 1.12(d, J = 6.31, 3H), 2.26(m, 2H), 2.57(m, 2H), 2.75(m, 1H), 4.91(s, 1H), 6.95–6.98(m, 2H), 7.29(dd, J = 2.47, 3.84, 1H)<br><br>IR(cm⁻¹) (KBr) 1665, 1607, 1562, 1423, 1404, 698<br><br>Mass (EI) 250(M⁺) | mp. 54–55° C.<br>Elemental analysis<br>Molecular formula C₁₃H₁₄O₃S<br>Calcd. C, 62.38; H, 5.64; S, 12.81<br>Found C, 62.22; H, 5.68; S, 12.76 |
|---|---|---|---|
| Compound 70 | 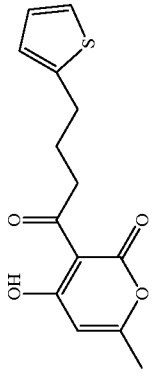 | NMR (ppm) (300 MHz, CD₃OD) 2.05 (quint, J = 7.30 Hz, 2H), 2.32 (d, J = 0.82 Hz, 3H), 2.95 (t, J = 7.30 Hz, 2H), 3.14 (t, J = 7.30 Hz, 2H), 6.18 (q, J = 0.82 Hz, 1H),6.85–6.87 (m, 1H), 6.92–6.95 (m, 1H), 7.19–7.22 (m, 1H).<br><br>IR(cm⁻¹) (KBr) 1725, 1649, 1620, 1560, 1460, 1433, 1334, 1249, 996, 924, 851, 688<br><br>Mass (EI) 278 (M⁺) | mp. 83.0–83.5° C.<br>Elemental analysis<br>Molecular formula C₁₄H₁₄O₄S<br>Calcd. C, 60.41; H, 5.07; S, 11.52.<br>Found C, 60.40; H, 5.06; S, 11.48. |
| Compound 71 | 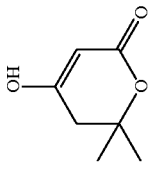 | NMR (ppm) (300 MHz, CD₃OD) 1.52–1.68 (m, 1H), 1.94–2.05 (m, 1H), 2.14–2.31 (m, 4H), 2.33 (d, J = 0.82 Hz, 3H), 3.84–3.95 (m, 1H), 5.75–5.77 (m, 2H), 6.19 (q, J = 0.82 Hz, 1H)<br><br>IR(cm⁻¹) (KBr) 2986, 2936, 2674, 2598, 1650, 1555, 1323, 1272, 1110, 1008, 911<br><br>Mass (EI) 142 (M⁺) | mp. 128–130° C.<br>Elemental analysis<br>Molecular formula C₇H₁₀O₃<br>Calcd. C, 59.14; H, 7.09.<br>Found C, 59.16; H, 7.02. |
| Compound 72 | 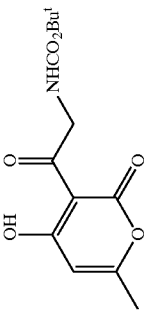 | NMR (ppm) (300 MHz, CD₃OD) 1.50 (s, 3H), 2.34 (d, J = 0.82 Hz, 3H), 4.49 (s, 2H), 6.23 (q, J = 0.82 Hz, 1H)<br><br>IR(cm⁻¹) (KBr) 3332, 2982, 1720, 1675, 1654, 1563, 1527, 1456, 1301, 1250, 1238, 1185, 1164, 995, 938, 857<br>Mass (EI) 283 (M⁺) | mp. 106–109° C. (dec)<br>Elemental analysis<br>Molecular formula C₁₃H₁₇O₆N<br>Calcd. C, 55.12; H, 6.05; N, 4.95.<br>Found C, 55.23; H, 6.04; N, 5.08. |

-continued

Compound 73

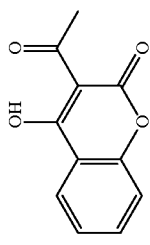

NMR (ppm) (300 MHz, CD$_3$OD)
2.76 (s, 3H), 7.37–7.41 (m, 1H), 7.80–7.86 (m, 1H), 8.11–8.15 (m, 1H).

IR(cm$^{-1}$) (KBr)
1734, 1612, 1545, 1498, 1444, 1370, 1170, 1034, 981, 764, 579

Mass (EI) 204 (M$^+$)

mp. 135–136° C.
Elemental analysis
Molecular formula C$_{11}$H$_8$O$_4$
Calcd. C, 64.70; H, 3.95.
Found C, 64.54; H, 4.04.

Compound 74

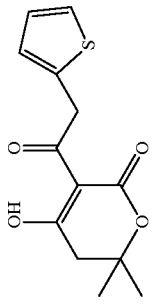

NMR (ppm) (300 MHz, CD$_3$OD)
1.47 (s, 6H), 2.89 (s, 2H), 4.58 (s, 2H), 6.69–7.02 (m, 2H), 7.30–7.33 (m, 1H).

IR(cm$^{-1}$) (KBr)
1692, 1572, 1543, 1311, 1067, 940, 768, 721

Mass (EI) 266 (M$^+$)

mp. 85.0–85.5° C.
Elemental analysis
Molecular formula C$_{13}$H$_{14}$O$_4$S
Calcd. C, 58.63; H, 5.30; S, 12.04.
Found C, 58.32; H, 5.30; S, 11.97.

Compound 75

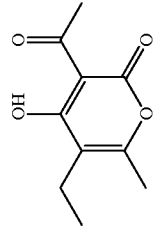

NMR (ppm) (300 MHz, CD$_3$OD)
1.12(d, J = 6.04, 3H), 2.28(m, 2H), 2.53(m, 2H), 2.77(m, 1H), 3.48(s, 3H), 4.70(d, J = 1.10, 2H)

IR(cm$^{-1}$)

Mass (EI) 198(M$^+$)

mp.
High resolution mass spectrum
Molecular formula C$_{10}$H$_{14}$O$_4$
Calcd. 198.089
Found 198.091

Compound 77

NMR (ppm) (300 MHz, CD$_3$OD)
1.14(t, J = 7.41, 3H), 2.35(s, 3H), 2.52(q, J = 7.41, 2H), 2.65(s, 3H), 5.44(s, 1H)

IR(cm$^{-1}$)

Mass (EI) 196(M$^+$)

mp.
High resolution mass spectrum
Molecular formula C$_{10}$H$_{12}$O$_4$
Calcd. 196.074
Found 196.075

-continued

| Compound 78 | 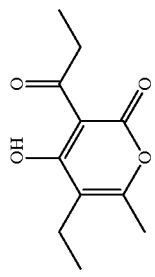 | NMR (ppm) (300 MHz, CD$_3$OD) 1.14(t, J = 7.41, 3H), 1.17(t, J = 7.41, 3H), 2.35(s, 3H), 2.52(q, J = 7.41, 2H), 3.11(q, J = 7.41, 2H)<br><br>IR(cm$^{-1}$)<br><br>Mass (EI) 196(M$^+$) | mp.<br>High resolution mass spectrum<br>Molecular formula C$_{11}$H$_{14}$O$_4$<br>Calcd. 210.089<br>Found 210.090 |
|---|---|---|---|
| Compound 79 | 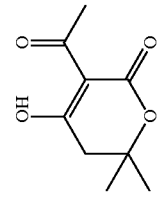 | NMR (ppm) (300 MHz, CD$_3$OD) 1.49 (s, 6H), 2.61(s, 3H), 2.87 (s, 2H).<br><br>IR(cm$^{-1}$) (KBr) 2984, 1710, 1562, 1465, 1414, 1256, 1181, 1064, 935, 842, 769<br><br>Mass (EI) 184 (M$^+$) | mp. 105–160° C.<br>Elemental analysis<br>Molecular formula C$_9$H$_{12}$O$_4$<br>Calcd. C, 58.68; H, 6.57.<br>Found C, 58.52; H, 6.48; |
| Compound 80 | 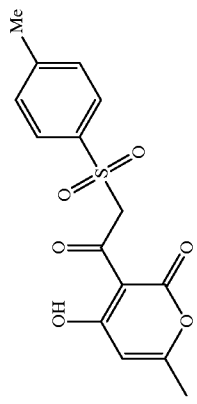 | NMR (ppm) (300 MHz, CD$_3$OD) 2.33 (d, J = 0.82 Hz, 3H), 2.50 (s, 3H), 4.48 (s, 2H), 6.23 (q, J = 0.82 Hz, 1H), 7.47 (d, J = 8.34 Hz, 2H), 7.84 (d, J = 8.34 Hz, 2H).<br><br>IR(cm$^{-1}$) (KBr) 2920, 1704, 1653, 1550, 1323, 1244, 1160, 1129, 997, 887, 814<br><br>Mass (EI) 322 (M$^+$) | mp. 174–175° C.<br>Elemental analysis<br>Molecular formula C$_{15}$H$_{14}$O$_6$<br>Calcd. C, 55.89; H, 4.38; S, 9.95.<br>Found C, 55.51; H, 4.41; S, 9.84. |
| Compound 81 | 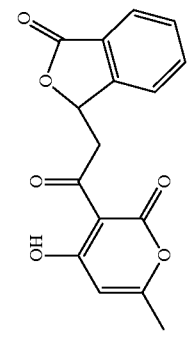 | NMR (ppm) (300 MHz, CD$_3$OD) 2.34 (d, J = 0.82 Hz, 3H), 3.61 (dd, J = 17.85 Hz, J = 7.96 Hz, 1H), 3.81 (dd, J = 17.85 Hz, J = 4.39 Hz, 1H), 6.15 (dd, J = 7.96 Hz, J = 4.39 Hz, 1H), 6.25 (q, J = 0.82 Hz, 1H), 7.63–7.94 (m, 4H).<br><br>IR(cm$^{-1}$) (KBr) 1757, 1739, 1641, 1566, 1458, 1296, 1215, 1069, 1001, 835<br><br>Mass (EI) 300 (M$^+$) | mp. 160–161° C.<br>Elemental analysis<br>Molecular formula C$_{16}$H$_{12}$O$_6$<br>Calcd. C, 63.99; H, 4.03.<br>Found C, 63.67; H, 4.12. |

-continued

| | |
|---|---|
| Compound 82 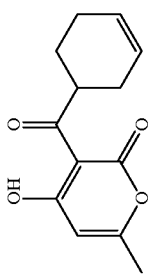 | NMR (ppm) (300 MHz, CD₃OD) 1.52–1.68 (m, 1H), 1.94–2.05 (m, 1H), 2.14–2.31 (m, 4H), 2.33 (d, J = 0.82 Hz, 3H), 3.84–3.95 (m, 1H), 5.75–5.77 (m, 2H), 6.19 (q, J = 0.82 Hz, 1H). IR(cm⁻¹) (KBr) 3096, 3026, 2916, 2838, 1713, 1647, 1655, 1455, 1352, 1236, 998, 867 Mass (EI) 234 (M⁺) | mp. 78–79° C. Elemental analysis Molecular formula C₁₃H₁₄O₄ Calcd. C, 66.65; H, 6.02. Found C, 66.77; H, 6.02. |
| Compound 83 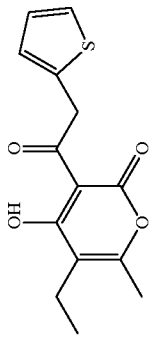 | NMR (ppm) (300 MHz, CD₃OD) 1.14(t, J = 7.41, 3H), 2.36(s, 3H), 4.63(s, 1.5H), 6.98–7.00(m, 2H), 7.31(m, 1H) IR(cm⁻¹) (neat) 1725, 1638, 1607, 1553, 1431 Mass (EI) 278(M⁺) | mp. High resolution mass spectrum Molecular formula C₁₄H₁₄O₄S Calcd. 278.061 Found 278.064 |
| Compound 84 | NMR (ppm) (300 MHz, CD₃OD) 2.33(s, 3H), 2.51(s, 3H), 5.46(s, 1H) IR(cm⁻¹) (KBr) 1688, 1663, 1615, 1599, 1545, 1493, 1357, 1278 Mass (EI) 168(M⁺) | mp. 160–163° C. Elemental analysis Molecular formula C₈H₈O₄ Calcd. C, 57.14; H, 4.80 Found C, 57.01; H, 4.81 |
| Compound 85 | NMR (ppm) (300 MHz, CD₃OD) 2.39(s, 3H), 2.55(s, 3H), 2.69(s, 3H) IR(cm⁻¹) (KBr) 1744, 1705, 1665, 1618, 1562, 1402 Mass (EI) 210(M⁺) | mp. 55–57° C. Molecular formula C₁₀H₁₀O₅ Calcd. C, 57.14; H, 4.80 Found |

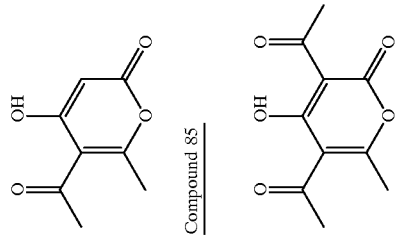

-continued

| | |
|---|---|
| Compound 86 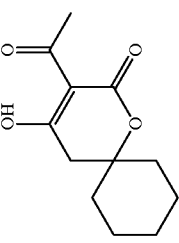 | NMR (ppm) (300 MHz, CD$_3$OD) 1.34–1.53 (m, 1H), 1.53–1.86 (m, 7H), 1.87–2.00 (m, 2H), 2.61 (s, 3H), 2.84 (s, 2H). IR(cm$^{-1}$) (KBr) 2952, 2870, 1707, 1560, 1464, 1415, 1238, 1077, 1054, 762 Mass (EI) 224 (M$^+$) | mp. 64–66° C. Elemental analysis Molecular formula C$_{12}$H$_{16}$O$_4$ Calcd. C, 64.27; H, 7.19. Found C, 64.28; H, 7.18. |
| Compound 87 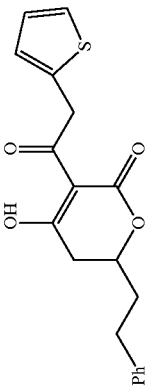 | NMR (ppm) (300 MHz, CD$_3$OD) 1.93–2.18 (m, 2H), 2.71–2.98 (m, 4H), 4.41–4.56 (m, 1H), 4.57 (s, 2H), 6.97–7.03 (m, 2H), 7.20–7.35 (m, 1H + 5H). IR(cm$^{-1}$) (KBr) 3090, 3032, 2926, 1714, 1573, 1433, 1283, 1265, 1076, 943, 908, 713, 698 Mass (EI) 342 (M$^+$) | mp. 65–67° C. Elemental analysis Molecular formula C$_{19}$H$_{18}$O$_4$S Calcd. C, 66.64; H, 5.30; S, 9.37. Found C, 66.54; H, 5.31; S, 9.27. |
| Compound 88 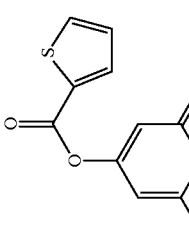 | NMR (ppm) (300 MHz, CD$_3$OD) 2.35 (m, 3H), 6.28 (m, 1H), 6.39 (m, 1H), 7.99–8.01 (m, 1H), 8.06–8.08 (m, 1H). IR(cm$^{-1}$) (KBr) 3086, 1751, 1650, 1574, 1522, 1248, 1225, 1162, 1056, 736 Mass (EI) 236 (M$^+$) | mp. 104–104.5° C. Elemental analysis Molecular formula C$_{11}$H$_8$O$_4$S Calcd. C, 55.92; H, 3.41; S, 13.57. Found C, 55.83; H, 3.49; S, 13.53. |
| Compound 89 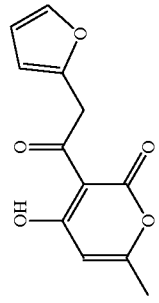 | NMR (ppm) (300 MHz, CD$_3$OD) 2.33(3H, d, J = 0.8 Hz), 4.45(1H, s, enolic proton), 6.20(1H, s), 6.28(1H,m), 6.38(1H,m), 7.45(1H, q, J = 0.82 Hz) IR(cm$^{-1}$) (KBr) 1773, 1752, 1657, 1613, 1460, 1249, 1127, 1052, 1017, 830 Mass | mp. 119.7–120.1° C. Molecular formula C$_{12}$H$_{10}$O$_5$ Calcd. C, 70.06; H, 6.61 Found C, 69.93; H, 6.65 |

-continued

Compound 90

NMR (ppm) (300 MHz, CD$_3$OD)
2.14 (s, 3H), 2.34 (d, J = 0.82 Hz, 3H), 3.85 (s, 2H), 6.22 (q, J = 0.82 Hz, 1H).

IR(cm$^{-1}$) (KBr)
1711, 1651, 1562, 1460, 996, 862, 528

Mass (EI) 214(M$^+$)

mp. 78–79° C.
Elemental analysis
Molecular formula C$_9$H$_{10}$O$_4$S
Calcd. C, 50.45; H, 4.71; S, 14.97.
Found C, 50.39; H, 4.66; S, 14.79.

Compound 91

NMR (ppm) (300 MHz, CD$_3$OD)
1.46 (d, J = 7.14 Hz, 3H), 2.26 (d, J = 0.82 Hz, 3H), 5.27 (q, J = 7.16 Hz, 1H), 6.14 (q, J = 0.82 Hz, 1H), 7.20–7.37 (m, 5H).

IR(cm$^{-1}$) (KBr)
3096, 3030, 2986, 2940, 1717, 1651, 1560, 1460, 1241, 1009, 998, 864, 752, 700

Mass (EI) 258 (M$^+$)

mp. 62–62.5° C.
Elemental analysis
Molecular formula C$_{15}$H$_{14}$O$_4$
Calcd. C, 69.75; H, 5.46.
Found C, 69.71; H, 5.51.

Compound 92

NMR (ppm) (300 MHz, CD$_3$OD)
0.91–0.97 (br m, 3H), 1.28–1.44 (br m, 14H), 1.62–1.84 (br m, 2H), 2.32 (d, J = 0.82 Hz, 3H), 3.09 (t, J = 7.14 Hz, 2H), 6.18 (q, J = 0.82 Hz, 1H).

IR(cm$^{-1}$) (KBr)
3090, 2960, 2924, 2854, 1719, 1653, 1611, 1557, 1458, 1249, 996, 930

Mass (EI) 294 (M$^+$)

mp. 84–85° C.
Elemental analysis
Molecular formula C$_{17}$H$_{26}$O$_4$
Calcd. C, 69.36; H, 8.90.
Found C, 69.38; H, 8.99.

Compound 93

NMR (ppm) (300 MHz, CD$_3$OD)
2.11–2.24 (m, 1H), 2.27–2.38 (m, 1H), 2.33 (d, J = 0.82 Hz, 3H), 3.81–4.08 (m, 4H), 4.33–4.42 (m, 1H), 6.21 (q, J = 0.82 Hz, 1H).

IR(cm$^{-1}$) (KBr)
3047, 2956, 2872, 1723, 1644, 1611, 1564, 1454, 1238, 1064, 998

Mass (EI) 224 (M$^+$)

mp. 83–84° C.
Elemental analysis
Molecular formula C$_{11}$H$_{12}$O$_5$
Calcd. C, 58.92; H, 5.40.
Found C, 58.95; H, 5.41.

-continued

| Compound 94 | 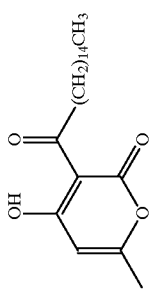 | NMR (ppm) (300 MHz, CD$_3$OD) 0.91–0.97 (br m, 3H), 1.28–1.44 (br m, 26H), 1.62–1.84 (br m, 2H), 2.32 (d, J = 0.82 Hz, 3H), 3.07 (t, J = 7.14 Hz, 2H), 6.18 (q, J = 0.82 Hz, 1H). IR(cm$^{-1}$) (KBr) 2918, 2854, 1719, 1655, 1562, 1473, 1245, 994, 716 Mass (EI) 364 (M$^+$) | mp. 89–90° C. Elemental analysis Molecular formula C$_{22}$H$_{36}$O$_4$ Calcd. C, 72.49; H, 9.96. Found C, 72.47; H, 9.95. |
|---|---|---|---|
| Compound 95 | 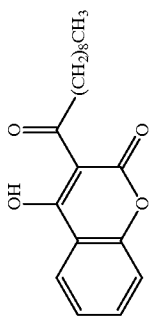 | NMR (ppm) (300 MHz, CDCl$_3$) 0.85–0.91 (br m, 3H), 1.24–1.43 (br m, 14H), 1.63–1.77 (br m, 2H), 3.20 (t, J = 7.42 Hz, 2H), 7.29–7.37 (m, 2H), 7.66–7.72 (m, 1H), 8.05–8.09 (m, 1H). IR(cm$^{-1}$) (KBr) 2924, 2858, 1719, 1609, 1549, 1433, 1228, 1201, 1031, 980, 899 Mass (EI) 316 (M$^+$) | mp. 109–110° C. Elemental analysis Molecular formula C$_{19}$H$_{24}$O$_4$ Calcd. C, 72.12; H, 7.64. Found C, 72.08; H, 7.68. |
| Compound 96 | 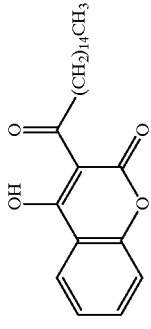 | NMR (ppm) (300 MHz, CDCl$_3$) 0.85–0.91 (br m, 3H), 1.24–1.46 (br m, 26H), 1.63–1.77 (br m, 2H), 3.20 (t, J = 7.42 Hz, 2H), 7.29–7.37 (m, 2H), 7.66–7.72 (m, 1H), 8.05–8.09 (m, 1H). IR(cm$^{-1}$) (KBr) 2956, 2920, 2856, 1715, 1607, 1551, 1437, 1230, 1031, 982, 899, 766 Mass (EI) 400 (M$^+$) | mp. 112–114° C. Elemental analysis Molecular formula C$_{25}$H$_{36}$O$_4$ Calcd. C, 74.96; H, 9.06. Found C, 74.98; H, 9.09. |
| Compound 97 | 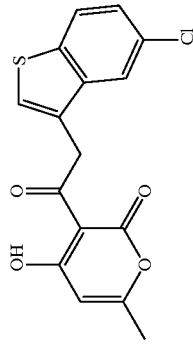 | NMR (ppm) (300 MHz, CD$_3$OD) 2.35 (d, J = 0.82 Hz, 3H), 4.66 (s, 2H), 6.21 (q, J = 0.82 Hz, 1H), 7.36–7.39 (m, 1H), 7.59 (s, 1H), 7.84–7.91 (m, 2H). IR(cm$^{-1}$) (KBr) 3096, 1717, 1636, 1618, 1572, 1450, 1419, 1077, 996, 942, 830, 787 Mass (EI) 334 (M$^+$) | mp. 172–173° C. Elemental analysis Molecular formula C$_{16}$H$_{11}$ClO$_4$S Calcd. C, 57.40; H, 3.31; Cl, 10.59; S, 9.58. Found C, 57.08; H, 3.50; Cl, 10.69; S, 9.56. |

-continued

| | |
|---|---|
| Compound 98 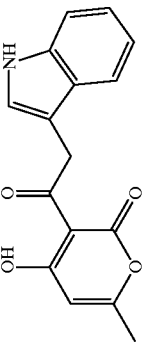 | NMR (ppm) (300 MHz, CD₃OD) 2.31 (d, J = 0.82 Hz, 3H), 4.51 (s, 2H), 6.15 (q, J = 0.82 Hz, 1H), 7.00–7.15 (m, 2H), 7.26 (s, 1H), 7.35–7.38 (m, 1H), 7.58–7.61 (m, 1H).<br><br>IR(cm⁻¹) (KBr)<br>3376, 3084, 1715, 1644, 1607, 1553, 1452, 1238, 1098, 996, 942, 855, 737<br><br>Mass (EI) 283 (M⁺) | mp. 161–162° C.<br>Elemental analysis<br>Molecular formula C₁₆H₁₃NO₄<br>Calcd. C, 67.84; H, 4.63; N, 4.95.<br>Found C, 67.50; H, 4.63; N, 4.95. |
| Compound 99 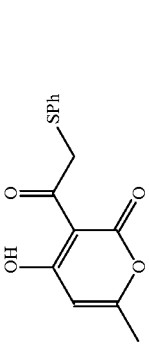 | NMR (ppm) (300 MHz, CD₃OD) 2.35 (d, J = 0.82 Hz, 3H), 4.34 (s, 2H), 6.22 (q, J = 0.82 Hz, 1H), 7.26–7.33 (m, 3H), 7.43–7.46 (m, 2H).<br><br>IR(cm⁻¹) (KBr)<br>1717, 1636, 1618, 1564, 1454, 1390, 1168, 994, 938, 743<br><br>Mass (EI) 276 (M⁺) | mp. 84–85° C.<br>Elemental analysis<br>Molecular formula C₁₄H₁₂O₄S<br>Calcd. C, 60.85; H, 4.38; S, 11.61.<br>Found C, 60.85; H, 4.51; S, 11.55. |
| Compound 100 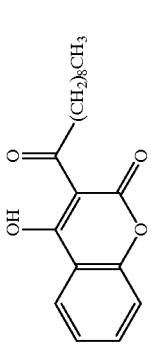 | NMR (ppm) (300 MHz, CD₃OD) 2.35 (d, J = 0.82 Hz, 3H), 2.39 (m, 3H), 4.71 (s, 2H), 6.22 (q, J = 0.82 Hz, 1H), 7.29–7.42 (m, 2H), 7.71–7.74 (m, 1H), 7.78–7.82 (m, 1H).<br><br>IR(cm⁻¹) (KBr)<br>1744, 1640, 1599, 1555, 1460, 1421, 1267, 1000, 938, 826, 758<br><br>Mass (EI) 314 (M⁺) | mp. 155–156° C.<br>Elemental analysis<br>Molecular formula C₁₇H₁₄O₄S<br>Calcd. C, 64.95; H, 4.49; S, 10.20.<br>Found C, 64.84; H, 4.53; S, 10.20. |
| Compound 101 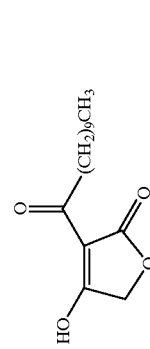 | NMR (ppm) (300 MHz, CDCl₃) 0.93(3H, t, J = 6.6Hz), 1.33(broad s, 14H), 1.65(2H, quint, J = 7.4Hz), 2.84(2H, t, J = 7.4Hz), 4.46(2H, s)<br><br>IR(cm⁻¹) (KBr)<br>1773, 1750, 1663, 1615<br><br>Mass (EI) 268(M⁺) | mp. 85.7–87.2° C.<br>Molecular formula C₁₅H₂₄O₄<br>Calcd. C, 67.14; H, 9.01<br>Found |

| | |
|---|---|
| Compound 102 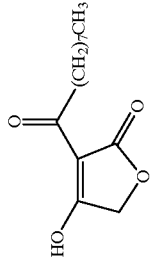 | NMR (ppm) (300 MHz, CDCl$_3$) 0.94(3H, t, J = 6.6Hz), 1.33(10H, broad s), 1.63(2H, quint, J = 7.4 Hz), 2.82(2H, t, J = 7.4Hz), 4.35(2H, s)<br>IR(cm$^{-1}$) (KBr) 1773, 1748, 1661,1615<br>Mass (EI) 240(M$^+$) | mp. 79.7–80.3° C.<br>Molecular formula C$_{13}$H$_{20}$O$_4$<br>Calcd. C, 64.98; H, 8.39<br>Found C, 65.20; H, 8.60 |
| Compound 103 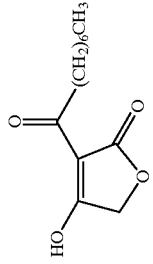 | NMR (ppm) (300 MHz, CDCl$_3$) 0.94(3H, t, J = 6.86 Hz), 1.42–1.34(m, 8H), 1.7(2H, quint, J = 7.4 Hz), 2.84(2H, t, J = 7.4 Hz), 4.72(2H, s)<br>IR(cm$^{-1}$) (KBr) 1773, 1750, 1661, 1615<br>Mass (EI) 226(M$^+$) | mp. 68.9–69.5° C.<br>Elemental analysis<br>Molecular formula C$_{12}$H$_{18}$O$_4$<br>Calcd. C, 63.70; H, 8.02<br>Found C, 63.68; H, 7.97 |
| Compound 104 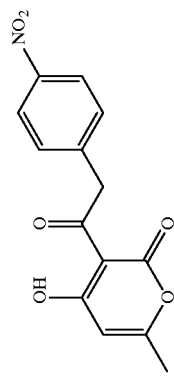 | NMR (ppm) (300 MHz, CD$_3$OD) 2.34 (d, J = 0.82 Hz, 3H), 4.58 (s, 2H), 6.22 (q, J = 0.82 Hz, 1H), 7.56 (d, J = 8.2 Hz, 2H), 8.23 (d, J = 8.2 Hz, 2H).<br>IR(cm$^{-1}$) (KBr) 1721, 1640, 1607, 1562, 1518, 1348, 996, 938, 830, 737<br>Mass (EI) 289 (M$^+$) | mp. 202–203° C.<br>Elemental analysis<br>Molecular formula C$_{14}$H$_{11}$NO$_6$<br>Calcd. C, 58.13; H, 3.83; N, 4.84.<br>Found C, 57.79; H, 3.94; N, 4.83. |
| Compound 105 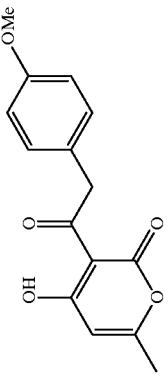 | NMR (ppm) (300 MHz, CD$_3$OD) 2.32 (d, J = 0.82 Hz, 3H), 3.80 (s, 3H), 4.33 (s, 2H), 6.18 (q, J = 0.82 Hz, 1H), 6.88 (d, J = 8.8 Hz, 2H), 7.24 (d, J = 8.8 Hz, 2H).<br>IR(cm$^{-1}$) (KBr) 3082, 2930, 1702, 1651, 1615, 1553, 1518, 1458, 1301, 1257, 1183, 1033, 994, 946, 791<br>Mass (EI) 274 (M$^+$) | mp. 109–110° C.<br>Elemental analysis<br>Molecular formula C$_{15}$H$_{14}$O$_5$<br>Calcd. C, 65.69; H, 5.15.<br>Found C, 65.66; H, 5.18. |

-continued

| | | |
|---|---|---|
| Compound 106 | 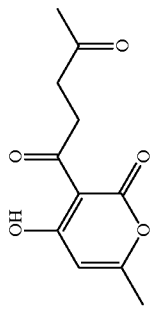 | NMR (ppm) (300 MHz, CD₃OD) 2.25 (s, 3H), 2.33 (d, J = 0.82 Hz, 3H), 2.88 (t, J = 6.3 Hz, 2H), 3.34 (t, J = 6.3 Hz, 2H), 6 19 (q, J = 0.82 Hz, 1H).<br><br>IR(cm⁻¹) (KBr) 3102, 2922, 1711, 1638, 1624, 1553, 1446, 1427, 1373, 1241, 1168, 994, 924, 855<br><br>Mass (EI) 224 (M⁺) | mp. 133–134° C.<br>Elemental analysis<br>Molecular formula C₁₁H₁₂O₅<br>Calcd. C, 58.92; H, 5.40.<br>Found C, 58.85; H, 5.35. |
| Compound 107 | 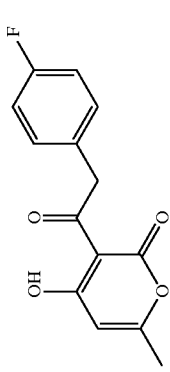 | NMR (ppm) (300 MHz, CD₃OD) 2.33 (d, J = 0.82 Hz, 3H), 4.40 (s, 2H), 6.20 (q, J = 0.82 Hz, 1H), 7.03–7.09 (m, 2H), 7.30–7.34 (m, 2H).<br><br>IR(cm⁻¹) (KBr) 1738, 1653, 1607, 1564, 1514, 1462, 1319, 1218, 992, 928, 845, 793<br><br>Mass (EI) 262 (M⁺) | mp. 159–160° C.<br>Elemental analysis<br>Molecular formula C₁₄H₁₁FO₄<br>Calcd. C, 64.12; H, 4.23.<br>Found C, 63.93; H, 4.27. |
| Compound 108 | 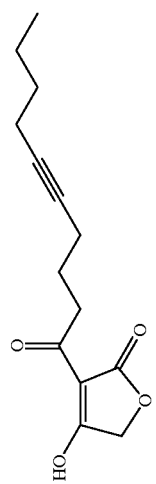 | NMR (ppm) (300 MHz, CDCl₃) 0.95(3H, t, J = 7.1 Hz), 1.47(4H, m), 1.85(2H, quint, J = 7.4Hz), 2.17(2H, m), 2.27(2H, m), 3.03(2H, t, J = 7.1 Hz), 4.74(2H, s)<br><br>IR(cm⁻¹) (KBr) 1773, 1752, 1657, 1607, 404<br><br>Mass | mp. 51.5–52° C.<br>Molecular formula C₁₄H₁₈O₄<br>Calcd. C, 67.18; H, 7.25<br>Found |
| Compound 109 | 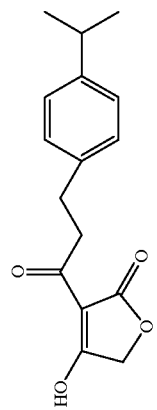 | NMR (ppm) (300 MHz, CDCl₃) 1.231(d,J = 6.86,1.8H), 1.234(d,J = 6.86,4.2H), 2.88(sept, J = 6.86,1H), 2.98(t, J = 7.96, 2H), 3.24(t, J = 7.96, 2H), 4.53(s, 0.60H),4.53(s, 1.40H),7.17(s, 4H)<br><br>IR(cm⁻¹) (KBr) 1773, 1752, 1657, 1613, 1460, 1249, 1127, 1052, 1017, 830<br><br>Mass (EI) 274(M⁺) | mp. 86.2–87.3° C.<br>Elemental analysis<br>Molecular formula C₁₆H₁₈O₄<br>Calcd. C, 70.06; H, 6.61<br>Found C, 69.93; H, 6.65 |

-continued

Compound 110

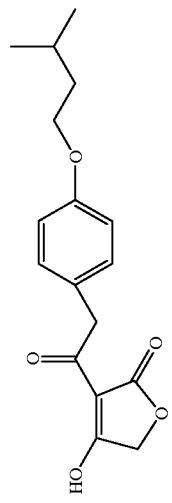

NMR (ppm) (300 MHz, CDCl$_3$)
0.95(d, J = 6.59, 6H), 1.66(dd, J = 13.59, 2H), 1.81(sept,J = 6.59, 1H), 3.96(t,J = 6.59, 2H), 4.13(s, 2H), 4.58(s, 0.6H),4.67(s, 1.4H), 6.86(d, J = 8.51, 6H), 7.26(d, J = 12.96, 2H)
IR(cm$^{-1}$) (KBr)
1752, 1671, 1605, 1510, 1388, 1286, 1249, 1178, 1040, 1013, 982, 870, 795

Mass (EI) 304(M$^+$)

mp. 82.1–82.9° C.
Elemental analysis
Molecular formula C$_{17}$H$_{20}$O$_5$
Calcd. C, 67.09; H, 6.62
Found C, 66.92; H, 6.64

Compound 111

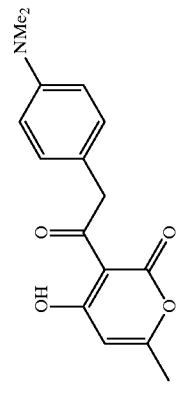

NMR (ppm) (300 MHz, CD$_3$OD)
2.31 (d, J = 0.82 Hz, 3H), 2.93 (s, 6H), 4.28 (s, 2H), 6.16 (q, J = 0.82 Hz, 1H), 6.77 (d, J = 8.8 Hz, 2H), 7.17 (d, J = 8.8 Hz, 2H).
IR(cm$^{-1}$) (KBr)
1711, 1655, 1620, 1562, 1531, 1462, 1359, 1238, 1170, 996, 783

Mass (EI) 287 (M$^+$)

mp. 158–159° C.
Elemental analysis
Molecular formula C$_{16}$H$_{17}$NO$_4$
Calcd. C, 66.88; H, 5.96; N, 4.88.
Found C, 66.70; H, 5.96; N, 4.98.

Compound 112

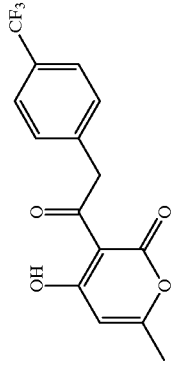

NMR (ppm) (300 MHz, CD$_3$OD)
2.33 (d, J = 0.82 Hz, 3H), 4.52 (s, 2H), 6.21 (q, J = 0.82 Hz, 1H), 7.50 (d, J =8.8 Hz, 2H), 7.64 (d, J = 8.8 Hz, 2H).
IR(cm$^{-1}$) (KBr)
1719, 1638, 1574, 1421, 1332, 1160, 1116, 1069, 998, 830

Mass (EI) 312 (M$^+$)

mp. 161–162° C.
Elemental analysis
Molecular formula C$_{15}$H$_{11}$F$_3$O$_4$
Calcd. C, 57.70; H, 3.55.
Found C, 57.54; H, 3.58.

Compound 113

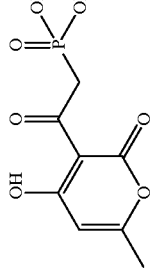

NMR (ppm) (300 MHz, CD$_3$OD)
2.33 (d, J = 0.82 Hz, 3H), 3.95 (d, J = 22.8 Hz, 2H), 6.21 (q, J = 0.82 Hz, 1H).
IR(cm$^{-1}$) (KBr)
2920, 2236, 1723, 1680, 1642, 1603, 1557, 1458, 1241, 1218, 1129, 1023, 1006, 951
Mass (EI) 248 (M$^+$)

mp. 196–197° C.
Elemental analysis
Molecular formula C$_9$H$_{11}$O$_7$P
Calcd. C, 38.73; H, 3.66.
Found C, 38.50; H, 3.64.

-continued

| Compound 114 | 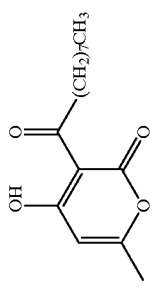 | NMR (ppm) (300 MHz, CD₃OD) 0.94 (br t, J = 6.8 Hz, 3H), 1.27–1.47 (br m, 10H), 1.68 (br m, 2H), 2.32 (d, J = 0.82 Hz, 3H), 3.06 (t, J = 7.4 Hz, 2H), 4.28 (s, 2H), 6.18 (q,J = 0.82 Hz, 1H). IR(cm⁻¹) (KBr) 3090, 2962, 2969, 2856, 1715, 1557, 1618, 1564, 1452, 1236, 1183, 996 Mass (EI) 266 (M⁺) | mp. 83–84° C. Elemental analysis Molecular formula C₁₅H₂₂O₄ Calcd. C, 67.64; H, 8.33. Found C, 67.59; H, 8.18. |
|---|---|---|---|
| Compound 115 | 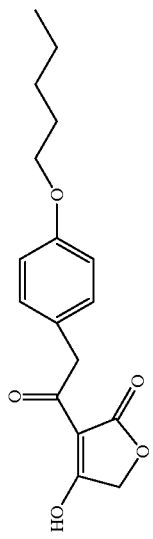 | NMR (ppm) (300 MHz, CDCl₃) 0.90–0.94(m, 3H), 1.36–1.44(m, 4H), 1.75–1.79(m, 2H), 3.91–3.95 (m, 2H), 4.13(s, 2H), 4.58(s, 0.6H), 4.67(s, 1.40H), 6.84–6.86(m, 2H), 7.26–7.29(m, 2H) IR(cm⁻¹) (KBr) 1752, 1671, 1657, 1609, 1514, 1421, 1390, 1253, 1180, 1038, 876, 801 Mass (EI) 304(M⁺) | mp. 84.9–86.5° C. Elemental analysis Molecular formula C₁₇H₂₀O₅ Calcd. C, 67.09; H, 6.62 Found C, 67.00; H, 6.54 |
| Compound 116 | 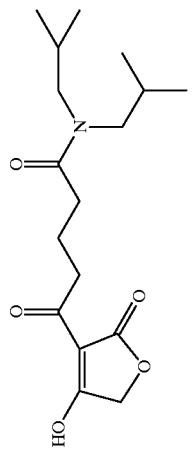 | NMR (ppm) (300 MHz, CDCl₃) 0.86–0.93(m, 12H), 1.88–2.11(m, 4H), 2.42–2.49(m, 3H), 2.99–3.22(m, 5H), 4.65(s, 1H) IR(cm⁻¹) (KBr) 1738, 1719, 1638, 1620, 1562, 1460, 1286, 1255, 1234, 849, 681, 629 Mass (EI) 325(M⁺) | mp. High resolution mass spectrum Molecular formula C₁₇H₂₇NO₅ Calcd. 325.189 Found 325.190 |
| Compound 117 | 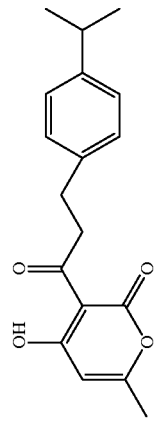 | NMR (ppm) (300 MHz, CDCl₃) 1.24(d, J = 6.87, 6H), 2.27(s, 3H), 2.89(sept, J = 6.87, 1H), 2.93(t, J = 7.41, 2H), 3.41(t, J = 7.41, 2H), 5.94(s, 1H), 7.14–7.26(m, 4H) IR(cm⁻¹) (KBr) 1738, 1719, 1642, 1609, 1562, 980, 932, 833, 822 Mass (EI) 300(M⁺) | mp. 80.6–81.4° C. Elemental analysis Molecular formula C₁₈H₂₀O₄ Calcd. C, 71.98; H, 6.71 Found C, 71.81; H, 6.66 |

-continued

Compound 118

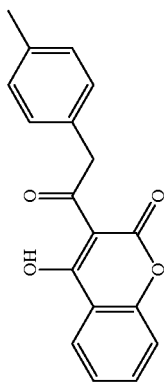

NMR (ppm) (360 MHz, CD$_3$OD)
2.35 (s, 3H), 4.49 (s, 2H), 7.14–7.24 (m, 4H), 7.38–7.48 (m, 2H), 7.80–7.86 (m, 1H), 8.11–8.14 (m, 1H).
IR(cm$^{-1}$) (KBr)
1729, 1622, 1549, 1508, 1444, 1185, 1029, 984, 758
Mass (EI) 294 (M$^+$)

mp. 122–123° C.
Elemental analysis
Molecular formula C$_{18}$H$_{14}$O$_4$
Calcd. C, 73.46; H, 4.80.
Found C, 73.25; H, 4.76.

Compound 119

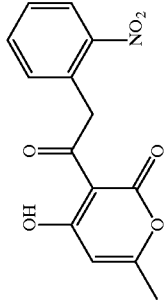

NMR (ppm) (300 MHz, CD$_3$OD)
2.37 (d, J = 0.82 Hz, 3H), 4.84 (s, 2H), 6.24 (q, J = 0.82 Hz, 1H), 7.47–7.51 (m, 1H), 7.55–7.61 (m, 1H), 7.69–7.75 (m, 1H), 8.16–8.19 (m, 1H).
IR(cm$^{-1}$) (KBr)
1721, 1653, 1624, 1562, 1520, 1456, 1350, 1317, 994, 731
Mass (EI) 289 (M$^+$)

mp. 170–172° C.
Elemental analysis
Molecular formula C$_{14}$H$_{11}$NO$_6$
Calcd. C, 58.15; H, 3.96; N, 5.09.
Found C, 58.13; H, 3.83; N, 4.84.

Compound 120

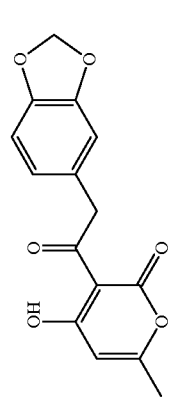

NMR (ppm) (300 MHz, CD$_3$OD)
2.32 (d, J = 0.82 Hz, 3H), 4.32 (s, 2H), 5.95 (s, 2H), 6.19 (q, J = 0.82 Hz, 1H), 6.77 (br s, 1H), 6.78 (s, 1H), 6.82 (br s, 1H).
IR(cm$^{-1}$) (KBr)
3082, 2930, 1707, 1651, 1622, 1560, 1497, 1450, 1259, 1040, 996, 944, 928, 793
Mass (EI) 288 (M$^+$)

mp. 187–188° C.
Elemental analysis
Molecular formula C$_{15}$H$_{12}$O$_6$
Calcd. C, 62.49; H, 4.20.
Found C, 62.37; H, 4.24.

Compound 121

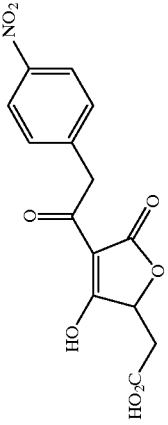

NMR (ppm) (300 MHz, CDCl$_3$)
2.84(dd,J1 = 6.6 Hz,J2 = 17.3 Hz, 1H), 3.05 (dd,J1 = 3.8 Hz,J2 = 17.3 Hz, 1H), 5.06 (dd, J1 = 3.8 Hz, J2 = 6.6 Hz, 1H), 7.61 (d, J = 8.8 Hz, 2H), 8.22 (d, J = 8.8 Hz, 2H)
IR(cm$^{-1}$) (KBr)
3278, 1748, 1659, 1605, 1514, 1352, 1241, 1170, 1021
Mass (EI) 321 (M$^+$)

mp. 194–196° C.
Elemental analysis
Molecular formula C$_{14}$H$_{11}$NO$_8$
Calcd. C, 81.92; H, 3.52; N, 4.28.
Found C, 52.34; H, 3.45; N, 4.36.

-continued

| Compound 122 | 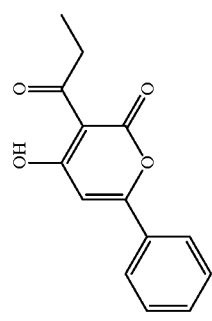 | NMR (ppm) (300 MHz, CD$_3$OD) 1.21 (t, J = 7.14 Hz, 3H), 3.17 (q, J = 7.14 Hz, 2H), 6.93 (s, 2H), 7.58–7.63 (m, 3H), 8.00–8.04 (m, 2H). IR(cm$^{-1}$) (KBr) 1722, 1632, 1558, 1437, 1240, 1057, 887, 773, 685 Mass (EI) 244 (M$^+$) | mp. 153–155° C. Elemental analysis Molecular formula C$_{14}$H$_{12}$O$_4$ Calcd. C, 68.84; H, 4.95. Found C, 68.67; H, 4.99. |
|---|---|---|---|
| Compound 123 | 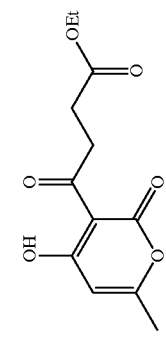 | NMR (ppm) (300 MHz, CD$_3$OD) 1.28 (t, J = 7.14 Hz, 3H), 2.33 (d, J = 0.82 Hz, 3H), 2.69 (t, J = 6.32 Hz, 2H), 3.40 (t, J = 6.32 Hz, 2H), 4.17 (q, J = 7.14 Hz, 2H), 6.20 (q, J = 0.82 Hz, 1H). IR(cm$^{-1}$) (KBr) 1734, 1719, 1651, 1562, 1180, 1156, 998, 861, 806 Mass (EI) 254 (M$^+$) | mp. 80.5–81.0° C. Elemental analysis Molecular formula C$_{12}$H$_{14}$O$_6$ Calcd. C, 56.69; H, 5.55. Found C, 56.52; H, 5.50. |
| Compound 124 | 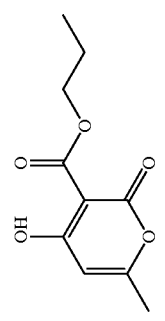 | NMR (ppm) (300 MHz, CD$_3$OD) 1.06 (t, J = 7.14 Hz, 3H), 1.82 (qd, J1 = 7.14 Hz, J2 = 6.59 Hz, 2H), 2.32 (d, J = 0.82 Hz, 3H), 4.34 (t, J = 6.59 Hz, 2H), 6.21 (q, J = 0.82 Hz, 1H). IR(cm$^{-1}$) (KBr) 3100, 2976, 2884, 1742, 1651, 1570, 1423, 1354, 1274, 1102, 996 Mass (EI) 212 (M$^+$) | mp. 64–68° C. Elemental analysis Molecular formula C$_{10}$H$_{12}$O$_5$ Calcd. C, 56.60; H, 5.70. Found C, 57.32; H, 5.66. |
| Compound 125 | 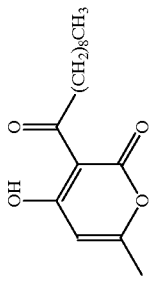 | NMR (ppm) (300 MHz, CD$_3$OD) 0.91–0.97 (br m, 3H), 1.28–1.44 (br m, 12H), 1.62–1.84 (br m, 2H), 2.32 (d, J = 0.82 Hz, 3H), 3.06 (t, J = 7.14 Hz, 2H), 6.18 (q, J = 0.82 Hz, 1H). IR(cm$^{-1}$) (KBr) 2954, 2918, 2854, 1720, 1656, 1562, 1474, 1460, 996 Mass (EI) 280 (M$^+$) | mp. 73–74° C. Elemental analysis Molecular formula C$_{16}$H$_{24}$O$_4$ Calcd. C, 68.54; H, 8.63. Found C, 68.44; H, 8.65. |

-continued

| Compound 126 | 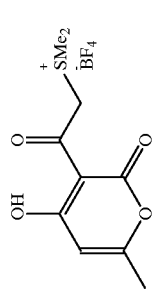 | NMR (ppm) (300 MHz, CD$_3$OD) 2.39 (d, J = 0.82 Hz, 3H), 3.03 (s, 6H), 6.33 (q, J = 0.82 Hz, 1H). IR(cm$^{-1}$) (KBr) 3046, 2994, 2974, 2928, 2880, 1740, 1721, 1642, 1576, 1452, 1259, 1083, 1036, 988 Mass (FAB) 230 ([M-BF$_4$]) | mp. 154–161° C. (dec) Elemental analysis Molecular formula C$_{10}$H$_{13}$BF$_4$O$_4$S Calcd. C, 38.00; H, 4.15; S, 10.15. Found C, 37.89; H, 4.15; S, 10.40. |
| Compound 127 | 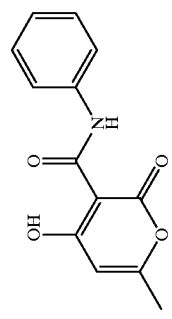 | NMR (ppm) (300 MHz, CD$_3$OD) 2.35 (d, J = 0.82 Hz, 3H), 6.27 (q, J = 0.82 Hz, 1H), 7.18–7.23 (m, 1H), 7.37–7.43 (m, 2H), 7.64–7.67 (m, 2H). IR(cm$^{-1}$) (KBr) 3070, 1707, 1603, 1547, 1450, 1251, 998, 965, 754 Mass (EI) 245 (M$^+$) | mp. 155–158° C. Elemental analysis Molecular formula C$_{13}$H$_{11}$NO$_4$ Calcd. C, 63.67; H, 4.52; N, 5.71. Found C, 63.68; H, 4.58 N, 5.93 |
| Compound 128 | 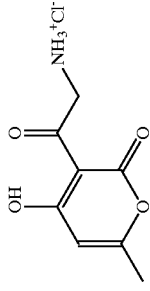 | NMR (ppm) (300 MHz, CD$_3$OD) 2.38 (br s, 3H), 4.48 (s, 2H), 6.32 (br s, 1H). IR(cm$^{-1}$) (KBr) 2970, 2840, 1709, 1640, 1557, 1417, 1272, 1228, 1170, 996, 862 Mass (FAB) 185 ([M-Cl]$^+$) | mp. 210–239° C. (dec) Elemental analysis Molecular formula C$_8$H$_{10}$ClNO$_4$ Calcd. C, 43.75; H, 4.59; N, 6.38; Cl, 16.14. Found C, 43.63; H, 4.61; N, 6.36; Cl, 16.22. |
| Compound 129 | 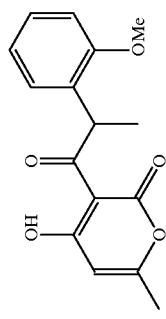 | NMR (ppm) (300 MHz, CD$_3$OD) 1.44 (d, J = 6.87 Hz, 3H), 2.29 (d, J = 0.82 Hz, 3H), 3.81 (s, 3H), 5.35 (q, J = 6.87 Hz, 1H), 6.17 (q, J = 0.82 Hz, 1H), 6.89–6.97 (m, 2H), 7.09–7.13 (m, 1H), 7.21–7.25(m,1H). IR(cm$^{-1}$) (KBr) 3020, 2980, 2954, 2934, 1734, 1640, 1609, 1553, 1448, 1255, 1033, 998, 911 Mass (EI) 288 (M$^+$) | mp. 125–126° C. Elemental analysis Molecular formula C$_{16}$H$_{16}$O$_5$ Calcd. C, 66.66; H, 5.94. Found C, 66.44; H, 5.63. |

-continued

| Compound 130 | 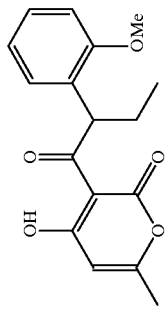 | NMR (ppm) (300 MHz, CD₃OD) 0.98 (t, J = 7.42 Hz, 3H), 1.71–1.86 (m, 1H), 1.99–2.24 (m, 1H), 2.28 (d, J = 0.82 Hz, 3H), 3.83 (s, 3H), 5.33 (t, J = 7.14 Hz, 1H), 6.15 (q, J = 0.82 Hz, 1H), 6.90–6.98 (m, 2H), 7.10–7.14 (m, 1H), 7.20–7.27 (m, 1H). IR(cm⁻¹)(KBr) 2974, 2932, 2874, 1744, 1638, 1603, 1560, 1460, 1241, 998<br><br>Mass (EI) 302 (M⁺) | mp. 69–71° C. Elemental analysis Molecular formula C₁₇H₁₈O₅ Calcd. C, 67.54; H, 6.00. Found C, 67.61; H, 6.01. |
|---|---|---|---|
| Compound 131 | 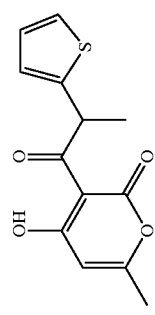 | NMR (ppm) (300 MHz, CD₃OD) 1.55 (d, J = 6.87 Hz, 3H), 2.31 (d, J = 0.82 Hz, 3H), 5.65 (q, J = 6.87 Hz, 1H), 6.18 (q, J = 0.82 Hz, 1H), 6.93–6.97 (m, 1H), 7.01–7.03 (m, 1H), 7.28–7.30 (m, 1H) IR(cm⁻¹)(KBr) 1729, 1644, 1609, 1562, 1458, 1236, 998, 913, 702<br><br>Mass (EI) 264 (M⁺) | mp. High resolution mass spectrum Molecular formula C₁₃H₁₂O₄S Calcd. 264.0456 Found 264.0426 |
| Compound 132 | 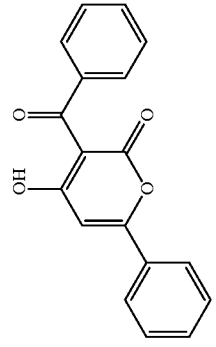 | NMR (ppm) (300 MHz, CDCl₃) 6.66(s, 1H), 7.43–7.58(m, 6H), 7.67–7.71(m, 2H), 7.89–7.93(m, 2H) IR(cm⁻¹) (KBr) 1742, 1628, 1549<br><br>Mass (CI) 293(M + H)⁺ | mp. 170–175° C. Elemental analysis Molecular formula C₁₈H₁₂O₄ Calcd. C, 73.97; H, 4.14 Found C, 73.98; H, 4.18 |
| Compound 133 | 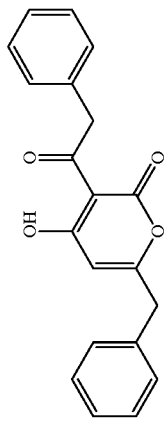 | NMR (ppm) (300 MHz, CDCl₃) 3.79(s, 2H), 4.41(s, 2H), 5.79(s, 1H), 7.23–7.39(m, 10H) IR(cm⁻¹) (KBr) 1729, 1649, 1564, 1454, 967, 731<br><br>Mass (EI) 320(M⁺) | mp. 122–127° C. Elemental analysis Molecular formula C₂₀H₁₆O₄ Calcd. C, 74.99; H, 5.03 Found C, 74.83; H, 5.04 |

-continued

| Compound 134 | 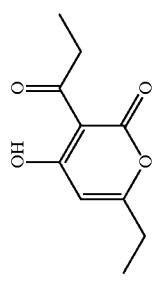 | NMR (ppm) (300 MHz, CDCl₃) 1.16(t, J = 7.14, 0.7H), 1.17(t, J = 7.14, 2.3H), 1.25(t, J = 7.41, 3H), 2.54(qd, J = 0.82, 7.41, 2H), 3.11(q, J = 7.14, 0.45H), 3.12(q, J = 7.14, 1.55H), 5.94(t, J = 0.82, 1H), IR(cm⁻¹) (KBr) 1738, 1642, 1572, 1396, 828 Mass (EI) 196(M⁺) | mp. 70–72° C. Elemental analysis Molecular formula C₁₀H₁₂O₄ Calcd. C, 61.22; H, 6.16 Found C, 61.22; H, 6.19 |

Compound 135

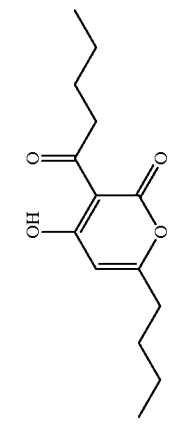

NMR (ppm) (300 MHz, CDCl₃)
0.99(t, J = 7.41, 3H), 1.00(t, J = 7.41, 3H), 1.65–1.76(m, 4H), 2.46(td, J = 0.55, 7.41, 2H), 3.06(t, J = 7.41, 2H), 5.92(d, J = 0.55, 1H)

IR(cm⁻¹) (neat)
2972, 1717, 1644, 1409, 1562, 1448, 996

Mass (EI) 224(M⁺)

mp. 91–98° C.
High resolution mass spectrum
Molecular formula C₁₂H₁₆O₄
Calcd. 224.105
Found 224.105

Compound 136

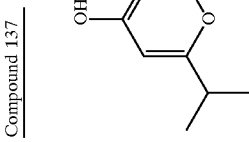

NMR (ppm) (300 MHz, CDCl₃)
0.94(t, J = 7.41, 6H), 1.35–1.46(m, 4H), 1.59–1.71(m, 4H), 2.49(t, J = 7.41, 2H), 3.08(t, J = 7.41, 2H), 5.92(d, J = 0.55, 1H)

IR(cm⁻¹) (KBr)
2964, 1725, 1638, 1562, 1452

Mass (EI) 252(M⁺)

mp. 40–41° C.
Elemental analysis
Molecular formula C₁₄H₂₀O₄
Calcd. C, 66.65; H, 7.99
Found C, 66.53; H, 7.95

Compound 137

NMR (ppm) (300 MHz, CDCl₃)
1.17(d, J = 6.86, 0.9H), 1.18(d, J = 6.86, 2.1H), 1.26(d, J = 6.86, 3H), 2.73(m, 1H), 3.95(m, 1H), 5.92(d, J = 0.55, 1H)

IR(cm⁻¹) (neat)
2978, 1736, 1625, 1607, 1560, 1236, 1075, 982

Mass (EI) 224(M⁺)

mp. 91° C.(0.02 mmHg)
High resolution mass spectrum
Molecular formula C₁₂H₁₆O₄
Calcd. 224.105
Found 224.104

-continued

| Compound 138 | 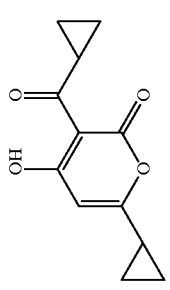 | NMR (ppm) (300 MHz, CDCl₃)<br>1.05–1.17(m, 6H), 1.20–1.30(m, 6H), 1.79(m, 1H), 3.54(m, 1H), 3.95(m, 1H), 5.97(d, J = 1.10, 1H)<br>IR(cm⁻¹) (KBr)<br>1721, 1640, 1547, 1437, 986<br>Mass (EI) 220(M⁺) | mp. 61–62° C.<br>Elemental analysis<br>Molecular formula C₁₂H₁₂O₄<br>Calcd. C, 65.45; H, 5.49<br>Found C, 65.34; H, 5.56 |
|---|---|---|---|
| Compound 139 | 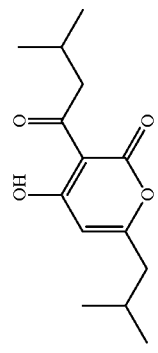 | NMR (ppm) (300 MHz, CDCl₃)<br>0.98(d, J = 6.86, 6H), 0.99(d, J = 6.86, 6H), 2.12(m, 1H), 2.22(m, 1H), 2.34(d, J = 7.14, 2H), 2.96(dd, J = 1.10, 6.86, 2H), 5.91(s, 1H)<br>IR(cm⁻¹) (neat)<br>1966, 1734, 1638, 1560, 1456, 1002, 936<br>Mass (EI) 252(M⁺) | mp. 103–104° C.(0.07 mmHg)<br>High resolution mass spectrum<br>Molecular formula C₁₄H₂₀O₄<br>Calcd. 252.136<br>Found 252.138 |
| Compound 140 | 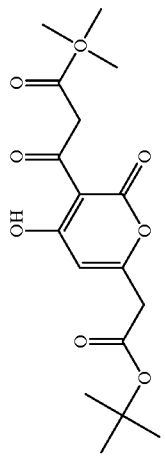 | NMR (ppm) (300 MHz, CDCl₃)<br>1.471(s, 9H), 1.475(s, 9H), 3.45(s, 2H), 3.94(d,J = 1.10, 2H), 6.14(s, 1H)<br>IR(cm⁻¹) (neat)<br>2984, 1734, 1653, 1570, 1456, 1396, 1373, 1336, 1257, 1230, 1145<br>Mass (EI) 368(M⁺) | mp.<br>High resolution mass spectrum<br>Molecular formula C₁₈H₂₄O₈<br>Calcd. 368.147<br>Found 368.149 |
| Compound 141 | 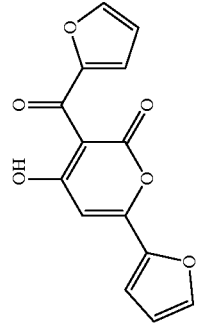 | NMR (ppm) (300 MHz, CDCl₃)<br>6.53(s, 1H), 6.62(dd, J = 1.65, 3.57, 2H), 7.22(dd, J = 0.55, 3.57, 1H), 7.64(dd, J = 0.82, 1.65, 1H), 7.72(dd, J = 0.55, 1.65, 1H), 7.98(dd, J = 0.82, 3.84, 0.3H), 8.05(dd, J = 0.55, 3.84, 0.7H)<br>IR(cm⁻¹) (KBr)<br>1731, 1649, 1545, 1520, 1456, 1031, 766<br>Mass (EI) 272(M⁺) | mp. 156–158° C.<br>Elemental analysis<br>Molecular formula C₁₄H₈O₆<br>Calcd. C, 61.77; H, 2.96<br>Found C, 61.67; H, 2.94 |

-continued

| Compound 142 | 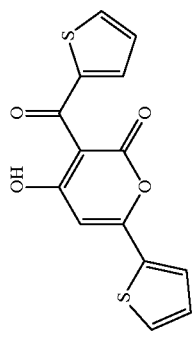 | NMR (ppm) (300 MHz, CDCl₃) 6.46(s, 1H), 7.14–7.21(m, 2H), 7.63(dd, J = 1.10, 4.95, 1H), 7.72–7.78(m, 2H), 8.33(dd, J = 1.10, 4.12, 0.25H), 8.39(dd, J = 1.10, 4.12, 0.75H)<br><br>IR(cm⁻¹) (KBr) 1758, 1620, 1578, 1537, 1415, 812, 714<br><br>Mass (EI) 304(M⁺) | mp. 152–154° C.<br>Elemental analysis<br>Molecular formula C₁₄H₈O₄S₂<br>Calcd. C, 55.25; H, 2.65; S, 21.07<br>Found C, 55.14; H, 2.72; S, 21.02 |
|---|---|---|---|
| Compound 143 | 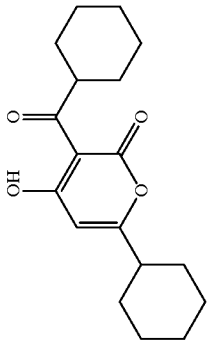 | NMR (ppm) (300 MHz, CDCl₃) 1.20–1.52(m, 10H), 1.70–1.98(m, 10H), 2.39(m, 1H), 3.68(m, 1H), 5.89(s, 1H)<br><br>IR(cm⁻¹) (KBr) 2930, 1729, 1638, 1553<br><br>Mass (EI) 304(M⁺) | mp. 94–95° C.<br>Elemental analysis<br>Molecular formula C₁₈H₂₄O₄<br>Calcd. C, 71.03; H, 7.95<br>Found C, 70.84; H, 7.89 |
| Compound 144 | 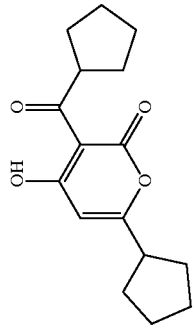 | NMR (ppm) (300 MHz, CDCl₃) 1.62–2.05(m, 16H), 2.87(m, 1H), 4.11(m, 1H), 5.94(s, 1H)<br><br>IR(cm⁻¹) (KBr) 1727, 1636, 1603, 1560<br><br>Mass (EI) 276(M⁺) | mp. 46–48° C.<br>Elemental analysis<br>Molecular formula C₁₆H₂₀O₄<br>Calcd. C, 69.55; H, 7.29<br>Found C, 69.11; H, 7.26 |
| Compound 145 | 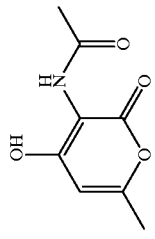 | NMR (ppm) (300 MHz, CD₃OD) 2.18(s, 3H), 2.27(d, J = 1.10, 3H), 6.07(d, J = 0.82, 1H)<br><br>IR(cm⁻¹) (KBr) 1684, 1568, 1452, 1400, 1346, 996, 766<br><br>Mass (EI) 183(M⁺) | mp. 200–201° C.<br>Elemental analysis<br>Molecular formula C₈H₉NO₄<br>Calcd. C, 52.46; H, 4.95; N, 7.65<br>Found C, 52.38; H, 4.93; N, 7.63 |

-continued

| Compound 146 | 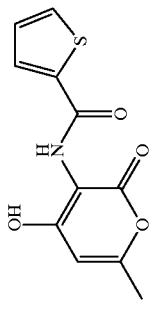 | NMR (ppm) (300 MHz, CD$_3$OD)<br>2.30(d, J = 1.10, 3H), 6.14(dd, J = 0.82, 1.64, 1H), 7.21(dd, J = 3.84, 5.22, 1H), 7.77(dd, J = 1.10, 4.96, 1H), 7.90(dd, J = 1.10, 3.84)<br><br>IR(cm$^{-1}$) (KBr)<br>1692, 1607, 1593, 1543, 1419, 1311, 733<br><br>Mass (EI) 251(M$^+$) | mp. 209–210° C.<br>Elemental analysis<br>Molecular formula C$_{11}$H$_9$NO$_4$S<br>Calcd. C, 52.58; H, 3.61; N, 5.57; S, 12.76<br>Found C, 52.48; H, 3.68; N, 5.59; S, 12.67 |
|---|---|---|---|
| Compound 147 | 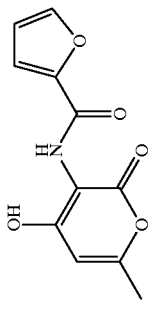 | NMR (ppm) (300 MHz, CD$_3$OD)<br>2.30(d, J = 0.82, 3H), 6.13(dd, J = 0.82, 1.64, 1H), 6.68(dd, J = 1.92, 3.57, 1H), 7.29(dd, J = 0.82, 3.57, 1H), 7.78(dd, J = 0.82, 1.92)<br><br>IR(cm$^{-1}$) (KBr)<br>5311698, 1591,<br><br>Mass (EI) 235(M$^+$) | mp. 188–191° C.<br>Elemental analysis<br>Molecular formula C$_{11}$H$_9$NO$_5$<br>Calcd. C, 56.17; H, 3.86; N, 5.96<br>Found C, 55.82; H, 3.95; N, 5.89 |
| Compound 148 | 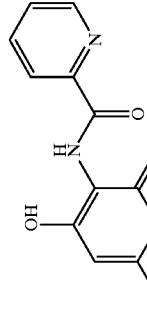 | NMR (ppm) (300 MHz, CD$_3$OD)<br>2.25(d, J = 1.10, 3H), 5.94(d, J = 1.10, 1H), 7.52(m, 1H), 7.92(td, J = 1.83, 7.69, 1H), 8.19(d, J = 7.69, 1H), 8.70(m, 1H), 10.61(br, 1H), 13.40(s, 1H)<br><br>IR(cm$^{-1}$) (KBr)<br>1692, 1671, 1582, 1547, 1446<br><br>Mass (EI) 246(M$^+$) | mp. 247–248° C.<br>Elemental analysis<br>Molecular formula C$_{12}$H$_{10}$N$_2$O$_4$<br>Calcd. C, 58.54; H, 4.09; N, 11.38<br>Found C, 58.42; H, 4.19; N, 11.31 |
| Compound 149 | 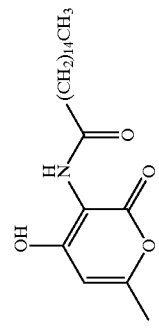 | NMR (ppm) (300 MHz, CDCl$_3$)<br>0.88(3H), 1.2–1.4(m, 22H), 1.70(m, 2H), 2.22(s, 3H), 2.43(t, J = 7.58, 2H), 5.90(s, 1H), 7.89(br, 1H), 13.18(s, 1H)<br><br>IR(cm$^{-1}$) (KBr)<br>2922, 2852, 1694, 1564<br><br>Mass (EI) 379(M$^+$) | mp. 108° C.<br>Elemental analysis<br>Molecular formula C$_{22}$H$_{37}$NO$_4$<br>Calcd. C, 69.62; H, 9.83; N, 3.69<br>Found C, 69.53; H, 9.82; N, 3.78 |

-continued

Compound 150

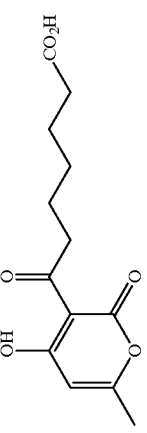

NMR (ppm) (300 MHz, CDCl₃)
1.45(m, 2H), 1.69(t, J = 7.30, 4H), 2.27(d, J = 0.77, 3H), 2.38(t, J = 7.30, 2H), 3.08(t, J = 7.30, 2H), 5.94(d, J = 0.77, 1H), 16.78(s, 1H)

IR(cm⁻¹) (KBr)
1748, 1702, 1649, 1605, 1557, 1462, 1259

Mass (EI) 268(M⁺)

mp. 112–113° C.
Elemental analysis Molecular formula $C_{13}H_{16}O_6$
Calcd. C, 58.20; H, 6.01
Found C, 58.14; H, 6.03

Compound 152

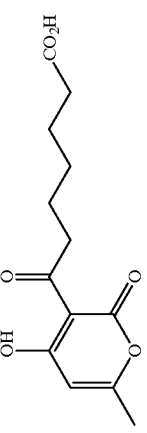

NMR (ppm) (300 MHz, CD₃OD)
1.12(t, J = 7.41, 3H), 2.29(s, 3H), 2.47(q, J = 7.41, 2H), 5.44(s, 1H)

IR(cm⁻¹) (KBr)
1678, 1605, 1564, 1491, 1265, 1257

Mass mp. 166–168° C.
Elemental analysis Molecular formula $C_8H_{10}O_3$
Calcd. C, 62.33; H, 6.54
Found C, 62.04; H, 6.53

Compound 153

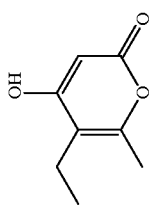

NMR (ppm) (300 MHz, CD₃OD)
2.36 (t, J = 0.82 Hz, 3H), 6.29–6.30 (m, 1H), 6.41–6.42 (m, 1H), 7.59–7.64 (m, 2H), 7.72–7.81 (m, 1H), 8.17–8.21 (m, 2H).

IR(cm⁻¹) (KBr)
1746, 1715, 1638, 1568, 1450, 1249, 1218, 1160, 1050, 1023, 716, 696

Mass (EI) 230 (M⁺)

mp. 88.0–89.0° C.
Elemental analysis Molecular formula $C_{13}H_{10}O_4$
Calcd. C, 67.82; H, 4.38.
Found C, 67.84; H, 4.43

Compound 154

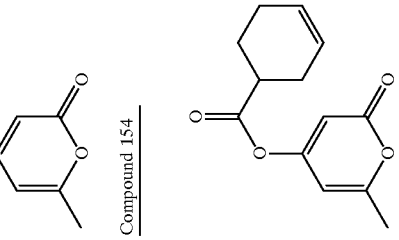

NMR (ppm) (300 MHz, CD₃OD)
1.73–1.91 (m, 1H), 2.10–2.2 (m, 3H), 2.32 (t, J = 0.82 Hz, 3H), 2.33–2.51 (m, 2H), 2.84–2.95 (m, 1H), 5.68–5.82 (m, 2H), 6.24 (m, 1H), 6.25 (m, 1H).

IR(cm⁻¹) (KBr)
2922, 1758, 1723, 1649, 1576, 1444, 1323, 1303, 1288, 1218, 1168, 1122, 996, 853, 665

Mass (EI) 234 (*)

mp. 46.5–47.0° C.
Elemental analysis Molecular formula $C_{13}H_{14}O_4$
Calcd. C, 66.65; H, 6.02.
Found C, 66.59; H, 6.09.

-continued

Compound 155

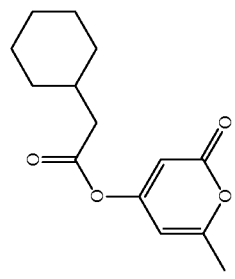

NMR (ppm) (300 MHz, CD$_3$OD)
1.00–1.43 (m, 5H), 1.67–1.90 (m, 6H), 2.32 (t, J = 0.82 Hz, 3H), 2.49 (d, J = 6.87 Hz, 2H), 6.09–6.11 (m, 1H), 6.22–6.23 (m, 1H).

IR(cm$^{-1}$) (KBr)
2936, 2856, 1777, 1725, 1638, 1572, 1543, 1450, 1216, 1154, 1089, 982

Mass (EI) 250 (M$^+$)

mp. 57.5–58.0° C.
Elemental analysis
Molecular formula C$_{14}$H$_{18}$O$_4$
Calcd. C, 67.18; H, 7.25.
Found C, 67.11; H, 7.30.

Compound 156

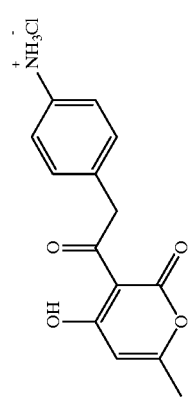

NMR (ppm) (300 MHz, CD$_3$OD)
2.34 (d, J = 0.82 Hz, 3H), 4.49 (s, 2H), 6.22 (q, J = 0.82 Hz, 1H), 7.38 (d, J = 8.8 Hz, 2H), 7.50 (d, J = 8.8 Hz, 2H).

IR(cm$^{-1}$) (KBr)
2928, 2586, 1721, 1642, 1560, 1512, 1460, 1000, 835, 789

Mass (FAB) 261 ([M-Cl]$^+$)

mp. 205–211° C. (dec)
Elemental analysis
Molecular formula C$_{14}$H$_{14}$ClNO$_4$
Calcd. C, 56.86; H, 4.77; Cl, 11.99; N, 4.74.
Found C, 56.23; H, 4.76; Cl, 12.34; N, 4.69.

Compound 157

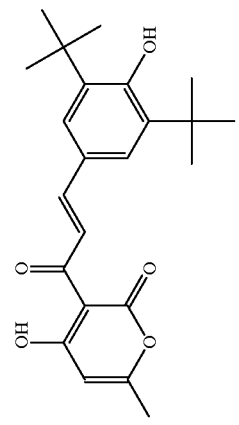

NMR (ppm) (300 MHz, CDCl$_3$)
1.47(s, 18H), 2.27(s, 3H), 5.66(s, 1H), 5.94(s, 1H), 7.54(s, 2H), 7.98(d, J = 15.56, 1H), 8.20(d, J = 15.56, 1H), 18.31(s, 1H)

IR(cm$^{-1}$) (KBr)
1717, 1626, 1522, 1433, 1207

Mass (EI) 384(M$^+$)

mp. 210–212° C.
Elemental analysis
Molecular formula C$_{23}$H$_{28}$O$_5$
Calcd. C, 71.85; H, 7.34
Found C, 71.72; H, 7.28

-continued

Compound 158

NMR (ppm) (300 MHz, CDCl₃)
2.28(d, J = 0.81, 3H), 2.52(s, 3H), 5.96(s, 1H), 7.22–7.28(m, 2H), 7.57–7.64(m, 2H), 7.93(d, J = 15.71, 1H), 8.27(d, J = 15.71, 1H), 18.04(s, 1H)

IR(cm⁻¹) (KBr)
1705, 1624, 1516, 1493, 1475, 998

Mass (EI) 302(M⁺)

mp. 176–180° C.
Elemental analysis
Molecular formula $C_{16}H_{14}O_4S$
Calcd. C, 63.56; H, 4.67; S, 10.60
Found C, 63.51; H, 4.70; S, 10.53

Compound 159

NMR (ppm) (300 MHz, CDCl₃)
1.43(s, 18H), 2.27(d, J = 0.70, 3H), 2.89(t, J = 7.65, 2H), 3.37(t, J = 7.65, 2H), 5.06(s, 1H), 5.94(s, 1H), 7.03(s, 2H), 16.77(s, 1H)

IR(cm⁻¹) (KBr)
3648, 2968, 1721, 1651, 1564, 1435, 996

Mass (EI) 386(M⁺)

mp. 163–165° C.
Elemental analysis
Molecular formula $C_{23}H_{30}O_5$
Calcd. C, 71.48; H, 7.82
Found C, 71.40; H, 7.74

Compound 160

NMR (ppm) (300 MHz, CD₃OD)
0.94(t, 3H), 1.25–1.50(m, 24H), 1.72(m, 2H), 2.93(t, J = 7.41, 2H), 3.97(m, 2H), 4.85(t, J = 2.74, 1H)

IR(cm⁻¹) (KBr)
2920, 2852, 1752, 1665, 1607, 1050

Mass (EI) 368(M⁺)

mp. 95–99° C.
Elemental analysis
Molecular formula $C_{21}H_{36}O_5$
Calcd. C, 68.45; H, 9.85
Found C, 68.23; H, 9.82

Compound 161

NMR (ppm) (300 MHz, CD₃OD)
2.34 (d, J = 0.82 Hz, 3H), 4.79 (s, 2H), 6.24 (q, J = 0.82 Hz, 1H).

IR(cm⁻¹) (KBr)
3282, 1728, 1642, 1573, 1457, 1240, 936, 993, 969, 936, 839

Mass (EI) 184 (M⁺)

mp. 128.0–129.5° C.
Elemental analysis
Molecular formula $C_8H_8O_5$
Calcd. C, 52.18; H, 4.38.
Found C, 52.11; H, 4.36.

-continued

| Compound 162 | 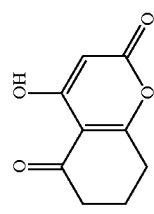 | NMR (ppm) (300 MHz, CD$_3$OD) 2.19(quint, J = 6.31, 2H), 2.69(dt, J = 1.65, 5.76, 2H), 2.95(t, J = 6.31, 2H), 5.43(s, 1H) IR(cm$^{-1}$) (KBr) 1738, 1678, 1566, 1460, 1381, 828, 810 Mass (EI) 180(M$^+$) | mp. 122–125° C. Elemental analysis Molecular formula C$_9$H$_8$O$_4$ Calcd. C, 60.00; H, 4.48 Found C, 60.00; H, 4.49 |
| --- | --- | --- | --- |
| Compound 163 | 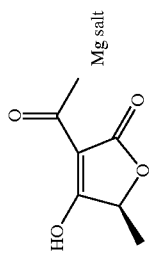 Mg salt | NMR (ppm) IR(cm$^{-1}$) (KBr) 1736, 1717, 1638, 1562, 1543, 1479, 1033 Mass | mp. molecular formula Calcd. Found |
| Compound 164 | 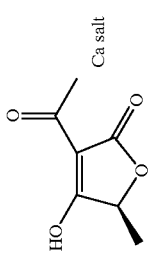 Ca salt | NMR (ppm) IR(cm$^{-1}$) (KBr) 3422, 1719, 1630, 1468, 1365, 1323, 1087, 1067, 1027, 975, 793 Mass | mp. Molecular formula Calcd. Found |
| Compound 165 | 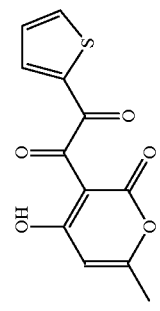 | NMR (ppm) (300 MHz, CD$_3$OD) 2.37 (d, J = 0.82 Hz, 3H), 6.35 (q, J = 0.82 Hz, 1H), 7.24–7.27 (m, 1H), 7.72–7.73 (m, 1H), 8.01–8.03 (m, 1H). IR(cm$^{-1}$) (KBr) 3436, 1744, 1734, 1649, 1632, 1574, 1410, 1232, 992 Mass (EI) 264 (M$^+$) | mp. 128–129° C. Elemental analysis Molecular formula C$_{12}$H$_8$O$_5$S Calcd. C, 54.54; H, 3.05 S, 12.14 Found C, 55.00; H, 3.44; S, 12.27 |

-continued

Compound 166

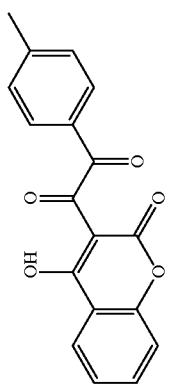

NMR (ppm) (300 MHz, CD$_3$OD)
2.45 (s, 3H), 7.37 (d, J = 8.5 Hz, 2H), 7.46–7.57 (m, 2H), 7.75 (d, J = 8.5 Hz, 2H), 7.89–7.95 (m, 1H), 8.17–8.21 (m, 1H).

IR(cm$^{-1}$)(KBr)
1729, 1680, 1613, 1560, 1267, 1228, 1180, 930, 764, 582

Mass (EI) 308 (M$^+$)

mp. 182–183° C.
Elemental analysis
Molecular formula C$_{18}$H$_{12}$O$_5$
Calcd; C, 70.13; H, 3.92.
Found C, 69.68; H, 4.08.

Compound 167

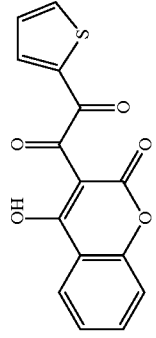

NMR (ppm) (300 MHz, CD$_3$OD)
7.26–7.29 (m, 1H), 7.44–7.53 (m, 2H), 7.77–7.79 (m, 1H), 7.87–7.93 (m, 1H), 8.02–8.05 (m, 1H), 8.19–8.23 (m, 1H).

IR(cm$^{-1}$) (KBr)
3082, 1725, 1661, 1613, 1557, 1412, 1253, 1230, 901, 758

Mass (EI) 300 (M$^+$)

mp. 155–157° C.
Elemental analysis
Molecular formula C$_{15}$H$_8$O$_5$S·0.2 H$_2$O
Calcd. C, 59.28; H, 2.79; S, 10.55.
Found C, 58.99; H, 2.92; S, 10.63.

Compound 168

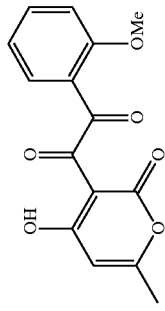

NMR (ppm) (300 MHz, CD$_3$OD)
2.40 (d, J = 0.82 Hz, 3H), 3.76 (s, 3H), 6.37 (q, J = 0.82 Hz, 1H), 7.14–7.19 (br m, 2H), 7.59–7.72 (m, 1H), 7.97–8.00 (m, 1H).

IR(cm$^{-1}$) (KBr)
1727, 1665, 1634, 1578, 1441, 1356, 1294, 1259, 992, 876

Mass (EI) 288 (M$^+$)

mp. 142–143° C.
Elemental analysis
Molecular formula C$_{15}$H$_{12}$O$_6$·0.2 H$_2$O
Calcd. C, 61.73; H, 4.28.
Found C, 61.88; H, 4.28.

Compound 169

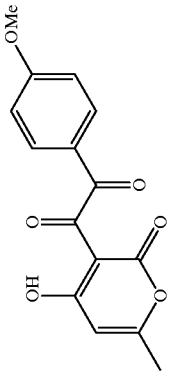

NMR (ppm) (300 MHz, CD$_3$OD)
2.38 (d, J = 0.82 Hz, 3H), 3.93 (s, 2H), 6.38 (q, J = 0.82 Hz, 1H), 7.09 (d, J = 8.8 Hz, 2H), 7.85 (d, J = 8.8 Hz, 2H).

IR(cm$^{-1}$)(KBr)
1731, 1640, 1603, 1564, 1431, 1270, 1168, 994, 882

Mass (EI) 288 (M$^+$)

mp. 182–184° C.
Elemental analysis
Molecular formula C$_{15}$H$_{12}$O$_6$·0.2 H$_2$O
Calcd. C, 61.73; H, 4.28.
Found C, 61.41; H, 4.32.

-continued

| Compound 170 | 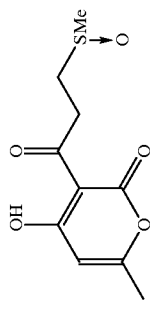 | NMR (ppm) (300 MHz, CD₃OD)<br>2.34 (d, J = 0.82 Hz, 3H), 2.73 (s, 3H), 3.06–3.14 (m, 1H), 3.26–3.32 (m, 1H), 3.56–3.61 (m, 2H), 6.22 (q, J = 0.82 Hz, 1H).<br>IR(cm⁻¹) (KBr)<br>1719, 1638, 1618, 1572, 1460, 1421, 1241, 1046, 996, 940<br>Mass (EI) 244 (M⁺) | mp. 124–126° C. (dec)<br>Elemental analysis<br>Molecular formula C₁₀H₁₂O₅S<br>Calcd. C, 50.00; H, 5.04; N, 11.66.<br>Found C, 49.07; H, 4.93; S, 13.10. |
| Compound 171 | 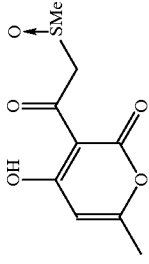 | NMR (ppm) (300 MHz, CD₃OD)<br>2.35 (d, J = 0.82 Hz, 3H), 2.83 (s, 3H), 3.85 (s, 2H), 4.52 (d, J = 14.8 Hz, 1H), 4.74 (d, J = 14.8 Hz, 1H), 6.28 (q, J = 0.82 Hz, 1H).<br>IR(cm⁻¹) (KBr)<br>1711, 1647, 1543, 1456, 1236, 1042, 996, 938, 853<br>Mass (EI) 230 (M⁺) | mp. 125–128° C. (dec)<br>Elemental analysis<br>Molecular formula C₉H₁₀O₅S<br>Calcd. C, 46.95; H, 4.38; S, 13.93.<br>Found C, 46.81; H, 4.34; S, 13.88. |
| Compound 172 | 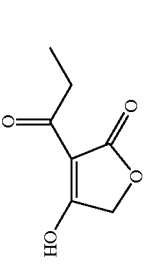 | NMR (ppm) (300 MHz, CDCl₃)<br>7.23(1H, bs), 4.69, 4.56(2H, s), 2.95(2H, q, J = 7.5), 1.25(3H, t, J = 7.5)<br>IR(cm⁻¹) (KBr)<br>2936, 1756, 1655, 1613, 1464, 1276, 1052, 855<br>Mass | mp. 105–107° C.<br>Molecular formula<br>Calcd.<br>Found |
| Compound 173 | 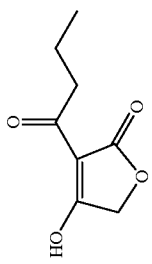 | NMR (ppm) (300 MHz, CDCl₃)<br>4.67, 4.55(2H, s), 2.73, 2.91(2H, t, J = 6.8), 1.75(2H, m), 1.02(3H, t, J = 7.0)<br>IR(cm⁻¹) (KBr)<br>2972, 1771, 1752, 1462, 1255, 104, 1011<br>Mass | mp. 79–80° C.<br>Molecular formula<br>Calcd.<br>Found |

-continued

| Compound 174 | NMR (ppm) (300 MHz, CDCl₃)<br>4.69, 4.55(2H, s), 3.69(1H, sep, J = 6.8), 1.26, 1.24(3H, d, J = 6.8)<br>IR(cm⁻¹) (KBr)<br>2974, 1758, 1661, 1603, 1460, 1261, 1050, 541<br>Mass | mp. 80–81° C.<br>Molecular formula<br>Calcd.<br>Found |
|---|---|---|
| Compound 175 | NMR (ppm) (300 MHz, CDCl₃)<br>4.65, 4.56(2H, s), 2.98(1H, m), 1.43(4H, m)<br>IR(cm⁻¹) (KBr)<br>1771, 1640, 1603, 1274, 1056, 961<br>Mass | mp. 120–121° C.<br>Molecular formula<br>Calcd.<br>Found |
| Compound 176 | NMR (ppm)<br>IR(cm⁻¹)<br>Mass | mp. |
| Compound 177 | NMR (ppm) (300 MHz, CD₃OD)<br>2.40(s, 3H), 3.50(s, 3H), 5.78(d, J = 2.75, 1H), 6.00(m, 1H)<br>IR(cm⁻¹) (KBr)<br>1638, 1626, 1543, 1537, 1528, 1493, 1328, 1232, 1203<br>Mass | mp. 239–243° C.<br>Molecular formula C₇H₉NO₂<br>Calcd. C, 60.42; H, 6.52; N, 10.07<br>Found |

-continued

| Compound 178 | 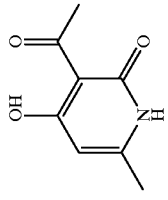 | NMR (ppm) (300 MHz, CDCl$_3$) 2.30(s, 3H), 2.72(s, 3H), 5.82(s, 1H), 11.26(br, 1H), 15.64(s, 1H) IR(cm$^{-1}$) (KBr) 1678, 1628, 1249 Mass (EI) 167(M$^+$) | mp. >240° C. (sublimation) Molecular formula C$_8$H$_9$NO$_3$ Calcd. C, 57.48; H, 5.43; N, 8.38 Found |
| --- | --- | --- | --- |
| Compound 179 | 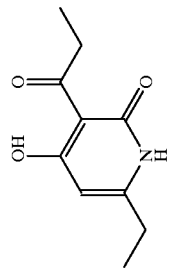 | NMR (ppm) (300 MHz, CDCl$_3$) 1.18(t, J = 7.32, 3H), 1.31(t, J = 7.32, 3H), 2.57(q, J = 7.32, 2H), 3.18(q, J = 7.32, 2H), 5 84(s, 1H), 11.37(br, 1H, —NH), 15.73(s, 1H, —OH) IR(cm$^{-1}$) (KBr) 1659, 1611, 1450, 1241, 1216 Mass (EI) 195(M$^+$) | mp. 158–160° C. Elemental analysis Molecular formula C$_{10}$H$_{13}$NO$_3$ Calcd. C, 61.53; H,6.71; N, 7.17 Found C, 61.30; H, 6.68; N, 7.14 |
| Compound 180 | 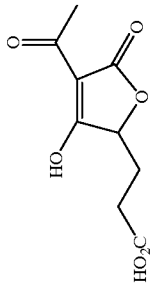 | NMR (ppm) (300 MHz, CD$_3$OD) 1.98(m, 1H), 2.27(m,1H), 2.52(m, 2H), 2.54(s,3H, 4.88(m, 1H) IR(cm$^{-1}$) (KBr) 1752, 1702, 1671, 1611, 1450, 1342, 1172 Mass (EI) 214(M$^+$) | mp. 155–158° C. Elemental analysis Molecular formula C$_9$H$_{10}$O$_6$ Calcd. C, 50.47; H, 4.71 Found C, 50.42; H, 4.70 |
| Compound 181 | 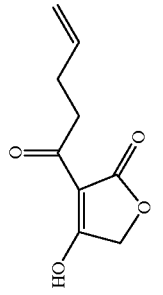 | NMR (ppm) (300 MHz CD$_3$OD) 2.44–2.49 (m, 2H), 2.99–3.05 (m, 2H), 4.75 (s, 2H), 5.00–5.16 (m, 2H), 5.94–5.98 (m, 1H) IR(cm$^{-1}$) (KBr) 3192, 1775, 1752, 1660, 1615, 1461, 1433, 1244, 1125, 1056, 1016, 953, 919, 843, 756 Mass (EI) 182 (M$^+$) | mp. 85.0–85.5° C. Elemental analysis Molecular formula C$_9$H$_{10}$O$_4$ Calcd. C, 59.33; H, 5.53. Found C, 59.28; H, 5.54. |

-continued

Compound 182

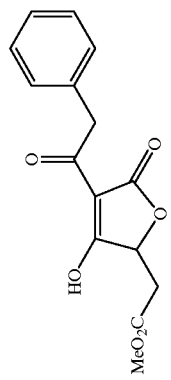

NMR (ppm) (300 MHz, CD$_3$OD)
2.94(dd, J = 6.04, 17.30, 1H), 3.09(dd, J = 4.39, 17.30, 1H), 3.69(s, 3H), 3.72(m, 0.5H), 4.24(m, 0.5H), 5.09(m, 1H), 7.25–7.40(m, 5H)
IR(cm$^{-1}$) (KBr)
1760, 1734, 1661, 1618, 1448, 1390, 1249, 1238, 1178, 1023, 719
Mass (EI) 290(M$^+$)
mp. 115–116° C.
Elemental analysis
Molecular formula C$_{15}$H$_{14}$O$_6$
Calcd. C, 62.07; H, 4.86
Found C, 61.82; H, 4.84

Compound 183

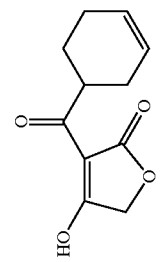

NMR (ppm) (300 MHz, CD$_3$OD)
2.32 (d, J = 0.82 Hz, 3H), 4.43 (s, 2H), 6.19 (q, J = 0.82 Hz, 1H), 7.05–7.08 (m, 1H), 7.24–7.27 (m, 1H), 7.35–7.38 (m, 1H).
IR(cm$^{-1}$) (KBr)
1738, 1711, 1653, 1560, 1460, 998, 938, 859, 770
Mass (EI) 250 (M$^+$)
mp. 100.0–100.5° C.
Elemental analysis
Molecular formula C$_{12}$H$_{10}$O$_4$S
Calcd. C, 57.58; H, 4.02; S, 12.81.
Found C, 57.57; H, 4.04; S, 12.66.

Compound 184

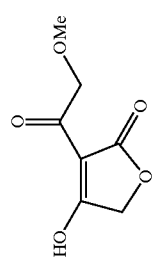

NMR (ppm) (300 MHz, CD$_3$OD)
3.48 (s, 3H), 4.59 (s, 2H), 4.79 (s, 2H).
IR(cm$^{-1}$) (KBr)
3470, 1763, 1673, 1657, 1607, 1595, 1475, 1437, 1274, 1046, 712
Mass (EI) 172 (M$^+$)
mp. 132.0–135.0° C.
Elemental analysis
Molecular formula C$_7$H$_8$O$_5$
Calcd. C, 48.84; H, 4.68.
Found C, 48.97; H, 4.70.

Compound 185

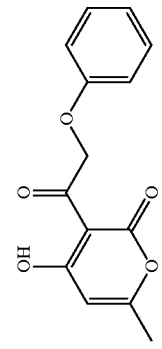

NMR (ppm) (300 MHz, CD$_3$OD)
2.36 (d, J = 0.82 Hz, 3H), 5.35 (s, 2H), 6.27 (q, J = 0.82 Hz, 1H), 6.95–7.02 (m, 3H), 7.28–7.34 (m, 2H).
IR(cm$^{-1}$) (KBr)
1725, 1653, 1601, 1566, 1493, 1456, 1427, 1234, 1091, 994, 975, 760, 752, 692
Mass (EI) 260 (M$^+$)
mp. 133.5–134.0° C.
Elemental analysis
Molecular formula C$_{14}$H$_{12}$O$_5$
Calcd. C, 64.61; H, 4.64.
Found C, 64.59; H, 4.63.

-continued

Compound 186

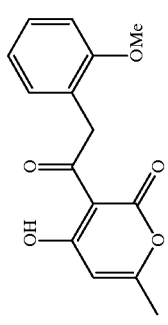

NMR (ppm) (300 MHz, CD$_3$OD)
2.34 (d, J = 0.82 Hz, 3H), 3.80 (s, 3H), 4.37 (s, 2H), 6.21 (q, J = 0.82 Hz, 1H), 6.90–7.00 (m, 2H), 7.11–7.15 (m, 1H), 7.26–7.32 (m, 1H).

IR(cm$^{-1}$)(KBr)
3082, 2922, 2842, 1711, 1651, 1557, 1460, 1330, 1249, 996, 748

Mass (EI) 274 (M$^+$)

mp. 103–105° C.
Elemental analysis
Molecular formula C$_{15}$H$_{14}$O$_5$
Calcd. C, 65.69; H, 5.15.
Found C, 65.67; H, 5.16.

Compound 187

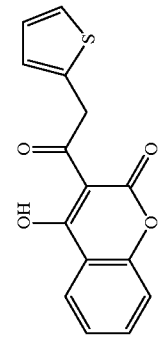

NMR (ppm) (300 MHz, CD$_3$OD)
4.91 (s, 2H), 6.99–7.06 (m, 2H), 7.32–7.49 (m, 2H + 1H), 7.80–7.87 (m, 1H), 8.11–8.15 (m, 1H).

IR(cm$^{-1}$) (KBr)
1727, 1620, 1610, 1555, 1422, 760, 704

Mass (EI) 286 (M$^+$)

mp. 130–132° C.
Elemental analysis
Molecular formula C$_{15}$H$_{10}$O$_4$S
Calcd. C, 62.92; H, 3.52; S, 11.20.
Found C, 62.90; H, 3.54; S, 11.38.

Compound 188

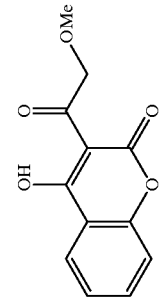

NMR (ppm) (300 MHz, CD$_3$OD)
3.36 (s, 3H), 4.85 (s, 2H), 7.39–7.51 (m, 2H), 7.82–7.88 (m, 1H), 8.13–8.17 (m, 1H).

IR(cm$^{-1}$) (KBr)
1717, 1615, 1560, 1431, 1207, 1093, 978, 766, 596

Mass (EI) 234 (M$^+$)

mp. 167–169° C.
Elemental analysis
Molecular formula C$_{12}$H$_{10}$O$_5$
Calcd. C, 61.54; H, 4.30.
Found C, 61.37; H, 4.36.

Compound 189

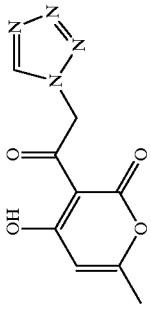

NMR (ppm) (300) CD$_3$OD)
2.39 (d, J = 0.82 Hz, 3H), 6.11 (s, 2H), 6.31 (q, J = 0.82 Hz, 1H), 9.19 (s, 1H).

IR(cm$^{-1}$) (KBr)
3164, 2956, 1731, 1638, 1578, 1450, 1421, 1096, 990, 731, 571

Mass (EI) 236 (M$^+$)

mp. 203–205° C.
Elemental analysis
Molecular formula C$_9$H$_8$N$_4$O$_4$
Calcd. C, 45.76; H, 3.41; N, 23.73.
Found C, 45.54; H, 3.52; N, 23.54.

-continued

| Compound | Structure | Data |
|---|---|---|
| Compound 190 | 3-(4-methylphenylacetyl)-4-hydroxy-6-methyl-2H-pyran-2-one | NMR (ppm) (300 MHz, CD₃OD) 2.31(3H, s), 2.34(3H, s), 4.35(2H, s), 6.17(1H, s), 7.12–7.20(m, 4H)<br><br>IR(cm⁻¹)<br><br>Mass (EI) (M+)<br><br>mp. 118–120° C.<br>Molecular formula $C_{15}H_{14}O_4$<br>Calcd. C, 69.76; H, 5.46<br>Found |
| Compound 191 | 3-(2-trifluoromethylphenylacetyl)-4-hydroxy-6-methyl-2H-pyran-2-one | NMR (ppm) (300 MHz, CD₃OD) 2.32 (d, J = 0.82 Hz, 3H), 4.32 (s, 2H), 5.95 (s, 2H), 6.19 (q, J = 0.82 Hz, 1H), 6.77 (br s, 1H), 6.78 (s, 1H), 6.82 (br s, 1H).<br><br>IR(cm⁻¹)(KBr)<br>3088, 1719, 1649, 1555, 1454, 1325, 1303, 1166, 1106, 994, 853, 770<br><br>Mass (EI) 312 (M⁺) | mp. 146–147° C.<br>Elemental analysis<br>Molecular formula $C_{15}H_{11}F_3O_4$<br>Calcd. C, 57.70; H, 3.55.<br>Found C, 57.50; H, 3.57. |
| Compound 192 | 4-(methoxycarbonyloxy)-6-methyl-2H-pyran-2-one | NMR (ppm) (300 MHz, CD₃OD) 2.33 (d, J = 0.82 Hz, 3H), 2.50 (s, 3H), 4.48 (s, 2H), 6.23 (q, J = 0.82 Hz, 1H), 7.47 (d, J = 8.34 Hz, 2H), 7.84 (d, J = 8.34 Hz, 2H).<br><br>IR(cm⁻¹)(KBr)<br>1782, 1740, 1721, 1650, 1577, 1443, 1282, 1255, 1220, 968<br><br>Mass (EI) 184 (M⁺) | mp. 46–48° C.<br>Elemental analysis<br>Molecular formula $C_{15}H_{14}O_6S$<br>Calcd. C, 55.89; H, 4.38; S, 9.95.<br>Found C, 55.51; H, 4.41; S, 9.84. |
| Compound 193 | 4-(N,N-dimethylcarbamoyloxy)-6-methyl-2H-pyran-2-one | NMR (ppm) (300 MHz, CD₃OD) 2.31–2.32 (m, 3H), 3.03 (s, 3H), 3.10 (s, 3H), 6.09–6.10 (m, 1H), 6.27–6.29 (m, 1H).<br><br>IR(cm⁻¹)(KBr)<br>3082, 2930, 1744, 1715, 1651, 1574, 1454, 1375, 1325, 1174, 1133, 847<br><br>Mass (EI) 197 (M⁺) | mp. 82–83° C.<br>Elemental analysis<br>Molecular formula $C_9H_{11}NO_4$<br>Calcd. C, 54.82; H, 5.62; N, 7.10.<br>Found C, 54.89; H, 5.59; N, 7.09. |

| | |
|---|---|
| Compound 194 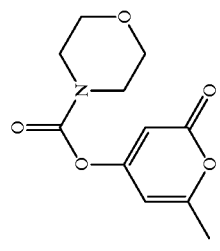 | NMR (ppm) (300 MHz, CD₃OD) 2.31–2.32 (m, 3H), 3.54–3.58 (m, 2H), 3.62–3.66 (m, 2H), 3.71–3.77 (m, 4H), 6.12–6.13 (m, 1H), 6.29–6.31 (m, 1H).<br><br>IR(cm⁻¹) (KBr) 1731, 1642, 1568, 1433, 1394, 1232, 1210, 1172, 1114, 1062, 835<br><br>Mass (EI) 239 (M⁺) | mp. 119–120° C.<br>Elemental analysis<br>Molecular formula $C_{11}H_{13}NO_5$<br>Calcd. C, 55.22; H, 5.48; N, 5.86.<br>Found C, 55.13; H, 5.46; N, 5.89. |
| Compound 195 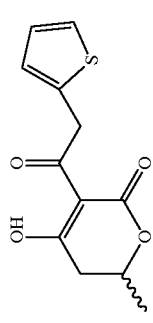 | NMR (ppm) (300 MHz, CD₃OD) 1.46 (d, J = 6.32 Hz, 3H), 2.71–2.89 (m, 2H), 4.51–4.70 (m, 1H + 2H), 6.96–7.02 (m, 2H), 7.30–7.33 (m, 1H).<br><br>IR(cm⁻¹) (KBr) 3110, 2976, 2932, 2902, 1696, 1562, 1444, 1290, 1267, 1069, 1050, 961, 905, 719<br><br>Mass (EI) 252 (M⁺) | mp. 93–95° C.<br>Elemental analysis<br>Molecular formula $C_{12}H_{12}O_4S$<br>Calcd. C, 57.13; H, 4.79; S, 12.71.<br>Found C, 57.08; H, 4.82; S, 12.61. |
| Compound 196 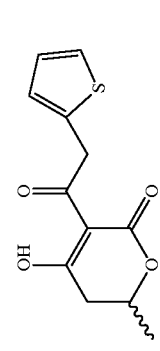 | NMR (ppm) (300 MHz, CD₃OD) 2.33 (d, J = 0.82 Hz, 3H), 6.18 (q, J = 0.82 Hz, 1H), 7.17–7.20 (m, 1H), 7.53–7.54 (m, 1H), 7.68–7.70 (m, 1H), 8.14 (s, 2H).<br><br>IR(cm⁻¹) (KBr) 3086, 1718, 1619, 1521, 1348, 1246, 1209, 994, 725<br><br>Mass (EI) 262 (M⁺) | mp. 157–159° C.<br>Elemental analysis<br>Molecular formula $C_{13}H_{10}O_4S$<br>Calcd. C, 59.53; H, 3.84; S, 12.23.<br>Found C, 59.16; H, 3.85; S, 12.16. |
| Compound 197 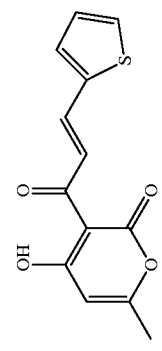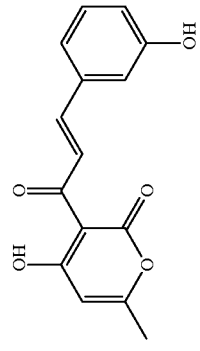 | NMR (ppm) (300 MHz, CD₃OD) 2.34 (d, J = 0.82 Hz, 3H), 3.70 (s, 1H), 6.20 (q, J = 0.82 Hz, 1H), 6.90–6.94 (m, 1H), 7.16–7.20 (m, 2H), 7.28–7.33 (m, 1H), 7.91 (d, J = 15.9 Hz, 1H), 8.30 (d, J = 15.9 Hz, 1H).<br><br>IR(cm⁻¹) (KBr) 3280, 1686, 1647, 1584, 1535, 1263, 1243, 998, 861<br><br>Mass (EI) 272 (M⁺) | mp. 224–226° C.<br>Elemental analysis<br>Molecular formula $C_{15}H_{12}O_5 \cdot 0.2H_2O$<br>Calcd. C, 65.31; H, 4.53.<br>Found C, 65.22; H, 4.73. |

| | | |
|---|---|---|
| Compound 198 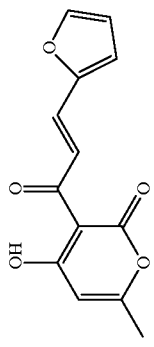 | NMR (ppm) (300 MHz, CD₃OD) 2.33 (d, J = 0.82 Hz, 3H), 6.18 (q, J = 0.82 Hz, 1H), 6.66 (dd, J =3.85 Hz, J3 =1.65 Hz, 1H), 6.97 (d, J = 3.85 Hz, 1H), 7.77 (d, J = 1.65 Hz, 1H), 7.78 (d, J = 15.7 Hz, 1H), 8.14 (d, J = 15.7 Hz, 1H). IR(cm⁻¹)(KBr) 1737, 1625, 1522, 1382, 1271, 1243, 1019, 997, 755<br><br>Mass (EI) 246 (M⁺) | mp. 127–130° C.<br>Elemental analysis<br>Molecular formula C₁₃H₁₀O₅<br>Calcd. C, 63.41; H, 4.12.<br>Found C, 63.44; H, 4.12. |
| Compound 199 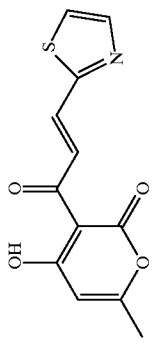 | NMR (ppm) (300 MHz, CD₃OD) 2.36 (d, J = 0.82 Hz, 3H), 6.25 (q, J = 0.82 Hz, 1H), 7.84 (d, J = 2.74 Hz, 1H), 8.01 (d, J = 15.7 Hz, 1H), 8.03 (d, J = 2.74 Hz, 1H), 8.53 (d, J = 15.7 Hz, 1H). IR(cm⁻¹)(KBr) 1721, 1638, 1539, 1477, 1359, 996, 505<br><br>Mass (EI) 263 (M⁺) | mp. 127–128° C.<br>Elemental analysis<br>Molecular formula C₁₂H₉NO₄S<br>Calcd. C, 54.74; H, 3.45; N, 5.32; S, 12.18.<br>Found C, 54.52; H, 3.52; N, 5.31; S, 12.10. |
| Compound 200 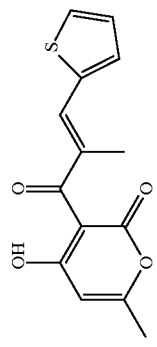 | NMR (ppm) (300 MHz, CD₃OD) 2.24 (d, J = 1.37 Hz, 3H), 2.34 (d, J = 0.82 Hz, 3H), 6.19 (q, J = 0.82 Hz, 1H), 7.19–7.22 (m, 1H), 7.40–7.42 (m, 1H), 7.52 (q, J = 1.37 Hz, 1H), 7.23–7.74 (m, 1H) IR(cm⁻¹)(KBr) 1719, 1657, 1537, 1365, 1277, 999, 696, 535<br><br>Mass (EI) 276 (M⁺) | mp. 138–140° C.<br>Elemental analysis<br>Molecular formula C₁₄H₁₂O₄S<br>Calcd. C, 60.85; H, 4.38.<br>Found C, 60.58; H, 4.56. |
| Compound 201 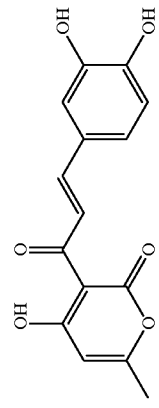 | NMR (ppm) (300 MHz, CD₃OD) 2.32(s, 3H), 3.39(s, 2H), 6.16(s, 1H), 6.85(d, 1H,J = 8.24 Hz), 7.10(dd, 1H, J = 1.92, 8.24 Hz), 7.22(d, 1H, J = 1.92 Hz), 7.90(d, 1H, J = 15.38 Hz), 8.15(d, 1H, J = 15.38) IR(cm⁻¹)(KBr) 3466, 3200(br), 1692, 1607, 1514, 1454, 1290, 1247<br><br>Mass (EI) 288(M⁺) | mp. 246–249° C.<br>Elemental analysis<br>Molecular formula C₁₅H₁₂O₆; MeOH<br>Calcd. C, 60.00; H, 5.03<br>Found C, 59.85; H, 5.07 |

-continued

| Compound 202 | 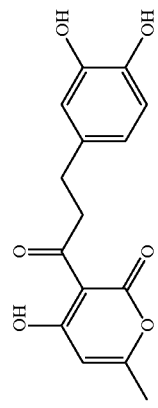 | NMR (ppm) (300 MHz, CD₃OD) 2.32(d, 3H, J = 0.82 Hz), 2.83(t, 2H, J = 7.96 Hz), 3.31(t, 2H, J = 7.96), 3.38(s, 2H), 6.18(d, 1H,J = 0.82 Hz), 6.58(m, 1H), 6.68–6.72(m, 2H)<br><br>IR(cm⁻¹) (KBr)<br>3520, 3200(br), 1686, 1649, 1551, 1439, 1245, 998<br><br>Mass (EI) 290(M⁺) | mp. 170–171° C.<br>Elemental analysis Molecular formula C₁₅H₁₄O₆ · H₂O<br>Calcd. C, 58.44; H, 5.23<br>Found C, 58.78; H, 5.39 |
|---|---|---|---|
| Compound 203 | 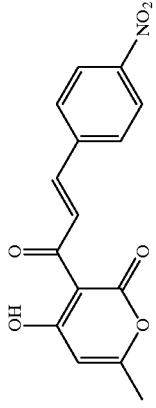 | NMR (ppm) (300 MHz, CD₃OD) 2.32 (d, J = 0.82 Hz, 3H), 4.32 (s, 2H), 5.95 (s, 2H), 6.19 (q, J = 0.82 Hz, 1H), 6.77 (br s, 1H), 6.78 (s, 1H), 6.82 (br s, 1H).<br><br>IR(cm⁻¹) (KBr)<br>1719, 1640, 1541, 1344, 1232<br><br>Mass (EI) 301 (M⁺) | mp. 247–250° C. (dec)<br>Elemental analysis Molecular formula C₁₅H₁₁NO₆<br>Calcd. C, 59.80; H, 3.68; N, 4.65.<br>Found C, 59.53; H, 3.70; N, 4.61. |
| Compound 204 | 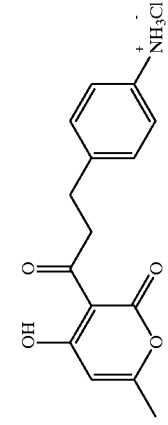 | NMR (ppm) (300 MHz, CD₃OD) 2.32 (d, J = 0.82 Hz, 3H), 4.32 (s, 2H), 5.95 (s, 2H), 6.19 (q, J = 0.82 Hz, 1H), 6.77 (br, s, 1H), 6.78 (s, 1H), 6.82 (br s, 1H)<br><br>IR(cm⁻¹) (KBr)<br>3522, 2846, 2584, 1719, 1642, 1562, 1514, 996<br><br>Mass (FAB) 275 ([M-Cl]⁺) | mp. 190–192° C. (dec)<br>Elemental analysis Molecular formula C₁₅H₁₆ClNO₄ · 0.2H₂O<br>Calcd. C, 57.49; H, 5.28; Cl, 11.31; N, 4.47.<br>Found C, 57.38; H, 5.31; Cl, 11.62; N, 4.50. |
| Compound 205 | 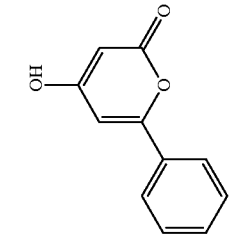 | NMR (ppm) (300 MHz, CD₃OD) 5.53 (d, J = 1.9 Hz, 1H), 6.75 (d, J = 1.9 Hz, 1H), 7.53–7.56 (m, 3H), 7.89–7.94 (m, 2H).<br><br>IR(cm⁻¹)<br>既知物質<br><br>Mass 188 (M⁺) | mp.<br>Molecular formula<br>Calcd.<br>Found |

-continued

| Compound 206 | 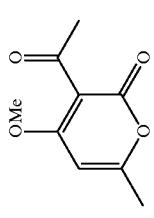 | NMR (ppm) (300 MHz, CDCl$_3$) 2.32 (d, J = 0.82 Hz, 3H), 2.51 (s, 3H), 3.95 (s, 3H), 6.09 (q, J = 0.82 Hz, 1H). IR(cm$^{-1}$) (KBr) 3106, 3010, 2964, 2928, 1714, 1666, 1497, 1474, 1344, 1236, 1224, 1015, 966, 769 Mass (EI) 182 (M$^+$) | mp. 89–91° C. Elemental analysis Molecular formula C$_9$H$_{10}$O$_4$ Calcd. C, 59.33; H, 5.53. Found C, 59.30; H, 5.54 |
|---|---|---|---|
| Compound 207 | 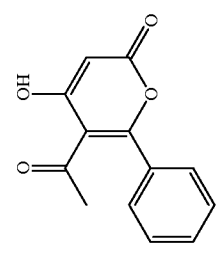 | NMR (ppm) (300 MHz, CD$_3$OD) 2.18(s, 3H), 5.48(s, 1H), 7.5–7.6(m, 2H), 7.70(m, 1H), 7.91–7.95(m, 2H) IR(cm$^{-1}$) (KBr) 1727, 1671, 1620, 1292 Mass (EI) 230(M$^+$) | mp. 224–227° C. Elemental analysis Molecular formula C$_{13}$H$_{10}$O$_4$ Calcd. C, 67.82; H, 4.38 Found C, 67.62; H, 4.47 |
| Compound 208 | 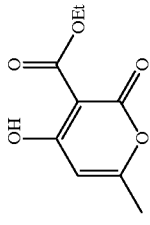 | NMR (ppm) (300 MHz, CD$_3$OD) 1.41 (t, J = 7.14 Hz, 1H), 2.32 (d, J = 0.82 Hz, 3H), 4.44 (q, J = 7.41 Hz, 2H), 6.22 (q, J = 0.82 Hz, 1H). IR(cm$^{-1}$) (KBr) 1744, 1650, 1564, 1424, 1340, 1263, 1099, 998 Mass (EI) 198 (M$^+$) | mp. 91–93° C. Elemental analysis Molecular formula C$_{13}$H$_{14}$O$_4$ Calcd. C, 66.65; H, 6.02. Found C, 66.77; H, 6.02. |
| Compound 209 | 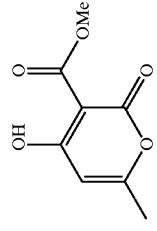 | NMR (ppm) (300 MHz, CD$_3$OD) 2.32 (d, J = 0.82 Hz, 3H), 3.96 (s, 3H), 6.23 (q, J = 0.82 Hz, 1H). IR(cm$^{-1}$) (KBr) 1750, 1655, 1564, 1462, 1367, 1338, 1253, 1098, 998 Mass (EI) 184 (M$^+$) | mp. 176–179° C. Elemental analysis Molecular formula C$_8$H$_8$O$_5$ Calcd. C, 52.58; H, 4.39. Found C, 52.18; H, 4.38. |

-continued
| Compound 210 | 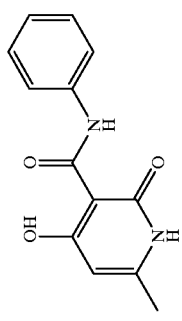 | NMR (ppm) (300 MHz, CDCl$_3$) 2.35(s, 3H), 5.96(s, 1H), 7.16(t, J = 6.59, 1H), 7.37(t, J = 7.32, 1H), 7.62(d, J = 7.69), 11.99(s, 1H), 15.49(s, 1H) IR(cm$^{-1}$) (KBr) 1644, 1601, 1551, 1491, 1448, 1263, 1249 Mass (EI) 244(M$^+$) | mp. 290–291° C. Elemental analysis Molecular formula C$_{13}$H$_{12}$N$_2$O$_3$ Calcd. C, 63.93; H, 4.95; N, 1.47 Found C, 63.82; H, 4.89; N, 11.34 |
| --- | --- | --- | --- |
| Compound 211 | 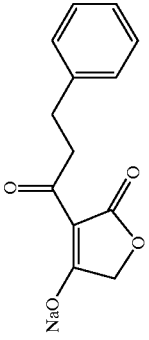 | NMR (ppm) IR(cm$^{-1}$) Mass | mp. Molecular formula Calcd. Found |
| Compound 212 | 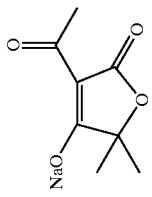 | NMR (ppm) IR(cm$^{-1}$) Mass | mp. Molecular formula Calcd. Found |
| Compound 213 | 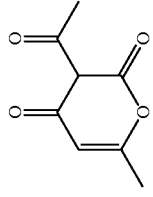 | NMR (ppm) IR(cm$^{-1}$) Mass | mp. Molecular formula Calcd. Found |

-continued

| Compound 214 | | |
|---|---|---|
| (structure) | NMR (ppm) | mp. |
| | IR(cm⁻¹) | Molecular formula Calcd. Found |
| | Mass | |

| Compound 215 | | |
|---|---|---|
| (structure) | NMR (ppm) | mp. |
| | IR(cm⁻¹) | Molecular formula Calcd. Found |
| | Mass | |

| Compound 216 | | |
|---|---|---|
| (structure) | NMR (ppm) | mp. |
| | IR(cm⁻¹) | Molecular formula Calcd. Found |
| | Mass | |

| Compound 217 | | |
|---|---|---|
| (structure) | NMR (ppm) | mp. |
| | IR(cm⁻¹) | Molecular formula Calcd. Found |
| | Mass | |

-continued
| Compound 218 | 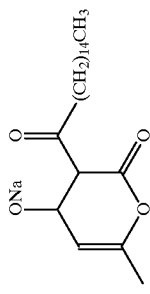 | NMR (ppm) IR(cm$^{-1}$) Mass | mp. Molecular formula Calcd. Found |
| --- | --- | --- | --- |
| Compound 219 | 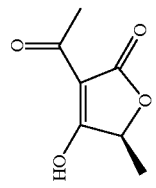 | NMR (ppm) IR(cm$^{-1}$) Mass | mp. Molecular formula Calcd. Found |
| Compound 220 | 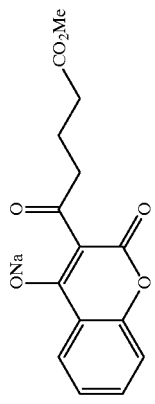 | NMR (ppm) IR(cm$^{-1}$) Mass | mp. Molecular formula Calcd. Found |
| Compound 221 | 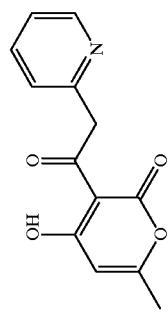 | NMR (ppm) IR(cm$^{-1}$) Mass | mp. Molecular formula Calcd. Found |

-continued
| Compound 222 | 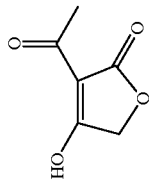 | NMR (ppm) IR(cm$^{-1}$) Mass | mp. Molecular formula Calcd. Found |
| --- | --- | --- | --- |
| Compound 223 | 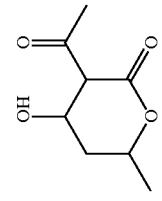 | NMR (ppm) IR(cm$^{-1}$) Mass | mp. Molecular formula Calcd. Found |
| Compound 224 | 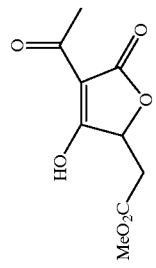 | NMR (ppm) IR(cm$^{-1}$) Mass | mp. Molecular formula Calcd. Found |
| Compound 225 | 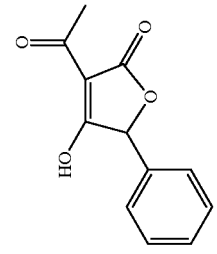 | NMR (ppm) IR(cm$^{-1}$) Mass | mp. Molecular formula Calcd. Found |

-continued
| Compound 226 | 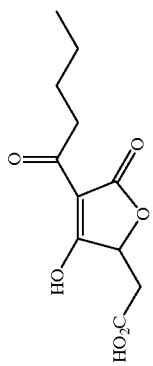 | NMR (ppm) IR(cm$^{-1}$) Mass | mp. Molecular formula Calcd. Found |
| --- | --- | --- | --- |
| Compound 227 | 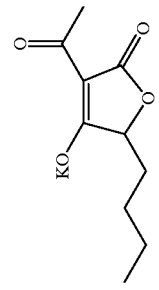 | NMR (ppm) IR(cm$^{-1}$) Mass | mp. Molecular formula Calcd. Found |
| Compound 228 | 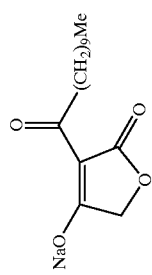 | NMR (ppm) IR(cm$^{-1}$) Mass | mp. Molecular formula Calcd. Found |
| Compound 229 | 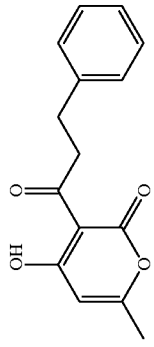 | NMR (ppm) IR(cm$^{-1}$) Mass | mp. Molecular formula Calcd. Found |

-continued

| | |
|---|---|
| | mp. |
| NMR (ppm) | |
| IR(cm$^{-1}$) | Molecular formula |
| | Calcd. |
| Mass | Found |

Compound 230

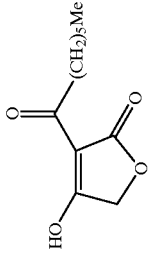

Compound 231

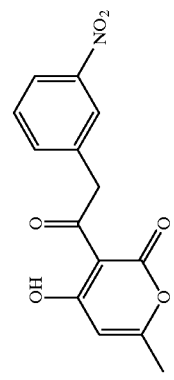

mp. 155–158
Elemental analysis
Molecular formula $C_{14}H_{11}NO_6$
Calcd. C, 58.13; H, 3.83; N, 4.84.
Found C, 58.06; H, 4.04; N, 5.20.

NMR (ppm) (300 MHz, CD$_3$OD)
2.34 (d, J = 0.82 Hz, 3H), 4.58 (s, 2H), 6.22 (q, J = 0.82 Hz, 1H), 7.57–7.64 (m, 1H), 7.70–7.73 (m, 1H), 8.15–8.23(m, 2H).

IR(cm$^{-1}$) (KBr)
3080, 2930, 1709, 1653, 1562, 1526, 1458, 1350, 1238, 996, 938, 857, 731

Mass (EI) 289 (M$^+$)

Compound 232

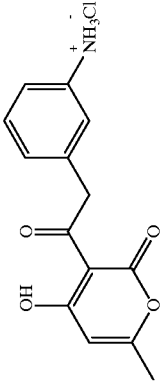

mp. 176–182° C. (dec)
Elemental analysis
Molecular formula $C_{14}H_{14}ClNO_4$
Calcd. C, 56.86; H, 4.77; N, 4.74.
Found C, 56.66; H, 5.01; N, 4.93.

NMR (ppm) (300 MHz, CD$_3$OD)
2.34 (d, J = 0.82 Hz, 3H), 4.51 (s, 2H), 6.23 (q, J = 0.82 Hz, 1H),7.33–7.36 (m, 1H), 7.39–7.40 (m, 1H), 7.44–7.56 (m, 2H).

IR(cm$^{-1}$) (KBr)
3436, 3784, 2578, 1719, 1642, 1562, 1460, 1415, 1238, 998, 781, 770

Mass (FAB) 261 ([M-Cl]$^+$)

Compound 233

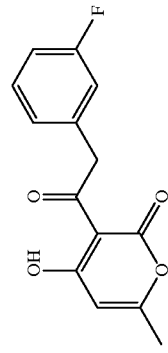

mp. 186–187° C.
Elemental analysis
Molecular formula $C_{14}H_{11}FO_4$
Calcd. C, 64.12; H, 4.43.
Found C, 63.97; H, 4.43.

NMR (ppm) (300 MHz, CD$_3$OD)
2.33 (d, J = 0.82 Hz, 3H), 4.43 (s, 2H), 6.20 (q, J = 0.82 Hz, 1H), 6.98–7.14 (m, 3H), 7.30–7.38 (m, 1H).

IR(cm$^{-1}$) (KBr)
3090, 1712, 1655, 1558, 1488, 1452, 1318, 1260, 1128, 998, 936, 778

Mass (EI) 262 (M$^+$)

-continued

| Compound 234 | 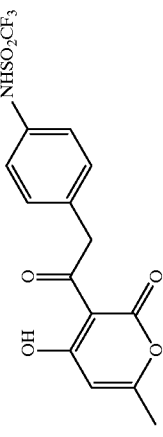 | NMR (ppm) (300 MHz, CD₃OD) 2.33 (d, J = 0.82 Hz, 3H), 4.42 (s, 2H), 6.20 (q, J = 0.82, 1H), 7.23–7.27 (m, 2H), 7.32–7.36 (m, 2H).<br>IR(cm⁻¹) (KBr) 3176, 1698, 1653, 1551, 1412, 1365, 1201, 1147, 1000, 955, 605, 507<br>Mass (EI) 391 (M⁺) | mp. 181–183° C.<br>Elemental analysis<br>Molecular formula C₁₅H₂F₃NO₆S<br>Calcd. C, 46.04; H, 3.09; N, 3.58.<br>Found C, 45.71; H, 3.19; N, 3.49. |
|---|---|---|---|
| Compound 235 | 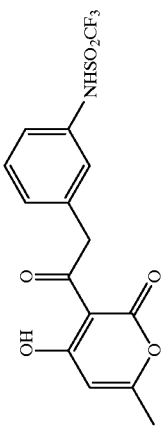 | NMR (ppm) (300 MHz, CD₃OD) 2.33 (d, J = 0.82 Hz, 3H), 4.43 (s, 2H), 6.20 (q, J = 0.82, 1H), 7.20–7.24 (m, 3H), 7.33–7.38 (m, 1H).<br>IR(cm⁻¹) (KBr) 3232, 1738, 1717, 1640, 1562, 1468, 1421, 1232, 1216, 1197, 141,1000, 700, 603<br>Mass (EI) 391 (M⁺) | mp. 147–148° C.<br>Elemental analysis<br>Molecular formula C₁₅H₁₂O₆F₃NS<br>Calcd. C, 46.04; H, 3.09; N, 3.58.<br>Found C, 45.96; H, 3.39; N, 3.52. |
| Compound 236 | 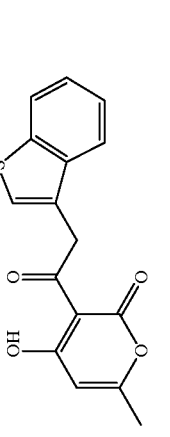 | NMR (ppm) (300 MHz, CD₃OD) 2.34 (d, J = 0.82 Hz, 3H), 4.68 (s, 2H), 6.21 (q, J = 0.82, 1H), 7.39–7.41 (m, 2H), 7.48 (brs, 1H), 7.79–7.83 (m, 1H), 7.91–7.93 (m, 1H).<br>IR(cm⁻¹) (KBr) 1717, 1642, 1555, 1456, 994, 940, 764, 632, 551, 501<br>Mass (EI) 300 (M⁺) | mp. 110–111° C.<br>Molecular formula<br>Calcd.<br>Found |
| Compound 237 | 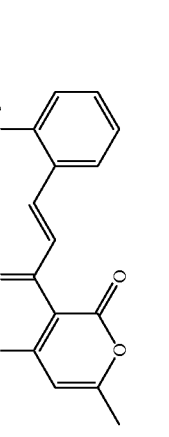 | NMR (ppm) (300 MHz, CD₃OD) 2.35 (d, J = 0.82 Hz, 3H), 6.25 (q, J = 0.82, 1H), 7.62–7.68 (m, 1H), 7.73–7.78 (m, 1H), 7.83 (d, J = 7.42 Hz, 1H), 8.04 (d, J = 7.42 Hz, 1H), 8.27–8.37 (m, 2H)<br>IR(cm⁻¹) (KBr) 1721, 1638, 1535, 1489, 1315, 1168, 1125, 1038, 998, 768, 462<br>Mass (EI) 325 (M⁺) | mp. 90–92° C.<br>Molecular formula<br>Calcd.<br>Found |

-continued
| Compound 238 | 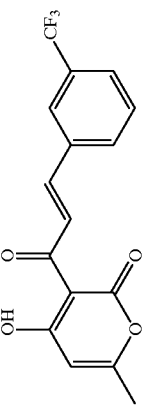 | NMR (ppm) (300 MHz, CD₃OD) 2.35 (d, J = 0.82 Hz, 3H), 6.24 (q, J = 0.82, 1H), 7.67–7.73 (m, 1H), 7.76–7.82 (m, 1H), 7.98–8.03 (m, 2H), 8.01 (d, J = 15.9 Hz, 1H), 8.41 (d, J = 15.9 Hz, 1H). IR(cm⁻¹) (KBr) 1727, 1632, 1541, 1441, 1367, 1336, 176, 1120, 998, 822, 690 Mass (EI) 324 (M⁺) | mp. 124–125° C. Molecular formula Calcd. Found |
|---|---|---|---|
| Compound 239 | 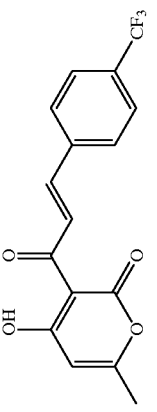 | NMR (ppm) (300 MHz, CD₃OD) 2.35 (q, J = 0.82, 1H),6.23 (q, J = 0.82, 1H), 7.78 (d, J = 8.24 Hz, 2H), 7.92 (d, J = 8.24 Hz, 2H), 7.98 (d, J = 15.9 Hz, 1H), 8.42 (d, J = 15.9 Hz, 1H). IR(cm⁻¹) (KBr) 1725, 1638, 1528, 1369, 1323, 1170, 1125, 1067, 1013, 996, 849, 833 Mass (EI) 324 (M⁺) | mp. 142–144° C. Molecular formula Calcd. Found |

Example 232

Hematopoietic Effect in Normal Mice

Each of the above test compounds was peritoneally administered to C57BL/6 mice (7-week old, male) for three days consecutively (n=6) at a dose of 10 mg/kg, and the peripheral blood cell count was measured 5 days after the beginning of the administration. Table 1 shows the rate of increase (%) with respect to the control group (100%) which were peritoneally administered 10 mg/kg of physiological saline.

Each of the above test compounds was peritoneally administered to C57BL/6 mice (7-week old, male) for three days consecutively (n=6) at doses of 1, 10, 33, and 100 mg/kg, and the peripheral blood cell count was measured 5 days after the beginning of the administration. Tables (Table 2:platelets, Table 3:red blood cells, and Table 4:white blood cells) shows the rate of increase (%) with respect to the control group (100%) which were peritoneally administered 10 mg/kg of physiological saline.

TABLE 1

| | Blood cell increasing rate (%) | | |
|---|---|---|---|
| Compound | Platelet (%) | Red blood cell (%) | White blood cell (%) |
| 4 | 108.8 | 101.2 | 59.0 |
| 5 | 95.1 | 100.2 | 121.2 |
| 6 | 105.6 | 99.7 | 69.3 |
| 8 | 91.8 | 102.8 | 105 |
| 11 | 104.5 | 105.0 | 70.2 |
| 12 | 110.6 | 102.1 | 59.3 |
| 13 | 111.1 | 104.0 | 55.8 |
| 15 | 104.4 | 102.9 | 82.0 |
| 16 | 88.5 | 99.7 | 130.9 |
| 18 | 106.3 | 99.5 | 51.2 |
| 19 | 109.3 | 102.7 | 72.0 |
| 23 | 94.6 | 100.4 | 143.5 |
| 24 | 109.0 | 100.4 | 48.5 |
| 25 | 111.6 | 100.2 | 55 |
| 26 | 113.3 | 100.5 | 60.0 |
| 27 | 108.8 | 100.7 | 81.6 |
| 28 | 109.5 | 102.7 | 65.8 |
| 29 | 118.5 | 100.5 | 72.6 |
| 30 | 110.2 | 100.5 | 74.3 |
| 31 | 106.7 | 101.0 | 55.8 |
| 32 | 104.8 | 104.0 | 69.4 |
| 33 | 107.6 | 105.2 | 76.8 |
| 34 | 103.7 | 105.6 | 68.5 |
| 36 | 105.6 | 100.0 | 76.9 |
| 39 | 104.1 | 102.7 | 88.4 |
| 40 | 104.5 | 100.6 | 73.0 |
| 41 | 103.1 | 103.3 | 57.2 |
| 42 | 97.8 | 104.1 | 80.3 |
| 44 | 107.3 | 101.4 | 50.4 |
| 46 | 103.3 | 99.0 | 115 |
| 47 | 110.7 | 99.5 | 59.5 |
| 49 | 93.7 | 107.0 | 99.8 |
| 51 | 99.8 | 108.2 | 80.9 |
| 52 | 97.7 | 105.4 | 49.1 |
| 53 | 99.8 | 102.4 | 69.1 |
| 56 | 97.4 | 104.6 | 61.6 |
| 57 | 99.6 | 102.1 | 74.9 |
| 58 | 99.4 | 102.0 | 84.1 |
| 59 | 109.4 | 103.5 | 62.3 |
| 60 | 100.4 | 103.2 | 70.2 |
| 64 | 109.4 | 102.4 | 50.6 |
| 66 | 107.6 | 101.6 | 57.9 |
| 67 | 110.6 | 98.5 | 68.8 |
| 69 | 108.7 | 98.4 | 58.7 |
| 70 | 98.4 | 104.5 | 95.3 |
| 71 | 108.1 | 103.9 | 70.7 |
| 72 | 100.1 | 104.8 | 63.9 |
| 73 | 111.1 | 105.2 | 70.0 |

TABLE 1-continued

| | Blood cell increasing rate (%) | | |
|---|---|---|---|
| Compound | Platelet (%) | Red blood cell (%) | White blood cell (%) |
| 74 | 100.6 | 104.4 | 65.2 |
| 75 | 96.7 | 102.2 | 54.1 |
| 77 | 108.3 | 102.8 | 51.5 |
| 78 | 106.2 | 103.3 | 47.7 |
| 79 | 101.3 | 98.6 | 110.9 |
| 83 | 102.3 | 101.4 | 124.4 |
| 84 | 94.9 | 102.8 | 96.9 |
| 85 | 102.8 | 100 | 111.1 |
| 86 | 88.4 | 96.5 | 179.6 |
| 87 | 95.5 | 96.5 | 140 |
| 88 | 106.3 | 99.9 | 96.2 |
| 95 | 91.7 | 102.9 | 78.7 |
| 96 | 96.5 | 104.9 | 80.5 |
| 99 | 100.7 | 98.6 | 120.9 |
| 101 | 107 | 98 | 96.8 |
| 105 | 106.1 | 97.6 | 115 |
| 107 | 95.5 | 95.6 | 111.5 |
| 110 | 95.2 | 101.7 | 112.9 |
| 111 | 105.6 | 97.4 | 93.7 |
| 112 | 94.1 | 104.1 | 89.5 |
| 113 | 108 | 98.2 | 142.4 |
| 117 | 102.5 | 102.4 | 108.2 |
| 129 | 100.2 | 102.5 | 98.4 |
| 130 | 96.5 | 101.9 | 127.4 |
| 131 | 106.6 | 101.4 | 85.3 |
| 132 | 105.3 | 104.5 | 46.6 |
| 133 | 98.2 | 104.2 | 41.2 |
| 134 | 101.6 | 102.4 | 61.6 |
| 137 | 111.6 | 104.2 | 58.3 |
| 138 | 103.0 | 102.1 | 41.9 |
| 140 | 108.1 | 102.2 | 75.2 |
| 143 | 113.3 | 104.7 | 57.2 |
| 146 | 96.9 | 101.6 | 112.4 |
| 147 | 100.3 | 99.8 | 127.7 |
| 153 | 112.4 | 102.7 | 78.5 |
| 154 | 105.5 | 105.5 | 62.6 |
| 155 | 111.9 | 101.6 | 56.1 |
| 159 | 104 | 102.5 | 84.7 |
| 161 | 104.6 | 102.7 | 53.4 |
| 162 | 101.5 | 102.8 | 74.6 |
| 163 | 98.3 | 102.9 | 89.7 |
| 168 | 108.8 | 98.5 | 86.8 |
| 171 | 108 | 98 | 96.5 |
| 172 | 112.0 | 87.0 | 103.0 |
| 173 | 98.0 | 101.0 | 126.9 |
| 176 | 97.0 | 104.0 | 70.0 |
| 177 | 108.9 | 99.1 | 83.3 |
| 180 | 112.7 | 99.5 | 67.3 |
| 182 | 102.2 | 99.6 | 143.2 |
| 183 | 97.6 | 104.1 | 70.2 |
| 187 | 98.6 | 102.1 | 85.9 |
| 188 | 104.9 | 100.5 | 143.4 |
| 193 | 99.4 | 102 | 129.7 |
| 195 | 89.1 | 96.5 | 158.4 |
| 196 | 109.6 | 99.6 | 81.7 |
| 198 | 93.7 | 102 | 94 |
| 206 | 89.1 | 96.8 | 144.4 |
| 208 | 109.8 | 101.4 | 88.4 |
| 215 | 109.1 | 98.6 | 93.8 |
| 216 | 97 | 100.4 | 120.3 |
| 218 | 95.1 | 98.2 | 110.5 |
| 221 | 115.1 | 105.0 | 63.4 |
| 211 | 106.0 | 97.0 | 110.0 |
| 212 | 104.0 | 104.0 | 131.0 |
| 213 | 110.0 | 107.0 | 94.0 |
| 214 | 100.0 | 103.0 | 93.0 |
| 219 | 109.2 | 99.6 | 81.9 |
| 220 | 105.5 | 99.3 | 61.7 |
| 222 | 102.0 | 100.0 | 129.0 |
| 223 | 119.0 | 104.0 | 61.0 |
| 224 | 115.0 | 107.0 | 67.0 |
| 225 | 113.0 | 100.0 | 74.0 |

TABLE 1-continued

Blood cell increasing rate (%)

| Compound | Platelet (%) | Red blood cell (%) | White blood cell (%) |
|---|---|---|---|
| 226 | 116.0 | 103.0 | 45.0 |
| 227 | 115.0 | 103.0 | 42.0 |

TABLE 2

Platelet increasing rate (%)

| | Dose (mg/kg) | | | |
|---|---|---|---|---|
| Compound | 1 | 10 | 33 | 100 |
| 10 |  | 104.5 | 94.8 | 112.3 |
| 11 |  | 99.7 | 103.0 | 110.9 |
| 12 | 110.7 | 101.7 |  | 103.8 |
| 14 | 107.0 | 111.1 |  | 98.7 |
| 15 | 99.5 | 99.3 |  | 112.7 |
| 18 | 117.3 | 112.7 |  | 113.2 |
| 19 | 113.3 | 106.3 |  | 107.0 |
| 24 | 108.5 | 110.7 |  | 108.4 |
| 25 | 106.7 | 109.0 |  | 113.7 |
| 26 | 109.9 | 111.6 |  | 103.7 |
| 28 | 107.6 | 108.8 |  | 111.5 |
| 29 | 112.6 | 109.5 |  | 108.9 |
| 30 | 109.0 | 109.1 |  | 111.9 |
| 31 | 99.6 | 110.2 |  | 112.3 |
| 32 | 110.0 | 108.2 |  | 113.5 |
| 42 | 114.7 | 109.3 |  | 107.7 |
| 172 |  | 112.0 | 111.0 | 119.0 |
| 182 | 113.6 | 101.3 |  | 97.4 |
| 212 |  | 112.0 | 122.0 | 110.0 |
| 214 |  | 100.0 | 112.0 | 106.0 |
| 219 |  | 109.2 | 117.5 | 120.2 |
| 220 | 106.2 | 113.3 |  | 101.7 |
| 222 |  | 102.0 | 108.0 | 113.0 |
| 223 |  | 119.0 | 110.0 | 124.0 |
| 224 |  | 115.0 | 122.0 | 126.0 |
| 225 |  | 113.0 | 115.0 | 122.0 |
| 226 |  | 116.0 | 107.0 | 115.0 |
| 227 |  | 115.0 | 109.0 | 111.0 |
| 228 | 110.9 | 110.6 |  | 106.8 |
| 229 | 115.4 | 102.6 |  | 105.1 |

TABLE 3

Red blood cell increasing rate (%)

| | Dose (mg/kg) | | | |
|---|---|---|---|---|
| Compound | 1.0 | 10.0 | 33.0 | 100.0 |
| 7 | 104.0 | 100.7 |  | 98.6 |
| 11 |  | 105.0 | 101.0 | 103.0 |
| 13 | 102.5 | 104.0 |  | 104.7 |
| 15 | 103.3 | 102.9 |  | 103.1 |
| 25 | 104.3 | 100.2 |  | 102.8 |
| 32 | 103.0 | 104.0 |  | 105.6 |
| 33 | 105.1 | 105.2 |  | 105.0 |
| 34 | 104.9 | 105.6 |  | 106.1 |
| 42 | 105.1 | 104.1 |  | 107.3 |
| 49 | 107.5 | 107.0 |  | 105.7 |
| 51 | 108.4 | 108.2 |  | 107.8 |
| 52 | 105.2 | 105.4 |  | 103.6 |
| 183 | 103.8 | 104.1 |  | 100.9 |
| 173 |  | 101.0 | 103.0 | 102.0 |
| 176 |  | 104.0 | 105.0 | 104.0 |
| 213 |  | 107.0 | 101.0 | 104.0 |
| 223 |  | 104.0 | 108.0 | 102.0 |
| 224 |  | 107.0 | 109.0 | 105.0 |

TABLE 3-continued

Red blood cell increasing rate (%)

| | Dose (mg/kg) | | | |
|---|---|---|---|---|
| Compound | 1.0 | 10.0 | 33.0 | 100.0 |
| 226 |  | 103.0 | 98.0 | 100.0 |
| 227 |  | 103.0 | 101.0 | 103.0 |

TABLE 4

White blood cell increasing rate (%)

| | Dose (mg/kg) | | | |
|---|---|---|---|---|
| Compound | 1 | 10 | 33 | 100 |
| 1 |  | 105.3 | 129.1 | 118.2 |
| 5 |  | 121.2 | 99.2 | 107.3 |
| 9 | 84.6 | 101.2 |  | 148.8 |
| 16 | 126.8 | 130.9 |  | 77.6 |
| 23 | 111.2 | 143.5 |  | 161.4 |
| 46 | 125 | 115 |  | 156.8 |
| 172 |  | 103.0 | 115.0 | 122.0 |
| 173 |  | 126.0 | 155.0 | 158.0 |
| 182 | 120.6 | 143.2 |  | 205.2 |
| 212 |  | 122.0 | 111.0 | 187.0 |
| 213 |  | 94.0 | 102.0 | 125.0 |
| 214 |  | 93.0 | 126.0 | 90.0 |
| 219 |  | 81.9 | 93.9 | 133.2 |
| 222 |  | 129.0 | 109.0 | 109.0 |
| 230 |  | 104.0 | 111.5 | 139.1 |

It was found from Tables 1 to 4 that the test compounds increased platelets, red blood cells, and white blood cells dose-dependently.

Industrial Applicability

As mentioned above, the ketone derivatives in the present invention increase platelets, red blood cells, and white blood cells and can preferably be applied to the medical field.

What is claimed is:

1. A ketone compound of the following general formula (I") or a pharmacologically acceptable salt thereof:

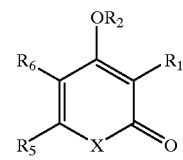

(I")

wherein $R_1$ is —CO(CH$_2$)$_q$Q wherein q is an integer of 0, 1, or from 3 to 10 and Q is a hydrogen atom, a hydrocarbon group having 1 to 6 carbon atoms (in which the hydrocarbon group may have one or more substituents selected from the group consisting of a chlorine atom, a bromine atom, a fluorine atom, a hydroxy group, a nitro group, a methoxy group, an ethoxy group, a carboxyl group, a carboethoxy group, a carbomethoxy group, a cyano group, a trifluoromethyl group, a methylthio group, a phenylthio group, and a t-butyl group, however, the hydrocarbon group must have a substituent when (CH$_2$)$_q$Q is an ethyl group), a heterocyclic ring having 1 to 9 carbon atoms (in which the heterocyclic ring may have one or more substituents selected from the group consisting of a chlorine atom, abromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group, a carboxyl group, a phosphoric ester group (in which the ester portion has 2 to 6 carbon atoms), a phosphoric group, a sulfonyl group having 1 to 7 carbon atoms, a t-butoxycarbonylamino group, a methylsulfoxide group, a primary amido group, or a secondary amide group, —COCO(CH$_2$)$_r$V$_3$ wherein r is an integer of 0 or 1 and V$_3$ is a hydrogen atom, a linear or branched alkyl group having 1 to 6 carbon atoms, an aryl group having 6 to 12 carbon atoms (in which the aryl group may have one or more substituents selected from the group consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), a heterocyclic ring having 1 to 9 carbon atoms (in which the heterocyclic ring may have one or more substituents selected from the group consisting of a chlorine atom, a bromide atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which ester portion has 1 to 6 carbon atoms), a carboxyl group, a primary amide group, or a secondary amide group, —COCH=CHV$_4$ wherein V$_4$ is an aryl group having 6 to 12 carbon atoms (in which the aryl group may have one or more substituents selected from the group consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group) or a heterocyclic ring having 1 to 9 carbon atoms (in which the heterocyclic ring may have one or more substituents selected from the group consisting of a chlorine atom, a bromine atom, a fluorine atom, a hydroxy group, a nitro group, a methoxy group, and an ethoxy group), —CO$_2$G wherein G is a hydrogen atom, a linear or branched alkyl group having 1 to 6 carbon atoms, an aryl group having 6 to 12 carbon atoms (in which the aryl group may have one or more substituents selected from the group consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group), —CONHV$_1$ wherein V$_1$ is a hydrogen atom, a linear or branched alkyl group having 1 to 10 carbon atoms, an aryl group having 6 to 12 carbon atoms (in which the aryl group may have one or more substituents selected from the group consisting of a chlorine atom, a bromine atom, a fluorine atom, a hydroxy group, a nitro group, a methoxy group, an ethoxy group, a carboxyl group, a carboethoxy group, a carbomethoxy group, and a cyano group) or a heterocyclic ring having 1 to 9 carbon atoms (in which the heterocyclic ring may have a substituent selected from the group consisting of a chlorine atom, a bromine atom, a fluorine atom, a hydroxy group, a nitro group, a methoxy group, and an ethoxy group), —NHCOV$_2$ wherein V$_2$ is a hydrogen atom, a linear or branched alkyl group having 1 to 10 carbon atoms, an aryl group having 6 to 12 carbon atoms (in which the aryl group may have one or more substituents selected from the group consisting of a chlorine atom, a bromine atom, a fluorine atom, a hydroxy group, a nitro group, a methoxy group, an ethoxy group, a carboxyl group, a carboethoxy group, a carbomethoxy group, and a cyano group), or a heterocyclic ring having 1 to 9 carbon atoms (in which the heterocyclic ring may have one or more substituents selected from the group consisting of a chlorine atom, a bromine atom, a fluorine atom, a hydroxy group, a nitro group, a methoxy group, and an ethoxy group), or —(CH$_2$)$_t$J wherein t is an integer of from 1 to 10, J is a heterocyclic ring having 1 to 9 carbon atoms (in which the heterocyclic ring may have one or more substituents selected from the group consisting of a chlorine atom, a bromine atom, a fluorine atom, a hydroxy group, a nitro group, a methoxy group, and an ethoxy group), a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, a primary amide group, or a secondary amide group;

R$_2$ is a hydrogen atom, a hydrocarbon group having 1 to 6 carbon atoms, or an acyl group having 2 to 10 carbon atoms;

X is O, S, CH$_2$, or NL wherein L is a hydrogen atom or a linear or branched alkyl group;

R$_5$ is independently a hydrogen atom, a hydrocarbon group having 1 to 15 carbon atoms, a 1-hydroxy-1-carboalkoxymethyl group, or a group represented by —(CH$_2$)$_1$Y wherein 1 is an integer of from 1 to 6 and Y is a hydroxy group, a thiol group, a thioether group having 1 to 6 carbon atoms, an alkoxy group having 1 to 6 carbon atoms, an acetyl group, an amino group, an acetamido group, a cyano group, a carboxyl ester group (in which the ester portion has 1 to 6 carbon atoms), a carboxyl group, an aldehyde group, a phosphoric group, a sulfonic group, a phosphoric ester group (in which the ester portion has 1 to 6 carbon atoms), a sulfonic ester group (in which the ester portion has 1 to 6 carbon atoms), a primary amide group, a secondary amide group, an indole group, a thiophene group, a furan group, a monosubstituted phenyl group, a disubstituted phenyl group, or a trisubstituted phenyl group whose substituent is selected from the group consisting of a chlorine atom, a bromine atom, a fluorine atom, a hydroxy group, a nitro group, a methoxy group, an ethoxy group, a carboxyl group, a carboethoxy group, a carbomethoxy group, and a cyano group;

R$_6$ is independently a hydrogen atom, a halogen atom, a hydrocarbon group having 1 to 6 carbon atoms, or an acyl group having 2 to 19 carbon atoms (in which the acyl group may have one or more substituents selected from the group consisting of a chlorine atom, a bromine atom, a fluorine atom, a hydroxy group, a nitro group, a methoxy group, an ethoxy group, a carboxyl group, a carboethoxy group, a carbomethoxy group, and a cyano group); or $R_5$ and $R_6$ may together form —CH=CH—CH=CH— or —CO(CH$_2$)$_3$.

2. A ketone derivative or a pharmacologically acceptable salt thereof as set forth in claim 1, wherein in the general formula (I"), X is O, S, or CH$_2$.

3. A ketone derivative or a pharmacologically acceptable salt thereof as set forth in claim 1, wherein in the general formula (I"), X is NL (L is defined as above).

4. A ketone derivative or a pharmacologically acceptable salt thereof as set forth in claim 1, wherein in the general formula (I"), the heterocyclic rings in J, Q, $V_1$, $V_2$, and $V_3$ are independently selected from the group essentially consisting of thiophene, furan, pyrrole, tetrahydrofuran, N-methylpyrrole, indole, imidazole, pyrrolidine, pyridine, benzothiophene, benzofuran, quinoline, isoquinoline, phthalimide, and phthalide groups (wherein the heterocyclic rings may have one or more substituents selected from the group essentially consisting of a chlorine atom, a bromine atom, a fluorine atom, a hydroxy group, a nitro group, a methoxy group, and an ethoxy group).

5. A ketone compound or a pharmacologically acceptable salt thereof as set forth in claim 1, wherein in the general formula (I"), X is O.

6. A ketone compound or a pharmacologically acceptable salt thereof as set forth in claim 1, wherein $R_1$ is —CO(CH$_2$)$_q$Q wherein q is an integer of 0, 1, or from 3 to 10 and Q is a heterocyclic ring having 1 to 9 carbon atoms in which the heterocyclic ring may have one or more substituents selected from the group consisting of a chlorine atom, a bromine atom, a fluorine atom, a hydroxy group, a nitro group, a methoxy group, and an ethoxy group, —COCO(CH$_2$)$_r$V$_3$ wherein r is an integer of 0 or 1 and $V_3$ is a heterocyclic ring having 1 to 9 carbon atoms in which the heterocyclic ring may have one or more substituents selected from the group consisting of a chlorine atom, a bromide atom, a fluorine atom, a hydroxy group, a nitro group, a methoxy group, and an ethoxy group, —COCH=CHV$_4$ wherein $V_4$ is a heterocyclic ring having 1 to 9 carbon atoms in which the heterocyclic ring may have one or more substituents selected from the group consisting of a chlorine atom, a bromine atom, a fluorine atom, a hydroxy group, a nitro group, a methoxy group, and an ethoxy group, —CONHV$_1$ wherein $V_1$ is a heterocyclic ring having 1 to 9 carbon atoms in which the heterocyclic ring may have a substituent selected from the group consisting of a chlorine atom, a bromine atom, a fluorine atom, a hydroxy group, a nitro group, a methoxy group, and an ethoxy group, —NHCOV$_2$ wherein $V_2$ is a heterocyclic ring having 1 to 9 carbon atoms in which the heterocyclic ring may have one or more substituents selected from the group consisting of a chlorine atom, a bromine atom, a fluorine atom, a hydroxy group, a nitro group, a methoxy group, and an ethoxy group, or —(CH$_2$)$_t$J wherein t is an integer of from 1 to 10, J is a heterocyclic ring having 1 to 9 carbon atoms in which the heterocyclic ring may have one or more substituents selected from the group consisting of a chlorine atom, a bromine atom, a fluorine atom, a hydroxy group, a nitro group, a methoxy group, and an ethoxy group.

7. A ketone compound or a pharmacologically acceptable salt thereof as set forth in claim 1, wherein $R_1$ is —CO(CH$_2$)$_q$Q wherein q is an integer of 0, 1, or from 3 to 10 and Q is a hydrocarbon group having 6 carbon atoms in which the hydrocarbon group may have one or more substituents selected from the group consisting of a chlorine atom, a brormine atom, a fluorine atom, a hydroxy group, a nitro group, a methoxy group, an ethoxy group, a carboxyl group, a carboethoxy group, a carbomethoxy group, a cyano group, a trifluoromethyl group, a methylthio group, a phenylthio group, and a t-butyl group, or a sulfonyl group having 6 to 7 carbon atoms, —COCO(CH$_2$)$_r$V$_3$ wherein r is an integer of 0 or 1 and $V_3$ is an aryl group having 6 to 12 carbon atoms in which the aryl group may have one or more substituents selected from the group consisting of a chlorine atom, a bromine atom, a fluorine atom, a hydroxy group, a nitro group, a methoxy group, an ethoxy group, a carboxyl group, a carboethoxy group, a carbomethoxy group, and a cyano group, —COCH=CHV$_4$ wherein $V_4$ is an aryl group having 6 to 12 carbon atoms in which the aryl group may have one or more substituents selected from the group consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group, —CO$_2$G wherein G is an aryl group having 6 to 12 carbon atoms in which the aryl group may have one or more substituents selected from the group consisting of a chlorine atom, a bromine atom, a hydroxy group, a nitro group, a methoxy group, an ethoxy group, a carboxyl group, a carboethoxy group, a carbomethoxy group, a cyano group, a trifluoromethyl group, a methylthio group, and a phenylthio group, —CONHV$_1$ wherein $V_1$ is an aryl group having 6 to 12 carbon atoms in which the aryl group may have one or more substituents selected from the group consisting of a chlorine atom, a bromine atom, a fluorine atom, a hydroxy group, a nitro group, a methoxy group, an ethoxy group, a carboxyl group, a carboethoxy group, a carbomethoxy group, and a cyano group, —NHCOV$_2$ wherein $V_2$ is an aryl group having 6 to 12 carbon atoms in which the aryl group may have one or more substituents selected from the group consisting of a chlorine atom, a bromine atom, a fluorine atom, a hydroxy group, a nitro group, a methoxy group, an ethoxy group, a carboxyl group, a carboethoxy group, a carbomethoxy group, and a cyano group.

* * * * *

UNITED STATES PATENT AND TRADEMARK OFFICE
CERTIFICATE OF CORRECTION

PATENT NO. : 6,215,016 B1  
DATED : April 10, 2001  
INVENTOR(S) : Hawai et al.

Page 1 of 1

It is certified that error appears in the above-identified patent and that said Letters Patent is hereby corrected as shown below:

<u>Column 94,</u>  
At "Compound 39", please change "104-167° C" to -- 104-107° C --.

<u>Column 114,</u>  
At "Compound 80", please change "$O_6$" to -- $O_6 S$ --.

<u>Column 191,</u>  
At "Compound 235", after "1197", please change "141" to -- 1141 --.

Signed and Sealed this

Fifth Day of February, 2002

Attest:

Attesting Officer

JAMES E. ROGAN  
*Director of the United States Patent and Trademark Office*